US007183270B2

(12) United States Patent
Cherney et al.

(10) Patent No.: US 7,183,270 B2
(45) Date of Patent: Feb. 27, 2007

(54) CYCLIC DERIVATIVES AS MODULATORS OF CHEMOKINE RECEPTOR ACTIVITY

(75) Inventors: Robert J. Cherney, Newark, DE (US); Percy H. Carter, Princeton, NJ (US); John V. Duncia, Newtown, PA (US); Daniel S. Gardner, Furlong, PA (US); Joseph B. Santella, Springfield, PA (US)

(73) Assignee: Bristol-Myers Squibb Company, Princeton, NJ (US)

( * ) Notice: Subject to any disclaimer, the term of this patent is extended or adjusted under 35 U.S.C. 154(b) by 232 days.

(21) Appl. No.: 10/776,828

(22) Filed: Feb. 11, 2004

(65) Prior Publication Data

US 2004/0186140 A1 Sep. 23, 2004

Related U.S. Application Data

(60) Provisional application No. 60/446,850, filed on Feb. 12, 2003.

(51) Int. Cl.
| | |
|---|---|
| A61K 31/397 | (2006.01) |
| A61K 31/5383 | (2006.01) |
| A61K 31/496 | (2006.01) |
| A61K 31/454 | (2006.01) |
| A61K 61/4015 | (2006.01) |
| C07D 413/12 | (2006.01) |
| C07D 403/12 | (2006.01) |
| C07D 401/12 | (2006.01) |
| C07D 207/77 | (2006.01) |
| C07D 207/00 | (2006.01) |
| C07D 205/04 | (2006.01) |

(52) U.S. Cl. ............... 514/210.18; 514/237.2; 514/254.01; 514/326; 514/422; 544/141; 544/372; 546/208; 548/518; 548/953

(58) Field of Classification Search .......... 548/550, 548/518, 953; 514/210.18, 237.2, 254.01, 514/326, 422; 544/141, 372; 546/208
See application file for complete search history.

(56) References Cited

U.S. PATENT DOCUMENTS

| 5,356,907 A | 10/1994 | Clemence et al. |
|---|---|---|
| 6,011,052 A | 1/2000 | Padia et al. |
| 6,706,712 B2 | 3/2004 | Cherney |
| 2003/0060459 A1 | 3/2003 | Cherney et al. |
| 2003/0216434 A1 | 11/2003 | Cherney |
| 2004/0110736 A1 | 6/2004 | Cherney |
| 2004/0186143 A1 | 9/2004 | Carter et al. |
| 2004/0235835 A1 | 11/2004 | Carter |
| 2004/0235836 A1 | 11/2004 | Cherney |

FOREIGN PATENT DOCUMENTS

| WO | WO 97/37975 | 10/1997 |
|---|---|---|
| WO | WO 97/44329 | 11/1997 |
| WO | WO 98/06703 | 2/1998 |
| WO | WO 98/08826 | 3/1998 |
| WO | WO 99/07351 | 2/1999 |
| WO | WO 99/07678 | 2/1999 |
| WO | WO 99/25686 | 5/1999 |
| WO | WO 99/37304 A2 * | 7/1999 |
| WO | WO 9937304 A1 * | 7/1999 |
| WO | WO 99/40913 | 8/1999 |
| WO | WO 99/40914 | 8/1999 |
| WO | WO 00/46196 | 8/2000 |
| WO | WO 00/69815 | 11/2000 |
| WO | WO 00/69820 | 11/2000 |
| WO | WO 01/19939 | 3/2001 |
| WO | WO 02/01416 | 1/2002 |
| WO | WO 02/26734 | 4/2002 |
| WO | WO 02/50019 | 6/2002 |
| WO | WO 02/060859 | 8/2002 |
| WO | WO 02060859 | 8/2002 |
| WO | WO 02/070523 | 9/2002 |
| WO | WO 02/102372 | 12/2002 |
| WO | WO 03/43988 | 5/2003 |
| WO | WO 03075853 | 9/2003 |
| WO | WO 2004071449 | 8/2004 |
| WO | WO 2004098512 | 11/2004 |
| WO | WO 2004098516 | 11/2004 |

OTHER PUBLICATIONS

Suga et al., "Glycosidase Antibodies Induced to a Half-Chair Transition-State Analog," *J. Am. Chem. Soc.*, vol. 116, pp. 11197-11198, 1994.

(Continued)

*Primary Examiner*—Kamal A. Saeed
*Assistant Examiner*—Joseph R. Kosack
(74) *Attorney, Agent, or Firm*—Mary K. VanAtten

(57) ABSTRACT

The present application describes modulators of MCP-1 of formula (I):

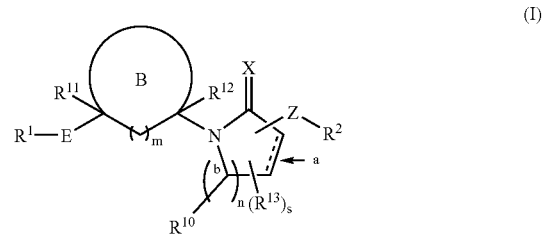

(I)

or pharmaceutically acceptable salt forms thereof, useful for the prevention of rheumatoid arthritis, multiple sclerosis, atherosclerosis and asthma, processes for preparing and intermediates thereof.

19 Claims, No Drawings

OTHER PUBLICATIONS

Fujita et al., "Regiocontrolled Iodoaminocyclization Reaction of an Ambident Nucleophile Mediated by Basic Metallic Reagent," *J. Org. Chem.,* vol. 62 pp. 7330-7335, 1997.
U.S. Appl. No. 10/922,406, filed Aug. 19, 2004, Carter et al.
U.S. Appl. No. 10/923,619, filed Aug. 19, 2004, Carter et al.
U.S. Appl. No. 10/922,726, filed Aug. 19, 2004, Carter et al.
U.S. Appl. No. 10/923,538, filed Aug. 19, 2004, Carter et al.

* cited by examiner

US 7,183,270 B2

CYCLIC DERIVATIVES AS MODULATORS OF CHEMOKINE RECEPTOR ACTIVITY

CROSS-REFERENCE TO RELATED APPLICATIONS

The present application claims the priority benefits of U.S. Provisional Application No. 60/446,850, filed Feb. 12, 2003, which is expressly incorporated fully herein by reference.

FIELD OF THE INVENTION

This invention relates generally to modulators of chemokine receptor activity, pharmaceutical compositions containing the same, and methods of using the same as agents for treatment and prevention of inflammatory diseases, allergic and autoimmune diseases, and in particular, asthma, rheumatoid arthritis, atherosclerosis, and multiple sclerosis, processes of forming and intermediates thereof.

BACKGROUND OF THE INVENTION

Chemokines are chemotactic cytokines, of molecular weight 6–15 kDa, that are released by a wide variety of cells to attract and activate, among other cell types, macrophages, T and B lymphocytes, eosinophils, basophils and neutrophils (reviewed in: Luster, *New Eng. J. Med.* 1998, 338, 436–445 and Rollins, *Blood* 1997, 90, 909–928). There are two major classes of chemokines, CXC and CC, depending on whether the first two cysteines in the amino acid sequence are separated by a single amino acid (CXC) or are adjacent (CC). The CXC chemokines, such as interleukin-8 (IL-8), neutrophil-activating protein-2 (NAP-2) and melanoma growth stimulatory activity protein (MGSA) are chemotactic primarily for neutrophils and T lymphocytes, whereas the CC chemokines, such as RANTES, MIP-1α, MIP-1β, the monocyte chemotactic proteins (MCP-1, MCP-2, MCP-3, MCP-4, and MCP-5) and the eotaxins (-1 and -2) are chemotactic for, among other cell types, macrophages, T lymphocytes, eosinophils, dendritic cells, and basophils. There also exist the chemokines lymphotactin-1, lymphotactin-2 (both C chemokines), and fractalkine (a $CX_3C$ chemokine) that do not fall into either of the major chemokine subfamilies.

The chemokines bind to specific cell-surface receptors belonging to the family of G-protein-coupled seven-transmembrane-domain proteins (reviewed in: Horuk, *Trends Pharm. Sci.* 1994, 15, 159–165) which are termed "chemokine receptors." On binding their cognate ligands, chemokine receptors transduce an intracellular signal though the associated trimeric G proteins, resulting in, among other responses, a rapid increase in intracellular calcium concentration, changes in cell shape, increased expression of cellular adhesion molecules, degranulation, and promotion of cell migration. There are at least ten human chemokine receptors that bind or respond to CC chemokines with the following characteristic patterns(reviewed in Zlotnik and Oshie *Immunity* 2000, 12, 121): CCR-1 (or "CKR-1" or "CC-CKR-1") [MIP-1α, MCP-3, MCP-4, RANTES] (Ben-Barruch, et al., *Cell* 1993, 72, 415–425, and Luster, *New Eng. J. Med.* 1998, 338, 436–445); CCR-2A and CCR-2B (or "CKR-2A"/"CKR-2B" or "CC-CKR-2A"/"CC-CKR-2B") [MCP-1, MCP-2, MCP-3, MCP-4, MCP-5] (Charo, et al., *Proc. Natl. Acad. Sci. USA* 1994, 91, 2752–2756, and Luster, *New Eng. J. Med.* 1998, 338, 436–445); CCR-3 (or "CKR-3" or "CC-CKR-3") [eotaxin-1, eotaxin-2, RANTES, MCP-3, MCP-4] (Combadiere, et al., *J. Biol. Chem.* 1995, 270, 16491–16494, and Luster, *New Eng. J. Med.* 1998, 338, 436–445); CCR-4 (or "CKR-4" or "CC-CKR-4") [TARC, MDC] (Power, et al., *J. Biol. Chem.* 1995, 270, 19495–19500, and Luster, *New Eng. J. Med.* 1998, 338, 436–445); CCR-5 (or "CKR-5" OR "CC-CKR-5") [MIP-1α, RANTES, MIP-1β] (Sanson, et al., *Biochemistry* 1996, 35, 3362–3367); CCR-6 (or "CKR-6" or "CC-CKR-6") [LARC] (Baba, et al., *J. Biol. Chem.* 1997, 272, 14893–14898); CCR-7 (or "CKR-7" or "CC-CKR-7") [ELC] (Yoshie et al., *J. Leukoc. Biol.* 1997, 62, 634–644); CCR-8 (or "CKR-8" or "CC-CKR-8") [I-309] (Napolitano et al., *J. Immunol.*, 1996, 157, 2759–2763); CCR-10 (or "CKR-10" or "CC-CKR-10") [MCP-1, MCP-3] (Bonini, et al., *DNA and Cell Biol.* 1997, 16, 1249–1256); and CCR-11 [MCP-1, MCP-2, and MCP-4] (Schweickert, et al., *J. Biol. Chem.* 2000, 275, 90550).

In addition to the mammalian chemokine receptors, mammalian cytomegaloviruses, herpesviruses and poxviruses have been shown to express, in infected cells, proteins with the binding properties of chemokine receptors (reviewed in: Wells and Schwartz, *Curr. Opin. Biotech.* 1997, 8, 741–748). Human CC chemokines, such as RANTES and MCP-3, can cause rapid mobilization of calcium via these virally encoded receptors. Receptor expression may be permissive for infection by allowing for the subversion of normal immune system surveillance and response to infection. Additionally, human chemokine receptors, such as CXCR4, CCR2, CCR3, CCR5 and CCR8, can act as co-receptors for the infection of mammalian cells by microbes as with, for example, the human immunodeficiency viruses (HIV).

The chemokines and their cognate receptors have been implicated as being important mediators of inflammatory, infectious, and immunoregulatory disorders and diseases, including asthma and allergic diseases, as well as autoimmune pathologies such as rheumatoid arthritis and atherosclerosis (reviewed in: P. H. Carter, *Current Opinion in Chemical Biology* 2002, 6, 510; Trivedi, et al, *Ann. Reports Med. Chem.* 2000, 35, 191; Saunders and Tarby, *Drug Disc. Today* 1999, 4, 80; Premack and Schall, *Nature Medicine* 1996, 2, 1174). For example, the chemokine monocyte chemoattractant-1 (MCP-1) and its receptor CC Chemokine Receptor 2 (CCR-2) play a pivotal role in attracting leukocytes to sites of inflammation and in subsequently activating these cells. When the chemokine MCP-1 binds to CCR-2, it induces a rapid increase in intracellular calcium concentration, increased expression of cellular adhesion molecules, cellular degranulation, and the promotion of leukocyte migration. Demonstration of the importance of the MCP-1/CCR-2 interaction has been provided by experiments with genetically modified mice. MCP-1 −/− mice had normal numbers of leukocytes and macrophages, but were unable to recruit monocytes into sites of inflammation after several different types of immune challenge (Bao Lu, et al., *J. Exp. Med.* 1998, 187, 601). Likewise, CCR-2 −/− mice were unable to recruit monocytes or produce interferon-γ when challenged with various exogenous agents; moreover, the leukocytes of CCR-2 null mice did not migrate in response to MCP-1 (Landin Boring, et al., *J. Clin. Invest.* 1997, 100, 2552), thereby demonstrating the specificity of the MCP-1/CCR-2 interaction. Two other groups have independently reported equivalent results with different strains of CCR-2 −/− mice (William A. Kuziel, et al., *Proc. Natl. Acad. Sci. USA* 1997, 94, 12053, and Takao Kurihara, et al., *J. Exp. Med.* 1997, 186, 1757). The viability and generally normal health of the MCP-1 −/− and CCR-2 −/− animals is noteworthy, in that disruption of the MCP-1/CCR-2 interaction does not induce physiological crisis. Taken together, these data lead one to the conclusion that molecules that block the actions of MCP-1 would be useful in treating a number of inflammatory and autoimmune disorders. This hypothesis has now been validated in a number of different animal disease models, as described below.

It is known that MCP-1 is upregulated in patients with rheumatoid arthritis (Alisa Koch, et al., *J. Clin. Invest.* 1992, 90, 772–779). Moreover, several studies have demonstrated the potential therapeutic value of antagonism of the MCP-1/CCR2 interaction in treating rheumatoid arthritis. A DNA vaccine encoding MCP-1 was shown recently to ameliorate chronic polyadjuvant-induced arthritis in rats (Sawsan Youssef, et al., *J. Clin. Invest.* 2000, 106, 361). Likewise, inflammatory disease symptoms could be controlled via direct administration of antibodies for MCP-1 to rats with collagen-induced arthritis (Hiroomi Ogata, et al., *J. Pathol.* 1997, 182, 106), or streptococcal cell wall-induced arthritis (Ralph C. Schimmer, et al., *J. Immunol.* 1998, 160, 1466). Perhaps most significantly, a peptide antagonist of MCP-1, MCP-1 (9–76), was shown both to prevent disease onset and to reduce disease symptoms (depending on the time of administration) in the MRL-lpr mouse model of arthritis (Jiang-Hong Gong, et al., *J. Exp. Med.* 1997, 186, 131).

It is known that MCP-1 is upregulated in atherosclerotic lesions, and it has been shown that circulating levels of MCP-1 are reduced through treatment with therapeutic agents, plays a role in disease progression (Abdolreza Rezaie-Majd, et al, *Arterioscler. Thromb. Vasc. Biol.* 2002, 22, 1194–1199). Four key studies have demonstrated the potential therapeutic value of antagonism of the MCP-1/CCR2 interaction in treating atherosclerosis. For example, when MCP-1 –/– mice are mated with LDL receptor-deficient mice, an 83% reduction in aortic lipid deposition was observed (Long Gu, et al., *Mol. Cell* 1998, 2, 275). Similarly, when MCP-1 was genetically ablated from mice which already overexpressed human apolipoprotein B, the resulting mice were protected from atherosclerotic lesion formation relative to the MCP-1 +/+ apoB control mice (Jennifa Gosling, et al., *J. Clin. Invest.* 1999, 103, 773). Likewise, when CCR-2 –/– mice are crossed with apolipoprotein E –/– mice, a significant decrease in the incidence of atherosclerotic lesions was observed (Landin Boring, et al, *Nature* 1998, 394, 894). Finally, when apolipoprotein E –/– mice are administered a gene encoding a peptide antagonist of CCR2, then lesion size is decreased and plaque stability is increased (W. Ni, et al. *Circulation* 2001, 103, 2096–2101).

It is known that MCP-1 is upregulated in human multiple sclerosis, and it has been shown that effective therapy with interferon b-1b reduces MCP-1 expression in peripheral blood mononuclear cells, suggesting that MCP-1 plays a role in disease progression (Carla Iarlori, et al., *J. Neuroimmunol.* 2002, 123, 170–179). Other studies have demonstrated the potential therapeutic value of antagonism of the MCP-1/CCR-2 interaction in treating multiple sclerosis; all of these studies have been demonstrated in experimental autoimmune encephalomyelitis (EAE), the conventional animal model for multiple scelerosis. Administration of antibodies for MCP-1 to animals with EAE significantly diminished disease relapse (K. J. Kennedy, et al., *J. Neuroimmunol.* 1998, 92, 98). Furthermore, two recent reports have now shown that CCR-2 –/– mice are resistant to EAE (Brian T. Fife, et al., *J. Exp. Med.* 2000, 192, 899; Leonid Izikson, et al., *J. Exp. Med.* 2000, 192, 1075).

It is known that MCP-1 is upregulated in patients who develop bronchiolitis obliterans syndrome after lung transplantation (Martine Reynaud-Gaubert, et al., *J. of Heart and Lung Transplant.*, 2002, 21, 721–730; John Belperio, et al., *J. Clin. Invest.* 2001, 108, 547–556). In a murine model of bronchiolitis obliterans syndrome, administration of an antibody to MCP-1 led to attenuation of airway obliteration; likewise, CCR2 –/– mice were resistant to airway obliteration in this same model (John Belperio, et al., *J. Clin. Invest.* 2001, 108, 547–556). These data suggest that antagonism of MCP-1/CCR2 may be beneficial in treating rejection of organs following transplantation.

Other studies have demonstrated the potential therapeutic value of antagonism of the MCP-1/CCR2 interaction in treating asthma. Sequestration of MCP-1 with a neutralizing antibody in ovalbumin-challenged mice resulted in marked decrease in bronchial hyperresponsiveness and inflammation (Jose-Angel Gonzalo, et al., *J. Exp. Med.* 1998, 188, 157). It proved possible to reduce allergic airway inflammation in *Schistosoma mansoni* egg-challenged mice through the administration of antibodies for MCP-1 (Nicholas W. Lukacs, et al., J. Immunol. 1997, 158, 4398). Consistent with this, MCP-1 –/– mice displayed a reduced response to challenge with *Schistosoma mansoni* egg (Bao Lu, et al., *J. Exp. Med.* 1998, 187, 601).

Other studies have demonstrated the potential therapeutic value of antagonism of the MCP-1/CCR2 interaction in treating kidney disease. Administration of antibodies for MCP-1 in a murine model of glomerularnephritis resulted in a marked decrease in glomerular crescent formation and deposition of type I collagen (Clare M. Lloyd, et al., *J. Exp. Med.* 1997, 185, 1371). In addition, MCP-1 –/– mice with induced nephrotoxic serum nephritis showed significantly less tubular damage than their MCP-1 +/+ counterparts (Gregory H. Tesch, et al., *J. Clin. Invest.* 1999, 103, 73).

One study has demonstrated the potential therapeutic value of antagonism of the MCP-1/CCR2 interaction in treating systemic lupus erythematosus. Crossing of MCP-1 –/– mice with MRL-FAS$^{lpr}$ mice—the latter of which have a fatal autoimmune disease that is analogous to human systemic lupus erythematosus—results mice that have less disease and longer survival than the wildtype MRL-FAS$^{lpr}$ mice (Gregory H. Tesch, et al., *J. Exp. Med.* 1999, 190, 1813).

One study has demonstrated the potential therapeutic value of antagonism of the MCP-1/CCR2 interaction in treating colitis. CCR-2 –/– mice were protected from the effects of dextran sodium sulfate-induced colitis (Pietro G. Andres, et al., *J. Immunol.* 2000, 164, 6303).

One study has demonstrated the potential therapeutic value of antagonism of the MCP-1/CCR2 interaction in treating alveolitis. When rats with IgA immune complex lung injury were treated intravenously with antibodies raised against rat MCP-1 (JE), the symptoms of alveolitis were partially aleviated (Michael L. Jones, et al., *J. Immunol.* 1992, 149, 2147).

One study has demonstrated the potential therapeutic value of antagonism of the MCP-1/CCR2 interaction in treating cancer. When immunodeficient mice bearing human breast carcinoma cells were treated with an anti-MCP-1 antibody, inhibition of lung micrometastases and increases in survival were observed (Rosalba Salcedo, et al., *Blood* 2000, 96, 34–40).

One study has demonstrated the potential therapeutic value of antagonism of the MCP-1/CCR2 interaction in treating restinosis. Mice deficient in CCR2 showed reductions in the intimal area and in the intima/media ratio (relative to wildtype littermates) after injury of the femoral artery (Merce Roque, et al. *Arterioscler. Thromb. Vasc. Biol.* 2002, 22, 554–559).

Other studies have provided evidence that MCP-1 is overexpressed in various disease states not mentioned above. These reports provide correlative evidence that MCP-1 antagonists could be useful therapeutics for such diseases. Two reports described the overexpression of MCP-1 in the intestinal epithelial cells and bowel mucosa of patients with inflammatory bowel disease (H. C. Reinecker, et al., *Gastroenterology* 1995, 108, 40, and Michael C. Grimm, et al., *J. Leukoc. Biol.* 1996, 59, 804). Two reports describe the overexpression of MCP-1 rats with induced brain trauma (J. S. King, et al., *J. Neuroimmunol.* 1994, 56, 127, and Joan W. Berman, et al., *J. Immunol.* 1996, 156, 3017). Another study has demonstrated the overexpression of MCP-1 in rodent cardiac allografts, suggesting a role for MCP-1 in the pathogenesis of transplant arteriosclerosis (Mary E. Russell, et al. *Proc. Natl. Acad. Sci. USA* 1993, 90, 6086). The overexpression of MCP-1 has been noted in the lung endothelial cells of patients with idiopathic pulmonary fibrosis (Harry N. Antoniades, et al., *Proc. Natl. Acad. Sci. USA* 1992, 89, 5371). Similarly, the overexpression of MCP-1 has been noted in the skin from patients with psoriasis (M. Deleuran, et al., *J. Dermatol. Sci.* 1996, 13, 228, and R. Gillitzer, et al., *J. Invest. Dermatol.* 1993, 101, 127). Finally, a recent report has shown that MCP-1 is overexpressed in the brains and cerebrospinal fluid of patients with HIV-1-associated dementia (Alfredo Garzino-Demo, WO 99/46991).

It should also be noted that CCR-2 has been implicated as a co-receptor for some strains of HIV (B. J. Doranz, et al., *Cell* 1996, 85, 1149). It has also been determined that the use of CCR-2 as an HIV co-receptor can be correlated with disease progression (Ruth I. Connor, et al., *J. Exp. Med.* 1997, 185, 621). This finding is consistent with the recent finding that the presence of a CCR-2 mutant, CCR2-64I, is positively correlated with delayed onset of HIV in the human population (Michael W. Smith, et al., *Science* 1997, 277, 959). Although MCP-1 has not been implicated in these processes, it may be that MCP-1 antagonists that act via binding to CCR-2 may have beneficial therapeutic effects in delaying the disease progression to AIDS in HIV-infected patients.

Recently, a number of groups have described the development of small molecule antagonists of MCP-1 (reviewed in: Bharat K. Trivedi, et al, *Ann. Reports Med. Chem.* 2000, 35, 191). Workers at Teijen and Combichem reported the use of cyclic amines (A) as MCP-1 (Tatsuki Shiota, et al., WO 99/25686; Tatsuki Shiota, et al., WO 00/69815) and MIP-1α (Christine Tarby and Wilna Moree, WO 00/69820) antagonists. These compounds are distinguished from those of the present invention (I) by the requirement for the central cyclic amine grouping.

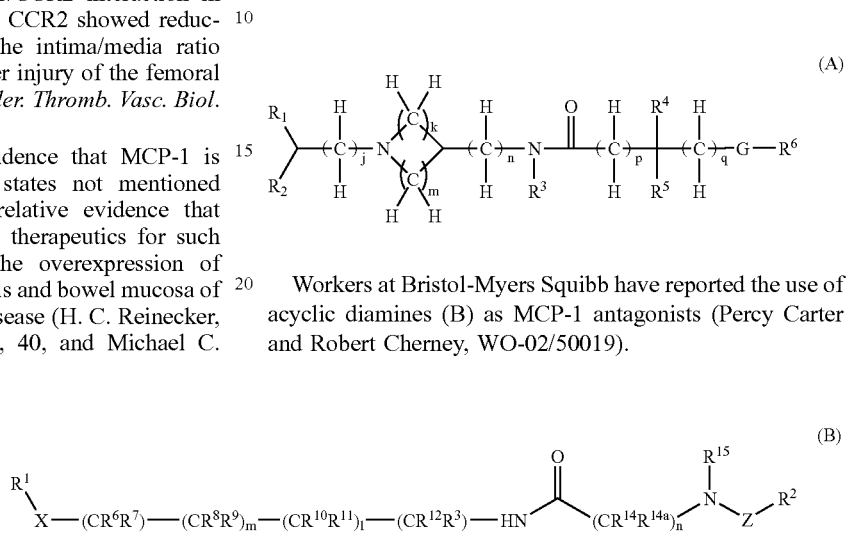

(A)

Workers at Bristol-Myers Squibb have reported the use of acyclic diamines (B) as MCP-1 antagonists (Percy Carter and Robert Cherney, WO-02/50019).

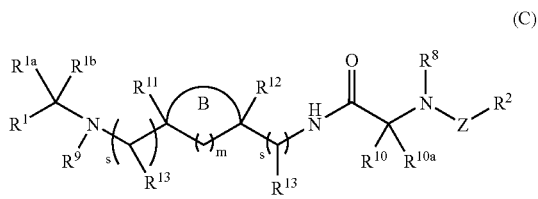

(B)

Workers at Bristol-Myers Squibb have reported the use of cyclic diamines (C) as MCP-1 antagonists (Robert Cherney, WO-02/060859).

(C)

Workers at Pfizer have reported the use of bicyclic diamines (D) as MCP-1 antagonists (Roberto Colon-Cruz, et al., WO-02/070523).

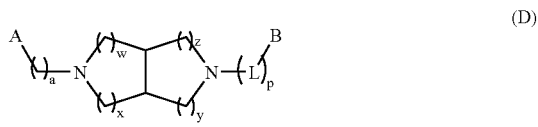

(D)

A number of other groups have also described the development of small molecule antagonists of the MCP-1/CCR-2 interaction. To date, indolopiperidines (Ian T. Forbes, et al., *Bioorg. Med. Chem. Lett.* 2000, 10, 1803), spiropiperidines (Tara Mirzadegan, et al., *J. Biol. Chem.* 2000, 275, 25562), quaternary amines (Masanori Baba, et al., *Proc. Natl. Acad. Sci.* 1999, 96, 5698), 2-substituted indoles (Alan Faull and Jason Kettle, WO 00/46196; Andrew John Barker, et al., WO 99/07351; Andrew John Barker, et al., WO 99/07678), pyrazolone derivatives (Janak Khimchand Padia, et al., U.S. Pat. No. 6,011,052, 2000), 2-substituted benzimidazoles (David Thomas Connor, et al., WO 98/06703), N,N-dialkylhomopiperazines (T. Shiota, et al., WO 97/44329), bicyclic pyrroles (Andrew J. Barker, et al., WO 99/40913 and Andrew J. Barker, et al., WO 99/40914), and 5-aryl pentadienamides (K. G. Carson, et al., Cambridge Health Tech Institute Chemokine Symposium, McLean, Va., USA, 1999) have all been reported as MCP-1 antagonists.

The foregoing reference compounds are readily distinguished structurally from the present invention by virtue of substantial differences in the terminal functionality, the attachment functionality, or the core functionality. The prior art does not disclose nor suggest the unique combination of structural fragments that embody in the novel compounds described herein. Furthermore, the prior art does not disclose or suggest that the compounds of the present invention would be antagonists of MCP-1.

It should be noted that CCR-2 is also the receptor for the chemokines MCP-2, MCP-3, MCP-4, and MCP-5 (Luster, New Eng. J. Med. 1998, 338, 436–445). Since the new compounds of formula (I) described herein antagonize MCP-1 by binding to the CCR-2 receptor, it may be that these compounds of formula (I) are also effective antagonists of the actions of MCP-2, MCP-3, MCP-4, and MCP-5 that are mediated by CCR-2. Accordingly, when reference is made herein to "antagonism of MCP-1," it is to be assumed that this is equivalent to "antagonism of chemokine stimulation of CCR-2."

SUMMARY OF THE INVENTION

Accordingly, the present invention provides novel antagonists or partial agonists/antagonists of MCP-1 receptor activity, or pharmaceutically acceptable salts or prodrugs thereof.

The present invention provides pharmaceutical compositions comprising a pharmaceutically acceptable carrier and a therapeutically effective amount of at least one of the compounds of the present invention or a pharmaceutically acceptable salt or prodrug form thereof.

The present invention provides a method for treating rheumatoid arthritis, multiple sclerosis, and atherosclerosis, comprising administering to a host in need of such treatment a therapeutically effective amount of at least one of the compounds of the present invention or a pharmaceutically acceptable salt or prodrug form thereof.

The present invention provides a method for treating inflammatory diseases, comprising administering to a host in need of such treatment a therapeutically effective amount of at least one of the compounds of the present invention or a pharmaceutically acceptable salt or prodrug form thereof.

The present invention provides novel cyclic derivatives for use in therapy.

The present invention provides the use of novel cyclic derivatives for the manufacture of a medicament for the treatment of inflammatory diseases.

The present invention is directed to methods of preparing the compounds of the present invention, and intermediates thereof.

These and other features of the invention, which will become apparent during the following detailed description, have been achieved by the inventors' discovery that compounds of formula (I):

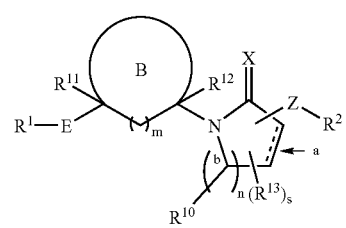

or stereoisomers or pharmaceutically acceptable salts thereof, wherein B, E, Z, m, n, s, carbon b, bond (a), $R^1$, $R^2$, $R^{10}$, $R^{11}$, $R^{12}$, and $R^{13}$ are defined below, are effective modulators of chemokine activity.

DETAILED DESCRIPTION OF EMBODIMENTS OF THE PRESENT INVENTION

[1] Thus, in another embodiment, the present invention provides novel compounds of formula (I):

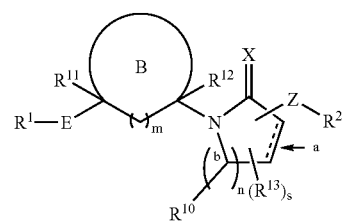

or a stereoisomer or a pharmaceutically acceptable salt thereof, wherein:

ring B is a cycloalkyl group of 3 to 8 carbon atoms wherein the cycloalkyl group is saturated or partially unsaturated; or a heterocycle of 3 to 7 atoms wherein the heterocycle is saturated or partially unsaturated, the heterocycle containing a heteroatom selected from —O—, —S—, —S(=O)—, —S(=O)$_2$—, and —N($R^4$)—, the heterocycle optionally containing a —C(O)—; ring B being substituted with 0–2 $R^5$;

X is selected from O or S;

Z is selected from a bond, —$NR^8C(O)$—, —$NR^8C(S)$—, —$NR^8C(O)NH$—, —$NR^8C(S)NH$—, —$NR^8SO_2$—, —$NR^8SO_2NH$—, —$C(O)NR^8$—, —$OC(O)NR^8$—, —$NR^8C(O)O$—, —$(CR^{15}R^{15})_1$—, —$CR^{14}$=$CR^{14}$—, —$CR^{15}R^{15}C(O)$—, —$C(O)CR^{15}R^{15}$—, —$CR^{15}R^{15}C$(=N—$OR^{16}$)—, —O—$CR^{14}R^{14}$—, —$CR^{14}R^{14}$—O—, —O—, —$NR^9$—, —$NR^9$—$CR^{14}R^{14}$—, —$CR^{14}R^{14}$—$NR^9$—, —$S(O)_p$—, —$S(O)_p$—$CR^{14}R^{14}$—, —$CR^{14}R^{14}$—$S(O)_p$—, and —$S(O)_p$—$NR^9$—;

wherein neither Z nor $R^{13}$ are connected to a carbon atom labeled (b);

bond (a) is a single or double bond;

alternatively, when n is equal to 2, two atoms labeled (b) may join through a double bond;

E is selected from —$S(O)_pCHR^e$—, —$CHR^eNR^e$—, —$C(O)$—$NR^e$—, —$NR^eC(O)NR^e$—, —$SO_2$—$NR^e$—, and —$NR^eSO_2NR^e$—;

$R^e$ is independently selected from H and $C_{1-3}$ alkyl;

$R^1$ is selected from a $C_{6-10}$ aryl group substituted with 0–5 $R^6$ and a 5–10 membered heteroaryl system containing 1–4 heteroatoms selected from N, O, and S, substituted with 0–3 $R^6$;

$R^2$ is selected from a $C_{6-10}$ aryl group substituted with 0–5 $R^7$ and a 5–10 membered heteroaryl system containing 1–4 heteroatoms selected from N, O, and S, substituted with 0–3 $R^7$;

$R^4$ is selected from H, $C_{1-6}$ alkyl, $C_{3-8}$ alkenyl, $C_{3-8}$ alkynyl, $(CRR)_tOH$, $(CRR)_tSH$, $(CRR)_tOR^{4d}$, $(CHR)_tSR^{4d}$, $(CRR)_tNR^{4a}R^{4a}$, $(CRR)_qC(O)OH$, $(CRR)_tC(O)R^{4b}$, $(CRR)_tC(O)NR^{4a}R^{4a}$, $(CRR)_tOC(O)NR^{4a}R^{4a}$, $(CRR)_tNR^{4a}C(O)OR^{4d}$, $(CRR)_tNR^{4a}C(O)R^{4b}$, $(CRR)_tC(O)OR^{4d}$, $(CRR)_tOC(O)R^{4b}$, $(CRR)_tS(O)_pR^{4b}$, $(CRR)_tS(O)_2NR^{4a}R^{4a}$, $(CRR)_tNR^{4a}S(O)_2R^{4b}$, $C_{1-6}$ haloalkyl, a $(CRR)_r$—$C_{3-10}$ carbocyclic residue substituted with 0–3 $R^{4e}$, and a $(CHR)_r$-4–10 membered heterocyclic system containing 1–4 heteroatoms selected from N, O, and S, substituted with 0–2 $R^{4e}$;

$R^{4a}$, at each occurrence, is independently selected from H, methyl substituted with 0–1 $R^{4c}$, $C_{2-6}$ alkyl substituted with 0–3 $R^{4e}$, $C_{3-8}$ alkenyl substituted with 0–3 $R^{4e}$, $C_{3-8}$ alkynyl substituted with 0–3 $R^{4e}$, a $(CH_2)_r$—$C_{3-10}$ carbocyclic residue substituted with 0–4 $R^{4e}$, and a $(CHR)_r$-4–10 membered heterocyclic system containing 1–4 heteroatoms selected from N, O, and S, substituted with 0–2 $R^{4e}$;

$R^{4b}$, at each occurrence, is selected from H, $C_{1-6}$ alkyl substituted with 0–3 $R^{4e}$, $C_{3-8}$ alkenyl substituted with 0–3 $R^{4e}$, $C_{3-8}$ alkynyl substituted with 0–3 $R^{4e}$, a $(CH_2)_r$—$C_{3-6}$ carbocyclic residue substituted with 0–2 $R^{4e}$, and a $(CHR)_r$-4–10 membered heterocyclic system containing 1–4 heteroatoms selected from N, O, and S, substituted with 0–2 $R^{4e}$;

$R^{4c}$ is independently selected from —$C(O)R^{4b}$, —$C(O)OR^{4d}$, —$C(O)NR^{4f}R^{4f}$, and $(CH_2)_r$phenyl;

$R^{4d}$, at each occurrence, is selected from methyl, $CF_3$, $C_{2-6}$ alkyl substituted with 0–3 $R^{4e}$, $C_{3-8}$ alkenyl substituted with 0–3 $R^{4e}$, $C_{3-8}$ alkynyl substituted with 0–3 $R^{4e}$, and a $C_{3-10}$ carbocyclic residue substituted with 0–3 $R^{4e}$;

$R^{4e}$, at each occurrence, is selected from $C_{1-6}$ alkyl, $C_{2-8}$ alkenyl, $C_{2-8}$ alkynyl, $(CH_2)_rC_{3-6}$ cycloalkyl, Cl, F, Br, I, CN, $NO_2$, $(CF_2)_rCF_3$, $(CH_2)_rOC_{1-5}$ alkyl, OH, SH, $(CH_2)_rSC_{1-5}$ alkyl, $(CH_2)_rNR^{4f}R^{4f}$, —$C(O)R^{4i}$, —$C(O)OR^{4j}$, —$C(O)NR^{4h}R^{4h}$, —$OC(O)NR^{4h}R^{4h}$, —$NR^{4h}C(O)NR^{4h}R^{4h}$, —$NR^{4h}C(O)OR^{4j}$, and $(CH_2)_r$phenyl;

$R^{4f}$, at each occurrence, is selected from H, $C_{1-6}$ alkyl, $C_{3-6}$ cycloalkyl, and phenyl;

$R^{4h}$, at each occurrence, is independently selected from H, $C_{1-6}$ alkyl, $C_{3-8}$ alkenyl, $C_{3-8}$ alkynyl, and a $(CH_2)_r$—$C_{3-10}$ carbocyclic;

$R^{4i}$, at each occurrence, is selected from H, $C_{1-6}$ alkyl, $C_{3-8}$ alkenyl, $C_{3-8}$ alkynyl, and a $(CH_2)_r$—$C_{3-6}$ carbocyclic residue;

$R^{4j}$, at each occurrence, is selected from $CF_3$, $C_{1-6}$ alkyl, $C_{3-8}$ alkenyl, $C_{3-8}$ alkynyl, and a $C_{3-10}$ carbocyclic residue;

$R^5$, at each occurrence, is independently selected from H, =O, $C_{1-6}$ alkyl, $C_{2-8}$ alkenyl, $C_{2-8}$ alkynyl, $(CRR)_rOH$, $(CRR)_rSH$, $(CRR)_rOR^{5d}$, $(CRR)_rSR^{5d}$, $(CRR)_rNR^{5a}R^{5a}$, $(CRR)_rN(\rightarrow O)R^{5a}R^{5a}$, $N_3$, $(CRR)_rC(O)OH$, $(CRR)_rC(O)R^{5b}$, $(CRR)_rC(O)NR^{5a}R^{5a}$, $(CRR)_rNR^{5a}C(O)R^{5b}$, $(CRR)_rOC(O)NR^{5a}R^{5a}$, $(CRR)_rNR^{5a}C(O)OR^{5d}$, $(CRR)_rNR^{5a}C(O)NR^{5a}R^{5a}$, $(CRR)_rNR^{5a}C(O)H$, $(CRR)_rC(O)OR^{5d}$, $(CRR)_rOC(O)R^{5b}$, $(CRR)_rS(O)_pR^{5b}$, $(CRR)_rS(O)_2NR^{5a}R^{5a}$, $(CRR)_rNR^{5a}S(O)_2R^{5b}$, $(CRR)_rNR^{5a}S(O)_2NR^{5a}R^{5a}$, $C_{1-6}$ haloalkyl, a $(CRR)_r$—$C_{3-10}$ carbocyclic residue substituted with 0–3 $R^{5c}$, and a $(CRR)_r$-5–10 membered heterocyclic system containing 1–4 heteroatoms selected from N, O, and S, substituted with 0–2 $R^{5c}$;

$R^{5a}$, at each occurrence, is independently selected from H, methyl substituted with 0–1 $R^{5g}$, $C_{2-6}$ alkyl substituted with 0–2 $R^{5e}$, $C_{3-8}$ alkenyl substituted with 0–2 $R^{5e}$, $C_{3-8}$ alkynyl substituted with 0–2 $R^{5e}$, a $(CH_2)_r$—$C_{3-10}$ carbocyclic residue substituted with 0–5 $R^{5e}$, and a $(CH_2)_r$-5–10 membered heterocyclic system containing 1–4 heteroatoms selected from N, O, and S, substituted with 0–3 $R^{5e}$;

$R^{5b}$, at each occurrence, is selected from $C_{1-6}$ alkyl substituted with 0–3 $R^{5e}$, $C_{3-8}$ alkenyl substituted with 0–2 $R^{5e}$, $C_{3-8}$ alkynyl substituted with 0–2 $R^{5e}$, a $(CH_2)_r$—$C_{3-6}$ carbocyclic residue substituted with 0–2 $R^{5e}$, and a $(CH_2)_r$-5–6 membered heterocyclic system containing 1–4 heteroatoms selected from N, O, and S, substituted with 0–3 $R^{5e}$;

$R^{5c}$, at each occurrence, is selected from $C_{1-6}$ alkyl, $C_{2-8}$ alkenyl, $C_{2-8}$ alkynyl, $(CH_2)_rC_{3-6}$ cycloalkyl, Cl, Br, I, F, $(CF_2)_rCF_3$, $NO_2$, CN, $(CH_2)_rNR^{5f}R^{5f}$, $(CH_2)_rOH$, $(CH_2)_rOC_{1-4}$ alkyl, $(CH_2)_rSC_{1-4}$ alkyl, $(CH_2)_rC(O)OH$, $(CH_2)_rC(O)R^{5b}$, $(CH_2)_rC(O)NR^{5f}R^{5f}$, $(CH_2)_rOC(O)NR^{5f}R^{5f}$, $(CH_2)_rNR^{5f}C(O)R^{5b}$, $(CH_2)_rC(O)OC_{1-4}$ alkyl, $(CH_2)_rNR_5C(O)OC_{1-4}$ alkyl, $(CH_2)_rOC(O)R^{5b}$, $(CH_2)_rC(=NR^{5f})NR^{5f}R^{5f}$, $(CH_2)_rS(O)_pR^{5b}$, $(CH_2)_rNHC(=NR^{5f})NR^{5f}R^{5f}$, $(CH_2)_rS(O)_2NR^{5f}R^{5f}$, $(CH_2)_rNR^{5f}S(O)_2R^{5b}$, and $(CH_2)_r$phenyl substituted with 0–3 $R^{5e}$;

$R^{5d}$, at each occurrence, is selected from methyl, $CF_3$, $C_{2-6}$ alkyl substituted with 0–2 $R^{5e}$, $C_{3-8}$ alkenyl substituted with 0–2 $R^{5e}$, $C_{3-8}$ alkynyl substituted with 0–2 $R^{5e}$, and a $C_{3-10}$ carbocyclic residue substituted with 0–3 $R^{5e}$;

$R^{5e}$, at each occurrence, is selected from $C_{1-6}$ alkyl, $C_{2-8}$ alkenyl, $C_{2-8}$ alkynyl, $C_{3-6}$ cycloalkyl, Cl, F, Br, I, CN, $NO_2$, $(CF_2)_rCF_3$, $(CH_2)_rOC_{1-5}$ alkyl, OH, SH, $(CH_2)_rSC_{1-5}$ alkyl, $(CH_2)_rNR^{5f}R^{5f}$, and $(CH_2)_r$phenyl;

$R^{5f}$, at each occurrence, is selected from H, $C_{1-6}$ alkyl, and $C_{3-6}$ cycloalkyl;

$R^{5g}$ is independently selected from —$C(O)R^{5b}$, —$C(O)OR^{5d}$, —$C(O)NR^{5f}R^{5f}$, —CN, and $(CH_2)_r$phenyl;

R, at each occurrence, is selected from H, $C_{1-6}$ alkyl substituted with $R^{5e}$, $C_{2-8}$ alkenyl, $C_{2-8}$ alkynyl, $(CH_2)_rC_{3-6}$ cycloalkyl, and $(CH_2)_r$phenyl substituted with $R^{5e}$;

$R^6$, at each occurrence, is selected from $C_{1-8}$ alkyl, $C_{2-8}$ alkenyl, $C_{2-8}$ alkynyl, $(CH_2)_rC_{3-6}$ cycloalkyl, Cl, Br, I, F, $NO_2$, CN, $(CR'R')_rNR^{6a}R^{6a}$, $(CR'R')_rOH$, $(CR'R')_rO(CR'R')_rR^{6d}$, $(CR'R')_rSH$, $(CR'R')_rC(O)H$, $(CR'R')_rS(CR'R')_rR^{6d}$, $(CR'R')_rSC(O)(CR'R')_rR^{6b}$, $(CR'R')_rC(O)OH$, $(CR'R')_rC(O)(CR'R')_rR^{6b}$, $(CR'R')_rNR^{6a}R^{6a}$, $(CR'R')_rC(O)NR^{6a}R^{6a}$, $(CR'R')_rNR^{6f}C(O)(CR'R')_rR^{6b}$, $(CR'R')_rC(O)O(CR'R')_rR^{6d}$, $(CR'R')_rOC(O)(CR'R')_rR^{6b}$, $(CR'R')_rOC(O)NR^{6a}(CR'R')_rR^{6d}$, $(CR'R')_rNR^{6a}C(O)NR^{6a}(CR'R')_rR^{6d}$, $(CR'R')_rNR^{6a}C(S)NR^{6a}(CR'R')_rR^{6d}$, $(CR'R')_rNR^{6f}C(O)O(CR'R')_rR^{6b}$, $(CR'R')_rC(=NR^{6f})NR^{6a}R^{6a}$, $(CR'R')_rNHC(=NR^{6f})NR^{6f}R^{6f}$, $(CR'R')_rS(O)_p(CR'R')_rR^{6b}$, $(CR'R')_rS(O)_2NR^{6a}R^{6a}$, $(CR'R')_rNR^{6f}S(O)_2NR^{6a}R^{6a}$, $(CR'R')_rNR^{6f}S(O)_2(CR'R')_rR^{6b}$, $C_{1-6}$ haloalkyl, $C_{2-8}$ alkenyl substituted with 0–3 R', $C_{2-8}$ alkynyl substituted with 0–3 R', $(CR'R')_r$phenyl substituted with 0–3 $R^{6e}$, and a $(CH_2)_r$-5–6 membered heterocyclic system containing 1–2 heteroatoms selected from N, O, and S, substituted with 0–2 $R^{6e}$;

alternatively, two $R^6$ on adjacent atoms on $R^1$ may join to form a cyclic acetal;

$R^{6a}$, at each occurrence, is selected from H, methyl substituted with 0–1 $R^{6g}$, $C_{2-6}$ alkyl substituted with 0–2 $R^{6e}$, $C_{3-8}$ alkenyl substituted with 0–2 $R^{6e}$, $C_{3-8}$ alkynyl substituted with 0–2 $R^{6e}$, a $(CH_2)_r$—$C_{3-10}$ carbocyclic residue substituted with 0–5 $R^{6e}$, and a $(CH_2)_r$-5–10 membered heterocyclic system containing 1–4 heteroatoms selected from N, O, and S, substituted with 0–2 $R^{6e}$;

$R^{6b}$, at each occurrence, is selected from H, $C_{1-6}$ alkyl substituted with 0–2 $R^{6e}$, $C_{3-8}$ alkenyl substituted with 0–2 $R^{6e}$, $C_{3-8}$ alkynyl substituted with 0–2 $R^{6e}$, a $(CH_2)_r$-$C_{3-6}$ carbocyclic residue substituted with 0–3 $R^{6e}$, and a $(CH_2)_r$-5–6 membered heterocyclic system containing 1–4 heteroatoms selected from N, O, and S, substituted with 0–2 $R^{6e}$;

$R^{6d}$, at each occurrence, is selected from $C_{3-8}$ alkenyl substituted with 0–2 $R^{6e}$, $C_{3-8}$ alkynyl substituted with 0–2 $R^{6e}$, methyl, $CF_3$, $C_{2-6}$ alkyl substituted with 0–3 $R^{6e}$, $C_{2-4}$ haloalkyl, a $(CH_2)_r$—$C_{3-10}$ carbocyclic residue substituted with 0–3 $R^{6e}$, and a $(CH_2)_r$-5–6 membered heterocyclic system containing 1–4 heteroatoms selected from N, O, and S, substituted with 0–3 $R^{6e}$;

$R^{6e}$, at each occurrence, is selected from $C_{1-6}$ alkyl, $C_{2-8}$ alkenyl, $C_{2-8}$ alkynyl, $(CH_2)_rC_{3-6}$ cycloalkyl, Cl, F, Br, I, CN, $NO_2$, $(CF_2)_rCF_3$, $(CH_2)_rOC_{1-5}$ alkyl, OH, SH, $(CH_2)_rSC_{1-5}$ alkyl, $(CH_2)_rNR^{6f}R^{6f}$, and $(CH_2)_r$phenyl;

$R^{6f}$, at each occurrence, is selected from H, $C_{1-5}$ alkyl, and $C_{3-6}$ cycloalkyl, and phenyl;

$R^{6g}$ is independently selected from —C(O)$R^{6b}$, —C(O)OR$^{6d}$, —C(O)NR$^{6f}R^{6f}$, and $(CH_2)_r$phenyl;

$R^7$, at each occurrence, is selected from $C_{1-8}$ alkyl, $C_{2-8}$ alkenyl, $C_{2-8}$ alkynyl, $(CH_2)_rC_{3-6}$ cycloalkyl, Cl, Br, I, F, $NO_2$, CN, $(CR'R')_rNR^{7a}R^{7a}$, $(CR'R')_rOH$, $(CR'R')_rO(CR'R')_rR^{7d}$, $(CR'R')_rSH$, $(CR'R')_rC(O)H$, $(CR'R')_rS(CR'R')_rR^{7d}$, $(CR'R')_rC(O)OH$, $(CR'R')_rC(O)(CR'R')_rR^{7b}$, $(CR'R')_rC(O)NR^{7a}R^{7a}$, $(CR'R')_rNR^{7f}C(O)(CR'R')_rR^{7b}$, $(CR'R')_rC(O)O(CR'R')_rR^{7d}$, $(CR'R')_rOC(O)(CR'R')_rR^{7b}$, $(CR'R')_rOC(O)NR^{7a}(CR'R')_rR^{7a}$, $(CR'R')_rNR^{7a}C(O)NR^{7a}(CR'R')_rR^{7a}$, $(CR'R')_rNR^{7f}C(O)O(CR'R')_rR^{7d}$, $(CR'R')_rC(=NR^{7f})NR^{7a}R^{7a}$, $(CR'R')_rNHC(=NR^{7f})NR^{7f}R^{7f}$, $(CR'R')_rS(O)_p(CR'R')_rR^{7b}$, $(CR'R')_rS(O)_2NR^{7a}R^{7a}$, $(CR'R')_rNR^{7a}S(O)_2NR^{7a}R^{7a}$, $(CR'R')_rNR^{7f}S(O)_2(CR'R')_rR^{7b}$, $C_{1-6}$ haloalkyl, $C_{2-8}$ alkenyl substituted with 0–3 R', $C_{2-8}$ alkynyl substituted with 0–3 R', $(CR'R')_r C_{3-10}$ carbocyclic residue and $(CR'R')_r$phenyl substituted with 0–3 $R^{7e}$;

alternatively, two $R^7$ on adjacent atoms on $R^2$ may join to form a cyclic acetal;

$R^{7a}$, at each occurrence, is independently selected from H, methyl substituted with 0–1 $R^{7g}$, $C_{2-6}$ alkyl substituted with 0–2 $R^{7e}$, $C_{3-8}$ alkenyl substituted with 0–2 $R^{7e}$, $C_{3-8}$ alkynyl substituted with 0–2 $R^{7e}$, a $(CH_2)_r$—$C_{3-10}$ carbocyclic residue substituted with 0–5 $R^{7e}$, and a $(CH_2)_r$-5–10 membered heterocyclic system containing 1–4 heteroatoms selected from N, O, and S, substituted with 0–2 $R^{7e}$;

$R^{7b}$, at each occurrence, is selected from $C_{1-6}$ alkyl substituted with 0–2 $R^{7e}$, $C_{3-8}$ alkenyl substituted with 0–2 $R^{7e}$, $C_{3-8}$ alkynyl substituted with 0–2 $R^{7e}$, a $(CH_2)_rC_{3-6}$ carbocyclic residue substituted with 0–3 $R^{7e}$, and a $(CH_2)_r$-5–6 membered heterocyclic system containing 1–4 heteroatoms selected from N, O, and S, substituted with 0–2 $R^{7e}$;

$R^{7d}$, at each occurrence, is selected from $C_{3-8}$ alkenyl substituted with 0–2 $R^{7e}$, $C_{3-8}$ alkynyl substituted with 0–2 $R^{7e}$, methyl, $CF_3$, $C_{2-4}$ haloalkyl, $C_{2-6}$ alkyl substituted with 0–3 $R^{7e}$, a $(CH_2)_r$—$C_{3-10}$ carbocyclic residue substituted with 0–3 $R^{7e}$, and a $(CH_2)_r$-5–6 membered heterocyclic system containing 1–4 heteroatoms selected from N, O, and S, substituted with 0–3 $R^{7e}$;

$R^{7e}$, at each occurrence, is selected from $C_{1-6}$ alkyl, $C_{2-8}$ alkenyl, $C_{2-8}$ alkynyl, $(CH_2)_rC_{3-6}$ cycloalkyl, Cl, F, Br, I, CN, $NO_2$, $(CF_2)_rCF_3$, $(CH_2)_rOC_{1-5}$ alkyl, OH, SH, C(O)OC$_{1-5}$ alkyl, $(CH_2)_rSC_{1-5}$ alkyl, $(CH_2)_rNR^{7f}R^{7f}$, and $(CH_2)_r$phenyl;

$R^{7f}$, at each occurrence, is selected from H, $C_{1-5}$ alkyl, and $C_{3-6}$ cycloalkyl, and phenyl;

$R^{7g}$ is independently selected from —C(O)$R^{7b}$, —C(O)OR$^{7d}$, —C(O)NR$^{7f}R^{7f}$, and $(CH_2)_r$phenyl;

R', at each occurrence, is selected from H, $C_{1-6}$ alkyl substituted with $R^{6e}$, $C_{2-8}$ alkenyl, $C_{2-8}$ alkynyl, $(CH_2)_rC_{3-6}$ cycloalkyl, and $(CH_2)_r$phenyl substituted with $R^{6e}$;

$R^8$ is selected from H, $C_{1-4}$ alkyl, and $C_{3-4}$ cycloalkyl;

$R^9$ is selected from H, $C_{1-4}$ alkyl, $C_{3-4}$ cycloalkyl, —C(O)H, and —C(O)—$C_{1-4}$alkyl;

$R^{10}$ is independently selected from H, and $C_{1-4}$alkyl substituted with 0–1 $R^{10b}$, alternatively, two $R^{10}$ form =O;

$R^{10b}$, at each occurrence, is independently selected from —OH, —SH, —NR$^{10c}R^{10c}$, —C(O)NR$^{10c}R^{10c}$, and —NHC(O)$R^{10c}$;

$R^{10c}$ is selected from H, $C_{1-4}$ alkyl and $C_{3-6}$ cycloalkyl;

$R^{11}$ is selected from H, $C_{1-4}$ alkyl, (CHR)$_q$OH, (CHR)$_q$SH, (CHR)$_q$OR$^{11d}$, (CHR)$_q$S(O)$_p$R$^{11d}$, (CHR)$_q$C(O)R$^{11b}$, (CHR)$_q$NR$^{11a}R^{11a}$, (CHR)$_q$C(O)NR$^{11a}R^{11a}$, (CHR)$_q$C(O)NR$^{11a}$OR$^{11d}$, (CHR)$_q$NR$^{11a}$C(O)R$^{11b}$, (CHR)$_q$NR$^{11a}$C(O)OR$^{11d}$, (CHR)$_q$OC(O)NR$^{11a}R^{11a}$, (CHR)$_r$C(O)OR$^{11d}$, a (CHR)$_r$—$C_{3-6}$ carbocyclic residue substituted with 0–5 $R^{11e}$, and a (CHR)$_r$-5–10 membered heterocyclic system containing 1–4 heteroatoms selected from N, O, and S, substituted with 0–3 $R^{11e}$;

$R^{11a}$, at each occurrence, is independently selected from H, $C_{1-4}$ alkyl, $C_{3-4}$ alkenyl, $C_{3-4}$ alkynyl, $(CH_2)_rC_{3-6}$ cycloalkyl, a $(CH_2)_r$—$C_{3-6}$ carbocyclic residue substituted with 0–5 $R^{11e}$, and a $(CH_2)_r$-5–6 membered heterocyclic system containing 1–4 heteroatoms selected from N, O, and S, substituted with 0–3 $R^{11e}$;

$R^{11b}$, at each occurrence, is independently selected from $C_{1-4}$ alkyl, $C_{2-4}$ alkenyl, $C_{2-4}$ alkynyl, a $(CH_2)_r$—$C_{3-6}$ carbocyclic residue substituted with 0–2 $R^{11e}$, and a $(CH_2)_r$-5–6 membered heterocyclic system containing 1–4 heteroatoms selected from N, O, and S, substituted with 0–3 $R^{11e}$;

$R^{11d}$, at each occurrence, is independently selected from H, methyl, —$CF_3$, $C_{2-4}$ alkyl, $C_{3-6}$ alkenyl, $C_{3-6}$ alkynyl, a $C_{3-6}$ carbocyclic residue substituted with 0–3 $R^{11e}$, and a $(CH_2)_r$-5–6 membered heterocyclic system containing 1–4 heteroatoms selected from N, O, and S, substituted with 0–3 $R^{11e}$;

$R^{11e}$, at each occurrence, is selected from $C_{1-6}$ alkyl, $C_{2-8}$ alkenyl, $C_{2-8}$ alkynyl, $C_{3-6}$ cycloalkyl, Cl, F, Br, I, CN, $NO_2$, $(CF_2)_rCF_3$, $(CH_2)_rOC_{1-5}$ alkyl, OH, —O—$C_{1-6}$ alkyl, SH, $(CH_2)_rSC_{1-5}$ alkyl, $(CH_2)_rNR^{11f}R^{11f}$, and $(CH_2)_r$phenyl;

$R^{11f}$, at each occurrence, is selected from H, $C_{1-6}$ alkyl, and $C_{3-6}$ cycloalkyl;

$R^{12}$ is selected from H, $C_{1-4}$ alkyl, (CHR)$_q$OH, (CHR)$_q$SH, (CHR)$_q$OR$^{12d}$, (CHR)$_q$S(O)$_p$R$^{12d}$, (CHR)$_q$C(O)R$^{12b}$, (CHR)$_r$NR$^{12a}R^{12a}$, (CHR)$_q$C(O)NR$^{12a}R^{12a}$, (CHR)$_q$C(O)NR$^{12a}$OR$^{12d}$, (CHR)$_q$NR$^{12a}$C(O)R$^{12b}$, (CHR)$_q$NR$^{12a}$C(O)OR$^{12d}$, (CHR)$_q$OC(O)NR$^{12a}R^{12a}$, (CHR)$_r$C(O)OR$^{12d}$, a (CHR)$_r$—$C_{3-6}$ carbocyclic residue substituted with 0–5 $R^{12e}$, and a (CHR)$_r$-5–10 membered heterocyclic system containing 1–4 heteroatoms selected from N, O, and S, substituted with 0–3 $R^{12e}$;

$R^{12a}$, at each occurrence, is independently selected from H, $C_{1-4}$ alkyl, $C_{3-4}$ alkenyl, $C_{3-4}$ alkynyl, $(CH_2)_rC_{3-6}$ cycloalkyl, a $(CH_2)_r$—$C_{3-6}$ carbocyclic residue substituted with 0–5 $R^{12e}$, and a $(CH_2)_r$-5–6 membered heterocyclic system containing 1–4 heteroatoms selected from N, O, and S, substituted with 0–3 $R^{12e}$;

$R^{12b}$, at each occurrence, is independently selected from $C_{1-4}$ alkyl, $C_{2-4}$ alkenyl, $C_{2-4}$ alkynyl, a $(CH_2)_r$-$C_{3-6}$ carbocyclic residue substituted with 0–2 $R^{12e}$, and a $(CH_2)_r$-5–6 membered heterocyclic system containing 1–4 heteroatoms selected from N, O, and S, substituted with 0–3 $R^{12e}$;

$R^{12d}$, at each occurrence, is independently selected from H, methyl, —$CF_3$, $C_{2-4}$ alkyl, $C_{3-6}$ alkenyl, $C_{3-6}$ alkynyl, a $C_{3-6}$ carbocyclic residue substituted with 0–3 $R^{12e}$, and a $(CH_2)_r$-5–6 membered heterocyclic system containing 1–4 heteroatoms selected from N, O, and S, substituted with 0–3 $R^{12e}$;

$R^{12e}$, at each occurrence, is selected from $C_{1-6}$ alkyl, $C_{2-8}$ alkenyl, $C_{2-8}$ alkynyl, $C_{3-6}$ cycloalkyl, Cl, F, Br, I, CN, $NO_2$, $(CF_2)_rCF_3$, $(CH_2)_rOC_{1-5}$ alkyl, OH, —O—$C_{1-6}$ alkyl, SH, $(CH_2)_rSC_{1-5}$ alkyl, $(CH_2)_rNR^{12f}R^{12f}$, and $(CH_2)_r$phenyl;

$R^{12f}$, at each occurrence, is selected from H, $C_{1-6}$ alkyl, and $C_{3-6}$ cycloalkyl;

$R^{13}$, at each occurrence, is independently selected from H, and $C_{1-4}$alkyl substituted with 0–1 $R^{13b}$, —OH, —$NH_2$, F, Cl, Br, I, —$OR^{13a}$, —$N(R^{13a})_2$, and $C_{1-4}$ alkyl substituted with 0–3 $R^{13b}$;

$R^{13a}$ is selected from H, $C_{1-4}$ alkyl and $C_{3-6}$ cycloalkyl;

$R^{13b}$, at each occurrence, is independently selected from —OH, —SH, $NR^{13c}R^{13c}$, —$C(O)NR^{13c}R^{13c}$, and —NHC$(O)R^{13c}$;

$R^{13c}$ is selected from H, $C_{1-4}$ alkyl and $C_{3-6}$ cycloalkyl;

$R^{14}$, at each occurrence, is independently selected from H and $C_{1-4}$alkyl;

alternatively, two $R^{14}$s, along with the carbon atom to which they are attached, join to form a $C_{3-6}$ carbocyclic ring;

$R^{15}$, at each occurrence, is independently selected from H, $C_{1-4}$alkyl, OH, $NH_2$, —O—$C_{1-4}$ alkyl, $NR^{15a}R^{15a}$, C(O)$NR^{15a}R^{15a}$, $NR^{15a}C(O)R^{15b}$, $NR^{15a}C(O)OR^{15d}$, OC(O)$NR^{15a}R^{15a}$, and $(CHR)_rC(O)OR^{15d}$;

alternatively, two $R^{15}$s, along with the carbon atom or atoms to which they are attached, join to form a $C_{3-6}$ carbocyclic ring;

$R^{15a}$, at each occurrence, is independently selected from H, and $C_{1-4}$ alkyl;

$R^{15b}$, at each occurrence, is independently selected from $C_{1-4}$ alkyl, $C_{3-6}$ alkenyl, and $C_{3-6}$ alkynyl;

$R^{15d}$, at each occurrence, is independently selected from $C_{1-4}$ alkyl, $C_{3-6}$ alkenyl, and $C_{3-6}$ alkynyl;

$R^{16}$ is selected from $C_{1-4}$ alkyl;

l is selected from 1, 2 and 3;

n is selected from 0, 1, 2, and 3;

m is selected from 0 and 1;

p, at each occurrence, is independently selected from 0, 1, and 2;

q, at each occurrence, is independently selected from 1, 2, 3, and 4;

r, at each occurrence, is independently selected from 0, 1, 2, 3, and 4;

t, at each occurrence, is independently selected from 2, 3, and 4;

s is selected from 0 and 1.

[2] Thus, in another embodiment, the present invention provides novel compounds of formula (I):

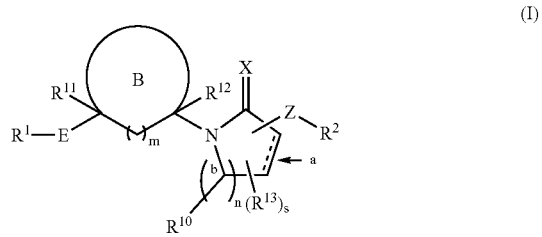

(I)

or a stereoisomer or a pharmaceutically acceptable salt thereof, wherein:

ring B is a cycloalkyl group of 3 to 8 carbon atoms wherein the cycloalkyl group is saturated or partially unsaturated; or a heterocycle of 3 to 7 atoms wherein the heterocycle is saturated or partially unsaturated, the heterocycle containing a heteroatom selected from —O—, —S—, —S(=O)—, —S(=O)$_2$—, and —N($R^4$)—, the heterocycle optionally containing a —C(O)—; ring B being substituted with 0–2 $R^5$;

X is selected from O or S;

Z is selected from a bond, —$NR^8C(O)$—, —$NR^8C(S)$—, —$NR^8C(O)NH$—, —$NR^8C(S)NH$—, —$NR^8SO_2$—, —$NR^8SO_2NH$—, —$C(O)NR^8$—, —$OC(O)NR^8$—, —$NR^8C(O)O$—, —$(CR^{15}R^{15})_t$—, —$CR^{14}$=$CR^{14}$—, —$CR^{15}R^{15}C(O)$—, —$C(O)CR^{15}R^{15}$—, $CR^{15}R^{15}C$(=N—$OR^{16}$)—, —O—$CR^{14}R^{14}$—, —$CR^{14}R^{14}$—O—, —O—, —$NR^9$—, —$NR^9$—$CR^{14}R^{14}$—, —$CR^{14}R^{14}$—$NR^9$—, —$S(O)_p$—, —$S(O)_p$—$CR^{14}R^{14}$—, —$CR^{14}R^{14}$—$S(O)_p$—, and —$S(O)_p$—$NR^9$—;

wherein neither Z nor $R^{13}$ are connected to a carbon atom labeled (b);

bond (a) is a single or double bond;

alternatively, when n is equal to 2, two atoms labeled (b) may join through a double bond;

E is selected from —$S(O)_pCHR^e$—, —$CHR^eNR^e$—, —$C(O)$—$NR^e$—, —$NR^eC(O)NR^e$—, —$SO_2$—$NR^e$—, and —$NR^eSO_2NR^e$—;

$R^e$ is independently selected from H and $C_{1-3}$ alkyl;

$R^1$ is selected from a $C_{6-10}$ aryl group substituted with 0–5 $R^6$ and a 5–10 membered heteroaryl system containing 1–4 heteroatoms selected from N, O, and S, substituted with 0–3 $R^6$;

$R^2$ is selected from a $C_{6-10}$ aryl group substituted with 0–5 $R^7$ and a 5–10 membered heteroaryl system containing 1–4 heteroatoms selected from N, O, and S, substituted with 0–3 $R^7$;

$R^4$ is selected from H, $C_{1-6}$ alkyl, $C_{3-8}$ alkenyl, $C_{3-8}$ alkynyl, $(CRR)_rOH$, $(CRR)_rSH$, $(CRR)_rOR^{4d}$, $(CHR)_rSR^{4d}$, $(CRR)_rNR^{4a}R^{4a}$, $(CRR)_qC(O)OH$, $(CRR)_rC(O)R^{4b}$, $(CRR)_rC(O)NR^{4a}R^{4a}$, $(CRR)_tOC(O)NR^{4a}R^{4a}$, $(CRR)_tNR^{4a}C(O)OR^{4d}$, $(CRR)_tNR^{4a}C(O)R^{4b}$, $(CRR)_rC(O)OR^{4d}$, $(CRR)_tOC(O)R^{4b}$, $(CRR)_rS(O)_pR^{4b}$, $(CRR)_rS(O)_2NR^{4a}R^{4a}$, $(CRR)_rNR^{4a}S(O)_2R^{4b}$, $C_{1-6}$ haloalkyl, a $(CRR)_r$—$C_{3-10}$ carbocyclic residue substituted with 0–3 $R^{4e}$, and a $(CHR)_r$-4–10 membered heterocyclic system containing 1–4 heteroatoms selected from N, O, and S, substituted with 0–2 $R^{4e}$;

$R^{4a}$, at each occurrence, is independently selected from H, methyl substituted with 0–1 $R^{4c}$, $C_{2-6}$ alkyl substituted with 0–3 $R^{4e}$, $C_{3-8}$ alkenyl substituted with 0–3 $R^{4e}$, $C_{3-8}$ alkynyl substituted with 0–3 $R^{4e}$, a $(CH_2)_r$—$C_{3-10}$ carbocyclic residue substituted with 0–4 $R^{4e}$, and a (CHR)$_r$-4–10 membered heterocyclic system containing 1–4 heteroatoms selected from N, O, and S, substituted with 0–2 $R^{4e}$;

$R^{4b}$, at each occurrence, is selected from H, $C_{1-6}$ alkyl substituted with 0–3 $R^{4e}$, $C_{3-8}$ alkenyl substituted with 0–3 $R^{4e}$, $C_{3-8}$ alkynyl substituted with 0–3 $R^{4e}$, a (CH$_2$)$_r$—$C_{3-6}$ carbocyclic residue substituted with 0–2 $R^{4e}$, and a (CHR)$_r$-4–10 membered heterocyclic system containing 1–4 heteroatoms selected from N, O, and S, substituted with 0–2 $R^{4e}$;

$R^{4c}$ is independently selected from —C(O)$R^{4b}$, —C(O)O$R^{4d}$, —C(O)NR$^{4f}$$R^{4f}$, and (CH$_2$)$_r$phenyl;

$R^{4d}$, at each occurrence, is selected from methyl, CF$_3$, $C_{2-6}$ alkyl substituted with 0–3 $R^{4e}$, $C_{3-8}$ alkenyl substituted with 0–3 $R^{4e}$, $C_{3-8}$ alkynyl substituted with 0–3 $R^{4e}$, and a $C_{3-10}$ carbocyclic residue substituted with 0–3 $R^{4e}$;

$R^{4e}$, at each occurrence, is selected from $C_{1-6}$ alkyl, $C_{2-8}$ alkenyl, $C_{2-8}$ alkynyl, (CH$_2$)$_r$$C_{3-6}$ cycloalkyl, Cl, F, Br, I, CN, NO$_2$, (CF$_2$)$_r$CF$_3$, (CH$_2$)$_r$OC$_{1-5}$ alkyl, OH, SH, (CH$_2$)$_r$SC$_{1-5}$ alkyl, (CH$_2$)$_r$NR$^{4f}$R$^{4f}$, —C(O)R$^{4i}$, —C(O)OR$^{4j}$, —C(O)NR$^{4h}$R$^{4h}$, —OC(O)NR$^{4h}$R$^{4h}$, —NR$^{4h}$C(O)NR$^{4h}$R$^{4h}$, —NR$^{4h}$C(O)OR$^{4j}$, and (CH$_2$)$_r$phenyl;

$R^{4f}$, at each occurrence, is selected from H, $C_{1-6}$ alkyl, $C_{3-6}$ cycloalkyl, and phenyl;

$R^{4h}$, at each occurrence, is independently selected from H, $C_{1-6}$ alkyl, $C_{3-8}$ alkenyl, $C_{3-8}$ alkynyl, and a (CH$_2$)$_r$—$C_{3-10}$ carbocyclic;

$R^{4i}$, at each occurrence, is selected from H, $C_{1-6}$ alkyl, $C_{3-8}$ alkenyl, $C_{3-8}$ alkynyl, and a (CH$_2$)$_r$—$C_{3-6}$ carbocyclic residue;

$R^{4j}$, at each occurrence, is selected from CF$_3$, $C_{1-6}$ alkyl, $C_{3-8}$ alkenyl, $C_{3-8}$ alkynyl, and a $C_{3-10}$ carbocyclic residue;

$R^5$, at each occurrence, is independently selected from H, =O, $C_{1-6}$ alkyl, $C_{2-8}$ alkenyl, $C_{2-8}$ alkynyl, (CRR)$_r$OH, (CRR)$_r$SH, (CRR)$_r$OR$^{5d}$, (CRR)$_r$SR$^{5d}$, (CRR)$_r$NR$^{5a}$R$^{5a}$, (CRR)$_r$C(O)OH, (CRR)$_r$C(O)R$^{5b}$, (CRR)$_r$C(O)NR$^{5a}$R$^{5a}$, (CRR)$_r$NR$^{5a}$C(O)R$^{5b}$, (CRR)$_r$OC(O)NR$^{5a}$R$^{5a}$, (CRR)$_r$NR$^{5a}$C(O)OR$^{5d}$, (CRR)$_r$NR$^{5a}$C(O)NR$^{5a}$R$^{5a}$, (CRR)$_r$NR$^{5a}$C(O)H, (CRR)$_r$C(O)OR$^{5d}$, (CRR)$_r$OC(O)R$^{5b}$, (CRR)$_r$S(O)$_p$R$^{5b}$, (CRR)$_r$S(O)$_2$NR$^{5a}$R$^{5a}$, (CRR)$_r$NR$^{5a}$S(O)$_2$R$^{5b}$, (CRR)$_r$NR$^{5a}$S(O)$_2$NR$^{5a}$R$^{5a}$, $C_{1-6}$ haloalkyl, a (CRR)$_r$—$C_{3-10}$ carbocyclic residue substituted with 0–3 $R^{5c}$, and a (CRR)$_r$-5–10 membered heterocyclic system containing 1–4 heteroatoms selected from N, O, and S, substituted with 0–2 $R^{5c}$;

$R^{5a}$, at each occurrence, is independently selected from H, methyl substituted with 0–1 $R^{5g}$, $C_{2-6}$ alkyl substituted with 0–2 $R^{5e}$, $C_{3-8}$ alkenyl substituted with 0–2 $R^{5e}$, $C_{3-8}$ alkynyl substituted with 0–2 $R^{5e}$, a (CH$_2$)$_r$—$C_{3-10}$ carbocyclic residue substituted with 0–5 $R^{5e}$, and a (CH$_2$)$_r$-5–10 membered heterocyclic system containing 1–4 heteroatoms selected from N, O, and S, substituted with 0–3 $R^{5e}$;

$R^{5b}$, at each occurrence, is selected from $C_{1-6}$ alkyl substituted with 0–3 $R^{5e}$, $C_{3-8}$ alkenyl substituted with 0–2 $R^{5e}$, $C_{3-8}$ alkynyl substituted with 0–2 $R^{5e}$, a (CH$_2$)$_r$—$C_{3-6}$ carbocyclic residue substituted with 0–2 $R^{5e}$, and a (CH$_2$)$_r$-5–6 membered heterocyclic system containing 1–4 heteroatoms selected from N, O, and S, substituted with 0–3 $R^{5e}$;

$R^{5c}$, at each occurrence, is selected from $C_{1-6}$ alkyl, $C_{2-8}$ alkenyl, $C_{2-8}$ alkynyl, (CH$_2$)$_r$$C_{3-6}$ cycloalkyl, Cl, Br, I, F, (CF$_2$)$_r$CF$_3$, NO$_2$, CN, (CH$_2$)$_r$NR$^{5f}$R$^{5f}$, (CH$_2$)$_r$OH, (CH$_2$)$_r$OC$_{1-4}$ alkyl, (CH$_2$)$_r$SC$_{1-4}$ alkyl, (CH$_2$)$_r$C(O)OH, (CH$_2$)$_r$C(O)R$^{5b}$, (CH$_2$)$_r$C(O)NR$^{5f}$R$^{5f}$, (CH$_2$)rOC(O)NR$^{5f}$R$^{5f}$, (CH$_2$)$_r$NR$^{5f}$C(O)R$^{5b}$, (CH$_2$)$_r$C(O)OC$_{1-4}$ alkyl, (CH$_2$)$_r$NR$^{5f}$C(O)OC$_{1-4}$ alkyl, (CH$_2$)$_r$OC(O)R$^{5b}$, (CH$_2$)$_r$C(=NR$^{5f}$)NR$^{5f}$R$^{5f}$, (CH$_2$)$_r$S(O)$_p$R$^{5b}$, (CH$_2$)$_r$NHC(=NR$^{5f}$)NR$^{5f}$R$^{5f}$, (CH$_2$)$_r$S(O)$_2$NR$^{5f}$R$^{5f}$, (CH$_2$)$_r$NR$^{5f}$S(O)$_2$R$^{5b}$, and (CH$_2$)$_r$phenyl substituted with 0–3 $R^{5e}$;

$R^{5d}$, at each occurrence, is selected from methyl, CF$_3$, $C_{2-6}$ alkyl substituted with 0–2 $R^{5e}$, $C_{3-8}$ alkenyl substituted with 0–2 $R^{5e}$, $C_{3-8}$ alkynyl substituted with 0–2 $R^{5e}$, and a $C_{3-10}$ carbocyclic residue substituted with 0–3 $R^{5e}$;

$R^{5e}$, at each occurrence, is selected from $C_{1-6}$ alkyl, $C_{2-8}$ alkenyl, $C_{2-8}$ alkynyl, $C_{3-6}$ cycloalkyl, Cl, F, Br, I, CN, NO$_2$, (CF$_2$)$_r$CF$_3$, (CH$_2$)$_r$OC$_{1-5}$ alkyl, OH, SH, (CH$_2$)$_r$SC$_{1-5}$ alkyl, (CH$_2$)$_r$NR$^{5f}$R$^{5f}$, and (CH$_2$)$_r$phenyl;

$R^{5f}$, at each occurrence, is selected from H, $C_{1-6}$ alkyl, and $C_{3-6}$ cycloalkyl;

$R^{5g}$ is independently selected from —C(O)$R^{5b}$, —C(O)OR$^{5d}$, —C(O)NR$^{5f}$R$^{5f}$, and (CH$_2$)$_r$phenyl;

R, at each occurrence, is selected from H, $C_{1-6}$ alkyl substituted with $R^{5e}$, $C_{2-8}$ alkenyl, $C_{2-8}$ alkynyl, (CH$_2$)$_r$$C_{3-6}$ cycloalkyl, and (CH$_2$)$_r$phenyl substituted with $R^{5e}$;

$R^6$, at each occurrence, is selected from $C_{1-8}$ alkyl, $C_{2-8}$ alkenyl, $C_{2-8}$ alkynyl, (CH$_2$)$_r$$C_{3-6}$ cycloalkyl, Cl, Br, I, F, NO$_2$, CN, (CR'R')$_r$NR$^{6a}$R$^{6a}$, (CR'R')$_r$OH, (CR'R')$_r$O(CR'R')$_r$R$^{6d}$, (CR'R')$_r$SH, (CR'R')$_r$C(O)H, (CR'R')$_r$S(CR'R')$_r$R$^{6d}$, (CR'R')$_r$SC(O)(CR'R')$_r$R$^{6b}$, (CR'R')$_r$C(O)OH, (CR'R')$_r$C(O)(CR'R')$_r$R$^{6b}$, (CR'R')$_r$NR$^{6a}$R$^{6a}$, (CR'R')$_r$C(O)NR$^{6a}$R$^{6a}$, (CR'R')$_r$NR$^{6f}$C(O)(CR'R')$_r$R$^{6b}$, (CR'R')$_r$C(O)O(CR'R')$_r$R$^{6d}$, (CR'R')$_r$OC(O)(CR'R')$_r$R$^{6b}$, (CR'R')$_r$OC(O)NR$^{6a}$(CR'R')$_r$R$^{6d}$, (CR'R')$_r$NR$^{6a}$C(O)NR$^{6a}$(CR'R')$_r$R$^{6d}$, (CR'R')$_r$NR$^{6a}$C(S)NR$^{6a}$(CR'R')$_r$R$^{6d}$, (CR'R')$_r$NR$^{6f}$C(O)O(CR'R')$_r$R$^{6b}$, (CR'R')$_r$C(=NR$^{6f}$)NR$^{6a}$R$^{6a}$, (CR'R')$_r$NHC(=NR$^{6f}$)NR$^{6f}$R$^{6f}$, (CR'R')$_r$S(O)$_p$(CR'R')$_r$R$^{6b}$, (CR'R')$_r$S(O)$_2$NR$^{6a}$R$^{6a}$, (CR'R')$_r$NR$^{6f}$S(O)$_2$NR$^{6a}$R$^{6a}$, (CR'R')$_r$NR$^{6f}$S(O)$_2$(CR'R')$_r$R$^{6b}$, $C_{1-6}$ haloalkyl, $C_{2-8}$ alkenyl substituted with 0–3 R', $C_{2-8}$ alkynyl substituted with 0–3 R', (CR'R')$_r$phenyl substituted with 0–3 $R^{6e}$, and a (CH$_2$)$_r$-5–6 membered heterocyclic system containing 1–2 heteroatoms selected from N, O, and S, substituted with 0–2 $R^{6e}$;

alternatively, two $R^6$ on adjacent atoms on $R^1$ may join to form a cyclic acetal;

$R^{6a}$, at each occurrence, is selected from H, methyl substituted with 0–1 $R^{6g}$, $C_{2-6}$ alkyl substituted with 0–2 $R^{6e}$, $C_{3-8}$ alkenyl substituted with 0–2 $R^{6e}$, $C_{3-8}$ alkynyl substituted with 0–2 $R^{6e}$, a (CH$_2$)$_r$—$C_{3-10}$ carbocyclic residue substituted with 0–5 $R^{6e}$, and a (CH$_2$)$_r$-5–10 membered heterocyclic system containing 1–4 heteroatoms selected from N, O, and S, substituted with 0–2 $R^{6e}$;

$R^{6b}$, at each occurrence, is selected from H, $C_{1-6}$ alkyl substituted with 0–2 $R^{6e}$, $C_{3-8}$ alkenyl substituted with 0–2 $R^{6e}$, $C_{3-8}$ alkynyl substituted with 0–2 $R^{6e}$, a (CH$_2$)$_r$$C_{3-6}$ carbocyclic residue substituted with 0–3 $R^{6e}$, and a (CH$_2$)$_r$-5–6 membered heterocyclic system containing 1–4 heteroatoms selected from N, O, and S, substituted with 0–2 $R^{6e}$;

$R^{6d}$, at each occurrence, is selected from $C_{3-8}$ alkenyl substituted with 0–2 $R^{6e}$, $C_{3-8}$ alkynyl substituted with 0–2 $R^{6e}$, methyl, CF$_3$, $C_{2-6}$ alkyl substituted with 0–3 $R^{6e}$, $C_{2-4}$ haloalkyl, a (CH$_2$)$_r$—$C_{3-10}$ carbocyclic residue substituted with 0–3 $R^{6e}$, and a (CH$_2$)$_r$-5–6 membered heterocyclic system containing 1–4 heteroatoms selected from N, O, and S, substituted with 0–3 $R^{6e}$;

$R^{6e}$, at each occurrence, is selected from $C_{1-6}$ alkyl, $C_{2-8}$ alkenyl, $C_{2-8}$ alkynyl, (CH$_2$)$_r$$C_{3-6}$ cycloalkyl, Cl, F, Br, I, CN, NO$_2$, (CF$_2$)$_r$CF$_3$, (CH$_2$)$_r$OC$_{1-5}$ alkyl, OH, SH, (CH$_2$)$_r$SC$_{1-5}$ alkyl, (CH$_2$)$_r$NR$^{6f}$R$^{6f}$, and (CH$_2$)$_r$phenyl;

$R^{6f}$, at each occurrence, is selected from H, $C_{1-5}$ alkyl, and $C_{3-6}$ cycloalkyl, and phenyl;

$R^{6g}$ is independently selected from —C(O)$R^{6b}$, —C(O)O$R^{6d}$, —C(O)N$R^{6f}R^{6f}$, and (CH$_2$)$_r$phenyl;

$R^7$, at each occurrence, is selected from C$_{1-8}$ alkyl, C$_{2-8}$ alkenyl, C$_{2-8}$ alkynyl, (CH$_2$)$_r$C$_{3-6}$ cycloalkyl, Cl, Br, I, F, NO$_2$, CN, (CR'R')$_r$NR$^{7a}$R$^{7a}$, (CR'R')$_r$OH, (CR'R')$_r$O(CR'R')$_r$R$^{7d}$, (CR'R')$_r$SH, (CR'R')$_r$C(O)H, (CR'R')$_r$S(CR'R')$_r$R$^{7d}$, (CR'R')$_r$C(O)OH, (CR'R')$_r$C(O)(CR'R')$_r$R$^{7b}$, (CR'R')$_r$C(O)NR$^{7a}$R$^{7a}$, (CR'R')$_r$NR$^{7f}$C(O)(CR'R')$_r$R$^{7b}$, (CR'R')$_r$C(O)O(CR'R')$_r$R$^{7d}$, (CR'R')$_r$OC(O)(CR'R')$_r$R$^{7b}$, (CR'R')$_r$OC(O)NR$^{7a}$(CR'R')$_r$R$^{7a}$, (CR'R')$_r$NR$^{7a}$C(O)NR$^{7a}$(CR'R')$_r$R$^{7a}$, (CR'R')$_r$NR$^{7f}$C(O)O(CR'R')$_r$R$^{7d}$, (CR'R')$_r$C(=NR$^{7f}$)NR$^{7a}$R$^{7a}$, (CR'R')$_r$NHC(=NR$^{7f}$)NR$^{7f}$R$^{7f}$, (CR'R')$_r$S(O)$_p$(CR'R')$_r$R$^{7b}$, (CR'R')$_r$S(O)$_2$NR$^{7a}$R$^{7a}$, (CR'R')$_r$NR$^{7a}$S(O)$_2$NR$^{7a}$R$^{7a}$, (CR'R')$_r$NR$^{7f}$S(O)$_2$(CR'R')$_r$R$^{7b}$, C$_{1-6}$ haloalkyl, C$_{2-8}$ alkenyl substituted with 0–3 R', C$_{2-8}$ alkynyl substituted with 0–3 R', and (CR'R')$_r$phenyl substituted with 0–3 R$^{7e}$;

alternatively, two R$^7$ on adjacent atoms on R$^2$ may join to form a cyclic acetal;

$R^{7a}$, at each occurrence, is independently selected from H, methyl substituted with 0–1 R$^{7g}$, C$_{2-6}$ alkyl substituted with 0–2 R$^{7e}$, C$_{3-8}$ alkenyl substituted with 0–2 R$^{7e}$, C$_{3-8}$ alkynyl substituted with 0–2 R$^{7e}$, a (CH$_2$)$_r$—C$_{3-10}$ carbocyclic residue substituted with 0–5 R$^{7e}$, and a (CH$_2$)$_r$-5–10 membered heterocyclic system containing 1–4 heteroatoms selected from N, O, and S, substituted with 0–2 R$^{7e}$;

$R^{7b}$, at each occurrence, is selected from C$_{1-6}$ alkyl substituted with 0–2 R$^{7e}$, C$_{3-8}$ alkenyl substituted with 0–2 R$^{7e}$, C$_{3-8}$ alkynyl substituted with 0–2 R$^{7e}$, a (CH$_2$)$_r$C$_{3-6}$ carbocyclic residue substituted with 0–3 R$^{7e}$, and a (CH$_2$)$_r$-5–6 membered heterocyclic system containing 1–4 heteroatoms selected from N, O, and S, substituted with 0–2 R$^{7e}$;

$R^{7d}$, at each occurrence, is selected from C$_{3-8}$ alkenyl substituted with 0–2 R$^{7e}$, C$_{3-8}$ alkynyl substituted with 0–2 R$^{7e}$, methyl, CF$_3$, C$_{2-4}$ haloalkyl, C$_{2-6}$ alkyl substituted with 0–3 R$^{7e}$, a (CH$_2$)$_r$—C$_{3-10}$ carbocyclic residue substituted with 0–3 R$^{7e}$, and a (CH$_2$)$_r$-5–6 membered heterocyclic system containing 1–4 heteroatoms selected from N, O, and S, substituted with 0–3 R$^{7e}$;

$R^{7e}$, at each occurrence, is selected from C$_{1-6}$ alkyl, C$_{2-8}$ alkenyl, C$_{2-8}$ alkynyl, (CH$_2$)$_r$C$_{3-6}$ cycloalkyl, Cl, F, Br, I, CN, NO$_2$, (CF$_2$)$_r$CF$_3$, (CH$_2$)$_r$OC$_{1-5}$ alkyl, OH, SH, C(O)OC$_{1-5}$ alkyl, (CH$_2$)$_r$SC$_{1-5}$ alkyl, (CH$_2$)$_r$NR$^{7f}$R$^{7f}$, and (CH$_2$)$_r$phenyl;

$R^{7f}$, at each occurrence, is selected from H, C$_{1-5}$ alkyl, and C$_{3-6}$ cycloalkyl, and phenyl;

$R^{7g}$ is independently selected from —C(O)R$^{7b}$, —C(O)OR$^{7d}$, —C(O)NR$^{7f}$R$^{7f}$, and (CH$_2$)$_r$phenyl;

R', at each occurrence, is selected from H, C$_{1-6}$ alkyl substituted with R$^{6e}$, C$_{2-8}$ alkenyl, C$_{2-8}$ alkynyl, (CH$_2$)$_r$C$_{3-6}$ cycloalkyl, and (CH$_2$)$_r$phenyl substituted with R$^{6e}$;

$R^8$ is selected from H, C$_{1-4}$ alkyl, and C$_{3-4}$ cycloalkyl;

$R^9$ is selected from H, C$_{1-4}$ alkyl, C$_{3-4}$ cycloalkyl, —C(O)H, and —C(O)—C$_{1-4}$alkyl;

$R^{10}$ is independently selected from H, and C$_{1-4}$alkyl substituted with 0–1 R$^{10b}$;

$R^{10b}$, at each occurrence, is independently selected from —OH, —SH, NR$^{10c}$R$^{10c}$, —C(O)NR$^{10c}$R$^{10c}$, and —NHC(O)R$^{10c}$;

$R^{10c}$ is selected from H, C$_{1-4}$ alkyl and C$_{3-6}$ cycloalkyl;

$R^{11}$ is selected from H, C$_{1-4}$ alkyl, (CHR)$_q$OH, (CHR)$_q$SH, (CHR)$_q$OR$^{11d}$, (CHR)$_q$S(O)$_p$R$^{11d}$, (CHR)$_r$C(O)R$^{11b}$, (CHR)$_r$NR$^{11a}$R$^{11a}$, (CHR)$_r$C(O)NR$^{11a}$R$^{11a}$, (CHR)$_r$C(O)NR$^{11a}$OR$^{11d}$, (CHR)$_q$NR$^{11a}$C(O)R$^{11b}$, (CHR)$_q$NR$^{11a}$C(O)OR$^{11d}$, (CHR)$_q$OC(O)NR$^{11a}$R$^{11a}$, (CHR)$_r$C(O)OR$^{11d}$, a (CHR)$_r$—C$_{3-6}$ carbocyclic residue substituted with 0–5 R$^{11e}$, and a (CHR)$_r$-5–10 membered heterocyclic system containing 1–4 heteroatoms selected from N, O, and S, substituted with 0–3 R$^{11e}$;

$R^{11a}$, at each occurrence, is independently selected from H, C$_{1-4}$ alkyl, C$_{3-4}$ alkenyl, C$_{3-4}$ alkynyl, (CH$_2$)$_r$C$_{3-6}$ cycloalkyl, a (CH$_2$)$_r$—C$_{3-6}$ carbocyclic residue substituted with 0–5 R$^{11e}$, and a (CH$_2$)$_r$-5–6 membered heterocyclic system containing 1–4 heteroatoms selected from N, O, and S, substituted with 0–3 R$^{11e}$;

$R^{11b}$, at each occurrence, is independently selected from C$_{1-4}$ alkyl, C$_{2-4}$ alkenyl, C$_{2-4}$ alkynyl, a (CH$_2$)$_r$—C$_{3-6}$ carbocyclic residue substituted with 0–2 R$^{11e}$, and a (CH$_2$)$_r$-5–6 membered heterocyclic system containing 1–4 heteroatoms selected from N, O, and S, substituted with 0–3 R$^{11e}$;

$R^{11d}$, at each occurrence, is independently selected from H, methyl, —CF$_3$, C$_{2-4}$ alkyl, C$_{3-6}$ alkenyl, C$_{3-6}$ alkynyl, a C$_{3-6}$ carbocyclic residue substituted with 0–3 R$^{11e}$, and a (CH$_2$)$_r$-5–6 membered heterocyclic system containing 1–4 heteroatoms selected from N, O, and S, substituted with 0–3 R$^{11e}$;

$R^{11e}$, at each occurrence, is selected from C$_{1-6}$ alkyl, C$_{2-8}$ alkenyl, C$_{2-8}$ alkynyl, C$_{3-6}$ cycloalkyl, Cl, F, Br, I, CN, NO$_2$, (CF$_2$)$_r$CF$_3$, (CH$_2$)$_r$OC$_{1-5}$ alkyl, OH, —O—C$_{1-6}$ alkyl, SH, (CH$_2$)$_r$SC$_{1-5}$ alkyl, (CH$_2$)$_r$NR$^{11f}$R$^{11f}$, and (CH$_2$)$_r$phenyl;

$R^{11f}$, at each occurrence, is selected from H, C$_{1-6}$ alkyl, and C$_{3-6}$ cycloalkyl;

$R^{12}$ is selected from H, C$_{1-4}$ alkyl, (CHR)$_q$OH, (CHR)$_q$SH, (CHR)$_q$OR$^{12d}$, (CHR)$_q$S(O)$_p$R$^{12d}$, (CHR)$_r$C(O)R$^{12b}$, (CHR)$_r$NR$^{12a}$R$^{12a}$, (CHR)$_r$C(O)NR$^{12a}$R$^{12a}$, (CHR)$_r$C(O)NR$^{12a}$OR$^{12d}$, (CHR)$_q$NR$^{12a}$C(O)R$^{12b}$, (CHR)$_q$NR$^{12a}$C(O)OR$^{12d}$, (CHR)$_q$OC(O)NR$^{12a}$R$^{12a}$, (CHR)$_r$C(O)OR$^{12d}$, a (CHR)$_r$—C$_{3-6}$ carbocyclic residue substituted with 0–5 R$^{12e}$, and a (CHR)$_r$-5–10 membered heterocyclic system containing 1–4 heteroatoms selected from N, O, and S, substituted with 0–3 R$^{12e}$;

$R^{12a}$, at each occurrence, is independently selected from H, C$_{1-4}$ alkyl, C$_{3-4}$ alkenyl, C$_{3-4}$ alkynyl, (CH$_2$)$_r$C$_{3-6}$ cycloalkyl, a (CH$_2$)$_r$—C$_{3-6}$ carbocyclic residue substituted with 0–5 R$^{12e}$, and a (CH$_2$)$_r$-5–6 membered heterocyclic system containing 1–4 heteroatoms selected from N, O, and S, substituted with 0–3 R$^{12e}$;

$R^{12b}$, at each occurrence, is independently selected from C$_{1-4}$ alkyl, C$_{2-4}$ alkenyl, C$_{2-4}$ alkynyl, a (CH$_2$)$_r$—C$_{3-6}$ carbocyclic residue substituted with 0–2 R$^{12e}$, and a (CH$_2$)$_r$-5–6 membered heterocyclic system containing 1–4 heteroatoms selected from N, O, and S, substituted with 0–3 R$^{12e}$;

$R^{12d}$, at each occurrence, is independently selected from H, methyl, —CF$_3$, C$_{2-4}$ alkyl, C$_{3-6}$ alkenyl, C$_{3-6}$ alkynyl, a C$_{3-6}$ carbocyclic residue substituted with 0–3 R$^{12e}$, and a (CH$_2$)$_r$-5–6 membered heterocyclic system containing 1–4 heteroatoms selected from N, O, and S, substituted with 0–3 R$^{12e}$;

$R^{12e}$, at each occurrence, is selected from C$_{1-6}$ alkyl, C$_{2-8}$ alkenyl, C$_{2-8}$ alkynyl, C$_{3-6}$ cycloalkyl, Cl, F, Br, I, CN, NO$_2$, (CF$_2$)$_r$CF$_3$, (CH$_2$)$_r$OC$_{1-5}$ alkyl, OH, —O—C$_{1-6}$ alkyl, SH, (CH$_2$)$_r$SC$_{1-5}$ alkyl, (CH$_2$)$_r$NR$^{12f}$R$^{12f}$, and (CH$_2$)$_r$phenyl;

$R^{12f}$, at each occurrence, is selected from H, C$_{1-6}$ alkyl, and C$_{3-6}$ cycloalkyl;

$R^{13}$, at each occurrence, is independently selected from H, and C$_{1-4}$alkyl substituted with 0–1 R$^{13b}$, —OH, —NH$_2$, F, Cl, Br, I, —OR$^{13a}$, —N(R$^{13a}$)$_2$, and C$_{1-4}$ alkyl substituted with 0–3 R$^{13b}$;

$R^{13a}$ is selected from H, $C_{1-4}$ alkyl and $C_{3-6}$ cycloalkyl;

$R^{13b}$, at each occurrence, is independently selected from —OH, —SH, $NR^{13c}R^{13c}$, —C(O)$NR^{13c}R^{13c}$, and —NHC(O)$R^{13c}$;

$R^{13c}$ is selected from H, $C_{1-4}$ alkyl and $C_{3-6}$ cycloalkyl;

$R^{14}$, at each occurrence, is independently selected from H and $C_{1-4}$ alkyl;

alternatively, two $R^{14}$s, along with the carbon atom to which they are attached, join to form a $C_{3-6}$ carbocyclic ring;

$R^{15}$, at each occurrence, is independently selected from H, $C_{1-4}$ alkyl, OH, $NH_2$, —O—$C_{1-4}$ alkyl, $NR^{15a}R^{15a}$, C(O)$NR^{15a}R^{15a}$, $NR^{15a}C(O)R^{15b}$, $NR^{15a}C(O)OR^{15d}$, OC(O)$NR^{15a}R^{15a}$, and $(CHR)_rC(O)OR^{15d}$;

alternatively, two $R^{15}$s, along with the carbon atom or atoms to which they are attached, join to form a $C_{3-6}$ carbocyclic ring;

$R^{15a}$, at each occurrence, is independently selected from H, and $C_{1-4}$ alkyl;

$R^{15b}$, at each occurrence, is independently selected from $C_{1-4}$ alkyl, $C_{3-6}$ alkenyl, and $C_{3-6}$ alkynyl;

$R^{15d}$, at each occurrence, is independently selected from $C_{1-4}$ alkyl, $C_{3-6}$ alkenyl, and $C_{3-6}$ alkynyl;

$R^{16}$ is selected from $C_{1-4}$ alkyl;

l is selected from 1, 2 and 3;

n is selected from 0, 1, 2, and 3;

m is selected from 0 and 1;

p, at each occurrence, is independently selected from 0, 1, and 2;

q, at each occurrence, is independently selected from 1, 2, 3, and 4;

r, at each occurrence, is independently selected from 0, 1, 2, 3, and 4;

t, at each occurrence, is independently selected from 2, 3, and 4;

s is selected from 0 and 1.

[3] Thus, in a another embodiment, the present invention provides novel compounds of formula (I):

m is 0.

In another embodiment, the present invention provides novel compounds of formula (I), wherein:

ring B is selected from

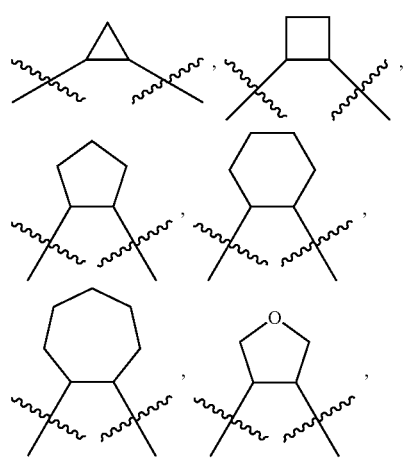

-continued

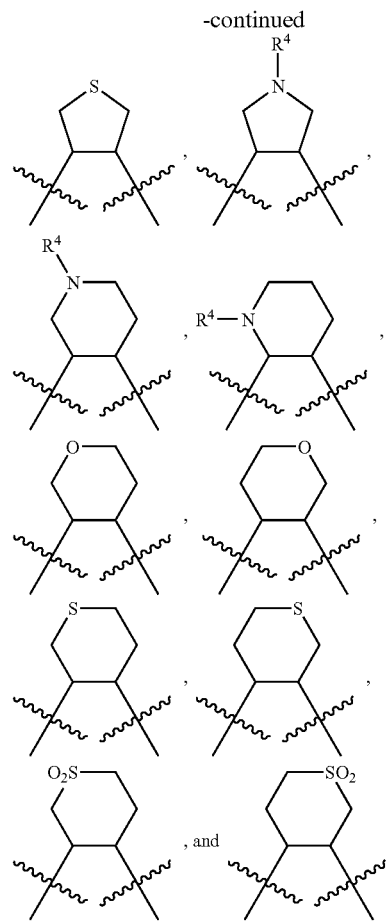

ring B being optionally substituted with 0–1 $R^5$; and $R^{11}$ and $R^{12}$ are H.

In another embodiment, the present invention provides novel compounds of formula (I), wherein:

$R^5$, at each occurrence, is independently selected from H, $C_{1-6}$ alkyl, $C_{2-8}$ alkenyl, $C_{2-8}$ alkynyl, $(CRR)_r$OH, $(CRR)_r$SH, $(CRR)_rOR^{5d}$, $(CRR)_rSR^{5d}$, $(CRR)_rNR^{5a}R^{5a}$, $(CRR)_r$C(O)OH, $(CRR)_rC(O)R^{5b}$, $(CRR)_rC(O)NR^{5a}R^{5a}$, $(CRR)_rNR^{5a}C(O)R^{5b}$, $(CRR)_rNR^{5a}C(O)OR^{5d}$, $(CRR)_rOC(O)NR^{5a}R^{5a}$, $(CHR)_rNR^{5a}C(O)NR^{5a}R^{5a}$, $CRR(CRR)_rNR^{5a}C(O)H$, $(CRR)_rC(O)OR^{5b}$, $(CRR)_rOC(O)R^{5b}$, $(CRR)_rS(O)_pR^{5b}$, $(CRR)_rS(O)_2NR^{5a}R^{5a}$, $(CRR)_rNR^{5a}S(O)_2R^{5b}$, and $C_{1-6}$ haloalkyl;

$R^{5a}$, at each occurrence, is independently selected from H, methyl, $C_{1-6}$ alkyl substituted with 0–2 $R^{5e}$ wherein the alkyl is selected from ethyl, propyl, i-propyl, butyl, i-butyl, pentyl, hexyl, $C_3$ alkenyl substituted with 0–1 $R^{5e}$, wherein the alkenyl is selected from allyl, $C_3$ alkynyl substituted with 0–1 $R^{5e}$ wherein the alkynyl is selected from propynyl, and a $(CH_2)_r$—$C_{3-4}$ carbocyclic residue substituted with 0–5 $R^{5e}$, wherein the carbocyclic residue is selected from cyclopropyl, and cyclobutyl;

$R^{5b}$, at each occurrence, is selected from $C_{1-6}$ alkyl substituted with 0–2 $R^{5e}$, wherein the alkyl is selected from methyl, ethyl, propyl, i-propyl, butyl, i-butyl, pentyl, and hexyl, a $(CH_2)_r$—$C_{3-4}$ carbocyclic residue substituted with 0–2 $R^{5e}$, wherein the carbocyclic residue is selected from cyclopropyl, and cyclobutyl; and $R^{5d}$, at each occurrence, is selected from methyl, $CF_3$, $C_{2-6}$ alkyl substituted with 0–2 $R^{5e}$, wherein the alkyl is selected from methyl, ethyl, propyl, i-propyl, butyl, i-butyl, pentyl, and hexyl, $C_{3-8}$ alkenyl, $C_{3-8}$ alkynyl, and a $C_{3-10}$ carbocyclic residue substituted with 0–3 $R^{5e}$.

In another embodiment, the present invention provides novel compounds of formula (I), wherein:

$R^5$, at each occurrence, is independently selected from H, $C_{1-6}$ alkyl, $C_{2-8}$ alkenyl, $C_{2-8}$ alkynyl, $(CRR)_rOH$, $(CRR)_r SH$, $(CRR)_rOR^{5d}$, $(CRR)_rSR^{5d}$, $(CRR)_rNR^{5a}R^{5a}$, $(CRR)_r N(O)R^{5a}R^{5a}$, $N_3$, $(CRR)_rC(O)OH$, $(CRR)_rC(O)R^{5b}$, $(CRR)_rC(O)NR^{5a}R^{5a}$, $(CRR)_rNR^{5a}C(O)R^{5b}$, $(CRR)_r NR^{5a}C(O)OR^{5d}$, $(CRR)_rOC(O)NR^{5a}R^{5a}$, $(CHR)_rNR^{5a}C(O)NR^{5a}R^{5a}$, $CRR(CRR)_rNR^{5a}C(O)H$, $(CRR)_rC(O) OR^{5b}$, $(CRR)_rOC(O)R^{5b}$, $(CRR)_rS(O)_pR^{5b}$, $(CRR)_rS(O)_2 NR^{5a}R^{5a}$, $(CRR)_rNR^{5a}S(O)_2R^{5b}$, and $C_{1-6}$ haloalkyl;

$R^{5a}$, at each occurrence, is independently selected from H, methyl, $C_{1-6}$ alkyl substituted with 0–2 $R^{5e}$ wherein the alkyl is selected from ethyl, propyl, i-propyl, butyl, i-butyl, pentyl, hexyl, $C_3$ alkenyl substituted with 0–1 $R^{5e}$, wherein the alkenyl is selected from allyl, $C_3$ alkynyl substituted with 0–1 $R^{5e}$ wherein the alkynyl is selected from propynyl, and a $(CH_2)_r$—$C_{3-4}$ carbocyclic residue substituted with 0–5 $R^{5e}$, wherein the carbocyclic residue is selected from cyclopropyl, and cyclobutyl;

$R^{5b}$, at each occurrence, is selected from $C_{1-6}$ alkyl substituted with 0–2 $R^{5e}$, wherein the alkyl is selected from methyl, ethyl, propyl, i-propyl, butyl, i-butyl, pentyl, and hexyl, a $(CH_2)_r$—$C_{3-4}$ carbocyclic residue substituted with 0–2 $R^{5e}$, wherein the carbocyclic residue is selected from cyclopropyl, and cyclobutyl; and $R^{5d}$, at each occurrence, is selected from methyl, $CF_3$, $C_{2-6}$ alkyl substituted with 0–2 $R^{5e}$, wherein the alkyl is selected from methyl, ethyl, propyl, i-propyl, butyl, i-butyl, pentyl, and hexyl, $C_{3-8}$ alkenyl, $C_{3-8}$ alkynyl, and a $C_{3-10}$ carbocyclic residue substituted with 0–3 $R^{5e}$.

In another embodiment, the present invention provides novel compounds of formula (I), wherein:

$R^4$ is selected from H, $C_{1-6}$ alkyl, $C_{3-8}$ alkenyl, $C_{3-8}$ alkynyl, $(CRR)_qOH$, $(CRR)_rSH$, $(CRR)_rOR^{4d}$, $(CRR)_rSR^{4d}$, $(CRR)_tNR^{4a}R^{4a}$, $(CRR)_qC(O)OH$, $(CRR)_rC(O)R^{4b}$, $(CRR)_rC(O)NR^{4a}R^{4a}$, $(CRR)_rNR^{4a}C(O)R^{4b}$, $(CRR)_tOC(O)NR^{4a}R^{4a}$, $(CRR)_rNR^{4a}C(O)OR^{4d}$, $(CRR)_rNR^{4a}C(O)R^{4b}$, $(CRR)_rC(O)OR^{4b}$, $(CRR)_rS(O)_pR^{4b}$, $(CRR)_rS(O)_2NR^{4a}R^{4a}$, $(CRR)_rNR^{4a}S(O)_2R^{4b}$;

R, at each occurrence, is independently selected from H, methyl, ethyl, propyl, allyl, propynyl, $(CH_2)_rC_{3-6}$ cycloalkyl, and $(CH_2)_r$phenyl substituted with $R^{6e}$;

$R^5$, at each occurrence, is independently selected from H, methyl, ethyl, propyl, i-propyl, butyl, i-butyl, allyl, propynyl, $(CH_2)_rOH$, $(CH_2)_rOR^{5d}$, $(CH_2)_rNR^{5a}R^{5a}$, $(CH_2)_rC(O)OH$, $(CH_2)_rC(O)R^{5b}$, $(CH_2)_rC(O)NR^{5a}R^{5a}$, $(CH_2)_r NR^{5a}C(O)R^{5b}$, $(CH_2)_rOC(O)NR^{5a}R^{5a}$, $(CH_2)_rNR^{5a}C(O) OR^{5d}$, $(CH_2)_rNR^{5a}C(O)R^{5b}$, $(CH_2)_rC(O)OR^{5b}$, $(CH_2)_r OC(O)R^{5b}$, $(CH_2)_rNR^{5a}S(O)_2R^{5b}$, and $C_{1-6}$ haloalkyl;

$R^{5a}$, at each occurrence, is independently selected from H, methyl, ethyl, propyl, i-propyl, butyl, i-butyl, pentyl, hexyl, cyclopropyl, and cyclobutyl; and r, at each occurrence, is selected from 0, 1, and 2.

In another embodiment, the present invention provides novel compounds of formula (I), wherein:

$R^1$ is selected from phenyl substituted with 0–2 $R^6$, naphthyl substituted with 0–2$R^6$, and a 5–10 membered heteroaryl system containing 1–4 heteroatoms selected from N, O, and S, substituted with 0–3 $R^6$ wherein the heteroaryl is selected from indolyl, benzimidazolyl, benzofuranyl, benzothiofuranyl, benzoxazolyl, benzthiazolyl, benztriazolyl, benztetrazolyl, benzisoxazolyl, benzisothiazolyl, benzimidazalonyl, cinnolinyl, furanyl, imidazolyl, indazolyl, indolyl, isoquinolinyl, isothiazolyl, isoxazolyl, oxazolyl, pyrazinyl, pyrazolyl, pyridazinyl, pyridyl, pyridinyl, pyrimidinyl, pyrrolyl, quinazolinyl, quinolinyl, thiazolyl, thienyl, and tetrazolyl;

$R^2$ is selected from phenyl substituted with 0–2 $R^7$, and a 5–10 membered heteroaryl system containing 1–4 heteroatoms selected from N, O, and S, substituted with 0–3 $R^7$ wherein the heteroaryl is selected from indolyl, benzimidazolyl, benzofuranyl, benzothiofuranyl, benzoxazolyl, benzthiazolyl, benztriazolyl, benztetrazolyl, benzisoxazolyl, benzisothiazolyl, benzimidazalonyl, cinnolinyl, furanyl, imidazolyl, indazolyl, indolyl, isoquinolinyl isothiazolyl, isoxazolyl, oxazolyl, phthalazinyl, pyrazinyl, pyrazolyl, pyridazinyl, pyridyl, pyridinyl, pyrimidinyl, pyrrolyl, quinazolinyl, quinolinyl, thiazolyl, thienyl, and tetrazolyl;

$R^4$ is selected from H, methyl, ethyl, propyl, i-propyl, butyl, i-butyl, allyl, propynyl, $(CRR)_qOH$, $(CRR)_rSH$, $(CRR)_t OR^{4d}$, $(CRR)_rSR^{4d}$, $(CRR)_rNR^{4a}R^{4a}$, $(CRR)_qC(O)OH$, $(CRR)_rC(O)R^{4b}$, $(CRR)_rC(O)NR^{4a}R^{4a}$, $(CRR)_tNR^{4a}C (O)R^{4b}$, $(CRR)_rOC(O)NR^{4a}R^{4a}$, $(CRR)_rNR^{4a}C(O)OR^{4d}$, $(CRR)_rNR^{4a}C(O)R^{4b}$, $(CRR)_rC(O)OR^{4b}$, $(CRR)_tOC(O) R^{4b}$, $(CRR)_rS(O)_pR^{4b}$, $(CRR)_rS(O)_2NR^{4a}R^{4a}$, $(CRR)_r NR^{4a}S(O)_2R^{4b}$;

$R^{4a}$, at each occurrence, is independently selected from H, methyl substituted with 0–1 $R^{4c}$, $C_{2-6}$ alkyl substituted with 0–3 $R^{4e}$ wherein $C_{2-6}$ is selected from ethyl, propyl, i-propyl, butyl, i-butyl, t-butyl, pentyl and hexyl, and a $(CH_2)_r$—$C_{3-6}$ carbocyclic residue substituted with 0–4 $R^{4e}$ wherein the carbocyclic residue is selected from cyclopropyl, cyclohexyl, and phenyl;

$R^{4b}$ is selected from H, methyl, ethyl, propyl, i-propyl, butyl, i-butyl, t-butyl, pentyl, and cyclopropyl;

$R^{4d}$ is selected from methyl, ethyl, propyl, i-propyl, butyl, i-butyl, t-butyl, pentyl, and cyclopropyl; and $R^8$ is selected from H, methyl, ethyl, propyl, i-propyl, and cyclopropyl.

In another embodiment, the present invention provides novel compounds of formula (I), wherein:

$R^1$ is selected from phenyl substituted with 0–2 $R^6$, naphthyl substituted with 0–2 $R^6$, and a 5–10 membered heteroaryl system containing 1–4 heteroatoms selected from N, O, and S, substituted with 0–3 $R^6$ wherein the heteroaryl is selected from indolyl, benzimidazolyl, benzofuranyl, benzothiofuranyl, benzoxazolyl, benzthiazolyl, benzo[b] thiophene, benztriazolyl, benztetrazolyl, benzisoxazolyl, benzisothiazolyl, benzimidazalonyl, cinnolinyl, furanyl, imidazolyl, indazolyl, indolyl, isoquinolinyl, isothiazolyl, isoxazolyl, oxazolyl, pyrazinyl, pyrazolyl, pyridazinyl, pyridyl, pyrido[2,3-d]pyrimidinyl, pyrimido[5,4-d]pyrimidinyl, thieno[3,2-d]pyrimidinyl, pyridinyl, pyrimidinyl, pyrrolyl, pyrrolo[2,1-f][1,2,4]triazine, quinazolinyl, quinolinyl, thiazolyl, thienyl, and tetrazolyl;

$R^2$ is selected from phenyl substituted with 0–2 $R^7$, and a 5–10 membered heteroaryl system containing 1–4 heteroatoms selected from N, O, and S, substituted with 0–3 $R^7$ wherein the heteroaryl is selected from indolyl, benzimidazolyl, benzofuranyl, benzothiofuranyl, benzoxazolyl, benzthiazolyl, benzo[b]thiophene, benztriazolyl, benztetrazolyl, benzisoxazolyl, benzisothiazolyl, benzimidazalonyl, cinnolinyl, furanyl, imidazolyl, indazolyl, indolyl, isoquinolinyl, isothiazolyl, isoxazolyl, oxazolyl, phthalazinyl, pyrazinyl, pyrazolyl, pyridazinyl, pyridyl, pyrido[2,3-d]pyrimidinyl, thieno[3,2-d]pyrimidinyl, pyridinyl, pyrimidinyl, pyrrolyl, pyrrolo[2,1-f][1,2,4]triazine, quinazolinyl, quinolinyl, thiazolyl, thienyl, and tetrazolyl;

$R^4$ is selected from H, methyl, ethyl, propyl, i-propyl, butyl, i-butyl, allyl, propynyl, $(CRR)_qOH$, $(CRR)_rSH$, $(CRR)_r OR^{4d}$, $(CRR)_rSR^{4d}$, $(CRR)_rNR^{4a}R^{4a}$, $(CRR)_qC(O)OH$, $(CRR)_rC(O)R^{4b}$, $(CRR)_rC(O)NR^{4a}R^{4a}$, $(CRR)_rNR^{4a}C(O)R^{4b}$, $(CRR)_rOC(O)NR^{4a}R^{4a}$, $(CRR)_rNR^{4a}C(O)OR^{4d}$, $(CRR)_rNR^{4a}C(O)R^{4b}$, $(CRR)_rC(O)OR^{4b}$, $(CRR)_rOC(O)R^{4b}$, $(CRR)_rS(O)_pR^{4b}$, $(CRR)_rS(O)_2NR^{4a}R^{4a}$, $(CRR)_r NR^{4a}S(O)_2R^{4b}$;

$R^{4a}$, at each occurrence, is independently selected from H, methyl substituted with 0–1 $R^{4c}$, $C_{2-6}$ alkyl substituted with 0–3 $R^{4e}$ wherein $C_{2-6}$ is selected from ethyl, propyl, i-propyl, butyl, i-butyl, t-butyl, pentyl and hexyl, and a $(CH_2)_r$—$C_{3-6}$ carbocyclic residue substituted with 0–4 $R^{4e}$ wherein the carbocyclic residue is selected from cyclopropyl, cyclohexyl, and phenyl;

$R^{4b}$ is selected from H, methyl, ethyl, propyl, i-propyl, butyl, i-butyl, t-butyl, pentyl, and cyclopropyl;

$R^{4d}$ is selected from methyl, ethyl, propyl, i-propyl, butyl, i-butyl, t-butyl, pentyl, and cyclopropyl; and $R^8$ is selected from H, methyl, ethyl, propyl, i-propyl, and cyclopropyl.

In another embodiment, the present invention provides novel compounds of formula (I), wherein:

$R^6$, at each occurrence, is selected from $C_{1-8}$ alkyl, $C_{2-8}$ alkenyl, $C_{2-8}$ alkynyl, $(CRR')_rC_{3-6}$ cycloalkyl, Cl, Br, I, F, $NO_2$, CN, $(CRR)_rNR^{6a}R^{6a}$, $(CRR)_rOH$, $(CRR)_rO(CRR)_r R^{6d}$, $(CRR)_rSH$, $(CRR)_rC(O)H$, $(CRR)_rS(CRR)_rR^{6d}$, $(CRR)_rC(O)OH$, $(CRR)_rC(O)(CRR)_rR^{6b}$, $(CRR)_rC(O) NR^{6a}R^{6a}$, $(CRR)_rNR^{6f}C(O)(CRR)_rR^{6b}$, $(CRR)_rC(O)O (CRR)_rR^{6d}$, $(CRR)_rNR^{6a}C(O)NR^{6a}R^{6a}$, $(CRR)_rNR^{6a}C (S)NR^{6a}R^{6a}$, $(CRR)_rOC(O)(CRR)_rR^{6b}$, $(CRR)_rS(O)_p (CRR)_rR^{6b}$, $(CRR)_rS(O)_2NR^{6a}R^{6a}$, $(CRR)_rNR^{6f}S(O)_2 (CRR)_rR^{6b}$, $(CRR)_rNR^{6f}S(O)_2NR^{6a}R^{6a}$, $C_{1-6}$ haloalkyl, and $(CRR)_r$phenyl substituted with 0–3 $R^{6e}$, and a $(CH_2)_r$-5–6 membered heterocyclic system containing 1–2 heteroatoms selected from N, O, and S, substituted with 0–2 $R^{6e}$;

$R^{6a}$, at each occurrence, is independently selected from H, methyl, ethyl, propyl, i-propyl, butyl, i-butyl, t-butyl, pentyl, hexyl, cyclopropyl and phenyl;

$R^{6b}$, at each occurrence, is selected from methyl, ethyl, propyl, i-propyl, butyl, i-butyl, t-butyl, pentyl, hexyl, cyclopropyl, and phenyl;

$R^{6d}$, at each occurrence, is selected from methyl, $CF_3$, ethyl, propyl, i-propyl, butyl, i-butyl, t-butyl, pentyl, hexyl, cyclopropyl, and phenyl;

$R^{6e}$, at each occurrence, is selected from $C_{1-6}$ alkyl, $C_{2-8}$ alkenyl, $C_{2-8}$ alkynyl, $(CH_2)_rC_{3-6}$ cycloalkyl, Cl, F, Br, I, CN, $NO_2$, $(CF_2)_rCF_3$, $(CH_2)_rOC_{1-5}$ alkyl, OH, SH, $(CH_2)_r SC_{1-5}$ alkyl, $(CH_2)_rNR^{6f}R^{6f}$, and $(CH_2)_r$phenyl;

$R^{6f}$, at each occurrence, is selected from H, methyl, ethyl, propyl, i-propyl, butyl, i-butyl, t-butyl, pentyl, hexyl, cyclopropyl, and phenyl;

$R^7$ is selected from methyl, ethyl, propyl, i-propyl, butyl, i-butyl, s-butyl, t-butyl, pentyl, hexyl, $(CRR)_rC_{3-6}$ cycloalkyl, Cl, Br, I, F, $NO_2$, CN, $(CRR)_rNR^{7a}R^{7a}$, $(CRR)_rOH$, $(CRR)_rO(CH)_rR^{7d}$, $(CRR)_rSH$, $(CRR)_rC(O) H$, $(CRR)_rS(CRR)_rR^{7d}$, $(CRR)_rC(O)OH$, $(CRR)_rC(O) (CRR)_rR^{7b}$, $(CRR)_rC(O)NR^{7a}R^{7a}$, $(CRR)_rNR^{7f}C(O) (CRR)_rR^{7b}$, $(CRR)_rC(O)O(CRR)_rR^{7d}$, $(CRR)_rOC (O)(CRR)_rR^{7b}$, $(CRR)_rNR^{7a}C(O)NR^{7a}R^{7a}$, $(CRR)_rNR^{7a}C (O)O(CRR)_rR^{7d}$, $(CRR)_rS(O)_p(CRR)_rR^{7b}$, $(CRR)_rS(O)_2 NR^{7a}R^{7a}$, $(CRR)_rNR^{7f}S(O)_2(CRR)_rR^{7b}$, $C_{1-6}$ haloalkyl, and $(CRR)_r$phenyl substituted with 0–3 $R^{7e}$;

$R^{7a}$, at each occurrence, is selected from H, methyl, ethyl, propyl, i-propyl, butyl, i-butyl, t-butyl, pentyl, hexyl, prop-2-enyl, 2-methyl-2-propenyl, cyclopropyl, cyclobutyl, cyclopentyl, cyclohexyl, $CH_2$cyclopropyl, and benzyl;

$R^{7b}$, at each occurrence, is selected from methyl, ethyl, propyl, i-propyl, butyl, i-butyl, t-butyl, pentyl, hexyl, cyclopropyl, cyclopentyl, $CH_2$-cyclopentyl, cyclohexyl, $CH_2$-cyclohexyl, $CF_3$, pyrrolidinyl, morpholinyl, piperizenyl substituted with 0–1 $R^{7e}$, and azetidinyl;

$R^{7d}$, at each occurrence, is selected from methyl, $CF_3$, $CF_2CF_3$, $CHF_2$, $CH_2F$, ethyl, propyl, i-propyl, butyl, i-butyl, t-butyl, pentyl, hexyl, and cyclopropyl;

$R^{7e}$, at each occurrence, is selected from $C_{1-6}$ alkyl, $C_{2-8}$ alkenyl, $C_{2-8}$ alkynyl, $(CH_2)_rC_{3-6}$ cycloalkyl, Cl, F, Br, I, CN, $NO_2$, $(CF_2)_rCF_3$, $(CH_2)_rOC_{1-5}$ alkyl, OH, SH, C(O) $OC_{1-5}$ alkyl, $(CH_2)_rSC_{1-5}$ alkyl, $(CH_2)_rNR^{7f}R^{7f}$, and $(CH_2)_r$phenyl;

$R^{7f}$, at each occurrence, is selected from H, methyl, ethyl, propyl, i-propyl, butyl, i-butyl, t-butyl, pentyl, hexyl, cyclopropyl, and phenyl; and r is 0 or 1.

In another embodiment, the present invention provides novel compounds of formula (I), wherein:

$R^6$, at each occurrence, is selected from $C_{1-8}$ alkyl, $C_{2-8}$ alkenyl, $C_{2-8}$ alkynyl, $(CR'R')_rC_{3-6}$ cycloalkyl, Cl, Br, I, F, $NO_2$, CN, $(CR'R')_rNR^{6a}R^{6a}$, $(CR'R')_rOH$, $(CR'R')_rO (CR'R')_rR^{6d}$, $(CR'R')_rSH$, $(CR'R')_rC(O)H$, $(CR'R')_rS (CR'R')_rR^{6d}$, $(CR'R')_rC(O)OH$, $(CR'R')_rC(O)(CR'R')_rR^{6b}$, $(CR'R')_rC(O)NR^{6a}R^{6a}$, $(CR'R')_rNR^{6f}C(O)(CR'R')_rR^{6b}$, $(CR'R')_rC(O)O(CR'R')_rR^{6d}$, $(CR'R')_rNR^{6a}C(O)NR^{6a}R^{6a}$, $(CR'R')_rNR^{6a}C(S)NR^{6a}R^{6a}$, $(CR'R')_rOC(O)(CR'R')_rR^{6b}$, $(CR'R')_rS(O)_p(CR'R')_rR^{6b}$, $(CR'R')_rS(O)_2NR^{6a}R^{6a}$, $(CR'R')_rNR^{6f}S(O)_2(CR'R')_rR^{6b}$, $(CR'R')_rNR^{6f}S(O)_2 NR^{6a}R^{6a}$, $C_{1-6}$ haloalkyl, and $(CR'R')_r$phenyl substituted with 0–3 $R^{6e}$, and a $(CH_2)_r$-5–6 membered heterocyclic system containing 1–2 heteroatoms selected from N, O, and S, substituted with 0–2 $R^{6e}$;

$R^{6a}$, at each occurrence, is independently selected from H, methyl, ethyl, propyl, i-propyl, butyl, i-butyl, t-butyl, pentyl, hexyl, cyclopropyl and phenyl;

$R^{6b}$, at each occurrence, is selected from methyl, ethyl, propyl, i-propyl, butyl, i-butyl, t-butyl, pentyl, hexyl, cyclopropyl, and phenyl;

$R^{6d}$, at each occurrence, is selected from methyl, $CF_3$, ethyl, propyl, i-propyl, butyl, i-butyl, t-butyl, pentyl, hexyl, cyclopropyl, and phenyl;

$R^{6e}$, at each occurrence, is selected from $C_{1-6}$ alkyl, $C_{2-8}$ alkenyl, $C_{2-8}$ alkynyl, $(CH_2)_rC_{3-6}$ cycloalkyl, Cl, F, Br, I, CN, $NO_2$, $(CF_2)_rCF_3$, $(CH_2)_rOC_{1-5}$ alkyl, OH, SH, $(CH_2)_r SC_{1-5}$ alkyl, $(CH_2)_rNR^{6f}R^{6f}$, and $(CH_2)_r$phenyl;

$R^{6f}$, at each occurrence, is selected from H, methyl, ethyl, propyl, i-propyl, butyl, i-butyl, t-butyl, pentyl, hexyl, cyclopropyl, and phenyl;

$R^7$ is selected from methyl, ethyl, propyl, i-propyl, butyl, i-butyl, s-butyl, t-butyl, pentyl, hexyl, $(CR'R')_rC_{3-6}$ cycloalkyl, Cl, Br, I, F, $NO_2$, CN, $(CR'R')_rNR^{7a}R^{7a}$, $(CR'R')_rOH$, $(CR'R')_rO(CH)_rR^{7d}$, $(CR'R')_rSH$, $(CR'R')_rC (O)H$, $(CR'R')_rS(CR'R')_rR^{7d}$, $(CR'R')_rC(O)OH$, $(CR'R')_rC (O)(CR'R')_rR^{7b}$, $(CR'R')_rC(O)NR^{7a}R^{7a}$, $(CR'R')_rNR^{7f}C (O)(CR'R')_rR^{7b}$, $(CR'R')_rC(O)O(CR'R')_rR^{7d}$, $(CR'R')_rOC (O)(CR'R')_rR^{7b}$, $(CR'R')_rNR^{7a}C(O)NR^{7a}R^{7a}$, $(CR'R')_r NR^{7a}C(O)O(CR'R')_rR^{7d}$, $(CR'R')_rS(O)_p(CR'R')_rR^{7b}$, $(CR'R')_rS(O)_2NR^{7a}R^{7a}$, $(CR'R')_rNR^{7f}S(O)_2(CR'R')_rR^{7b}$, $C_{1-6}$ haloalkyl, adamantyl, and $(CR'R')_r$phenyl substituted with 0–3 $R^{7e}$;

$R^{7a}$, at each occurrence, is selected from H, methyl, ethyl, propyl, i-propyl, butyl, i-butyl, t-butyl, pentyl, hexyl, prop-2-enyl, 2-methyl-2-propenyl, cyclopropyl, cyclobutyl, cyclopentyl, cyclohexyl, $CH_2$cyclopropyl, and benzyl;

$R^{7b}$, at each occurrence, is selected from methyl, ethyl, propyl, i-propyl, butyl, i-butyl, t-butyl, pentyl, hexyl, cyclopropyl, cyclopentyl, $CH_2$-cyclopentyl, cyclohexyl, $CH_2$-cyclohexyl, $CF_3$, pyrrolidinyl, morpholinyl, piperizenyl substituted with 0–1 $R^{7e}$, and azetidinyl;

$R^{7d}$, at each occurrence, is selected from methyl, $CF_3$, $CF_2CF_3$, $CHF_2$, $CH_2F$, ethyl, propyl, i-propyl, butyl, i-butyl, t-butyl, pentyl, hexyl, and cyclopropyl;

$R^{7e}$, at each occurrence, is selected from $C_{1-6}$ alkyl, $C_{2-8}$ alkenyl, $C_{2-8}$ alkynyl, $(CH_2)_rC_{3-6}$ cycloalkyl, Cl, F, Br, I, CN, $NO_2$, $(CF_2)_rCF_3$, $(CH_2)_rOC_{1-5}$ alkyl, OH, SH, C(O) $OC_{1-5}$ alkyl, $(CH_2)_rSC_{1-5}$ alkyl, $(CH_2)_rNR^{7f}R^{7f}$, and $(CH_2)_r$phenyl;

$R^{7f}$, at each occurrence, is selected from H, methyl, ethyl, propyl, i-propyl, butyl, i-butyl, t-butyl, pentyl, hexyl, cyclopropyl, and phenyl; and r is 0 or 1.

In another embodiment, the present invention provides novel compounds of formula (I), wherein:

$R^7$ is selected from methyl, ethyl, propyl, i-propyl, butyl, i-butyl, s-butyl, pentyl, hexyl, Cl, Br, I, F, CN, $NO_2$, $NR^{7a}R^{7a}$, $NHC(O)NHR^{7a}$, $NR^{7a}C(O)R^{7b}$, $NR^{7a}C(O)OR^{7d}$, $CF_3$, $CF_2CF_3$, $CHF_2$, $CH_2F$, $OCF_3$, $C(O)R^{7b}$, $C(O)OR^{7d}$, $NR^{7f}C(O)NR^{7a}R^{7a}$, $NHS(O)_2R^{7b}$,

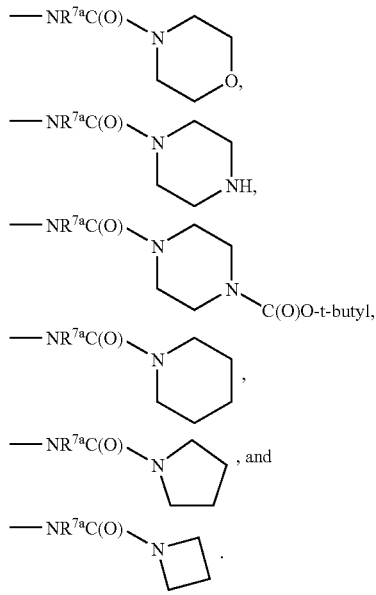

In another embodiment, the present invention provides novel compounds of formula (I), wherein:

$R^7$ is selected from methyl, ethyl, propyl, i-propyl, butyl, i-butyl, s-butyl, pentyl, hexyl, Cl, Br, I, F, CN, $NO_2$, $NR^{7a}R^{7a}$, $NHC(O)NHR^{7a}$, $NR^{7a}C(O)R^{7b}$, $NR^{7a}C(O)OR^{7d}$, $CF_3$, $CF_2CF_3$, $CHF_2$, $CH_2F$, $OCF_3$, $C(O)R^{7b}$, $C(O)OR^{7d}$, $NR^{7f}C(O)NR^{7a}R^{7a}$, $NHS(O)_2R^{7b}$, adamantyl,

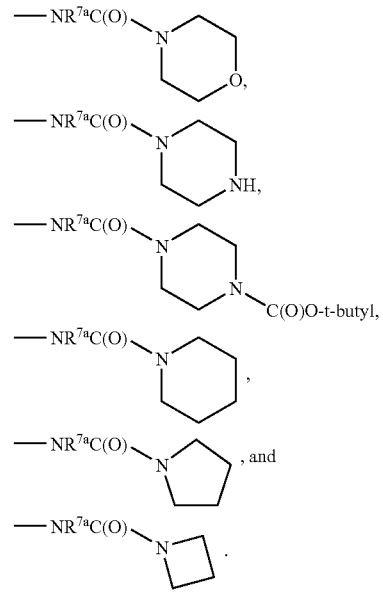

In another embodiment, the present invention provides novel compounds of formula (I), wherein:
ring B is selected from

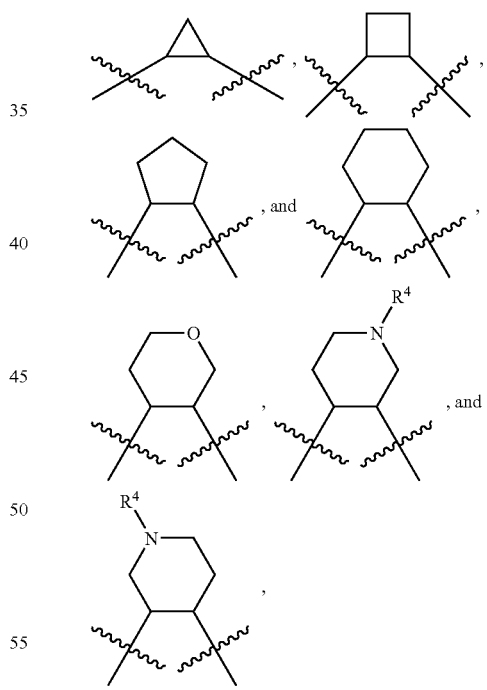

ring B being optionally substituted with 0–1 $R^5$;

Z is selected from a bond, —$NR^8C(O)$—, —$C(O)NH$—, and —$NHC(O)NH$—;

$R^1$ is selected from a $C_{6-10}$ aryl group substituted with 0–3 $R^6$ wherein the aryl group is selected from phenyl and naphthyl, and a 5–10 membered heteroaryl system containing 1–4 heteroatoms selected from N and O, substituted with 0–3 $R^6$ wherein the heteroaryl system is selected from indolyl and pyridinyl;

$R^2$ is phenyl substituted with 0–2 $R^7$;

$R^4$ is selected from H, methyl, ethyl, propyl, i-propyl, butyl, i-butyl, t-butyl, pentyl, hexyl, and $(CH_2)_rC(O)R^{4b}$;

$R^6$ is selected from methyl, ethyl, propyl, i-propyl, butyl, F, Cl, Br, I, $NO_2$, CN, $O(CH_2)_rR^{6d}$, C(O)H, $C(O)R^{6d}$, C(O)OH, $SR^{6d}$, $NR^{6a}R^{6a}$, $NC(O)R^{6b}$, $OC(O)R^{6b}$, $S(O)_pR^{6b}$, $(CHR')_rS(O)_2NR^{6a}R^{6a}$, and $CF_3$;

$R^{6a}$ is H, methyl, or ethyl;

$R^{6b}$ is H, methyl, ethyl, propyl, i-propyl or butyl;

$R^{6d}$ is methyl, phenyl, $CF_3$, and $(CH_2)$-phenyl; and r is 0 or 1.

In another embodiment, the present invention provides novel compounds of formula (I), wherein:

$R^1$ is selected from a $C_{6-10}$ aryl group substituted with 0–3 $R^6$ wherein the aryl group is selected from phenyl and naphthyl, and a 5–10 membered heteroaryl system containing 1–4 heteroatoms selected from N and O, substituted with 0–3 $R^6$ wherein the heteroaryl system is selected from indolyl, pyridinyl, pyrimidinyl, pyrido[2,3-d]pyrimidinyl, thieno[3,2-d]pyrimidinyl, imidazolyl, and pyrrolyl.

In another embodiment, the present invention provides novel compounds of formula (I), wherein:

ring B is selected from

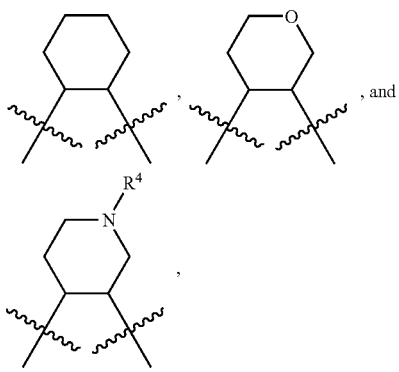

ring B being substituted with 0–1 $R^5$;

$R^1$ is selected from a $C_{6-10}$ aryl group substituted with 0–3 $R^6$ wherein the aryl group is selected from phenyl, and a 5–10 membered heteroaryl system containing 1–4 heteroatoms selected from N and O, substituted with 0–3 $R^6$ wherein the heteroaryl system is selected from indolyl and pyridinyl;

$R^4$ is selected from H, methyl, ethyl, propyl, i-propyl, butyl, i-butyl, t-butyl, pentyl, hexyl, allyl and $(CH_2)_rC(O)R^{4b}$;

$R^5$ is selected from H, OH, $OCH_3$, and $NR^{5a}R^{5a}$;

$R^{5a}$ is selected from H, methyl, ethyl, propyl, i-propyl, butyl, s-butyl, i-butyl, t-butyl, pentyl, hexyl, allyl, propargyl, cyclopropyl, cyclopropylmethyl, acetyl, methysulfonyl, —$C(O)CF_3$, C(=N)$NH_2$, benzyl, and —C(O)O-t-butyl;

$R^6$ is selected from methyl, ethyl, propyl, i-propyl, butyl, vinyl, F, Cl, Br, I, CN, $NR^{6a}R^{6a}$, C(O)H, C(O)OH, $C(O)R^{6b}$, $SR^{6d}$, $S(O)_pR^{6d}$, $S(O)_2NR^{6a}R^{6a}$, $CF_3$, and $CH_2OH$;

$R^{6b}$ is H, methyl, ethyl, propyl, i-propyl or butyl;

$R^{6d}$ is methyl;

$R^7$ is selected from methyl, ethyl, propyl, i-propyl, butyl, i-butyl, s-butyl, pentyl, hexyl, Cl, Br, I, F, CN, $NO_2$, $NR^{7a}R^{7a}$, $NHC(O)NHR^{7a}$, $NR^{7a}C(O)R^{7b}$, $NR^{7a}C(O)$ $OR^{7d}$, $CF_3$, $CF_2CF_3$, $CHF_2$, $CH_2F$, $OCF_3$, $OCF_2CF_3$, $OCHF_2$, and $OCH_2F$, $C(O)OR^{7d}$, $C(O)R^{7b}$, $NR^{7f}C(O)$ $NR^{7a}R^{7a}$, $NHS(O)_2R^{7b}$,

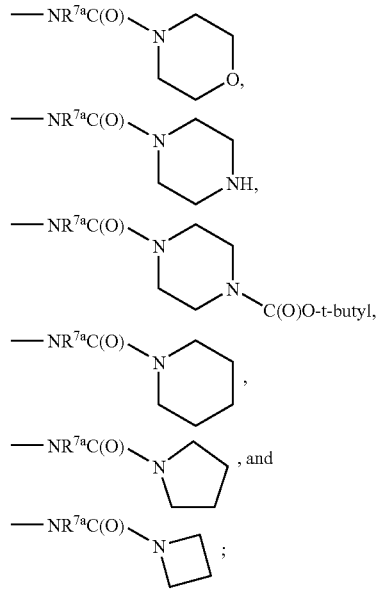

$R^{7a}$ is selected from H, methyl, ethyl, propyl, i-propyl, butyl, i-butyl, t-butyl, pentyl, neo-pentyl, cyclopropyl, cyclobutyl, cyclopentyl, and cyclohexyl;

$R^{7b}$ is selected from cyclohexyl and $CF_3$; and $R^{7d}$ is selected from methyl, ethyl, propyl, i-propyl, butyl, i-butyl, and t-butyl.

In another embodiment, the present invention provides novel compounds of formula (I), wherein:

ring B is selected from

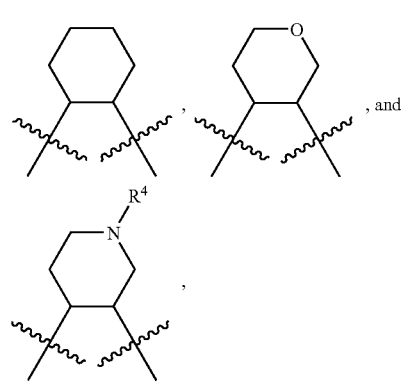

ring B being substituted with 0–1 $R^5$;

$R^1$ is selected from a $C_{6-10}$ aryl group substituted with 0–3 $R^6$ wherein the aryl group is selected from phenyl, and a 5–10 membered heteroaryl system containing 1–4 heteroatoms selected from N and O, substituted with 0–3 $R^6$ wherein the heteroaryl system is selected from indolyl and pyridinyl;

$R^4$ is selected from H, methyl, ethyl, propyl, i-propyl, butyl, i-butyl, t-butyl, pentyl, hexyl, allyl and $(CH_2)_rC(O)R^{4b}$;

$R^5$ is selected from H, OH, $OCH_3$, N(→O)$R^{5a}R^{5a}$a, $N_3$, $NR^{5a}C(O)R^{5b}$, $NR^{5a}C(O)H$, $NR^{5a}C(O)OR^{5d}$, $NR^{5a}C(O)$ $NR^{5a}R^{5a}$, and $NR^{5a}R^{5a}$, and a $(CH_2)_r$-5–6 membered heterocyclic system containing 1–2 heteroatoms selected from N, O, and S, substituted with 0–2 $R^{5e}$, wherein the heterocyclic system is selected from pyrrolidinyl, piperidinyl, pyrrolidin-2-one, and isothiazolidine 1,1-dioxide;

$R^{5a}$ is selected from H, methyl substituted with 0–1 $R^{5g}$, ethyl substituted with 0–1 $R^{5e}$, propyl, i-propyl, butyl, s-butyl, i-butyl, t-butyl, pentyl, hexyl, allyl, propargyl, cyclopropyl, cyclopropylmethyl, phenyl, benzyl, pyridin-3-yl, thiazolyl;

$R^6$ is selected from methyl, ethyl, propyl, i-propyl, butyl, vinyl, F, Cl, Br, I, CN, $NR^{6a}R^{6a}$, C(O)H, C(O)OH, C(O)$R^{6b}$, $SR^{6d}$, S(O)$_p R^{6d}$, S(O)$_2 NR^{6a}R^{6a}$, $CF_3$, and $CH_2OH$;

$R^{6b}$ is H, methyl, ethyl, propyl, i-propyl or butyl;

$R^{6d}$ is methyl;

$R^7$ is selected from methyl, ethyl, propyl, i-propyl, butyl, i-butyl, s-butyl, t-butyl, pentyl, hexyl, phenyl, adamantyl, benzyl, Cl, Br, I, F, CN, $NO_2$, $NR^{7a}R^{7a}$, $OR^{7d}$, NHC(O)NHR$^{7a}$, $NR^{7a}C(O)R^{7b}$, $NR^{7a}C(O)OR^{7d}$, $CF_3$, $CF_2CF_3$, $CHF_2$, $CH_2F$, $OCF_3$, $OCF_2CF_3$, $OCHF_2$, and $OCH_2F$, C(O)$OR^{7d}$, C(O)$R^{7b}$, $NR^{7f}C(O)NR^{7a}R^{7a}$, $NHS(O)_2R^{7b}$,

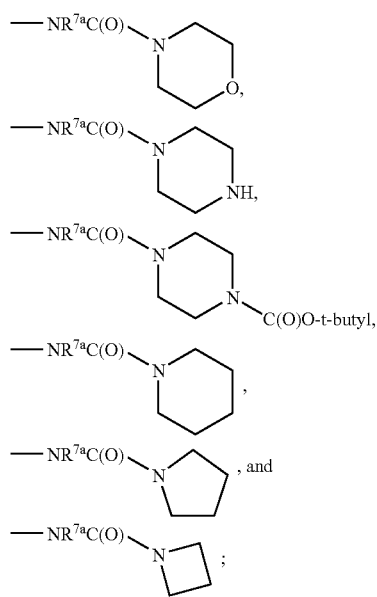

$R^{7a}$ is selected from H, methyl, ethyl, propyl, i-propyl, butyl, i-butyl, t-butyl, pentyl, neo-pentyl, cyclopropyl, cyclobutyl, cyclopentyl, and cyclohexyl;

$R^{7b}$ is selected from cyclohexyl and $CF_3$; and $R^{7d}$ is selected from methyl, ethyl, propyl, i-propyl, butyl, i-butyl, and t-butyl.

In another embodiment, the present invention provides novel compounds of formula (I), wherein:
ring B is selected from

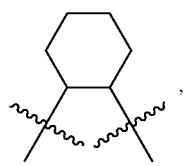

ring B being substituted with 0–1 $R^5$;

$R^1$ is selected from a $C_{6-10}$ aryl group substituted with 0–3 $R^6$ wherein the aryl group is phenyl, and a 5–10 membered heteroaryl system containing 1 heteroatoms selected from N and O, substituted with 0–3 $R^6$ wherein the heteroaryl system is indolyl;

$R^5$ is selected from H, OH, $OCH_3$, and $NR^{5a}R^{5a}$;

$R^{5a}$ is selected from H, methyl, ethyl, propyl, i-propyl, butyl, s-butyl, i-butyl, t-butyl, pentyl, hexyl, allyl, propargyl, cyclopropyl, cyclopropylmethyl, acetyl, methysulfonyl, —C(O)$CF_3$, C(=N)$NH_2$, benzyl, and —C(O)O-t-butyl;

$R^6$ is selected from methyl, ethyl, propyl, i-propyl, Cl, Br, CN, C(O)$CH_3$, C(O)OH, $OCH_3$, $NR^{6a}R^{6a}$, $SCH_3$, S(O)$_2$ $NR^{6a}R^{6a}$, and $CF_3$;

$R^{6a}$ is H, methyl, ethyl, propyl, i-propyl, butyl, propargyl, cyclopropyl, allyl;

$R^7$ is selected from Cl, Br, CN, $NR^{7a}R^{7a}$, $CF_3$, $CF_2CF_3$, $CHF_2$, $CH_2F$, $OCF_3$, $OCF_2CF_3$, $OCHF_2$, and $OCH_2F$; and $R^{7a}$ is selected from H, methyl, ethyl, propyl, i-propyl, butyl, i-butyl, t-butyl, pentyl, neo-pentyl, cyclopropyl, cyclobutyl, cyclopentyl, and cyclohexyl.

In another embodiment, the present invention provides novel compounds of formula (I), wherein:
ring B is selected from

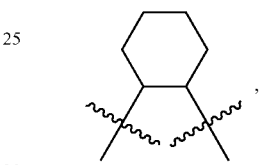

ring B being substituted with 0–1 $R^5$;

$R^1$ is selected from a $C_{6-10}$ aryl group substituted with 0–3 $R^6$ wherein the aryl group is phenyl;

$R^6$ is selected from methyl, ethyl, propyl, i-propyl, F, Cl, Br, CN, $SCH_3$, and $CF_3$;

$R^7$ is selected from methyl, ethyl, propyl, i-propyl, butyl, i-butyl, s-butyl, t-butyl, pentyl, hexyl, phenyl, adamantyl, benzyl, Cl, Br, I, F, CN, $NO_2$, $NR^{7a}R^{7a}$, $OR^{7d}$, NHC(O)NHR$^{7a}$, $NR^{7a}C(O)R^{7b}$, $NR^{7a}C(O)OR^{7d}$, $CF_3$, $CF_2CF_3$, $CHF_2$, $CH_2F$, $OCF_3$, $OCF_2CF_3$, $OCHF_2$, and $OCH_2F$, C(O)$OR^{7d}$, C(O)$R^{7b}$, and $NR^{7f}C(O)NR^{7a}R^{7a}$;

$R^{7a}$ is selected from H, methyl, ethyl, propyl, i-propyl, butyl, i-butyl, t-butyl, pentyl, neo-pentyl, cyclopropyl, cyclobutyl, cyclopentyl, and cyclohexyl.

In another embodiment, the present invention provides novel compounds of formula (I), wherein:
E is selected from —$CH_2$—NH—, —C(O)—NH— and —$SO_2$—$CH_2$—.

In another embodiment, the present invention provides novel compounds of formula (I), wherein:
B is

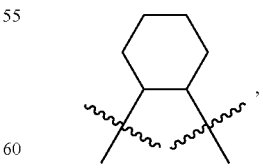

ring B being substituted with 0–1 $R^5$; and $R^5$ is selected from H and $NR^{5a}R^{5a}$;

$R^{5a}$ is selected from H, methyl, ethyl, propyl, i-propyl, butyl, s-butyl, i-butyl, t-butyl, pentyl, hexyl, propargyl, allyl, cyclopropylmethyl, cyclopropyl, and phenyl.

In another embodiment, the present invention provides novel compounds of formula (I), wherein:

Z is selected from a bond, —NR$^8$C(O)—, —C(O)NH—, and —NHC(O)NH—.

In another embodiment, the present invention provides novel compounds of formula (I), wherein:

R$^6$ is selected from methyl, ethyl, propyl, i-propyl, butyl, vinyl, F, Cl, Br, I, C(O)H, C(O)R$^{6b}$, SR$^{6d}$, S(O)$_p$R$^{6d}$, CF$_3$, and CH$_2$OH;

R$^{6b}$ is H, methyl, ethyl, propyl, i-propyl or butyl;

R$^{6d}$ is methyl;

R$^7$ is selected from Cl, Br, NR$^{7a}$R$^{7a}$, NR$^{7a}$C(O)OR$^{7d}$, NHC(O)NHR$^{7a}$, OCF$_3$, and CF$_3$;

R$^{7a}$ is selected from H, methyl, ethyl, propyl, i-propyl, butyl, i-butyl, t-butyl, pentyl, neo-pentyl, cyclopropyl, cyclobutyl, cyclopentyl, and cyclohexyl;

R$^{7d}$ is selected from methyl, ethyl, propyl, i-propyl, butyl, i-butyl, and t-butyl.

In another embodiment, the present invention provides novel compounds of formula (Ia) or (Ic), wherein:

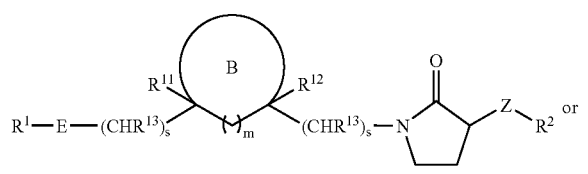

(Ia)

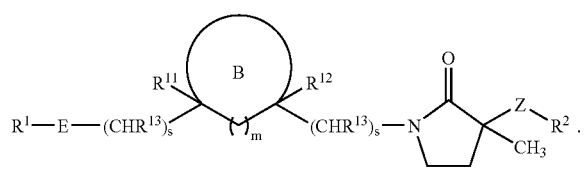

(Ic)

In another embodiment, the present invention provides novel compounds of formula (Ib), wherein:

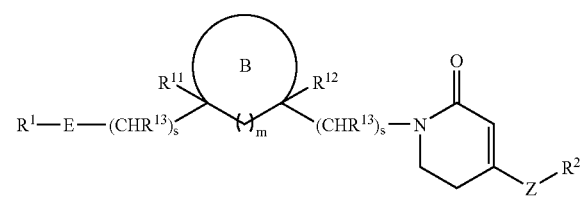

(Ib)

In another embodiment, the present invention provides novel compounds of formula (I), wherein the compound is selected from the compounds of the examples.

In another embodiment, the present invention is directed to a pharmaceutical composition, comprising a pharmaceutically acceptable carrier and a therapeutically effective amount of a compound of Formula (I).

In another embodiment, the present invention is directed to a method for modulation of chemokine or chemokine receptor activity comprising administering to a patient in need thereof a therapeutically effective amount of a compound of Formula (I).

In another embodiment, the present invention is directed to a method for modulation of CCR-2 receptor activity comprising administering to a patient in need thereof a therapeutically effective amount of a compound of Formula (I).

In another embodiment, the present invention is directed to a method for modulation of MCP-1, MCP-2, MCP-3 and MCP-4, and MCP-5 activity that is mediated by the CCR2 receptor comprising administering to a patient in need thereof a therapeutically effective amount of a compound of Formula (I).

In another embodiment, the present invention is directed to a method for modulation of MCP-1 activity comprising administering to a patient in need thereof a therapeutically effective amount of a compound of Formula (I).

In another embodiment, the present invention is directed to a method for treating disorders, comprising administering to a patient in need thereof a therapeutically effective amount of a compound of Formula (I), said disorders being selected from osteoarthritis, aneurism, fever, cardiovascular effects, Crohn's disease, congestive heart failure, autoimmune diseases, HIV-infection, HIV-associated dementia, psoriasis, idiopathic pulmonary fibrosis, transplant arteriosclerosis, physically- or chemically-induced brain trauma, inflammatory bowel disease, alveolitis, colitis, systemic lupus erythematosus, nephrotoxic serum nephritis, glomerularnephritis, asthma, multiple sclerosis, artherosclerosis, rheumatoid arthritis, restinosis, organ transplantation, and cancer.

In another embodiment, the present invention is directed to a method for treating disorders, of Formula (I), wherein said disorders being selected from psoriasis, idiopathic pulmonary fibrosis, transplant arteriosclerosis, physically- or chemically-induced brain trauma, inflammatory bowel disease, alveolitis, colitis, systemic lupus erythematosus, nephrotoxic serum nephritis, glomerularnephritis, asthma, multiple sclerosis, artherosclerosis, and rheumatoid arthritis, restinosis, organ transplantation, and cancer.

In another embodiment, the present invention is directed to a method for treating disorders, of Formula (I), wherein said disorders being selected from alveolitis, colitis, systemic lupus erythematosus, nephrotoxic serum nephritis, glomerularnephritis, asthma, multiple sclerosis, artherosclerosis, and rheumatoid arthritis, restinosis, organ transplantation, and cancer.

In another embodiment, the present invention is directed to a method for treating disorders, of Formula (I), wherein said disorders being selected from asthma, multiple sclerosis, artherosclerosis, and rheumatoid arthritis.

In another embodiment, the present invention is directed to a method for treating disorders, of Formula (I), wherein said disorders being selected from restinosis, organ transplantation, and cancer.

In another embodiment, the present invention is directed to a method for treating rheumatoid arthritis, comprising administering to a patient in need thereof a therapeutically effective amount of a compound of Formula (I).

In another embodiment, the present invention is directed to a method for treating multiple sclerosis, comprising administering to a patient in need thereof a therapeutically effective amount of a compound of Formula (I).

In another embodiment, the present invention is directed to a method for treating atherosclerosis, comprising administering to a patient in need thereof a therapeutically effective amount of a compound of Formula (I).

In another embodiment, the present invention is directed to a method for treating asthma, comprising administering to a patient in need thereof a therapeutically effective amount of a compound of Formula (I).

In another embodiment, the present invention is directed to a method for treating restinosis, comprising administering to a patient in need thereof a therapeutically effective amount of a compound of Formula (I).

In another embodiment, the present invention is directed to a method for treating organ transplantation, comprising administering to a patient in need thereof a therapeutically effective amount of a compound of Formula (I).

In another embodiment, the present invention is directed to a method for treating cancer, comprising administering to a patient in need thereof a therapeutically effective amount of a compound of Formula (I).

In another embodiment, the present invention is directed to a method for treating inflammatory diseases, comprising administering to a patient in need thereof a therapeutically effective amount of a compound of Formula (I).

In another embodiment, the present invention is directed to a method for treating inflammatory diseases which are at least partially mediated by CCR-2, comprising administering to a patient in need thereof a therapeutically effective amount of a compound of Formula (I).

In another embodiment, the present invention is directed to a method for modulation of CCR2 activity comprising administering to a patient in need thereof a therapeutically effective amount of a compound of Formula (I).

In another embodiment, the present invention is directed the use of a compound of Formula (I) in the preparation of a medicament for the treatment of osteoarthritis, aneurism, fever, cardiovascular effects, Crohn's disease, congestive heart failure, autoimmune diseases, HIV-infection, HIV-associated dementia, psoriasis, idiopathic pulmonary fibrosis, transplant arteriosclerosis, physically- or chemically-induced brain trauma, inflammatory bowel disease, alveolitis, colitis, systemic lupus erythematosus, nephrotoxic serum nephritis, glomerularnephritis, asthma, multiple sclerosis, artherosclerosis, and rheumatoid arthritis.

In another embodiment, the present invention is directed to a compound of formula (I) for use in therapy.

In another embodiment, the present invention is directed to a compound of formula (Ia)

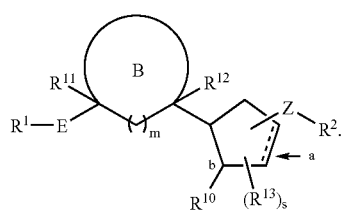

(Ia)

In another embodiment, the present invention is directed to a compound of formula (Ib)

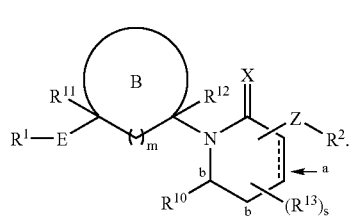

(Ib)

In another embodiment, the present invention is directed to a compound of formula (Ic)

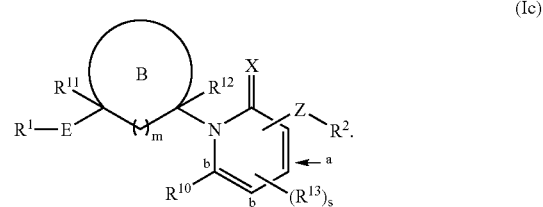

(Ic)

In another embodiment, ring B is selected from

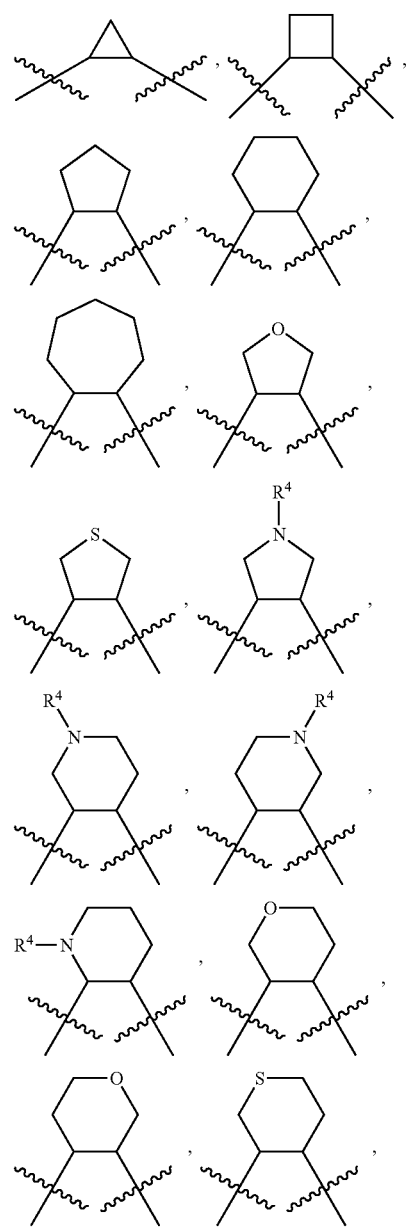

-continued

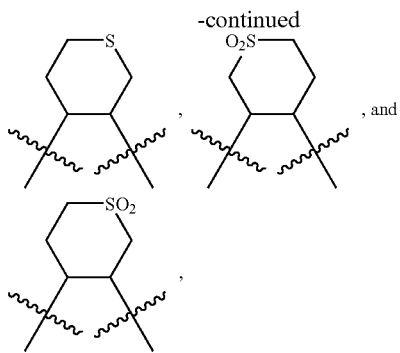

ring B being optionally substituted with 0–1 $R^5$.

In another embodiment, ring B is selected from

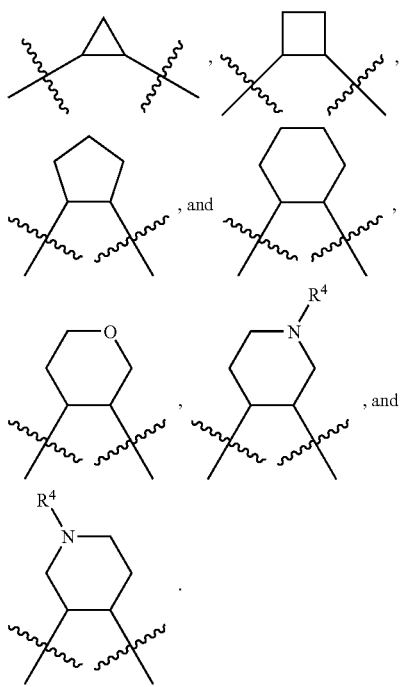

In another embodiment, ring B is selected from

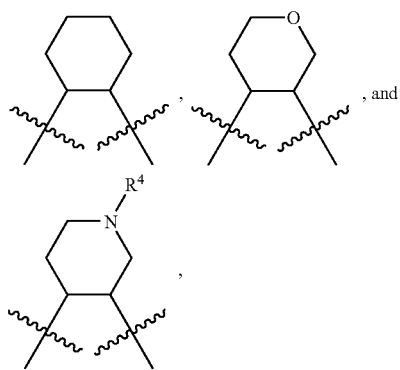

ring B being substituted with 0–

In another embodiment, ring B is

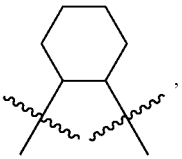

ring B being substituted with 0–1 $R^5$;

In another embodiment, E is $—S(O)_pCH_2—$.
In another embodiment, E is $—C(O)NH—$.
In another embodiment, E is $—CH_2NH—$.
In another embodiment, Z is selected from a bond, $—NR^8C(O)—$, $—NR^8C(O)NH—$, $—NR^8SO_2—$, $—NR^8SO_2NH—$, $—C(O)NR^8—$, $—(CR^{15}R^{15})_r—$, $—CR^{14}=CR^{14}—$, $—CR^{15}R^{15}C(O)—$, $—C(O)CR^{15}R^{15}—$, $—O—CR^{14}R^{14}—$, $—CR^{14}R^{14}—O—$, $—O—$, $—NR^9—$, $—NR^9—CR^{14}R^{14}—$, $—CR^{14}R^{14}—NR^9—$, $—S(O)_p—$, $—S(O)_p—CR^{14}R^{14}—$, $—CR^{14}R^{14}—S(O)_p—$, and $—S(O)_p—NR^9—$.

In another embodiment, Z is selected from a bond, $—NR^8C(O)—$, $—NR^8C(O)NH—$, $—C(O)NR^8—$, $—(CR^{15}R^{15})_r—$, $—CR^{15}R^{15}C(O)—$, $—C(O)CR^{15}R^{15}—$, $—O—CR^{14}R^{14}—$, $—CR^{14}R^{14}—O—$, $—O—$, $—NR^9—$, $—NR^9—CR^{14}R^{14}—$, $—CR^{14}R^{14}—NR^9—$, $—S(O)_p—$, $—S(O)_p—CR^{14}R^{14}—$, and $—S(O)_p—NR^9—$.

In another embodiment, Z is selected from a bond, $—NR^8C(O)—$, $—NR^8C(O)NH—$, and $—C(O)NR^8—$.

In another embodiment, z is selected from a bond, $—NR^8C(O)—$, $—C(O)NH—$, and $—NHC(O)NH—$.

In another embodiment, Z is selected from $—C(O)NH—$.

In another embodiment, Z is selected from a bond, and $—NHC(O)—$;

In another embodiment, Z is a bond.

In another embodiment, $R^4$ is selected from H, $C_{1-6}$ alkyl, $C_{3-8}$ alkenyl, $C_{3-8}$ alkynyl, $(CRR)_qOH$, $(CHR)_sSH$, $(CRR)_tOR^{4d}$, $(CHR)_tSR^{4d}$, $(CHR)_tNR^{4a}R^{4a}$, $(CHR)_qC(O)OH$, $(CHR)_tC(O)R^{4b}$, $(CHR)_rC(O)NR^{4a}R^{4a}$, $(CHR)_tNR^{4a}C(O)R^{4b}$, $(CHR)_tOC(O)NR^{4a}R^{4a}$, $(CHR)_tNR^{4a}C(O)OR^{4d}$, $(CHR)_tNR^{4a}C(O)R^{4b}$, $(CHR)_tC(O)OR^{4b}$, $(CHR)_tOC(O)R^{4b}$, $(CHR)_tS(O)_pR^{4b}$, $(CHR)_tS(O)_2NR^{4a}R^{4a}$, $(CHR)_tNR^{4a}S(O)_2R^{4b}$; and R, at each occurrence, is independently selected from H, methyl, ethyl, propyl, allyl, propynyl, $(CH_2)_rC_{3-6}$ cycloalkyl, and $(CH_2)_r$phenyl substituted with $R^{6e}$.

In another embodiment, $R^4$ is selected from H, methyl, ethyl, propyl, i-propyl, butyl, i-butyl, allyl, propynyl, $(CRR)_qOH$, $(CRR)_sSH$, $(CRR)_tOR^{4d}$, $(CRR)_tSR^{4d}$, $(CRR)_tNR^{4a}R^{4a}$, $(CRR)_qC(O)OH$, $(CRR)_rC(O)R^{4b}$, $(CRR)_rC(O)NR^{4a}R^{4a}$, $(CRR)_tNR^{4a}C(O)R^{4b}$, $(CRR)_tOC(O)NR^{4a}R^{4a}$, $(CRR)_tNR^{4a}C(O)OR^{4d}$, $(CRR)_tNR^{4a}C(O)R^{4b}$, $(CRR)_rC(O)OR^{4b}$, $(CRR)_tOC(O)R^{4b}$, $(CRR)_rS(O)_pR^{4b}$, $(CRR)_rS(O)_2NR^{4a}R^{4a}$, $(CRR)_tNR^{4a}S(O)_2R^{4b}$.

$R^{4b}$ is selected from H, methyl, ethyl, propyl, i-propyl, butyl, i-butyl, t-butyl, pentyl, and cyclopropyl; and $R^{4d}$ is selected from methyl, ethyl, propyl, i-propyl, butyl, i-butyl, t-butyl, pentyl, and cyclopropyl.

In another embodiment, $R^4$ is selected from H, methyl, ethyl, propyl, i-propyl, butyl, i-butyl, allyl, propynyl, $(CH_2)_rC(O)R^{4b}$.

In another embodiment, $R^5$, at each occurrence, is independently selected from H, $C_{1-6}$ alkyl, $C_{2-8}$ alkenyl, $C_{2-8}$ alkynyl, $(CRR)_rOH$, $(CRR)_rSH$, $(CRR)_rOR^{5d}$, $(CRR)_rSR^{5d}$, $(CRR)_rNR^{5a}R^{5a}$, $(CRR)_rN(O)R^{5a}R^{5a}$, $N_3$, $(CRR)_r$ C(O)OH, (CRR)$_r$C(O)R$^{5b}$, (CRR)$_r$C(O)NR$^{5a}$R$^{5a}$, (CRR)$_r$NR$^{5a}$C(O)R$^{5b}$, (CRR)$_r$NR$^{5a}$C(O)OR$^{5d}$, (CRR)$_r$OC(O)NR$^{5a}$R$^{5a}$, (CHR)$_r$NR$^{5a}$C(O)NR$^{5a}$R$^{5a}$, (CRR)$_r$NR$^{5a}$C(O)H, (CRR)$_r$C(O)OR$^{5b}$, (CRR)$_r$OC(O)R$^{5b}$, (CRR)$_r$S(O)$_p$R$^{5b}$, (CRR)$_r$S(O)$_2$NR$^{5a}$R$^{5a}$, (CRR)$_r$NR$^{5a}$S(O)$_2$R$^{5b}$, and C$_{1-6}$ haloalkyl.

In another embodiment, R$^5$ is selected from H, OH, OCH$_3$, N(→O)R$^{5a}$R$^{5a}$, N$_3$, NR$^{5a}$C(O)R$^{5b}$, NR$^{5a}$C(O)H, NR$^{5a}$C(O)OR$^{5d}$, NR$^{5a}$C(O)NR$^{5a}$R$^{5a}$, and NR$^{5a}$R$^{5a}$, and a (CH$_2$)$_r$-5–6 membered heterocyclic system containing 1–2 heteroatoms selected from N, O, and S, substituted with 0–2 R$^{5e}$, wherein the heterocyclic system is selected from pyrrolidinyl, piperidinyl, pyrrolidin-2-one, and isothiazolidine 1,1-dioxide;

R$^{5a}$ is selected from H, methyl substituted with 0–1 R$^{5g}$, ethyl substituted with 0–1 R$^{5e}$, propyl, i-propyl, butyl, s-butyl, i-butyl, t-butyl, pentyl, hexyl, allyl, propargyl, cyclopropyl, cyclopropylmethyl, phenyl, benzyl, pyridin-3-yl, thiazolyl.

In another embodiment, R$^5$ is selected from H, N(→O) R$^{5a}$R$^{5a}$, N$_3$, NR$^{5a}$C(O)R$^{5b}$, NR$^{5a}$C(O)H, NR$^{5a}$C(O)OR$^{5d}$, NR$^{5a}$C(O)NR$^{5a}$R$^{5a}$, and NR$^{5a}$R$^{5a}$, and a (CH$_2$)$_r$-5–6 membered heterocyclic system containing 1–2 heteroatoms selected from N, O, and S, substituted with 0–2 R$^{5e}$, wherein the heterocyclic system is selected from pyrrolidinyl, piperidinyl, pyrrolidin-2-one, and isothiazolidine 1,1-dioxide.

In another embodiment, R$^5$, at each occurrence, is independently selected from H, C$_{1-6}$ alkyl, C$_{2-8}$ alkenyl, C$_{2-8}$ alkynyl, (CH$_2$)$_r$OH, (CH$_2$)$_r$SH, (CH$_2$)$_r$OR$^{5d}$, (CH$_2$)$_r$SR$^{5d}$, (CH$_2$)$_r$NR$^{5a}$R$^{5a}$, (CH$_2$)$_r$N(O)R$^{5a}$R$^{5a}$, N$_3$, (CH$_2$)$_r$C(O)OH, (CH$_2$)$_r$C(O)R$^{5b}$, (CH$_2$)$_r$C(O)NR$^{5a}$R$^{5a}$, (CH$_2$)$_r$NR$^{5a}$C(O)R$^{5b}$, (CH$_2$)$_r$NR$^{5a}$C(O)OR$^{5d}$, (CH$_2$)$_r$OC(O)NR$^{5a}$R$^{5a}$, (CHR)$_r$NR$^{5a}$C(O)NR$^{5a}$R$^{5a}$, (CH$_2$)$_r$NR$^{5a}$C(O)H, (CH$_2$)$_r$C(O)OR$^{5b}$, (CH$_2$)$_r$OC(O)R$^{5b}$, (CH$_2$)$_r$S(O)$_p$R$^{5b}$, (CH$_2$)$_r$S(O)$_2$NR$^{5a}$R$^{5a}$, (CH$_2$)$_r$NR$^{5a}$S(O)$_2$R$^{5b}$, and C$_{1-6}$ haloalkyl.

In another embodiment, R$^5$, at each occurrence, is independently selected from H, methyl, ethyl, propyl, i-propyl, butyl, i-butyl, allyl, propynyl, (CH$_2$)$_r$OH, (CH$_2$)$_r$OR$^{5d}$, (CH$_2$)$_r$NR$^{5a}$R$^{5a}$, (CH$_2$)$_r$C(O)OH, (CH$_2$)$_r$C(O)R$^{5b}$, (CH$_2$)$_r$C(O)NR$^{5a}$R$^{5a}$, (CH$_2$)$_r$NR$^{5a}$C(O)R$^{5b}$, (CH$_2$)$_r$OC(O)NR$^{5a}$R$^{5a}$, (CH$_2$)$_r$NR$^{5a}$C(O)OR$^{5d}$, (CH$_2$)$_r$NR$^{5a}$C(O)R$^{5b}$, (CH$_2$)$_r$C(O)OR$^{5b}$, (CH$_2$)$_r$OC(O)R$^{5b}$, (CH$_2$)$_r$NR$^{5a}$S(O)$_2$R$^{5b}$, and C$_{1-6}$ haloalkyl; and R$^{5a}$, at each occurrence, is independently selected from H, methyl, ethyl, propyl, i-propyl, butyl, i-butyl, pentyl, hexyl, cyclopropyl, and cyclobutyl.

In another embodiment, R$^5$, at each occurrence, is independently selected from H, OH, OR$^{5d}$, (CH$_2$)$_r$NR$^{5a}$R$^{5a}$, (CH$_2$)$_r$NR$^{5a}$C(O)R$^{5b}$, and (CH$_2$)$_r$NR$^{5a}$C(O)R$^{5d}$.

In another embodiment, R$^1$ is selected from phenyl substituted with 0–2 R$^6$, naphthyl substituted with 0–2 R$^6$, and a 5–10 membered heteroaryl system containing 1–4 heteroatoms selected from N, O, and S, substituted with 0–3 R$^6$ wherein the heteroaryl is selected from indolyl, benzimidazolyl, benzofuranyl, benzothiofuranyl, benzoxazolyl, benzthiazolyl, benztriazolyl, benztetrazolyl, benzisoxazolyl, benzisothiazolyl, benzimidazalonyl, cinnolinyl, furanyl, imidazolyl, indazolyl, indolyl, isoquinolinyl isothiazolyl, isoxazolyl, oxazolyl, pyrazinyl, pyrazolyl, pyridazinyl, pyridyl, pyridinyl, pyrimidinyl, pyrrolyl, quinazolinyl, quinolinyl, thiazolyl, thienyl, and tetrazolyl.

In another embodiment, R$^1$ is selected from a C$_{6-10}$ aryl group substituted with 0–3 R$^6$ wherein the aryl group is selected from phenyl and naphthyl, and a 5–10 membered heteroaryl system containing 1–4 heteroatoms selected from N and O, substituted with 0–3 R$^6$ wherein the heteroaryl system is selected from furanyl, indolyl, benzothiazolyl, and benzotriazolyl.

In another embodiment, R$^1$ is selected from phenyl substituted with 0–2 R$^6$, naphthyl substituted with 0–2 R$^6$, and a 5–10 membered heteroaryl system containing 1–4 heteroatoms selected from N, O, and S, substituted with 0–3 R$^6$ wherein the heteroaryl is selected from indolyl, benzimidazolyl, benzofuranyl, benzothiofuranyl, benzoxazolyl, benzthiazolyl, benzo[b]thiophene, benztriazolyl, benztetrazolyl, benzisoxazolyl, benzisothiazolyl, benzimidazalonyl, cinnolinyl, furanyl, imidazolyl, indazolyl, indolyl, isoquinolinyl, isothiazolyl, isoxazolyl, oxazolyl, pyrazinyl, pyrazolyl, pyridazinyl, pyridyl, pyrido[2,3-d]pyrimidinyl, pyrimido[5,4-d]pyrimidinyl, thieno[3,2-d]pyrimidinyl, pyridinyl, pyrimidinyl, pyrrolyl, pyrrolo[2,1-f][1,2,4]triazine, quinazolinyl, quinolinyl, thiazolyl, thienyl, and tetrazolyl.

In another embodiment, R$^1$ is selected from a C$_{6-10}$ aryl group substituted with 0–3 R$^6$ wherein the aryl group is selected from phenyl and naphthyl, and a 5–10 membered heteroaryl system containing 1–4 heteroatoms selected from N and O, substituted with 0–3 R$^6$ wherein the heteroaryl system is selected from indolyl, pyridinyl, pyrimidinyl, pyrido[2,3-d]pyrimidinyl, thieno[3,2-d]pyrimidinyl, imidazolyl, and pyrrolyl.

In another embodiment, R$^1$ is selected from a C$_{6-10}$ aryl group substituted with 0–3 R$^6$ wherein the aryl group is selected from phenyl, and a 5–10 membered heteroaryl system containing 1–4 heteroatoms selected from N and O, substituted with 0–3 R$^6$ wherein the heteroaryl system is selected from indolyl and pyridinyl.

In another embodiment, R$^1$ is selected from a C$_{6-10}$ aryl group substituted with 0–3 R$^6$ wherein the aryl group is phenyl.

In another embodiment, R$^2$ is selected from phenyl substituted with 0–2 R$^7$, and a 5–10 membered heteroaryl system containing 1–4 heteroatoms selected from N, O, and S, substituted with 0–3 R$^7$ wherein the heteroaryl is selected from benzimidazolyl, benzofuranyl, benzothiofuranyl, benzoxazolyl, benzthiazolyl, benztriazolyl, benztetrazolyl, benzisoxazolyl, benzisothiazolyl, benzimidazalonyl, cinnolinyl, furanyl, imidazolyl, indazolyl, indolyl, isoquinolinyl isothiazolyl, isoxazolyl, oxazolyl, pyrazinyl, pyrazolyl, pyridazinyl, pyridyl, pyridinyl, pyrimidinyl, pyrrolyl, quinazolinyl, quinolinyl, thiazolyl, thienyl, and tetrazolyl.

In another embodiment, R$^2$ is selected from phenyl substituted with 0–2 R$^7$.

In another embodiment, R$^2$ is selected from phenyl substituted with 0–2 R$^7$, and a 5–10 membered heteroaryl system containing 1–4 heteroatoms selected from N, O, and S, substituted with 0–3 R$^7$ wherein the heteroaryl is selected from indolyl, naphthalenyl, phthalazinyl, cinnolinyl, quinolinyl, isoquinolinyl, indazolyl, and quinazolinyl, benzimidazolyl, benzofuranyl, benzothiofuranyl, benzoxazolyl, benzthiazolyl, benzisoxazolyl, and benzisothiazolyl.

In another embodiment, R$^2$ is selected from phenyl substituted with 0–2 R$^7$, and a 5–10 membered heteroaryl system containing 1–4 heteroatoms selected from N, O, and S, substituted with 0–3 R$^7$ wherein the heteroaryl is selected from indolyl, benzimidazolyl, benzofuranyl, benzothiofuranyl, benzoxazolyl, benzthiazolyl, benzo[b]thiophene, benztriazolyl, benztetrazolyl, benzisoxazolyl, benzisothiazolyl, benzimidazalonyl, cinnolinyl, furanyl, imidazolyl, indazolyl, indolyl, isoquinolinyl isothiazolyl, isoxazolyl, oxazolyl, phthalazinyl, pyrazinyl, pyrazolyl, pyridazinyl, pyridyl, pyrido[2,3-d]pyrimidinyl, thieno[3,2-d]pyrimidinyl, pyridinyl, pyrimidinyl, pyrrolyl, pyrrolo[2,1-f][1,2,4]triazine, quinazolinyl, quinolinyl, thiazolyl, thienyl, and tetrazolyl.

In another embodiment, Z is a bond and $R^2$ is selected from a 5–10 membered heteroaryl system containing 1–4 heteroatoms selected from N, O, and S, substituted with 0–3 $R^7$ wherein the heteroaryl is selected from indolyl, naphthalenyl, phthalazinyl, cinnolinyl, quinolinyl, isoquinolinyl, indazolyl, and quinazolinyl, benzimidazolyl, benzofuranyl, benzothiofuranyl, benzoxazolyl, benzthiazolyl, benzisoxazolyl, and benzisothiazolyl.

In another embodiment, $R^6$, at each occurrence, is selected from $C_{1-8}$ alkyl, $C_{2-8}$ alkenyl, $C_{2-8}$ alkynyl, $(CH_2)_rC_{3-6}$ cycloalkyl, Cl, Br, I, F, $NO_2$, CN, $(CH_2)_rNR^{6a}R^{6a}$, $(CH_2)_r$OH, $(CH_2)_rO(CH_2)_rR^{6d}$, $(CH_2)_rSH$, $(CH_2)_rC(O)H$, $(CH_2)_rS(CH_2)_rR^{6d}$, $(CH_2)_rC(O)OH$, $(CH_2)_rC(O)(CH_2)_rR^{6b}$, $(CH_2)_rC(O)NR^{6a}R^{6a}$, $(CH_2)_rNR^{6f}C(O)(CH_2)_rR^{6b}$, $(CH_2)_rC(O)O(CH_2)_rR^{6d}$, $(CH_2)_rOC(O)(CH_2)_rR^{6b}$, $(CH_2)_rS(O)_p(CH_2)_rR^{6b}$, $(CH_2)_rS(O)_2NR^{6a}R^{6a}$, $(CH_2)_rNR^{6f}S(O)_2(CH_2)_rR^{6b}$, $(CH_2)_rNR^{6f}S(O)_2NR^{6a}R^{6a}$, $C_{1-6}$ haloalkyl, and $(CH_2)_r$phenyl substituted with 0–3 $R^{6e}$;

$R^{6a}$, at each occurrence, is independently selected from H, methyl, ethyl, propyl, i-propyl, butyl, i-butyl, t-butyl, pentyl, hexyl, cyclopropyl and phenyl;

$R^{6b}$, at each occurrence, is selected from methyl, ethyl, propyl, i-propyl, butyl, i-butyl, t-butyl, pentyl, hexyl, cyclopropyl, and phenyl;

$R^{6d}$, at each occurrence, is selected from methyl, $CF_3$, ethyl, propyl, i-propyl, butyl, i-butyl, t-butyl, pentyl, hexyl, cyclopropyl, and phenyl;

$R^{6e}$, at each occurrence, is selected from $C_{1-6}$ alkyl, $C_{2-8}$ alkenyl, $C_{2-8}$ alkynyl, $(CH_2)_rC_{3-6}$ cycloalkyl, Cl, F, Br, I, CN, $NO_2$, $(CF_2)_rCF_3$, $(CH_2)_rOC_{1-5}$ alkyl, OH, SH, $(CH_2)_r$ $SC_{1-5}$ alkyl, $(CH_2)_rNR^{6f}R^{6f}$, and $(CH_2)_r$phenyl; and $R^{6f}$, at each occurrence, is selected from H, methyl, ethyl, propyl, i-propyl, butyl, i-butyl, t-butyl, pentyl, hexyl, cyclopropyl, and phenyl.

In another embodiment, $R^6$ is selected from methyl, ethyl, propyl, i-propyl, butyl, F, Cl, Br, I, $NO_2$, CN, $O(CH_2)_r$ $R^{6d}$, C(O)H, $SR^{6d}$, $NR^{6a}R^{6a}$, $OC(O)R^{6b}$, $S(O)_pR^{6b}$, $(CHR')_rS(O)_2NR^{6a}R^{6a}$, $CF_3$;

$R^{6a}$ is H, methyl, or ethyl;

$R^{6b}$ is H or methyl; and $R^{6d}$ is methyl, phenyl, $CF_3$, and $(CH_2)$-phenyl.

In another embodiment, $R^7$ is selected from methyl, ethyl, propyl, i-propyl, butyl, i-butyl, s-butyl, t-butyl, pentyl, hexyl, $(CH_2)_rC_{3-6}$ cycloalkyl, Cl, Br, I, F, $NO_2$, CN, $(CH_2)_rNR^{7a}R^{7a}$, $(CH_2)_rOH$, $(CH_2)_rO(CH)_rR^{7d}$, $(CH_2)_r$ SH, $(CH_2)_rC(O)H$, $(CH_2)_rS(CH_2)_rR^{7d}$, $(CH_2)_rC(O)OH$, $(CH_2)_rC(O)(CH_2)_rR^{7b}$, $(CH_2)_rC(O)NR^{7a}R^{7a}$, $(CH_2)_r$ $NR^{7f}C(O)(CH_2)_rR^{7b}$, $(CH_2)_rC(O)O(CH_2)_rR^{7d}$, $(CH_2)_rOC(O)(CH_2)_rR^{7b}$, $(CH_2)_rNR^{7a}C(O)NR^{7a}R^{7a}$, $(CH_2)_rNR^{7a}C(O)O(CH_2)_rR^{7d}$, $(CH_2)_rS(O)_p(CH_2)_rR^{7b}$, $(CH_2)_rS(O)_2NR^{7a}R^{7a}$, $(CH_2)_rNR^{7f}S(O)_2(CH_2)_rR^{7b}$, $C_{1-6}$ haloalkyl, and $(CH_2)_r$phenyl substituted with 0–3 $R^{7e}$;

$R^{7a}$, at each occurrence, is selected from H, methyl, ethyl, propyl, i-propyl, butyl, i-butyl, t-butyl, pentyl, hexyl, and cyclopropyl;

$R^{7b}$, at each occurrence, is selected from methyl, ethyl, propyl, i-propyl, butyl, i-butyl, t-butyl, pentyl, hexyl, and cyclopropyl;

$R^{7d}$, at each occurrence, is selected from methyl, $CF_3$, ethyl, propyl, i-propyl, butyl, i-butyl, t-butyl, pentyl, hexyl, and cyclopropyl;

$R^{7e}$, at each occurrence, is selected from $C_{1-6}$ alkyl, $C_{2-8}$ alkenyl, $C_{2-8}$ alkynyl, $(CH_2)_rC_{3-6}$ cycloalkyl, Cl, F, Br, I, CN, $NO_2$, $(CF_2)_rCF_3$, $(CH_2)_rOC_{1-5}$ alkyl, OH, SH, $(CH_2)_r$ $SC_{1-5}$ alkyl, $(CH_2)_rNR^{7f}R^{7f}$, and $(CH_2)_r$phenyl; and $R^{7f}$, at each occurrence, is selected from H, methyl, ethyl, propyl, i-propyl, butyl, i-butyl, t-butyl, pentyl, hexyl, cyclopropyl, and phenyl.

In another embodiment, $R^7$ is selected from methyl, ethyl, propyl, i-propyl, butyl, i-butyl, s-butyl, pentyl, hexyl, Cl, Br, I, F, $NO_2$, $NR^{7a}R^{7a}$, $NHC(O)NHR^{7a}$, $NR^{7a}C(O)R^{7b}$, $NR^{7a}C(O)OR^{7d}$, $CF_3$, $OCF_3$, $C(O)R^{7b}$, $NR^{7f}C(O)NHR^{7a}$, and $NHS(O)_2R^{7b}$.

In another embodiment, $R^7$ is selected from methyl, ethyl, propyl, i-propyl, butyl, i-butyl, s-butyl, t-butyl, pentyl, hexyl, (CR'R')$_rC_{3-6}$ cycloalkyl, Cl, Br, I, F, $NO_2$, CN, (CR'R')$_rNR^{7a}R^{7a}$, (CR'R')$_r$OH, (CR'R')$_r$O(CH)$_rR^{7d}$, (CR'R')$_r$SH, (CR'R')$_r$C(O)H, (CR'R')$_r$S(CR'R')$_rR^{7d}$, (CR'R')$_r$C(O)OH, (CR'R')$_r$C(O)(CR'R')$_rR^{7b}$, (CR'R')$_r$C(O)NR$^{7a}R^{7a}$, (CR'R')$_r$NR$^{7f}$C(O)(CR'R')$_rR^{7b}$, (CR'R')$_r$C(O)O(CR'R')$_rR^{7d}$, (CR'R')$_r$OC(O)(CR'R')$_rR^{7b}$, (CR'R')$_r$NR$^{7a}$C(O)NR$^{7a}R^{7a}$, (CR'R')$_r$NR$^{7a}$C(O)O(CR'R')$_rR^{7d}$, (CR'R')$_r$S(O)$_p$(CR'R')$_rR^{7b}$, (CR'R')$_r$S(O)$_2$NR$^{7a}R^{7a}$, (CR'R')$_r$NR$^{7f}$S(O)$_2$(CR'R')$_rR^{7b}$, $C_{1-6}$ haloalkyl, adamantyl, and (CR'R')$_r$phenyl substituted with 0–3 $R^{7e}$.

In another embodiment, $R^7$ is selected from methyl, ethyl, propyl, i-propyl, butyl, i-butyl, s-butyl, t-butyl, pentyl, hexyl, Cl, Br, I, F, CN, $NO_2$, $NR^{7a}R^{7a}$, $NHC(O)NHR^{7a}$, $NR^{7a}C(O)R^{7b}$, $NR^{7a}C(O)OR^{7d}$, $CF_3$, $CF_2CF_3$, $CHF_2$, $CH_2F$, $OCF_3$, $C(O)R^{7b}$, $C(O)OR^{7d}$, $NR^{7f}C(O)NR^{7a}R^{7a}$, $NHS(O)_2R^{7b}$, adamantyl,

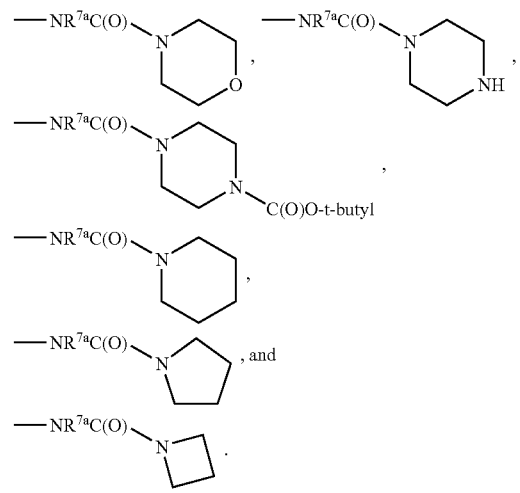

In another embodiment, $R^7$ is selected from methyl, ethyl, propyl, i-propyl, butyl, i-butyl, s-butyl, t-butyl, pentyl, hexyl, phenyl, adamantyl, benzyl, Cl, Br, I, F, CN, $NO_2$, $NR^{7a}R^{7a}$, $OR^{7d}$, $NHC(O)NHR^{7a}$, $NR^{7a}C(O)R^{7b}$, $NR^{7a}C(O)OR^{7d}$, $CF_3$, $CF_2CF_3$, $CHF_2$, $CH_2F$, $OCF_3$, $OCF_2CF_3$, $OCHF_2$, and $OCH_2F$, $C(O)OR^{7d}$, $C(O)R^{7b}$, $NR^{7f}C(O)NR^{7a}R^{7a}$, $NHS(O)_2R^{7b}$,

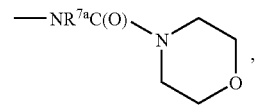

-continued

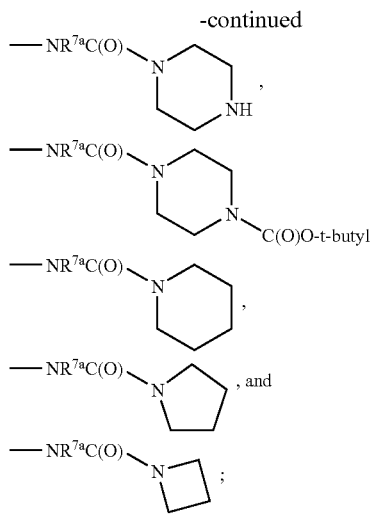

R$^{7a}$ is selected from H, methyl, ethyl, propyl, i-propyl, butyl, i-butyl, t-butyl, pentyl, neo-pentyl, cyclopropyl, cyclobutyl, cyclopentyl, and cyclohexyl;

R$^{7b}$ is selected from cyclohexyl and CF$_3$; and

R$^{7d}$ is selected from methyl, ethyl, propyl, i-propyl, butyl, i-butyl, and t-butyl.

In another embodiment, R$^7$ is selected from methyl, ethyl, propyl, i-propyl, butyl, i-butyl, s-butyl, t-butyl, pentyl, hexyl, phenyl, adamantyl, benzyl, Cl, Br, I, F, CN, NO$_2$, NR$^{7a}$R$^{7a}$, OR$^{7d}$, NHC(O)NHR$^{7a}$, NR$^{7a}$C(O)R$^{7b}$, NR$^{7a}$C(O)OR$^{7d}$, CF$_3$, CF$_2$CF$_3$, CHF$_2$, CH$_2$F, OCF$_3$, OCF$_2$CF$_3$, OCHF$_2$, and OCH$_2$F, C(O)OR$^{7d}$, C(O)R$^{7b}$, and NR$^{7f}$C(O)NR$^{7a}$R$^{7a}$;

R$^{7a}$ is selected from H, methyl, ethyl, propyl, i-propyl, butyl, i-butyl, t-butyl, pentyl, neo-pentyl, cyclopropyl, cyclobutyl, cyclopentyl, and cyclohexyl.

In another embodiment, R$^7$ is selected from methyl, ethyl, propyl, i-propyl, butyl, i-butyl, s-butyl, pentyl, hexyl, Cl, Br, I, F, NO$_2$, NR$^{7a}$R$^{7a}$, NHC(O)NHR$^{7a}$, NR$^{7a}$C(O)R$^{7b}$, NR$^{7a}$C(O)OR$^{7d}$, CF$_3$, OCF$_3$, C(O)OR$^{7d}$, C(O)R$^{7b}$, NR$^{7f}$C(O)NR$^{7a}$R$^{7a}$, NHS(O)$_2$R$^{7b}$,

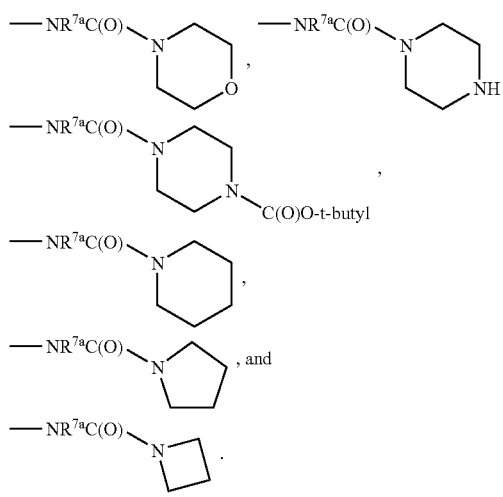

In another embodiment, R$^{7a}$ is selected from H, methyl, ethyl, propyl, i-propyl, butyl, i-butyl, t-butyl, pentyl, neo-pentyl, cyclopropyl, cyclobutyl, cyclopentyl, and cyclohexyl;

R$^{7b}$ is selected from cyclohexyl and CF$_3$; and

R$^{7d}$ is selected from methyl, ethyl, propyl, i-propyl, butyl, i-butyl, and t-butyl.

In another embodiment, R$^8$ is H.

In another embodiment, R$^{11}$ and R$^{12}$ are H.

In another embodiment, if ring B is not substituted with at least one R$^5$ which is to —NR$^{5a}$R$^{5a}$, than Z must be —NR$^8$C(O)— or —NR$^8$C(O)NH—.

In another embodiment, the present invention is directed to compounds of formula (II) which are useful as intermediates is the preparation of compounds of formula (I), wherein (II)

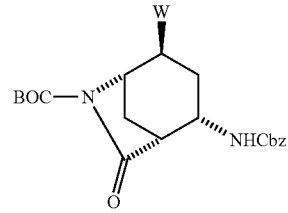

W is H or I.

In another embodiment, the present invention is directed to compounds of formula (III) which are useful as intermediates in the preparation of compounds of formula (I), wherein (III)

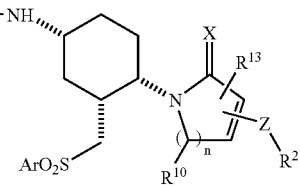

X, Z, R$^2$, R$^{13}$, and n are as described above.

In another embodiment, the present invention is directed to process of preparing compounds of formula (II), wherein (II)

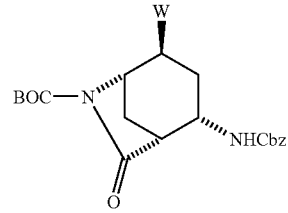

W is H or I;

comprising converting a compound of formula (IV)

(IV)

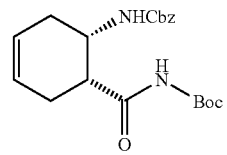

into a compound of formula (II) by use of an electrophile and base.

In another embodiment, the present invention is directed to process of preparing a compound of formula (III),

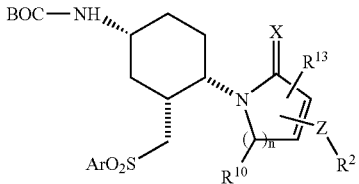
(III)

X, Z, R², R¹³, and n are as described above,
comprising converting a compound of formula (IV)

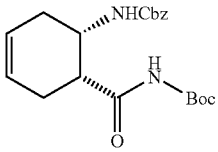
(IV)

into a compound of formula (II) by use of an electrophile and base.

In another embodiment, the present invention is directed to process of preparing compounds of formula (I), comprising
converting a compound of formula (IV)

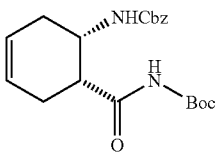
(IV)

into a compound of formula (II) by use of an electrophile and base

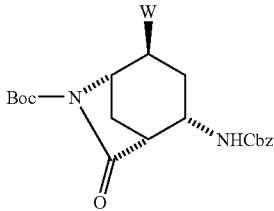
(II)

In another embodiment, the present invention is directed to process of preparing compounds of formula (I), comprising
converting a compound of formula (IV)

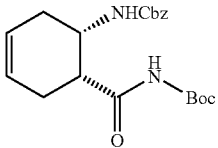
(IV)

into a compound of formula (II) by use of an electrophile and base, wherein the base is Butyl lithium and the electrophile is iodine

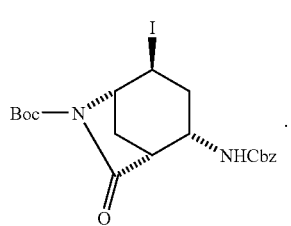
(II)

In another embodiment, the present invention is directed compound of Formula (II)

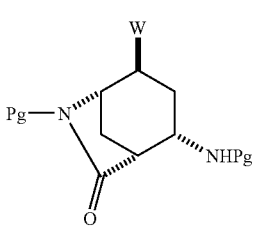
(II)

or salt or stereoisomer thereof, wherein
W is selected from H, I, and Br;
Pg, at each occurrence, is independently selected from an amine protecting group.

In another embodiment, the present invention is directed to a compound of formula (II), wherein
W is selected from H, I, and Br; and
Pg, at each occurrence, is independently selected from benzyloxycarbonyl (Cbz) and tert-butyloxycarbonyl (Boc).

In another embodiment, the present invention is directed to a process of preparing a compound of formula (Ia),

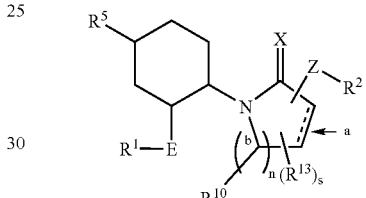
(Ia)

or salt or stereoisomer thereof: wherein
E is selected from —S(O)$_p$CHR$^e$—, —CHR$^e$NR$^e$—, —C(O)—NR$^e$—, —NR$^e$C(O)NR$^e$—, —SO$_2$—NR$^e$—, and —NR$^e$SO$_2$NR$^e$—;
R$^e$ is independently selected from H and C$_{1-3}$ alkyl;
X is selected from O or S;
Z is selected from a bond, —NR$^8$C(O)—, —NR$^8$C(S)—, —NR$^8$C(O)NH—, —NR$^8$C(S)NH—, —NR$^8$SO$_2$—, —NR$^8$SO$_2$NH—, —C(O)NR$^8$—, —OC(O)NR$^8$—, —NR$^8$C(O)O—, —(CR$^{15}$R$^{15}$)$_t$—, —CR$^{14}$=CR$^{14}$—, —CR$^{15}$R$^{15}$C(O)—, —C(O)CR$^{15}$R$^{15}$—, —CR$^{15}$R$^{15}$C(=N—OR$^{16}$)—, —O—CR$^{14}$R$^{14}$—, —CR$^{14}$R$^{14}$—O—, —O—, —NR$^9$—, —NR$^9$—CR$^{14}$R$^{14}$—, —CR$^{14}$R$^{14}$—NR$^9$—, —S(O)$_p$—, —S(O)$_p$—CR$^{14}$R$^{14}$—, —CR$^{14}$R$^{14}$—S(O)$_p$—, and —S(O)$_p$—NR$^9$—;
wherein neither Z nor R$^{13}$ are connected to a carbon atom labeled (b);
bond (a) is a single or double bond;
alternatively, when n is equal to 2, two atoms labeled (b) may join through a double bond;
R$^1$ is selected from a C$_{6-10}$ aryl group substituted with 0–5 R$^6$ and a 5–10 membered heteroaryl system containing 1–4 heteroatoms selected from N, O, and S, substituted with 0–3 R$^6$;
R$^2$ is selected from a C$_{6-10}$ aryl group substituted with 0–5 R$^7$ and a 5–10 membered heteroaryl system containing 1–4 heteroatoms selected from N, O, and S, substituted with 0–3 R$^7$;
R$^5$, at each occurrence, is independently selected from H, (CRR)$_r$OH, (CRR)$_r$SH, (CRR)$_r$OR$^{5d}$, (CRR)$_r$SR$^{5d}$, (CRR)$_r$NR$^{5a}$R$^{5a}$, (CRR)$_r$N(→O)R$^{5a}$R$^{5a}$, (CRR)$_r$NR$^{5a}$C(O)R$^{5b}$, (CRR)$_r$OC(O)NR$^{5a}$R$^{5a}$, (CRR)$_r$NR$^{5a}$C(O)OR$^{5d}$, (CRR)$_r$NR$^{5a}$C(O)NR$^{5a}$R$^{5a}$, (CRR)$_r$NR$^{5a}$C(O)H, (CRR)$_r$ OC(O)R$^{5b}$, (CRR)$_r$S(O)$_p$R$^{5b}$, (CRR)$_r$S(O)$_2$NR$^{5a}$R$^{5a}$, (CRR)$_r$NR$^{5a}$S(O)$_2$R$^{5b}$, (CRR)$_r$NR$^{5a}$S(O)$_2$NR$^{5a}$R$^{5a}$, and a (CRR)$_r$-5–10 membered heterocyclic system containing 1–4 heteroatoms selected from N, O, and S, substituted with 0–2 R$^{5c}$;

R$^{5a}$, at each occurrence, is independently selected from H, methyl substituted with 0–1 R$^{5g}$, C$_{2-6}$ alkyl substituted with 0–2 R$^{5e}$, C$_{3-8}$ alkenyl substituted with 0–2 R$^{5e}$, C$_{3-8}$ alkynyl substituted with 0–2 R$^{5e}$, a (CH$_2$)$_r$—C$_{3-10}$ carbocyclic residue substituted with 0–5 R$^{5e}$, and a (CH$_2$)$_r$-5–10 membered heterocyclic system containing 1–4 heteroatoms selected from N, O, and S, substituted with 0–3 R$^{5e}$;

R$^{5b}$, at each occurrence, is selected from C$_{1-6}$ alkyl substituted with 0–3 R$^{5e}$, C$_{3-8}$ alkenyl substituted with 0–2 R$^{5e}$, C$_{3-8}$ alkynyl substituted with 0–2 R$^{5e}$, a (CH$_2$)$_r$—C$_{3-6}$ carbocyclic residue substituted with 0–2 R$^{5e}$, and a (CH$_2$)$_r$-5–6 membered heterocyclic system containing 1–4 heteroatoms selected from N, O, and S, substituted with 0–3 R$^{5e}$;

R$^{5c}$, at each occurrence, is selected from C$_{1-6}$ alkyl, C$_{2-8}$ alkenyl, C$_{2-8}$ alkynyl, (CH$_2$)$_r$C$_{3-6}$ cycloalkyl, Cl, Br, I, F, (CF$_2$)$_r$CF$_3$, NO$_2$, CN, (CH$_2$)$_r$NR$^{5f}$R$^{5f}$, (CH$_2$)$_r$OH, (CH$_2$)$_r$OC$_{1-4}$ alkyl, (CH$_2$)$_r$SC$_{1-4}$ alkyl, (CH$_2$)$_r$C(O)OH, (CH$_2$)$_r$C(O)R$^{5b}$, (CH$_2$)$_r$C(O)NR$^{5f}$R$^{5f}$, (CH$_2$)$_r$OC(O)NR$^{5f}$R$^{5f}$, (CH$_2$)$_r$NR$^{5f}$C(O)R$^{5b}$, (CH$_2$)$_r$C(O)OC$_{1-4}$ alkyl, (CH$_2$)$_r$NR$_5$C(O)OC$_{1-4}$ alkyl, (CH$_2$)$_r$OC(O)R$^{5b}$, (CH$_2$)$_r$C(=NR$^{5f}$)NR$^{5f}$R$^{5f}$, (CH$_2$)$_r$S(O)$_p$R$^{5b}$, (CH$_2$)$_r$NHC(=NR$^{5f}$)NR$^{5f}$R$^{5f}$, (CH$_2$)$_r$S(O)$_2$NR$^{5f}$R$^{5f}$, (CH$_2$)$_r$NR$^{5f}$S(O)$_2$R$^{5b}$, and (CH$_2$)$_r$phenyl substituted with 0–3 R$^{5e}$;

R$^{5d}$, at each occurrence, is selected from methyl, CF$_3$, C$_{2-6}$ alkyl substituted with 0–2 R$^{5e}$, C$_{3-8}$ alkenyl substituted with 0–2 R$^{5e}$, C$_{3-8}$ alkynyl substituted with 0–2 R$^{5e}$, and a C$_{3-10}$ carbocyclic residue substituted with 0–3 R$^{5e}$;

R$^{5e}$, at each occurrence, is selected from C$_{1-6}$ alkyl, C$_{2-8}$ alkenyl, C$_{2-8}$ alkynyl, C$_{3-6}$ cycloalkyl, Cl, F, Br, I, CN, NO$_2$, (CF$_2$)$_r$CF$_3$, (CH$_2$)$_r$OC$_{1-5}$ alkyl, OH, SH, (CH$_2$)$_r$SC$_{1-5}$ alkyl, (CH$_2$)$_r$NR$^{5f}$R$^{5f}$, and (CH$_2$)$_r$phenyl;

R$^{5f}$, at each occurrence, is selected from H, C$_{1-6}$ alkyl, and C$_{3-6}$ cycloalkyl;

R$^{5g}$ is independently selected from —C(O)R$^{5b}$, —C(O)OR$^{5d}$, —C(O)NR$^{5f}$R$^{5f}$, —CN, and (CH$_2$)$_r$phenyl;

R, at each occurrence, is selected from H, C$_{1-6}$ alkyl substituted with R$^{5e}$, C$_{2-8}$ alkenyl, C$_{2-8}$ alkynyl, (CH$_2$)$_r$C$_{3-6}$ cycloalkyl, and (CH$_2$)$_r$phenyl substituted with R$^{5e}$;

R$^6$, at each occurrence, is selected from C$_{1-8}$ alkyl, C$_{2-8}$ alkenyl, C$_{2-8}$ alkynyl, (CH$_2$)$_r$C$_{3-6}$ cycloalkyl, Cl, Br, I, F, NO$_2$, CN, (CR'R')$_r$NR$^{6a}$R$^{6a}$, (CR'R')$_r$OH, (CR'R')$_r$O(CR'R')$_r$R$^{6d}$, (CR'R')$_r$SH, (CR'R')$_r$C(O)H, (CR'R')$_r$S(CR'R')$_r$R$^{6d}$, (CR'R')$_r$SC(O)(CR'R')$_r$R$^{6b}$, (CR'R')$_r$C(O)OH, (CR'R')$_r$C(O)(CR'R')$_r$R$^{6b}$, (CR'R')$_r$NR$^{6a}$R$^{6a}$, (CR'R')$_r$C(O)NR$^{6a}$R$^{6a}$, (CR'R')$_r$NR$^{6f}$C(O)(CR'R')$_r$R$^{6b}$, (CR'R')$_r$C(O)O(CR'R')$_r$R$^{6d}$, (CR'R')$_r$OC(O)(CR'R')$_r$R$^{6b}$, (CR'R')$_r$OC(O)NR$^{6a}$(CR'R')$_r$R$^{6d}$, (CR'R')$_r$NR$^{6a}$C(O)NR$^{6a}$(CR'R')$_r$R$^{6d}$, (CR'R')$_r$NR$^{6a}$C(S)NR$^{6a}$(CR'R')$_r$R$^{6d}$, (CR'R')$_r$NR$^{6f}$C(O)O(CR'R')$_r$R$^{6b}$, (CR'R')$_r$C(=NR$^{6f}$)NR$^{6a}$R$^{6a}$, (CR'R')$_r$NHC(=NR$^{6f}$)NR$^{6f}$R$^{6f}$, (CR'R')$_r$S(O)$_p$(CR'R')$_r$R$^{6b}$, (CR'R')$_r$S(O)$_2$NR$^{6a}$R$^{6a}$, (CR'R')$_r$NR$^{6f}$S(O)$_2$NR$^{6a}$R$^{6a}$, (CR'R')$_r$NR$^{6f}$S(O)$_2$(CR'R')$_r$R$^{6b}$, C$_{1-6}$ haloalkyl, C$_{2-8}$ alkenyl substituted with 0–3 R', C$_{2-8}$ alkynyl substituted with 0–3 R', (CR'R')$_r$phenyl substituted with 0–3 R$^{6e}$, and a (CH$_2$)$_r$-5–6 membered heterocyclic system containing 1–2 heteroatoms selected from N, O, and S, substituted with 0–2 R$^{6e}$;

alternatively, two R$^6$ on adjacent atoms on R$^1$ may join to form a cyclic acetal;

R$^{6a}$, at each occurrence, is selected from H, methyl substituted with 0–1 R$^{6g}$, C$_{2-6}$ alkyl substituted with 0–2 R$^{6e}$, C$_{3-8}$ alkenyl substituted with 0–2 R$^{6e}$, C$_{3-8}$ alkynyl substituted with 0–2 R$^{6e}$, a (CH$_2$)$_r$—C$_{3-10}$ carbocyclic residue substituted with 0–5 R$^{6e}$, and a (CH$_2$)$_r$-5–10 membered heterocyclic system containing 1–4 heteroatoms selected from N, O, and S, substituted with 0–2 R$^{6e}$;

R$^{6b}$, at each occurrence, is selected from H, C$_{1-6}$ alkyl substituted with 0–2 R$^{6e}$, C$_{3-8}$ alkenyl substituted with 0–2 R$^{6e}$, C$_{3-8}$ alkynyl substituted with 0–2 R$^{6e}$, a (CH$_2$)$_r$C$_{3-6}$ carbocyclic residue substituted with 0–3 R$^{6e}$, and a (CH$_2$)$_r$-5–6 membered heterocyclic system containing 1–4 heteroatoms selected from N, O, and S, substituted with 0–2 R$^{6e}$;

R$^{6d}$, at each occurrence, is selected from C$_{3-8}$ alkenyl substituted with 0–2 R$^{6e}$, C$_{3-8}$ alkynyl substituted with 0–2 R$^{6e}$, methyl, CF$_3$, C$_{2-6}$ alkyl substituted with 0–3 R$^{6e}$, C$_{2-4}$ haloalkyl, a (CH$_2$)$_r$—C$_{3-10}$ carbocyclic residue substituted with 0–3 R$^{6e}$, and a (CH$_2$)$_r$-5–6 membered heterocyclic system containing 1–4 heteroatoms selected from N, O, and S, substituted with 0–3 R$^{6e}$;

R$^{6e}$, at each occurrence, is selected from C$_{1-6}$ alkyl, C$_{2-8}$ alkenyl, C$_{2-8}$ alkynyl, (CH$_2$)$_r$C$_{3-6}$ cycloalkyl, Cl, F, Br, I, CN, NO$_2$, (CF$_2$)$_r$CF$_3$, (CH$_2$)$_r$OC$_{1-5}$ alkyl, OH, SH, (CH$_2$)$_r$SC$_{1-5}$ alkyl, (CH$_2$)$_r$NR$^{6f}$R$^{6f}$, and (CH$_2$)$_r$phenyl;

R$^{6f}$, at each occurrence, is selected from H, C$_{1-5}$ alkyl, and C$_{3-6}$ cycloalkyl, and phenyl;

R$^{6g}$ is independently selected from —C(O)R$^{6b}$, —C(O)OR$^{6d}$, —C(O)NR$^{6f}$R$^{6f}$, and (CH$_2$)$_r$phenyl;

R$^7$, at each occurrence, is selected from C$_{1-8}$ alkyl, C$_{2-8}$ alkenyl, C$_{2-8}$ alkynyl, (CH$_2$)$_r$C$_{3-6}$ cycloalkyl, Cl, Br, I, F, NO$_2$, CN, (CR'R')$_r$NR$^{7a}$R$^{7a}$, (CR'R')$_r$OH, (CR'R')$_r$O(CR'R')$_r$R$^{7d}$, (CR'R')$_r$SH, (CR'R')$_r$C(O)H, (CR'R')$_r$S(CR'R')$_r$R$^{7d}$, (CR'R')$_r$C(O)OH, (CR'R')$_r$C(O)(CR'R')$_r$R$^{7b}$, (CR'R')$_r$C(O)NR$^{7a}$R$^{7a}$, (CR'R')$_r$NR$^{7f}$C(O)(CR'R')$_r$R$^{7b}$, (CR'R')$_r$C(O)O(CR'R')$_r$R$^{7d}$, (CR'R')$_r$OC(O)(CR'R')$_r$R$^{7b}$, (CR'R')$_r$OC(O)NR$^{7a}$(CR'R')$_r$R$^{7a}$, (CR'R')$_r$NR$^{7a}$C(O)NR$^{7a}$(CR'R')$_r$R$^{7a}$, (CR'R')$_r$NR$^{7f}$C(O)O(CR'R')$_r$R$^{7d}$, (CR'R')$_r$C(=NR$^{7f}$)NR$^{7a}$R$^{7a}$, (CR'R')$_r$NHC(=NR$^{7f}$)NR$^{7f}$R$^{7f}$, (CR'R')$_r$S(O)$_p$(CR'R')$_r$R$^{7b}$, (CR'R')$_r$S(O)$_2$NR$^{7a}$R$^{7a}$, (CR'R')$_r$NR$^{7a}$S(O)$_2$NR$^{7a}$R$^{7a}$, (CR'R')$_r$NR$^{7f}$S(O)$_2$(CR'R')$_r$R$^{7b}$, C$_{1-6}$ haloalkyl, C$_{2-8}$ alkenyl substituted with 0–3 R', C$_{2-8}$ alkynyl substituted with 0–3 R', (CR'R')$_r$C$_{3-10}$ carbocyclic residue and (CR'R')$_r$phenyl substituted with 0–3 R$^{7e}$;

alternatively, two R$^7$ on adjacent atoms on R$^2$ may join to form a cyclic acetal;

R$^{7a}$, at each occurrence, is independently selected from H, methyl substituted with 0–1 R$^{7g}$, C$_{2-6}$ alkyl substituted with 0–2 R$^{7e}$, C$_{3-8}$ alkenyl substituted with 0–2 R$^{7e}$, C$_{3-8}$ alkynyl substituted with 0–2 R$^{7e}$, a (CH$_2$)$_r$—C$_{3-10}$ carbocyclic residue substituted with 0–5 R$^{7e}$, and a (CH$_2$)$_r$-5–10 membered heterocyclic system containing 1–4 heteroatoms selected from N, O, and S, substituted with 0–2 R$^{7e}$;

R$^{7b}$, at each occurrence, is selected from C$_{1-6}$ alkyl substituted with 0–2 R$^{7e}$, C$_{3-8}$ alkenyl substituted with 0–2 R$^{7e}$, C$_{3-8}$ alkynyl substituted with 0–2 R$^{7e}$, a (CH$_2$)$_r$C$_{3-6}$ carbocyclic residue substituted with 0–3 R$^{7e}$, and a (CH$_2$)$_r$-5–6 membered heterocyclic system containing 1–4 heteroatoms selected from N, O, and S, substituted with 0–2 R$^{7e}$;

R$^{7d}$, at each occurrence, is selected from C$_{3-8}$ alkenyl substituted with 0–2 R$^{7e}$, C$_{3-8}$ alkynyl substituted with 0–2 R$^{7e}$, methyl, CF$_3$, C$_{2-4}$ haloalkyl, C$_{2-6}$ alkyl substituted with 0–3 R$^{7e}$, a (CH$_2$)$_r$—C$_{3-10}$ carbocyclic residue substituted with 0–3 R$^{7e}$, and a (CH$_2$)$_r$-5–6 membered heterocyclic system containing 1–4 heteroatoms selected from N, O, and S, substituted with 0–3 $R^{7e}$;

$R^{7e}$, at each occurrence, is selected from $C_{1-6}$ alkyl, $C_{2-8}$ alkenyl, $C_{2-8}$ alkynyl, $(CH_2)_rC_{3-6}$ cycloalkyl, Cl, F, Br, I, CN, $NO_2$, $(CF_2)_rCF_3$, $(CH_2)_rOC_{1-5}$ alkyl, OH, SH, C(O)$OC_{1-5}$ alkyl, $(CH_2)_rSC_{1-5}$ alkyl, $(CH_2)_rNR^{7f}R^{7f}$, and $(CH_2)_r$phenyl;

$R^{7f}$, at each occurrence, is selected from H, $C_{1-5}$ alkyl, and $C_{3-6}$ cycloalkyl, and phenyl;

$R^{7g}$ is independently selected from —C(O)$R^{7b}$, —C(O)$OR^{7d}$, —C(O)$NR^{7f}R^{7f}$, and $(CH_2)_r$phenyl;

R', at each occurrence, is selected from H, $C_{1-6}$ alkyl substituted with $R^{6e}$, $C_{2-8}$ alkenyl, $C_{2-8}$ alkynyl, $(CH_2)_rC_{3-6}$ cycloalkyl, and $(CH_2)_r$phenyl substituted with $R^{6e}$;

$R^8$ is selected from H, $C_{1-4}$ alkyl, and $C_{3-4}$ cycloalkyl;

$R^9$ is selected from H, $C_{1-4}$ alkyl, $C_{3-4}$ cycloalkyl, —C(O)H, and —C(O)—$C_{1-4}$alkyl;

$R^{10}$ is independently selected from H, and $C_{1-4}$alkyl substituted with 0–1 $R^{10b}$, alternatively, two $R^{10}$ form =O;

$R^{10b}$, at each occurrence, is independently selected from —OH, —SH, —$NR^{10c}R^{10c}$, —C(O)$NR^{10c}R^{10c}$, and —NHC(O)$R^{10c}$;

$R^{10c}$ is selected from H, $C_{1-4}$ alkyl and $C_{3-6}$ cycloalkyl;

$R^{14}$, at each occurrence, is independently selected from H and $C_{1-4}$alkyl;

alternatively, two $R^{14}$s, along with the carbon atom to which they are attached, join to form a $C_{3-6}$ carbocyclic ring;

$R^{15}$, at each occurrence, is independently selected from H, $C_{1-4}$alkyl, OH, $NH_2$, —O—$C_{1-4}$ alkyl, $NR^{15a}R^{15a}$, C(O)$NR^{15a}R^{15a}$, $NR^{15a}C(O)R^{15b}$, $NR^{15a}C(O)OR^{15d}$, OC(O)$NR^{15a}R^{15a}$, and $(CHR)_rC(O)OR^{15d}$;

alternatively, two $R^{15}$s, along with the carbon atom or atoms to which they are attached, join to form a $C_{3-6}$ carbocyclic ring;

$R^{15a}$, at each occurrence, is independently selected from H, and $C_{1-4}$ alkyl;

$R^{15b}$, at each occurrence, is independently selected from $C_{1-4}$ alkyl, $C_{3-6}$ alkenyl, and $C_{3-6}$ alkynyl;

$R^{15d}$, at each occurrence, is independently selected from $C_{1-4}$ alkyl, $C_{3-6}$ alkenyl, and $C_{3-6}$ alkynyl;

$R^{16}$ is selected from $C_{1-4}$ alkyl;

l is selected from 1, 2 and 3;

n is selected from 0, 1, 2, and 3;

p, at each occurrence, is independently selected from 0, 1, and 2;

q, at each occurrence, is independently selected from 1, 2, 3, and 4;

r, at each occurrence, is independently selected from 0, 1, 2, 3, and 4;

s is selected from 0 and 1; and t, at each occurrence, is independently selected from 2, 3, and 4;

the steps comprising reacting a compound of Formula IV,

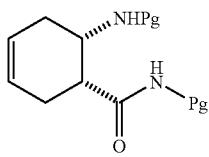

with an electrophile and base to give a compound of Formula II;

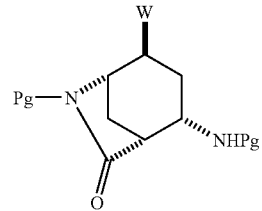

wherein

W is selected from H, I, and Br;

Pg, at each occurrence, is independently selected from an amine protecting group;

reacting a compound of Formula II to give the compound of Formula (Ia).

In another embodiment, the present invention is directed to a process of preparing a compound of Formula (II), wherein

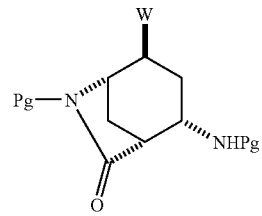

or salt or stereoisomer thereof, comprising reacting a compound of Formula (IV)

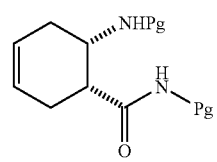

with an electrophile and a base, wherein

W is selected from I and Br;

Pg, at each occurrence, is independently selected from an amine protecting group.

In another embodiment, the present invention is directed to a process of preparing a compound of Formula (II), wherein the electrophile is selected from iodine, bromine, N-bromosuccimide, and N-iodosuccinimide; and the base is selected from n-butyl lithium, lithium diisopropylamide (LDA), sodium hydride, lithium bis(trimethylsilyl)amide, potassium bis(trimethylsilyl)amide, sodium bis(trimethylsilyl)-amide, and Li—Al(O-tButyl)$_4$.

In another embodiment, the present invention is directed to a process of preparing a compound of Formula (IIa), wherein

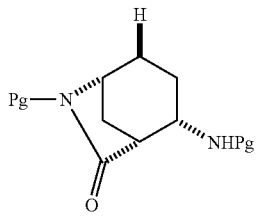

(IIa)

comprising reduction of a compound of Formula (II) with a reducing agent;

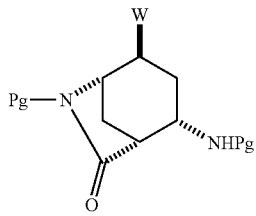

(II)

wherein W is selected from I and Br, and

Pg, at each occurrence, is independently selected from an amine protecting group.

In another embodiment, the present invention is directed to a process of preparing a compound of Formula (IIa), wherein the reducing agent is selected from tris-(trimethylsilyl)silane, zinc metal, tributyltin hydride and AIBN.

The invention may be embodied in other specific forms without departing from the spirit or essential attributes thereof. This invention also encompasses all combinations of alternative aspects of the invention noted herein. It is understood that any and all embodiments of the present invention may be taken in conjunction with any other embodiment to describe additional embodiments of the present invention. Furthermore, any elements of an embodiment are meant to be combined with any and all other elements from any of the embodiments to describe additional embodiments.

DEFINITIONS

The compounds herein described may have asymmetric centers. Compounds of the present invention containing an asymmetrically substituted atom may be isolated in optically active or racemic forms. It is well known in the art how to prepare optically active forms, such as by resolution of racemic forms or by synthesis from optically active starting materials. Many geometric isomers of olefins, C=N double bonds, and the like can also be present in the compounds described herein, and all such stable isomers are contemplated in the present invention. Cis and trans geometric isomers of the compounds of the present invention are described and may be isolated as a mixture of isomers or as separated isomeric forms. All chiral, diastereomeric, racemic forms and all geometric isomeric forms of a structure are intended, unless the specific stereochemistry or isomeric form is specifically indicated.

The processes of the present invention are contemplated to be practiced on at least a multigram scale, kilogram scale, multikilogram scale, or industrial scale. Multigram scale, as used herein, is preferably the scale wherein at least one starting material is present in 10 grams or more, more preferably at least 50 grams or more, even more preferably at least 100 grams or more. Multikilogram scale, as used herein, is intended to mean the scale wherein more than one kilogram of at least one starting material is used. Industrial scale as used herein is intended to mean a scale which is other than a laboratory scale and which is sufficient to supply product sufficient for either clinical tests or distribution to consumers.

Suitable ether solvents include, but are not intended to be limited to, dimethoxymethane, tetrahydrofuran, 1,3-dioxane, 1,4-dioxane, furan, diethyl ether, ethylene glycol dimethyl ether, ethylene glycol diethyl ether, diethylene glycol dimethyl ether, diethylene glycol diethyl ether, triethylene glycol dimethyl ether, or t-butyl methyl ether. Suitable hydrocarbon solvents include, but are not intended to be limited to, benzene, cyclohexane, pentane, hexane, toluene, cycloheptane, methylcyclohexane, heptane, ethylbenzene, m-, o-, or p-xylene, octane, indane, nonane, or naphthalene.

As used herein, the term "amine protecting group" (or "N-protected") refers to any group known in the art of organic synthesis for the protection of amine groups. As used herein, the term "amine protecting group reagent" refers to any reagent known in the art of organic synthesis for the protection of amine groups which may be reacted with an amine to provide an amine protected with an amine protecting group. The "amine protecting group" should be compatible with other reaction conditions. Such amine protecting groups include those listed in Greene and Wuts, "Protective Groups in Organic Synthesis" John Wiley & Sons, New York (1991) and "The Peptides: Analysis, Synthesis, Biology, Vol. 3, Academic Press, New York (1981), the disclosure of which is hereby incorporated by reference. Examples of amine protecting groups include, but are not limited to, the following: 1) acyl types such as formyl, trifluoroacetyl, and p-toluenesulfonyl; 2) aromatic carbamate types such as benzyloxycarbonyl (Cbz) and substituted benzyloxycarbonyls, 1-(p-biphenyl)-1-methylethoxycarbonyl, and 9-fluorenylmethyloxycarbonyl (Fmoc); 3) aliphatic carbamate types such as tert-butyloxycarbonyl (Boc), ethoxycarbonyl, diisopropylmethoxycarbonyl, and allyloxycarbonyl; and 4) cyclic alkyl carbamate types such as cyclopentyloxycarbonyl and adamantyloxycarbonyl.

Amine protecting groups may include, but are not limited to the following: 2,7-di-t-butyl-[9-(10,10-dioxo-10,10,10,10-tetrahydrothio-xanthyl)]methyloxycarbonyl; 2-trimethylsilylethyloxycarbonyl; 2-phenylethyloxycarbonyl; 1,1-dimethyl-2,2-dibromoethyloxycarbonyl; 1-methyl-1-(4-biphenylyl)ethyloxycarbonyl; benzyloxycarbonyl; p-nitrobenzyloxycarbonyl; 2-(p-toluenesulfonyl)ethyloxycarbonyl; m-chloro-p-acyloxybenzyloxycarbonyl; 5-benzyisoxazolylmethyloxycarbonyl; p-(dihydroxyboryl)benzyloxycarbonyl; m-nitrophenyloxycarbonyl; o-nitrobenzyloxycarbonyl; 3,5-dimethoxybenzyloxycarbonyl; 3,4-dimethoxy-6-nitrobenzyloxycarbonyl; N'-p-toluenesulfonylaminocarbonyl; t-amyloxycarbonyl; p-decyloxybenzyloxycarbonyl; diisopropylmethyloxycarbonyl; 2,2-dimethoxycarbonylvinyloxycarbonyl; di(2-pyridyl)methyloxycarbonyl; or 2-furanylmethyloxycarbonyl.

A suitable selective reducing agent is a reagent or combination of reagents which will selectively reduce the W group in the compound of Formula (II) to a hydrogen without altering the character of the other substitutents. Suitable selective reducing agents include, but are not limited to, tris-(trimethylsilyl)silane, zinc metal, tributyltin hydride and catalytic versions, see Gregory Fu, Org. Syn. (2002), 78, 239–248 which is hereby incorporated by reference, and AIBN (2,2'-Azobisisobutyronitrile).

One enantiomer of a compound of Formula I may display superior activity compared with the other. Thus, all of the stereochemistries are considered to be a part of the present invention. When required, separation of the racemic material can be achieved by HPLC using a chiral column or by a resolution using a resolving agent such as camphonic chloride as in Steven D. Young, et al, *Antimicrobial Agents and Chemotheraphy*, 1995, 2602–2605.

The term "substituted," as used herein, means that any one or more hydrogens on the designated atom or ring is replaced with a selection from the indicated group, provided that the designated atom's or ring atom's normal valency is not exceeded, and that the substitution results in a stable compound. When a substituent is keto (i.e., =O), then 2 hydrogens on the atom are replaced.

When any variable (e.g., $R^{10}$) occurs more than one time in any constituent or formula for a compound, its definition at each occurrence is independent of its definition at every other occurrence. Thus, for example, if a group is shown to be substituted with 0–2 $R^{10}$, then said group may optionally be substituted with up to two $R^{10}$ groups and $R^{10}$ at each occurrence is selected independently from the definition of $R^{10}$. Also, combinations of substituents and/or variables are permissible only if such combinations result in stable compounds.

When a bond to a substituent is shown to cross a bond connecting two atoms in a ring, then such substituent may be bonded to any atom on the ring. When a substituent is listed without indicating the atom via which such substituent is bonded to the rest of the compound of a given formula, then such substituent may be bonded via any atom in such substituent. Combinations of substituents and/or variables are permissible only if such combinations result in stable compounds.

As used herein, "$C_{1-8}$ alkyl" is intended to include both branched and straight-chain saturated aliphatic hydrocarbon groups having the specified number of carbon atoms, examples of which include, but are not limited to, methyl, ethyl, n-propyl, i-propyl, n-butyl, i-butyl, sec-butyl, t-butyl, pentyl, and hexyl. $C_{1-8}$ alkyl, is intended to include $C_1$, $C_2$, $C_3$, $C_4$, $C_5$, $C_6$, $C_7$, and $C_8$ alkyl groups. "Alkenyl" is intended to include hydrocarbon chains of either a straight or branched configuration and one or more unsaturated carbon-carbon bonds which may occur in any stable point along the chain, such as ethenyl, propenyl, and the like. "Alkynyl" is intended to include hydrocarbon chains of either a straight or branched configuration and one or more unsaturated triple carbon-carbon bonds which may occur in any stable point along the chain, such as ethynyl, propynyl, and the like. "$C_{3-6}$ cycloalkyl" is intended to include saturated ring groups having the specified number of carbon atoms in the ring, including mono-, bi-, or poly-cyclic ring systems, such as cyclopropyl, cyclobutyl, cyclopentyl, cyclohexyl, and cycloheptyl in the case of $C_7$ cycloalkyl. $C_{3-6}$ cycloalkyl, is intended to include $C_3$, $C_4$, $C_5$, and $C_6$ cycloalkyl groups.

"Halo" or "halogen" as used herein refers to fluoro, chloro, bromo, and iodo; and "haloalkyl" is intended to include both branched and straight-chain saturated aliphatic hydrocarbon groups, for example $CF_3$, having the specified number of carbon atoms, substituted with 1 or more halogen (for example —$C_vF_w$ where v=1 to 3 and w=1 to (2v+1)).

As used herein, the term "5–6-membered cyclic ketal" is intended to mean 2,2-disubstituted 1,3-dioxolane or 2,2-disubstituted 1,3-dioxane and their derivatives.

As used herein, "carbocycle" or "carbocyclic residue" is intended to mean any stable 3, 4, 5, 6, or 7-membered monocyclic or bicyclic or 7, 8, 9, 10, 11, 12, or 13-membered bicyclic or tricyclic, any of which may be saturated, partially unsaturated, or aromatic. Examples of such carbocycles include, but are not limited to, cyclopropyl, cyclobutyl, cyclopentyl, cyclohexyl, cycloheptyl, adamantyl, cyclooctyl, [3.3.0]bicyclooctane, [4.3.0]bicyclononane, [4.4.0]bicyclodecane (decalin), [2.2.2]bicyclooctane, fluorenyl, phenyl, naphthyl, indanyl, adamantyl, or tetrahydronaphthyl (tetralin).

As used herein, the term "heterocycle" or "heterocyclic system" is intended to mean a stable 5, 6, or 7-membered monocyclic or bicyclic or 7, 8, 9, or 10-membered bicyclic heterocyclic ring which is saturated, partially unsaturated or unsaturated (aromatic), and which consists of carbon atoms and 1, 2, 3, or 4 heteroatoms independently selected from the group consisting of N, NH, O and S and including any bicyclic group in which any of the above-defined heterocyclic rings is fused to a benzene ring. The nitrogen and sulfur heteroatoms may optionally be oxidized. The heterocyclic ring may be attached to its pendant group at any heteroatom or carbon atom which results in a stable structure. The heterocyclic rings described herein may be substituted on carbon or on a nitrogen atom if the resulting compound is stable. If specifically noted, a nitrogen in the heterocycle may optionally be quaternized. It is preferred that when the total number of S and O atoms in the heterocycle exceeds 1, then these heteroatoms are not adjacent to one another. As used herein, the term "aromatic heterocyclic system" or "heteroaryl" is intended to mean a stable 5- to 7-membered monocyclic or bicyclic or 7- to 10-membered bicyclic heterocyclic aromatic ring which consists of carbon atoms and from 1 to 4 heterotams independently selected from the group consisting of N, O and S and is aromatic in nature.

Examples of heterocycles include, but are not limited to, 1H-indazole, 2-pyrrolidonyl, 2H,6H-1,5,2-dithiazinyl, 2H-pyrrolyl, 1H-indolyl, 4-piperidonyl, 4aH-carbazole, 4H-quinolizinyl, 6H-1,2,5-thiadiazinyl, acridinyl, azocinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, benzimidazalonyl, carbazolyl, 4aH-carbazolyl, β-carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, indazolyl, indolenyl, indolinyl, indolizinyl, indolyl, isobenzofuranyl, isochromanyl, isoindazolyl, isoindolinyl, isoindolyl, isoquinolinyl (benzimidazolyl), isothiazolyl, isoxazolyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolidinylperimidinyl, phenanthridinyl, phenanthrolinyl, phenarsazinyl, phenazinyl, phenothiazinyl, phenoxathiinyl, phenoxazinyl, phthalazinyl, piperazinyl, piperidinyl, pteridinyl, piperidonyl, 4-piperidonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, pyrrolyl, quinazolinyl, quinolinyl, 4H-quinolizinyl, quinoxalinyl, quinuclidinyl, carbolinyl, tetrahydrofuranyl, tetrahydroisoquinolinyl, tetrahydroquinolinyl, 6H-1,2, 5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, tetrazolyl, and xanthenyl. In another aspect of the invention, the heterocycles include, but are not limited to, pyridinyl, thiophenyl, furanyl, indazolyl, benzothiazolyl, benzimidazolyl, benzothiaphenyl, benzofuranyl, benzoxazolyl, benzisoxazolyl, quinolinyl, isoquinolinyl, imidazolyl, indolyl, isoidolyl, piperidinyl, piperidonyl, 4-piperidonyl, piperonyl, pyrrazolyl, 1,2,4-triazolyl, 1,2,3-triazolyl, tetrazolyl, thiazolyl, oxazolyl, pyrazinyl, and pyrimidinyl. Also included are fused ring and spiro compounds containing, for example, the above heterocycles.

Examples of heteroaryls are 1H-indazole, 2H,6H-1,5,2-dithiazinyl, indolyl, 4aH-carbazole, 4H-quinolizinyl, 6H-1,2,5-thiadiazinyl, acridinyl, azocinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, benzimidazalonyl, carbazolyl, 4aH-carbazolyl, β-carbolinyl, chromanyl, chromenyl, cinnolinyl, decahydroquinolinyl, 2H,6H-1,5,2-dithiazinyl, dihydrofuro [2,3-b]tetrahydrofuran, furanyl, furazanyl, imidazolidinyl, imidazolinyl, imidazolyl, indazolyl, indolenyl, indolinyl, indolizinyl, indolyl, isobenzofuranyl, isochromanyl, isoindazolyl, isoindolinyl, isoindolyl, isoquinolinyl (benzimidazolyl), isothiazolyl, isoxazolyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolidinylperimidinyl, phenanthridinyl, phenanthrolinyl, phenarsazinyl, phenazinyl, phenothiazinyl, phenoxathiinyl, phenoxazinyl, phthalazinyl, piperazinyl, piperidinyl, pteridinyl, piperidonyl, 4-piperidonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, pyrrolyl, quinazolinyl, quinolinyl, 4H-quinolizinyl, quinoxalinyl, quinuclidinyl, carbolinyl, tetrahydrofuranyl, tetrahydroisoquinolinyl, tetrahydroquinolinyl, 6H-1,2, 5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, tetrazolyl, and xanthenyl. In another aspect of the invention, examples of heteroaryls are indolyl, benzimidazolyl, benzofuranyl, benzothiofuranyl, benzoxazolyl, benzthiazolyl, benztriazolyl, benztetrazolyl, benzisoxazolyl, benzisothiazolyl, benzimidazalonyl, cinnolinyl, furanyl, imidazolyl, indazolyl, indolyl, isoquinolinyl isothiazolyl, isoxazolyl, oxazolyl, pyrazinyl, pyrazolyl, pyridazinyl, pyridyl, pyridinyl, pyrimidinyl, pyrrolyl, quinazolinyl, quinolinyl, thiazolyl, thienyl, and tetrazolyl.

As used herein, the term "cyclic acetal" or the phrase when two variables "join to form a cyclic acetal" is intended to mean the substituent —O—CH$_2$—O—.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences*, 17th ed., Mack Publishing Company, Easton, Pa., 1985, p. 1418, the disclosure of which is hereby incorporated by reference.

Since prodrugs are known to enhance numerous desirable qualities of pharmaceuticals (e.g., solubility, bioavailability, manufacturing, etc . . . ) the compounds of the present invention may be delivered in prodrug form. Thus, the present invention is intended to cover prodrugs of the presently claimed compounds, methods of delivering the same and compositions containing the same. "Prodrugs" are intended to include any covalently bonded carriers which release an active parent drug of the present invention in vivo when such prodrug is administered to a mammalian subject. Prodrugs the present invention are prepared by modifying functional groups present in the compound in such a way that the modifications are cleaved, either in routine manipulation or in vivo, to the parent compound. Prodrugs include compounds of the present invention wherein a hydroxy, amino, or sulfhydryl group is bonded to any group that, when the prodrug of the present invention is administered to a mammalian subject, it cleaves to form a free hydroxyl, free amino, or free sulfhydryl group, respectively. Examples of prodrugs include, but are not limited to, acetate, formate and benzoate derivatives of alcohol and amine functional groups in the compounds of the present invention.

"Stable compound" and "stable structure" are meant to indicate a compound that is sufficiently robust to survive isolation to a useful degree of purity from a reaction mixture, and formulation into an efficacious therapeutic agent. The present invention is intended to embody stable compounds.

"Therapeutically effective amount" is intended to include an amount of a compound of the present invention alone or an amount of the combination of compounds claimed or an amount of a compound of the present invention in combination with other active ingredients effective to inhibit MCP-1 or effective to treat or prevent inflammatory disorders.

As used herein, "treating" or "treatment" cover the treatment of a disease-state in a mammal, particularly in a human, and include: (a) preventing the disease-state from occurring in a mammal, in particular, when such mammal is predisposed to the disease-state but has not yet been diagnosed as having it; (b) inhibiting the disease-state, i.e., arresting it development; and/or (c) relieving the disease-state, i.e., causing regression of the disease state.

SYNTHESIS

The compounds of the present invention can be prepared in a number of ways well known to one skilled in the art of organic synthesis. The compounds of the present invention can be synthesized using the methods described below, together with synthetic methods known in the art of synthetic organic chemistry, or variations thereon as appreciated by those skilled in the art. Preferred methods include, but are not limited to, those described below. All references cited herein are hereby incorporated in their entirety herein by reference.

The novel compounds of this invention may be prepared using the reactions and techniques described in this section. The reactions are performed in solvents appropriate to the reagents and materials employed and are suitable for the transformations being effected. Also, in the description of the synthetic methods described below, it is to be understood that all proposed reaction conditions, including choice of solvent, reaction atmosphere, reaction temperature, duration of the experiment and work up procedures, are chosen to be the conditions standard for that reaction, which should be readily recognized by one skilled in the art. It is understood by one skilled in the art of organic synthesis that the functionality present on various portions of the molecule must be compatible with the reagents and reactions proposed. Such restrictions to the substituents which are compatible with the reaction conditions will be readily apparent to one skilled in the art and alternate methods must then be used. This will sometimes require a judgment to modify the order of the synthetic steps or to select one particular process scheme over another in order to obtain a desired compound of the invention. It will also be recognized that another major consideration in the planning of any synthetic route in this field is the judicious choice of the protecting group used for protection of the reactive functional groups present in the compounds described in this invention. An authoritative account describing the many alternatives to the trained practitioner is Greene and Wuts (*Protective Groups In Organic Synthesis*, Wiley and Sons, 1999).

A series of compounds of formula 4 can be synthesized as shown in Scheme 1. Many cyclic amines 1 are available (Cherney, R. J. PCT 02/060859 and PCT 03/075853; and in U.S. Patent Application No. 60/362,604, filed Mar. 8, 2002, both of which are hereby incorporated by reference) and can be coupled to acid 2. The resulting amide 3 can be cyclized (Freidinger et al., *J. Org. Chem.* 1982, 47, 104) via the activated thioether to the desired lactam 4.

Scheme 1

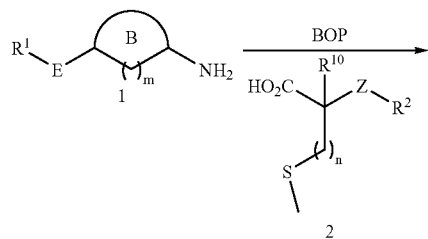

-continued

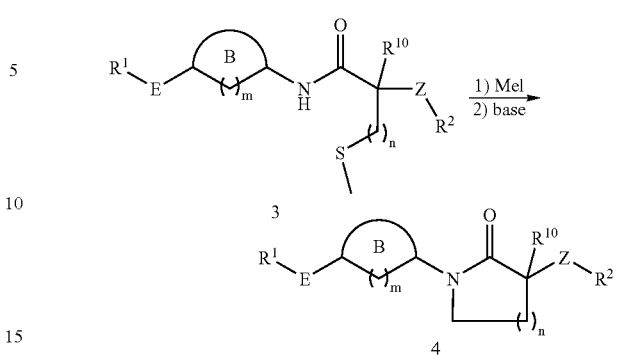

A series of compounds of formula 7 can be synthesized as shown in Scheme 2. The cyclic amine 1 can be coupled to an appropriate carboxylate to afford amide 5. This material can be cyclized under Mitsunobu conditions to afford β-lactam 6 (Townsend et al., *J. Amer. Chem. Soc.* 1990, 112, 760). The protecting group can be removed and an appropriate group can be installed (through coupling or another methodology) to deliver the desired target 7.

Scheme 2

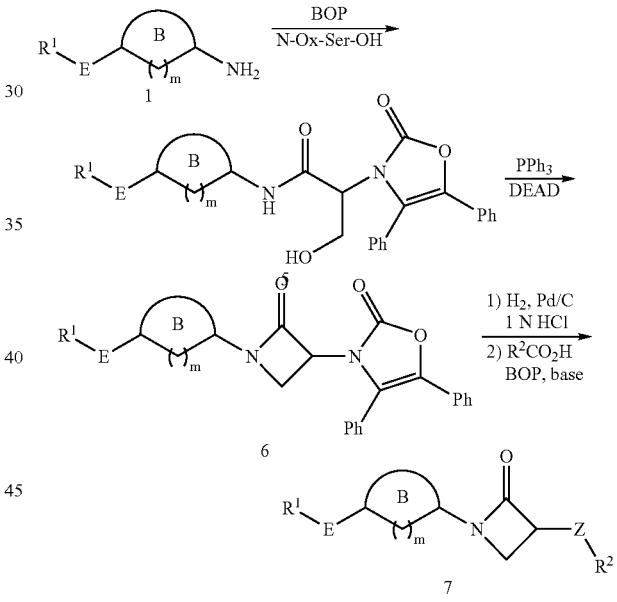

A series of compounds of formula 10 can be synthesized by the methods shown in Scheme 3. Amine 1 can be coupled to an appropriate carboxylate 8. The resulting amide 9 can be cyclized via the aldehyde to afford the target 10.

Scheme 3

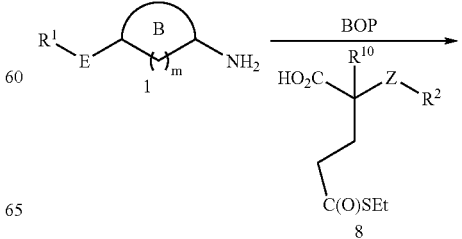

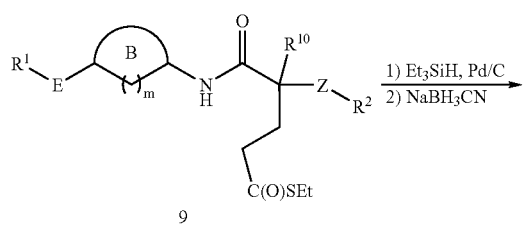

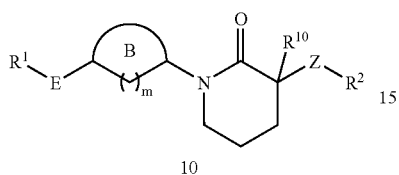

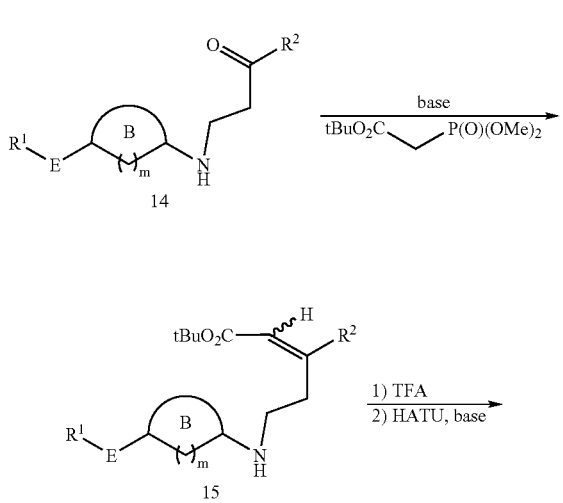

A series of compounds of formula 4 can also be synthesized as shown in Scheme 4. Amine 1 can be converted into 12 via a reductive amination. The secondary amine 12 can be cyclized under a variety of conditions to give the target 4.

Scheme 4

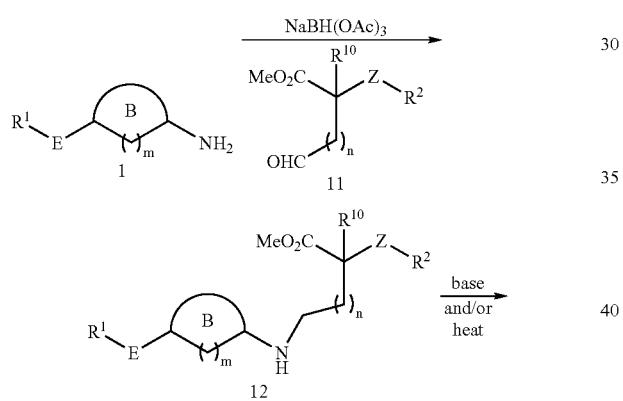

A series of compounds of formula 16 can be synthesized as shown in Scheme 5. Amine 1 can be converted into 14 via a Michael reaction. Treatment of 14 with a phosphonate and base affords 15. This material can be cyclized through the carboxylate to give 16.

Scheme 5

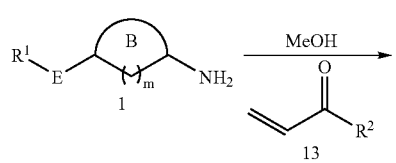

A series of compounds of formula 21 can be synthesized as shown in Scheme 6. The appropriate thioester 17 can be converted into the aldehyde 18. Reductive amination of 1 with 18 gives the secondary amine 19. This material can be cyclized through the carboxylate to give 20. The protecting group can be removed and an appropriate $R^2$ group can be coupled to afford target 21.

Scheme 6

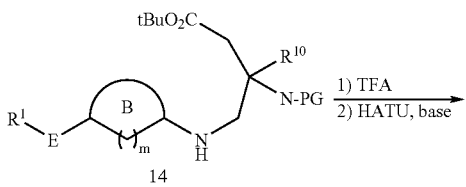

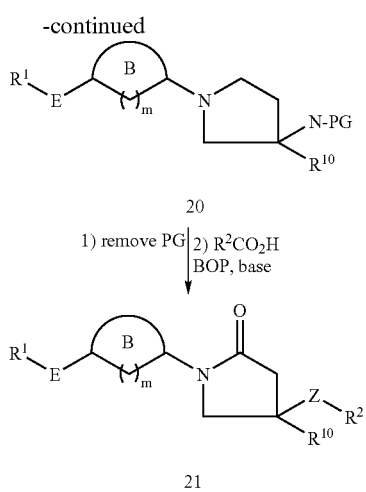

The synthesis of R²=pyrimido[5,4-d]pyrimidin-4-ol is shown in Scheme 7.

Intermediates such as 27 can be saponified and coupled to 20 where PG=H₂. The bromine can also be removed via hydrogenation, or used in Suzuki-type couplings for further elaboration. The conversion of 27 to 28 is performed by the method of Buchwald and Yin, *J. Am. Chem. Soc.*, (124), 6043, 2002.

The synthesis of R²=quinazolines and their analogs wherein the benzene moiety can also be replaced by a heterocycle are made by the procedures illustrated in Schemes 8 and 8a. Note that for clarity, benzoic acids and derivatives were drawn. However, it is to be understood that the benzene ring can be replaced with heterocycles. R¹ in Schemes 8 and 8a represents everything to the left of Z in formula (I) where Z=NH. R² and R³ are the usual substituents found on amines such as H, alkyl, etc., familiar to one skilled in the art and within the scope of $R^{7a}$ in this application.

Substituted anthranilic acids in Scheme 8 can be synthesized from BOC-protected anilines via ortho-directed metallation followed by quenching with CO₂. Bromo or iodo substituted quinazolines in Schemes 8 and 8a can undergo Suzuki-type couplings for further elaboration.

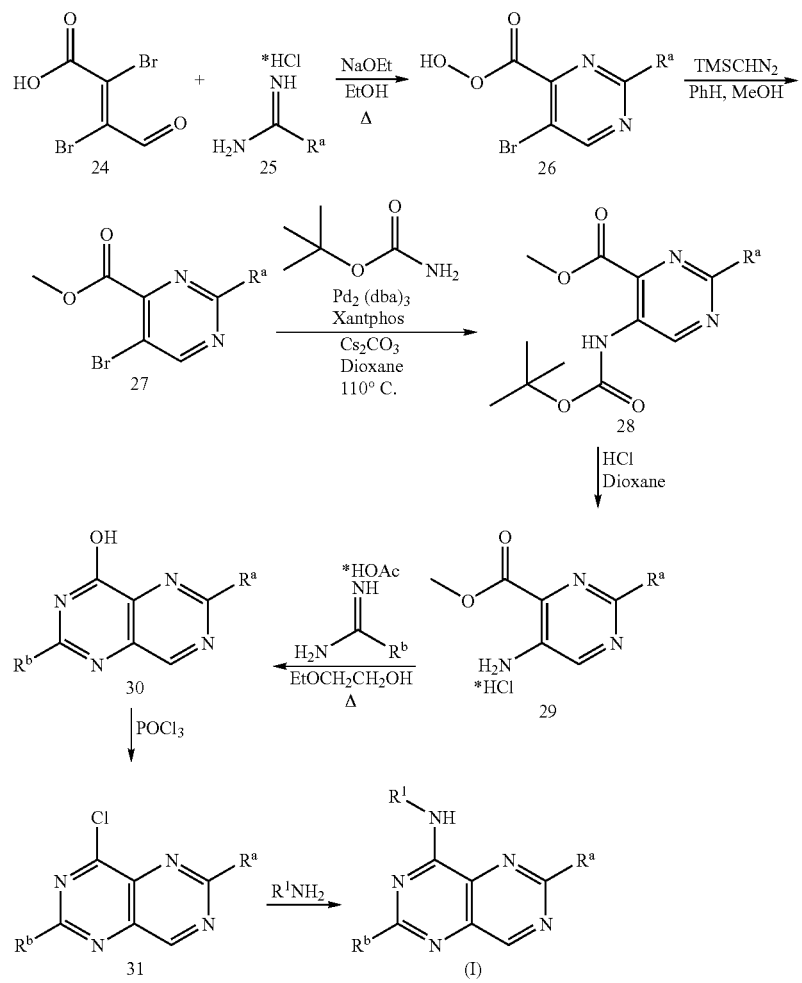

Scheme 8
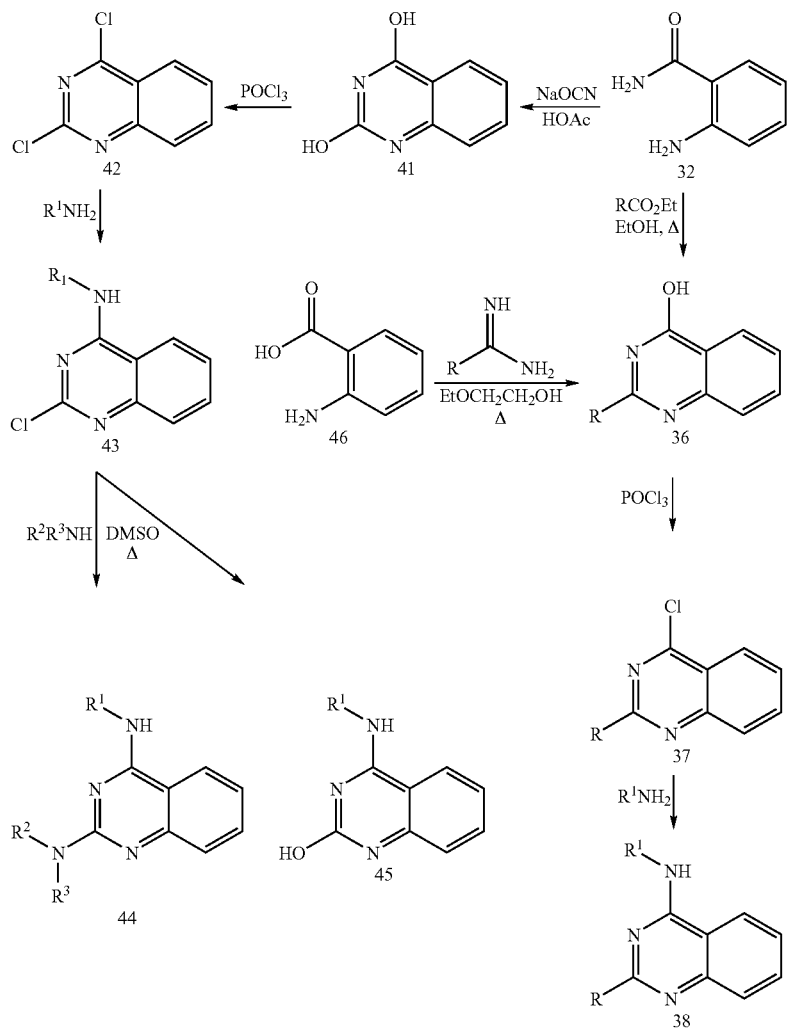
Scheme 8a
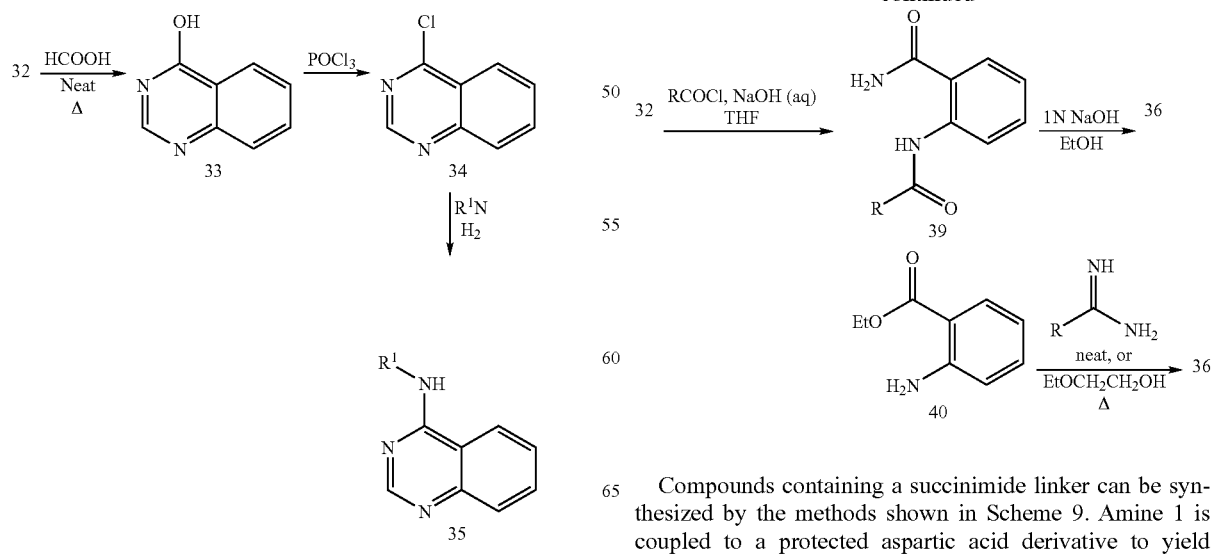
Compounds containing a succinimide linker can be synthesized by the methods shown in Scheme 9. Amine 1 is coupled to a protected aspartic acid derivative to yield succinimide 47 which can be deprotected and coupled to a carboxylic acid by the usual means familiar to one skilled in the art to yield the compounds of this invention, 48.

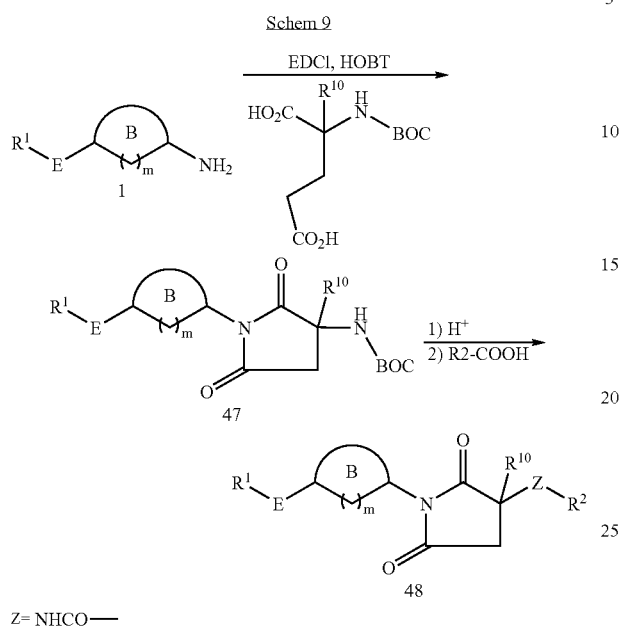

Z= NHCO—

Many core rings 1 have been described (see Cherney PTC WO/03075853 and others above). Others can be synthesized from anhydride openings or the corresponding amino esters (52) or acid esters (51) as shown in Scheme 10. As described (see Bolm et al. *J. Org. Chem.* 2000, 65, 6984), anhydride 50 can be opened to the acid ester 51. A Curtius reaction, or another rearrangement, on the carboxylate of 51 can provide the carbamate 52. Hydrolysis of the ester gives the acid 53 which can be converted to the primary amide 54. This primary amide 54 can be converted in one pot to the bicyclic 57 (through the intermediate 55) or transformed in a discrete step to acyl carbamate 55 and cyclized with the use of many different electrophiles and bases (see Taguchi et al. *J. Org. Chem.* 1997, 62, 7330) to give the bicyclic 57. The carboxylate 53 can also undergo cyclizations to the lactone 56. These compounds (56, 57, 58) serve as versatile intermediates because they can be opened in many ways to give substituted rings 59. These substituted rings 59 can then be incorporated into Schemes 1, 2, 3, 4, 5, 6, and 9 acting as compound 1.

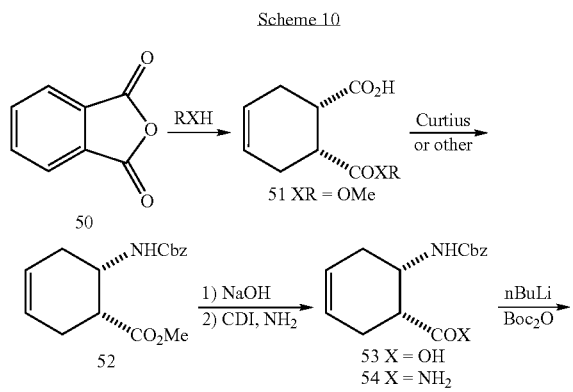

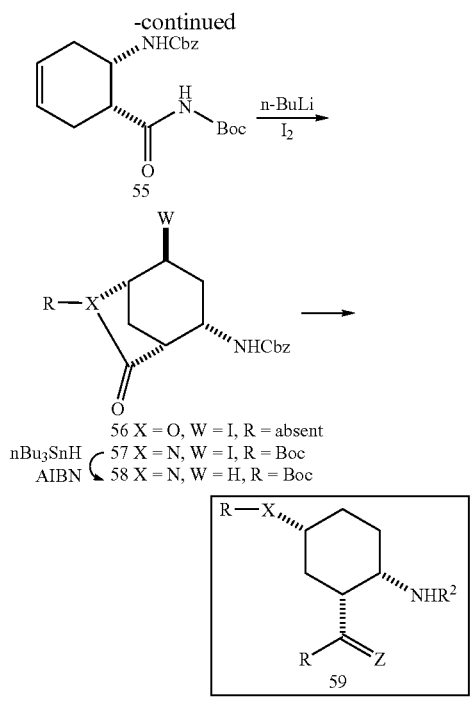

More generally, compounds 55–58 may be prepared as described in Scheme 10a. Compounds of Formula (IV), wherein an amine protecting group is as described above, are converted into compounds of Formula (II) by way of an electrophile and base in a suitable solvent.

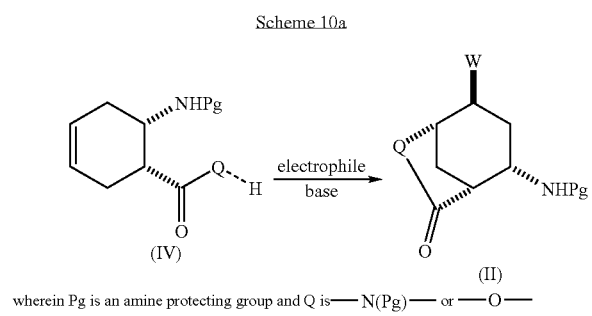

wherein Pg is an amine protecting group and Q is —N(Pg)— or —O—

Suitable solvents for the reaction are generally the ether solvents or non reactive hydrocarbon solvents as described above, or mixtures thereof. In particular, the solvents are selected from THF, toluene, and mixtures thereof. Additional non-reactive solvents such as other aromatic solvents (e.g., benzene, anisole, or quinoline) can also be used.

Suitable electrophiles for the reaction include, but are not limited to, iodine, bromine, N-bromosuccinimide, N-iodosuccinimide, N-(phenylseleno)phthalimide, and benzenesulfenyl chloride. Suitable bases for the reaction include, but are not limited to, alkyl lithium such as n-butyl lithium, lithium diisopropylamide (LDA), sodium hydride, lithium bis(trimethylsilyl)amide, potassium bis(trimethylsilyl) amide, sodium bis(trimethylsilyl)amide, Li—Al(O-tButyl)$_4$.

The reaction may be run at temperatures from about −22° C. to about room temperature and alternatively, from about 0° C. to about room temperature.

The amine protecting group includes all of those defined above and each may be selected independently to allow for differential removal of the protecting groups from the amine.

Scheme 11 shows how compounds like 59 can be converted into the final compounds of interest. A compound like 58 can be reductively opened to compound 59 (RX=BocHN, R'=HO, Z=H$_2$, R$^2$=Cbz). Treatment of 59 with Mitsunobu-like conditions (ArSSAr and nBu$_3$P, wherein Ar may be any of the substituents described by R$^1$ in the claims) or substitution conditions yields compound 60. This can be oxidized a number of ways to give the sulfone 61. Removal of the benzyl carbamate gives the primary amine 62. This can be incorporated into one of the Schemes 1–6 to afford 63. The Boc carbamate can then be removed, and the primary amine can be substituted in a variety of ways to the desired final compound 64.

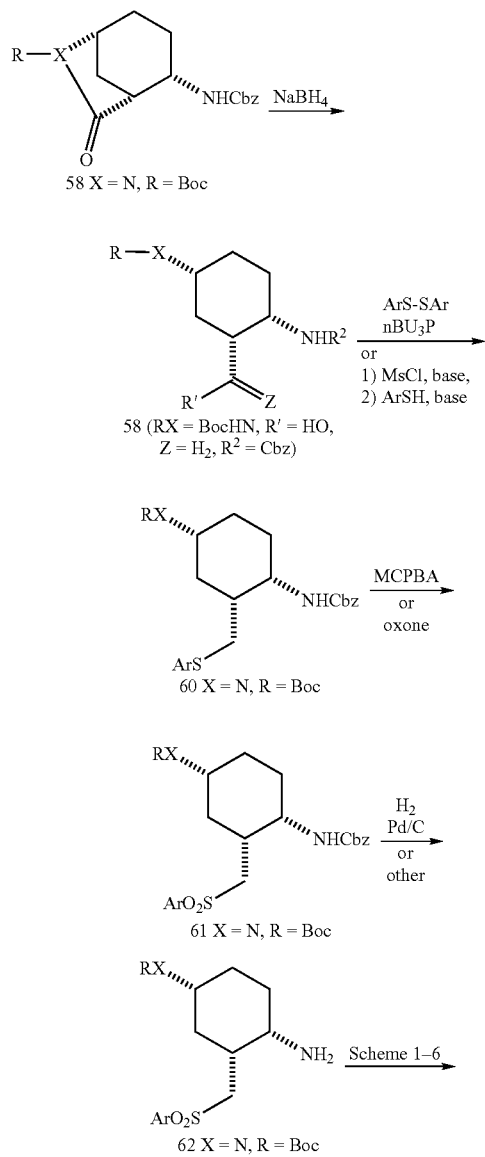

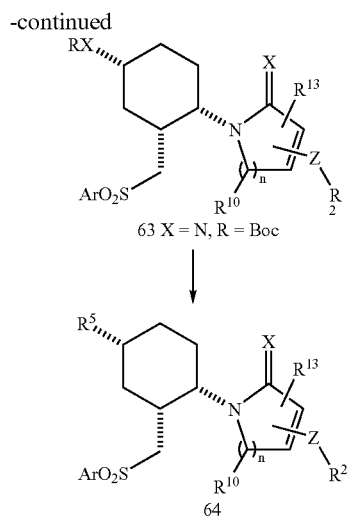

In a similar way, Scheme 12 shows how a compound like 58 can be converted into a final compound of interest by changing the order of Scheme 11. The benzyl carbamate of 58 can be removed to give the primary amine 65. This can be incorporated into one of the Schemes 1–6 to afford 66. The reductive opening of 66 gives 67. Treatment of 67 with Mitsunobu-like conditions (ArSSAr and nBu$_3$P) or substitution conditions yields compound 68, which can be oxidized to the same compound 63 as above.

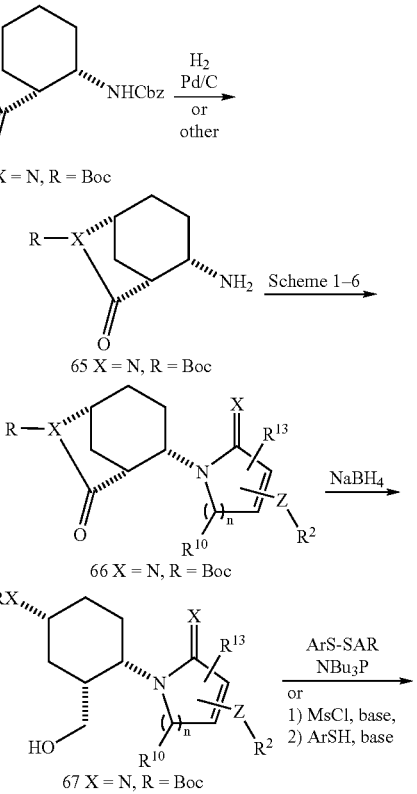

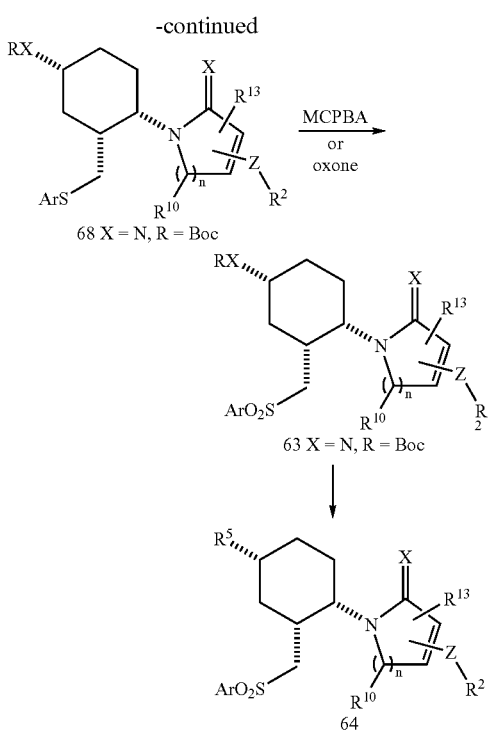

68 X = N, R = Boc

63 X = N, R = Boc

64

The variables described in the schemes may be the same or different than those described in the claims. They are not meant to limit the claims.

When required, separation of the racemic material can be achieved by HPLC using a chiral column or by a resolution using a resolving agent such as camphonic chloride as in Steven D. Young, et al, *Antimicrobial Agents and Chemotheraphy*, 1995, 2602–2605.

Other features of the invention will become apparent in the course of the following descriptions of exemplary embodiments which are given for illustration of the invention and are not intended to be limiting thereof.

EXAMPLES

Abbreviations used in the Examples are defined as follows: "1×" for once, "2×" for twice, "3×" for thrice, "° C." for degrees Celsius, "g" for gram or grams, "mg" for milligram or milligrams, "mL" for milliliter or milliliters, "$^1$H" for proton, "h" for hour or hours, "M" for molar, "min" for minute or minutes, "MHz" for megahertz, "MS" for mass spectroscopy, "NMR" for nuclear magnetic resonance spectroscopy, "rt" for room temperature, "tlc" for thin layer chromatography, "EtOAc" for ethyl acetate, "v/v" for volume to volume ratio, "aq" for aqueous solutions. "R" and "S" are stereochemical designations familiar to those skilled in the art. Compound names are provided by the program ChemDraw Ultra (6.0).

Example 1

2-{(3S)-1-[(1,2-cis)-2-(4-Methylsulfanyl-benzoylamino)-cyclohexyl]-2-oxo-pyrrolidin-3-ylcarbamoyl}-4-trifluoromethyl-phenyl)-carbamic acid tert-butyl ester (1a) Cis(±)-(2-amino-cyclohexyl)-carbamic acid benzyl ester trifluoroacetic acid salt (620 mg) (Cherney, R. J. PCT Int Appl. (2000), WO 0260859) was dissolved in DMF (6 mL) prior to the addition of 4-methylmorpholine (0.56 mL) and N-Boc-L-Met-OH (512.0 mg). After cooling to 0° C., BOP Reagent (907.1 mg) was added. The resulting mixture was warmed to rt and was stirred overnight. EtOAc was added along with 1 N HCl solution. The EtOAc layer was washed with 1 N HCl (aq), NaHCO$_3$ solution (aq), and brine. The EtOAc was dried (MgSO$_4$), filtered, and concentrated. Flash chromatography of the resulting residue gave an inseparable mixture of diastereomers cis-[2-(2(S)-tert-butoxycarbonylamino-4-methylsulfanyl-butyrylamino)-cyclohexyl]-carbamic acid benzyl ester (921 mg) which was taken forward. MS found: (M+Na)$^+$=502.4.

(1b) A portion (910 mg) of the above derivative (1a) was dissolved in MeI (12 mL). After stirring overnight at rt, the solution was concentrated and dried. The resulting material was dissolved in DMF (15 mL) and CH$_2$Cl$_2$ (15 mL) and cooled to 0° C. prior to the addition of 60% NaH (258.4 mg). After stirring 3 h at rt, EtOAc and brine were added. The EtOAc layer was washed with brine, dried (MgSO$_4$), filtered, and concentrated. Flash chromatography of the resulting residue gave the mixture of diastereomers cis-[1-(2-benzyloxycarbonylamino-cyclohexyl)-2-oxo-pyrrolidin-3(S)-yl]-carbamic acid benzyl ester (358 mg). MS found: (M+Na)$^+$=454.4.

(1c) A portion (340 mg) of the above derivative (1b) was dissolved in CH$_2$Cl$_2$ (2 mL) and cooled to 0° C. prior to the addition of TFA. After 1 h at rt, the mixture was concentrated. A portion (270 mg) of the resulting residue was dissolved in DMF (5 mL) prior to the addition of 4-methylmorpholine (0.24 mL) and 2-(tert-butoxycarbonyl)amino-5-trifluoromethylbenzoic acid (220 mg) (Takagishi et al., *Synlett* 1992, 360). After cooling to 0° C., BOP Reagent (322 mg) was added. The resulting mixture was warmed to rt and was stirred overnight. EtOAc was added along with 1 N HCl solution. The EtOAc layer was washed with 1 N HCl (aq), NaHCO$_3$ solution (aq), and brine. The EtOAc was dried (MgSO$_4$), filtered, and concentrated. Flash chromatography of the resulting residue gave the mixture of diastereomers cis-{2-[1-(2-benzyloxycarbonylamino-cyclohexyl)-2-oxo-pyrrolidin-3(S)-ylcarbamoyl]-4-trifluoromethyl-phenyl}-carbamic acid tert-butyl ester (196 mg). MS found: (M+Na)$^+$=641.4.

(1d) A portion (180 mg) of the above derivative (1c) was dissolved in MeOH prior to the addition of 10% Pd/C (40 mg). A hydrogen balloon was added and the mixture was stirred for 3 h. The Pd/C was filtered off and the solvent was concentrated to a mixture of diastereomers cis-{2-[1-(2-amino-cyclohexyl)-2-oxo-pyrrolidin-3(S)-ylcarbamoyl]-4-trifluoromethyl-phenyl}-carbamic acid tert-butyl ester (140 mg). MS found: (M+H)$^+$=485.4.

(1e) A portion (70 mg) of the above derivative (1d) was dissolved in DMF (5 mL) prior to the addition of 4-methylmorpholine (0.05 mL) and 4-(methylthio)benzoic acid (52 mg). After cooling to 0° C., BOP Reagent (77 mg) was added. The resulting mixture was warmed to rt and was stirred overnight. EtOAc was added along with 1 N HCl solution. The EtOAc layer was washed with 1 N HCl (aq), NaHCO$_3$ solution (aq), and brine. The EtOAc was dried (MgSO$_4$), filtered, and concentrated. Flash chromatography of the resulting residue gave the title mixture of diastereomers (76 mg). MS found: (M+H)$^+$=635.4.

Example 2

2-{(3S)-1-[(1,2-cis)2-(4-Methylsulfanyl-benzoylamino)-cyclohexyl]-2-oxo-pyrrolidin-3-ylcarbamoyl}-4-trifluoromethyl-phenyl)-amino (2a) A portion (19 mg) of the above Example 1 was dissolved in $CH_2Cl_2$ (2 mL) and cooled to 0° C. prior to the addition of TFA. After 1 h at rt, the mixture was concentrated and dried. This gave the title compound (17 mg). MS found: $(M+H)^+=535.4$.

Example 3

N-{(3S)-1-[(1S,2R,4R)-(Isopropyl-methyl-amino)-2-(toluene-4-sulfonylmethyl)-cyclohexyl]-2-oxo-pyrrolidin-3-yl}-3-trifluoromethyl-benzamide (3a) 1,4-Cyclohexanedione mono-ethylene ketal (25 g) was dissolved in THF and cooled to −78° C. 1M Lithium bis(trimethylsily)amide (160 mL) in THF was added dropwise. After 30 min, ethyl cyanoformate (15.9 mL) was added dropwise. After 60 min, the solution was poured into EtOAc and water containing ice. The organic layer was washed with water and brine before it was dried and concentrated. This crude was filtered through a plug of silica to give the 8-oxo-1,4-dioxa-spiro[4.5]decane-7-carboxylic acid ethyl ester (32.4 g). MS found: $(M+H)^+=228.9$ (3b) The above derivative (3a) (36.5 g) was dissolved in toluene (500 mL) prior to the addition of (S)-methylbenzyl amine (23 mL) and ytterbium (III) triflate (0.37 g). This miture was stirred at reflux for 3 h. After cooling to rt overnight, the solvent was removed to a golden oil. This oil was dissolved in acetonitrile (420 ml) prior to the addition of acetic acid (100 mL) and $NaBH(OAc)_3$ (67.8 g). The mixture was stirred for 5 days at rt. The solvent was removed before being redissolved in $CH_2Cl_2$. After cooling in an ice bath, 1N NaOH was added (pH=8). The organic layer was washed with brine, dried, filtered, and concentrated. Flash chromatography of the resulting residue gave 8(S)-(1(S)-phenyl-ethylamino)-1,4-dioxa-spiro[4.5]decane-7(R)-carboxylic acid ethyl ester (26.2 g): $^1H$ NMR ($CDCl_3$, δ ppm, 300 mHz) 1.31 (m, 6H), 1.46 (m, 1H), 1.6–1.84 (m, 4H), 2.1 (t, 1H), 2.85 (m, 1H), 3.16 (m, 1H), 3.76 (m, 1H), 3.93 (m, 4H), 4.19 (q, 2H), 7.2–7.4 (m, 5H).

(3c) The above derivative (3b) (16.3 g) was dissolved in $Et_2O$ (160 mL) and cooled to 0° C. 1M Lithium aluminum hydride in THF (117.3 mL) was added dropwise. After the addition, the solution was stirred for 2 hr at 0° C. The reaction was quenched with water (4.4 mL) and then 1N NaOH (17.6 mL). The solids were filtered off through a pad of celite. The filtrate was concentrated to an oil. This material was dissolved in MeOH (20 mL) prior to the addition of 20% $Pd(OH)_2$ (3 g). This solution was placed on a Parr aparatus at 50 psi. The solution was mixed overnight. The palladium was filtered off and the solution was concentrated. The resulting oil was dissolved in THF (160 mL) and water (20 mL) prior to the addition of triethylamine (8.8 mL). After cooling to 0° C., dibenzyl dicarbonate (18.2 g) was added. The solution was warmed to rt and was stirred overnight. Ethyl acetate was added along with brine. The organic layer was washed with brine, dried, filtered, and concentrated. Flash chromatography of the resulting residue gave (7R,8S)-(7-hydroxymethyl-1,4-dioxa-spiro[4.5]dec-8-yl)-carbamic acid benzyl ester (9.8 g). MS found: $(M+H)^+=322.2$.

(3d) A portion (100 mg) of the above derivative (3c) was dissolved in THF (10 mL) prior to the addition of tri-n-butylphosphine (0.86 mL). 4-Bromophenyl disulfide (233 mg) was added and the solution was stirred in a 75° C. oil bath. After 5 h, the reaction was cooled to rt and flash chromatography gave (7R,8S)-[7-(4-bromo-phenylsulfanyl-methyl)-1,4-dioxa-spiro[4.5]dec-8-yl]-carbamic acid benzyl ester (137 mg). $^1H$ NMR ($CDCl_3$, δ ppm, 300 mHz) 1.39 (t, 1H), 1.5–1.9 (m, 9H), 2.05 (m, 1H), 2.73 (m, 1H), 3.0 (dd, 1H), 3.93 (m, 4H), 4.08 (m, 1H), 4.9 (br d, 1H), 5.1 (s, 2H), 7.17 (d, 2H), 7.36 (m, 7H).

(3e) A portion (2.5 g) of the above derivative (3d) was dissolved in $CH_2Cl_2$ (100 mL) and cooled to 0° C. prior to the addition 65% m-CPBA (3.1 g). After 2 h, the solution was washed with saturated $NaHCO_3$ solution, brine solution, dried, filtered, and concentrated. Flash chromatography of the resulting residue gave (7R,8S)-[7-(4-bromo-benzenesulfonylmethyl)-1,4-dioxa-spiro[4.5]dec-8-yl]-carbamic acid benzyl ester (2.59 g). MS found: $(M+H)^+=525.9$.

(3f) A portion (2.1 g) of the above derivative (3e) was dissolved in DMF (10 mL) prior to the addition of $PdCl_2(PPh_3)_2$ (56 mg) and $Sn(Me)_4$ (0.8 mL). The resulting solution was heated in an oil bath at 80° C. Four addition portions of $Sn(Me)_4$ (0.8 mL each) were added over 3 days. After cooling, EtOAc and brine were added. The organic layer was washed with brine, dried, filtered, and concentrated. Flash chromatography of the resulting residue gave (7R,8S)-([7-(toluene-4-sulfonylmethyl)-1,4-dioxa-spiro[4.5]dec-8-yl]-carbamic acid benzyl ester (1.0 g). MS found: $(M+H)^+=460.3$.

(3g) A portion (1.0 g) of the above derivative (3f) was dissolved in MeOH prior to the addition of 10% Pd/C (120 mg). A hydrogen balloon was added and the mixture was stirred for 1.5 h. The Pd/C was filtered off and the solvent was concentrated to (7R,8S)-7-(toluene-4-sulfonylmethyl)-1,4-dioxa-spiro[4.5]dec-8-ylamine (740 mg). MS found: $(M+H)^+=326.3$.

(3h) A portion (730 mg) of the above derivative (3g) was dissolved in DMF prior to the addition of 4-methylmorpholine (0.74 mL) and N-Cbz-L-Met-OH (889.8 mg). After cooling to 0° C., BOP Reagent (1.4 g) was added. The resulting mixture was warmed to rt and was stirred overnight. EtOAc was added along with 1 N HCl solution. The EtOAc layer was washed with 1 N HCl (aq), $NaHCO_3$ solution (aq), and brine. The EtOAc was dried ($MgSO_4$), filtered, and concentrated. Flash chromatography of the resulting residue gave {(1S)3-methylsulfanyl-1-[(7R,8S)-7-(toluene-4-sulfonylmethyl)-1,4-dioxa-spiro[4.5]dec-8-ylcarbamoyl]-propyl}-carbamic acid benzyl ester (1.1 g). MS found: $(M+Na)^+=613.4$.

(3i) A portion (330 mg) of the above derivative (3h) was dissolved in MeI (6 mL). After stirring overnight at rt, the solution was concentrated and dried. A portion (50 mg) of the resulting material was dissolved in DMF (1.5 mL) prior to the addition of $Cs_2CO_3$ (133 mg). After stirring overnight at rt, EtOAc and brine were added. The EtOAc layer was washed with brine, dried ($MgSO_4$), filtered, and concentrated. Flash chromatography of the resulting residue gave {(3S)-2-oxo-1-[(7R,8S)-7-(toluene-4-sulfonylmethyl)-1,4-dioxa-spiro[4.5]dec-8-yl]-pyrrolidin-3-yl}-carbamic acid benzyl ester (19 mg). MS found: $(M+Na)^+=565.3$.

(3j) A portion (580 mg) of the above derivative (3i) was dissolved in $CH_3CN$ (10 mL) prior to the addition of 1N HCl (10 mL). The mixture was stirred in a 60° C. oil bath for 4 h. After cooling the solution was concentrated. Flash chromatography of the resulting residue gave {(3S)-2-oxo-1-

[(1S,2R)-4-oxo-2-(toluene-4-sulfonylmethyl)-cyclohexyl]-pyrrolidin-3-yl}-carbamic acid benzyl ester (270 mg). MS found: $(M+Na)^+=521.2$.

(3k) The above derivative (3j) (270 mg) was dissolved in Ti(OiPr)$_4$ (4 mL) prior to the addition of isopropylamine (0.4 mL). After 1.5 h, MeOH (7 mL) was added followed by NaBH$_4$ (57 mg). After 1 h, the reaction was quenched by the addition of 0.1N NaOH and filtered through celite. The filtrate was concentrated to a mixture of diastereomers. Flash chromatography of the resulting mixture gave two diastereomers: ({(3S)-1-[(1S,2R,4R)-isopropylamino-2-(toluene-4-sulfonylmethyl)-cyclohexyl]-2-oxo-pyrrolidin-3-yl}-carbamic acid benzyl ester (3ka) (59 mg), MS found: $(M+H)^+=542.3$; and ({(3S)-1-[(1S,2R,4S)-isopropylamino-2-(toluene-4-sulfonylmethyl)-cyclohexyl]-2-oxo-pyrrolidin-3-yl}-carbamic acid benzyl ester (3kb) (28 mg), MS found: $(M+H)^+=542.4$.

(3l) The above derivative (3ka) (57 mg) was dissolved in MeOH (1.3 mL) prior to the addition of 37% formaldehyde in water (53 mg). After 1.5 h, NaBH$_3$CN (10.4 mg) was added. After 1 h, saturated NaHCO$_3$ was added and some of the MeOH was removed. EtOAc was added and the organic layer was washed with brine, dried, filtered, and concentrated. The resulting residue was dissolved in MeOH prior to the addition of 5% Pd/BaSO$_4$ (100 mg). A hydrogen balloon was added and the mixture was stirred. Two more portions (50 mg each) of 5% Pd/BaSO$_4$ were added. The reaction was stirred for a total of 8 h. The Pd/BaSO$_4$ was filtered off and the solvent was concentrated. The resulting residue was dissolved in DMF prior to the addition of 4-methylmorpholine (34 mg) and 3-trifluoromethyl-benzoic acid (32 mg). After cooling to 0° C., HATU (64 mg) was added. The resulting mixture was warmed to rt and was stirred overnight. EtOAc was added along with saturated NaHCO$_3$ solution. The EtOAc layer was washed with NaHCO$_3$ solution (aq), dried (MgSO$_4$), filtered, and concentrated. Reverse phase HPLC purification (gradient elution, water/acetonitrile/TFA) of the resulting residue provided the title compound (36 mg). MS found: $(M+H)^+=594.3$.

Example 4

N-{(3S)-1-[(1S,2R,4S)-(Isopropyl-methyl-amino)-2-(toluene-4-sulfonylmethyl)-cyclohexyl]-2-oxo-pyrrolidin-3-yl}-3-trifluoromethyl-benzamide (4a) Derviative (3kb) (28 mg) was incorporated into Example (3l) to give the title compound (8.1 mg). MS found: $(M+H)^+=594.3$.

Example 5

N-{(3S)-1-[(1S,2R,4R)-2-Benzenesulfonylmethyl-(isopropyl-methyl-amino)-cyclohexyl]-2-oxo-pyrrolidin-3-yl}-3-trifluoromethyl-benzamide (5a) Phenyl disulfide was incorporated into Example 3—step (3d) and step (3f) was skipped to give two diastereomers. The first diastereomer was the title compound (12.3 mg). MS found: $(M+H)^+=580.3$.

Example 6

N-{(3S)-1-[(1S,2R,4S)-2-Benzenesulfonylmethyl-4-(isopropyl-methyl-amino)-cyclohexyl]-2-oxo-pyrrolidin-3-yl}-3-trifluoromethyl-benzamide (6a) The second diastereomer from above (5a) was isolated as the title compound. MS found: $(M+H)^+=580.3$.

Example 7

N-{(3S)-1-[(1S,2R,4R)-2-Benzenesulfonylmethyl-4-(isopropyl-ethyl-amino)-cyclohexyl]-2-oxo-pyrrolidin-3-yl}-3-trifluoromethyl-benzamide (7a) Acetaldehyde was incorporated into Example 5 (in the analogous step to 3l) to give two diastereomers. The first diastereomer was the title compound (30 mg). MS found: $(M+H)^+=594.3$.

Example 8

N-{(3S)-1-[(1S,2R,4S)-2-Benzenesulfonylmethyl-4-(isopropyl-ethyl-amino)-cyclohexyl]-2-oxo-pyrrolidin-3-yl}-3-trifluoromethyl-benzamide (8a) The second diastereomer from above (7a) was the title compound (7 mg). MS found: $(M+H)^+=594.3$.

Example 9

N-{(3S)-1-[(1S,2R,4R)-2-Benzenesulfonylmethyl-4-(isopropyl-cyclopropylmethyl-amino)-cyclohexyl]-2-oxo-pyrrolidin-3-yl}-3-trifluoromethyl-benzamide (9a) Cyclopropanecarboxaldehyde was incorporated into Example 5 (in the analogous step to 3l) to give the title compound (25 mg). MS found: $(M+H)^+=620.3$.

Example 10

(±) N-{(3S*)-1-[(1S*,2R*,4R*)-4-Azido-2-(4-methylsulfanyl-benzenesulfonylmethyl)-cyclohexyl]-3-methyl-2-oxo-pyrrolidin-3-yl}-3-trifluoromethyl-benzamide (10a) 1-Methanesulfonyl-4-methylsulfanyl-benzene (3.4 g) was dissolved in THF (40 mL) and cooled to −78° C. prior to the addition of 1.6 M nBuLi (10.4 mL). After 0.5 h, BF$_3$.Et$_2$O (2.1 mL) was added followed by cis(±)-4-(benzyloxy)-1,2-epoxycyclohexane (2.3 g) (Chini et al. *J. Org. Chem.* 1990, 55, 4265) in THF (20 mL). After an addition 1 h at −78° C., the solution was warmed to 0° C. After 2 h, the solution was cooled to −78° C. and 1N HCl solution (aq) was added. The solution was warmed to rt and EtOAc was added. The organic layer was washed with brine, dried, filtered, and concentrated. Flash chromatography of the resulting residue gave (±) (1R*,2R*,4S*)-4-benzyloxy-2-(4-methylsulfanyl-benzenesulfonylmethyl)-cyclohexanol (2.9 g) as the major product. MS found: $(M+H)^+=407.1$.

(10b) A portion of the above material (1.9 g) was dissolved in CH$_2$Cl$_2$ (15 mL) and cooled to 0° C. prior to the addition of Et$_3$N (2 mL) and methanesulfonyl chloride (0.55 mL). After 1 h, the CH$_2$Cl$_2$ was removed and EtOAc was added. This was washed with 1N HCl, saturated NaHCO$_3$, and brine. The organic layer was dried, filtered, and concentrated. This solid was dissolved in DMSO (20 mL) prior to the addition of NaN$_3$ (2.35 g). This was heated at 80° C. for 18 h. After cooling to 0° C., water was added and it was extracted with EtOAc. The organic layer was washed with brine, dried, filtered, and concentrated. Flash chromatography of the resulting residue gave (±) (1S*,2R*,4S*)-4-benzyloxy-2-(4-methylsulfanyl-benzenesulfonylmethyl)-azidocyclohexane (1.4 g). MS found: $(M-N_3)^+=388.5$.

(10c) A portion of the above material (1.3 g) was dissolved in CH$_2$Cl$_2$ (15 mL) and cooled to −78° C. prior to the addition of 1.0M BCl$_3$ (3.9 mL) in CH$_2$Cl$_2$. The reaction was stirred at 0° C. for 2 h. After cooling to −78° C., MeOH (8 mL) was added. The reaction was warmed to 0° C. and then rt. The resulting solution was extracted with CH$_2$Cl$_2$. The organic layer was washed with saturated NaHCO$_3$ solution (aq), brine, dried, filtered, and concentrated. Flash chromatography of the resulting residue gave (±) (1S*,2R*,4S*)-4-hydroxy-2-(4-methylsulfanyl-benzenesulfonylmethyl)-azidocyclohexane (1.1 g). MS found: (M−HN$_3$)$^+$=298.1.

(10d) The above material (1.1 g) was dissolved in MeOH (10 mL) prior to the addition of 5% Pd/BaSO$_4$ (800 mg). A hydrogen balloon was added and the solution was stirred for 4.0 h. The palladium was filtered off and the solution was concentrated to (±) (1S*,2R*,4S*)-4-hydroxy-2-(4-methylsulfanyl-benzenesulfonylmethyl)-cyclohexylamine: MS found: (M+H)$^+$=316.2. The resulting residue was dissolved in THF (10 mL) and water (2 mL) prior to the addition of Et$_3$N (0.88 mL). This was cooled to 0° C. and Boc$_2$O (761 mg) was added. The reaction was warmed to rt and was stirred overnight. The reaction was quenched with water and EtOAc. The EtOAc layer was washed with 1 N HCl solution, NaHCO$_3$ solution, and brine. The organic layer was dried, filtered, and concentrated (1.44 g). This material (1.44 g) was dissolved in CH$_2$Cl$_2$ (15 mL) and cooled to 0° C. prior to the addition of Et$_3$N (1.3 mL) and methanesulfonyl chloride (0.37 mL). After 1 h, the CH$_2$Cl$_2$ was removed and EtOAc was added. This was washed with 1N HCl, saturated NaHCO$_3$, and brine. The organic layer was dried, filtered, and concentrated. This solid was dissolved in DMSO (10 mL) prior to the addition of NaN$_3$ (1.03 g). This was heated at 80° C. for 18 h. After cooling to 0° C., water was added and it was extracted with EtOAc. The organic layer was washed with brine, dried, filtered, and concentrated. Flash chromatography of the resulting residue gave (±) (1S*,2R*,4R*)-[4-azido-2-(4-methylsulfanyl-benzenesulfonylmethyl)-cyclohexyl]-carbamic acid tert-butyl ester (1.2 g). MS found: (M+Na+CH$_3$CN)$^+$=504.3.

(10e) A portion of the above material (114 mg) was dissolved in CH$_2$Cl$_2$ (2 mL) and cooled to 0° C. prior to the addition of TFA (2 mL). After the reaction was warmed to rt over 45 min, it was concentrated and dried. The resulting residue was dissolved in DMF (4 mL) prior to the addition of HATU (166.7 mg) and N-Boc-α-methyl-dl-Met-OH (101.7 mg). After cooling to 0° C., diisopropylethylamine (0.74 mL) was added. The resulting mixture was warmed to rt and was stirred overnight before being concentrated. Flash chromatography of the resulting residue gave {1-[4-azido-2-(4-methylsulfanyl-benzenesulfonylmethyl)-cyclohexylcarbamoyl]-1-methyl-3-methylsulfanyl-propyl}-carbamic acid tert-butyl ester (113 mg) as a mixture of diastereomers. MS found: (M+H)$^+$=586.5.

(10f) The above derivative was dissolved in MeI (5 mL). After stirring overnight at rt, the solution was concentrated and dried. The resulting material was dissolved in DMF (4 mL) prior to the addition of CS$_2$CO$_3$ (380 mg). After stirring overnight the solution was filtered and concentrated. Flash chromatography of the resulting residue provided the bottom diastereomer (TLC 80% EtOAc/Hex) (±) {(3S*)-1-[(1S*,2R*,4R*)-4-azido-2-(4-methylsulfanyl-benzenesulfonylmethyl)-cyclohexyl]-3-methyl-2-oxo-pyrrolidin-3-yl}-carbamic acid tert-butyl ester (36 mg). MS found: (M+Na)$^+$=538.5.

(10 g) The above material was dissolved in CH$_2$Cl$_2$ (1 mL) and cooled to 0° C. prior to the addition of TFA (1 mL). After the reaction was warmed to rt over 30 min, it was concentrated and dried. The resulting residue was dissolved in CH$_2$Cl$_2$ prior to the addition of diisopropylethylamine (0.05 mL) and 3-(trifluoromethyl)benzoyl chloride (28 mg). After stirring for 1.5 h, the reaction was diluted with CH$_2$Cl$_2$ and washed with water, 10% citric acid solution, NaHCO$_3$ solution, and brine. The CH$_2$Cl$_2$ layer was dried (MgSO$_4$), filtered, and concentrated. Flash chromatography of the resulting residue provided the title compound (24 mg). MS found: (M+H)$^+$=610.5.

Example 11

(±) N-{(3S*)-1-[(1S*,2R*,4R*)-4-Amino-2-(4-methylsulfanyl-benzenesulfonylmethyl)-cyclohexyl]-3-methyl-2-oxo-pyrrolidin-3-yl}-3-trifluoromethyl-benzamide (11a) Example 10 (20 mg) was dissolved in MeOH (2 mL) prior to the addition of 5% Pd/BaSO$_4$ (10 mg). A hydrogen balloon was added and the mixture was stirred. After stirring 45 min, the Pd/BaSO$_4$ was filtered off and the solvent was concentrated to give the title compound. MS found: (M+H)$^+$=584.5.

Example 12

(±) N-{(3S*)-1-[(1S*,2R*,4R*)-4-Isopropylamino-2-(4-methylsulfanyl-benzenesulfonylmethyl)-cyclohexyl]-3-methyl-2-oxo-pyrrolidin-3-yl}-3-trifluoromethyl-benzamide (12a) Example 11 (16 mg) was dissolved in dichloroethane (1 mL) prior to the adddition of glacial acetic acid (8 mg), acetone (8 mg), and NaBH(OAc)$_3$ (30 mg). After 20 h, the solution was concentrated. The resulting residue was dissolved in EtOAc and washed with saturated NaHCO$_3$, water, and brine. The organic layer was dried, filtered, and concentrated. Reverse phase HPLC purification (gradient elution, water/acetonitrile/TFA) of the resulting residue provided the title compound (13 mg). MS found: (M+H)$^+$=626.6.

Example 13

(±) N-{(3S*)-1-[(1S*,2R*,4R*)-4-(Isopropyl-methyl-amino)-2-(4-methylsulfanyl-benzenesulfonylmethyl)-cyclohexyl]-3-methyl-2-oxo-pyrrolidin-3-yl}-3-trifluoromethyl-benzamide (13a) Example 12 (22 mg) was dissolved in MeOH (1 mL) prior to the addition of 37% formaldehyde in water (4 mg). After 15 min, NaBH$_3$CN (4 mg) was added. After 1 h, saturated NaHCO$_3$ was added and some of the MeOH was removed. EtOAc was added and the organic layer was dried, filtered, and concentrated. Reverse phase HPLC purification (gradient elution, water/acetonitrile/TFA) of the resulting residue provided the title compound (13 mg). MS found: (M+H)$^+$=640.6.

Example 14

(±) N-{(3S*)-1-[(1S*,2R*,4R*)-4-(Isopropyl-prop-2-ynyl-amino)-2-(4-methylsulfanyl-benzenesulfonylmethyl)-cyclohexyl]-3-methyl-2-oxo-pyrrolidin-3-yl}-3-trifluoromethyl-benzamide (14a) Example 12 (20 mg) was dissolved in acetonitrile (1 mL) prior to the addition of K$_2$CO$_3$ (22 mg) and propargyl bromide (8 mg). After 4.75 h at 45° C., the reaction was cooled to rt. Saturated NaHCO$_3$ was added and the reaction was extracted with EtOAc. The organic layer was dried, filtered, and concentrated. Reverse phase HPLC purification (gradient elution, water/acetonitrile/TFA) of the resulting residue provided the title compound (7 mg). MS found: (M+H)$^+$=664.6.

Example 15

(±) N-{(3S*)-1-[(1S*,2R*,4R*)-4-(Cyclopropylmethyl-isopropyl-amino)-2-(4-methylsulfanyl-benzenesulfonylmethyl)-cyclohexyl]-3-methyl-2-oxo-pyrrolidin-3-yl}-3-trifluoromethyl-benzamide (15a) Cyclopropanecarboxaldehyde was incorporated into Example 13 to give the title compound (11 mg). MS found: (M+H)$^+$=680.6.

Example 16

N-{(3S)-1-[4-(Isopropyl-methyl-amino)-2-(4-methylsulfanyl-benzenesulfonylmethyl)-cyclohexyl]-2-oxo-pyrrolidin-3-yl}-N-methyl-3-trifluoromethyl-benzamide (16a) N(Me)Boc-L-Met-OH was incorporated into Example 10, step (10e), and advanced in an analogous way to Example 12. This procedure gave the title compound (31 mg) as a mixture of diastereomers. MS found: (M+H)$^+$=640.3.

Example 17

N-{(3S)-1-[(1S,2R,4R)-4-(Isopropyl-methyl-amino)-2-(4-methylsulfanyl-benzenesulfonylmethyl)-cyclohexyl]-2-oxo-pyrrolidin-3-yl}-3-trifluoromethyl-benzamide (17a) N-Boc-L-Met-OH was incorporated into Example 16 to give the title compound. MS found: (M+H)$^+$=626.3.

Example 18

1-{(3S)-1-[(1S,2R,4R)-4-(Isopropyl-methyl-amino)-2-(4-methylsulfanyl-benzenesulfonylmethyl)-cyclohexyl]-2-oxo-pyrrolidin-3-yl}-3-(3-trifluoromethyl-phenyl)-urea (18a) {(3S)-1-[(1S,2R,4R)-4-Azido-2-(4-methylsulfanyl-benzenesulfonylmethyl)-cyclohexyl]-2-oxo-pyrrolidin-3-yl}-carbamic acid tert-butyl ester (350 mg), from the synthesis of Example 17 (analogous to 10f), was dissolved in MeOH (5 mL) prior to the addition of 5% Pd/BaSO$_4$ (300 mg). A hydrogen balloon was added and the mixture was stirred. After stirring 1 h, the Pd/BaSO$_4$ was filtered off and the solvent was concentrated to give {(3S)-1-[(1S,2R,4R)-4-amino-2-(4-methylsulfanyl-benzenesulfonylmethyl)-cyclohexyl]-2-oxo-pyrrolidin-3-yl}-carbamic acid tert-butyl ester (497 mg). MS found: (M−H)$^−$=496.5.

(18b) A portion of the above material (341 mg) was dissolved in dichloroethane (5 mL) prior to the adddition of acetone (0.25 mL) and NaBH(OAc)$_3$ (436 mg). After 2 h, the solution was concentrated. The resulting residue was dissolved in EtOAc and washed with saturated NaHCO$_3$. The organic layer was dried, filtered, and concentrated. The resulting residue was dissolved in MeOH (2 mL) prior to the addition of 37% formaldehyde in water (0.1 mL). After 15 min, NaBH$_3$CN (111 mg) was added. After 2 h, saturated NaHCO$_3$ was added and some of the MeOH was removed. EtOAc was added and the organic layer was dried, filtered, and concentrated. This material was passed through a plug of silica and concentrated. This material (300 mg) was dissolved in CH$_2$Cl$_2$ (5 mL) prior to the addition of TFA (2.5 mL). After 30 min, it was concentrated and dried. A portion of the resulting residue (35 mg) was dissolved in DMF (1 mL) prior to the addition of 4-methylmorpholine (0.02 mL) and 3-trifluoromethylphenyl isocyanate (0.013 mL). After 2 h, the solution was concentrated. Reverse phase HPLC purification (gradient elution, water/acetonitrile/TFA) of the resulting residue provided the title compound (7 mg). MS found: (M+H)$^+$=641.3.

Example 19

N-{(3S)-1-[(1S,2R,4R)-4-(Isopropyl-methyl-amino)-2-(4-methylsulfanyl-benzenesulfonylmethyl)-cyclohexyl]-2-oxo-pyrrolidin-3-yl}-3-trifluoromethyl-benzenesulfonamide (19a) 3-(Trifluoromethyl)phenylsulfonyl chloride (instead of 3-trifluoromethylphenyl isocyanate) and pyridine (instead of 4-methylmorpholine) were incorporated into Example 18 to give the title compound. MS found: (M+H)$^+$=662.3.

Example 20

N-{(3S)-1-[(1S,2R,4R)-4-(Isopropyl-methyl-amino)-2-(4-methylsulfanyl-benzenesulfonylmethyl)-cyclohexyl]-2-oxo-pyrrolidin-3-yl}-benzamide (20a) Benzoic acid was incorporated into Example 17 to give the title compound. MS found: (M+H)$^+$=558.3.

Example 21

{(3S)-1-[(1S,2R,4R)-2-Benzenesulfonylmethyl-4-(isopropyl-methyl-amino)-cyclohexyl]-2-oxo-pyrrolidin-3-yl}-3-(3-trifluoromethyl-phenyl)-urea (21a) Example 18 (15 mg) was dissolved in MeOH (1 mL) prior to the addition of 20% Pd(OH)$_2$ (20 mg). A hydrogen balloon was added and the mixture was stirred. After stirring overnight, the palladium was filtered off and the solvent was concentrated. Reverse phase HPLC purification (gradient elution, water/acetonitrile/TFA) of the resulting residue provided the title compound. MS found: (M+H)$^+$=595.3.

Example 22

N-[(3S)-1-((1S,2R,4R)-2-Benzenesulfonylmethyl-4-isopropylamino-cyclohexyl)-2-oxo-pyrrolidin-3-yl]-3-trifluoromethyl-benzamide (22a) {(3S)-1-[(1S,2R,4R)-4-Azido-2-(4-methylsulfanyl-benzenesulfonylmethyl)-cyclohexyl]-2-oxo-pyrrolidin-3-yl}-carbamic acid tert-butyl ester (240 mg), see example 18, was dissolved in CH$_2$Cl$_2$ (5 mL) prior to the addition of TFA (2.5 mL). After 30 min, it was concentrated and dried. The resulting residue was dissolved in DMF prior to the addition of 4-methylmorpholine (0.25 mL) and 3-trifluoromethyl-benzoic acid (104.5 mg). BOP Reagent (64 mg) was added and the mixture was stirred for 40 min. After concentration, EtOAc was added along with 1N HCl solution. The EtOAc layer was washed with NaHCO$_3$ solution (aq) and brine, dried (MgSO$_4$), filtered, and concentrated. This material was passed through a plug of silica and concentrated. The resulting material (178 mg) was dissolved in MeOH (5 mL) prior to the addition of 20% Pd(OH)$_2$ (100 mg). A hydrogen balloon was added and the mixture was stirred. After stirring overnight, the palladium was filtered off and the solvent was concentrated. A portion of this material (68 mg) was dissolved in dichloroethane (2.5 mL) prior to the adddition of acetone (0.04 mL) and NaBH(OAc)$_3$ (64 mg). After 40 min, the solution was concentrated. The resulting residue was dissolved in EtOAc and washed with saturated NaHCO$_3$. The organic layer was dried, filtered, and concentrated. Reverse phase HPLC purification (gradient elution, water/acetonitrile/TFA) of the resulting residue provided the title compound (66 mg). MS found: (M+H)$^+$=566.4.

Example 23

N-{(3S)-1-[(1S,2R,4R)-4-(Allyl-isopropyl-amino)-2-benzenesulfonylmethyl-cyclohexyl]-2-oxo-pyrrolidin-3-yl}-3-trifluoromethyl-benzamide (23a) Example 22 (17 mg) was dissolved in DMF (1 mL) prior to the addition of K$_2$CO$_3$ (11 mg) and allyl bromide (0.003 mL). After stirring overnight, the reaction was filtered and concentrated. Reverse phase HPLC purification (gradient elution, water/acetonitrile/TFA) of the resulting residue provided the title compound (5 mg). MS found: (M+H)$^+$=606.3.

Example 24

1-((1S,2R)-2-Benzenesulfonylmethyl-4-isopropylamino-cyclohexyl)-2-oxo-pyrrolidine-3-carboxylic acid (3-trifluoromethyl-phenyl)-amide (24a) Phenyl disulfide was incorporated into Example 3, step 3d (in place of 4-bromophenyl disulfide), and advanced to step 3e to give (7R,8S)-(7-benzenesulfonylmethyl-1,4-dioxa-spiro[4.5]dec-8-yl)-carbamic acid benzyl ester. This material (1.2 g) was dissolved in MeOH prior to the addition of 10% Pd/C (250 mg). A hydrogen balloon was added and the mixture was stirred for 5 h. The Pd/C was filtered off and the solvent was concentrated to give (7R,8S)-7-benzenesulfonylmethyl-1,4-dioxa-spiro[4.5]dec-8-ylamine (826 mg). MS found: (M+H)$^+$=312.3.

(24b) A portion of this material (239 mg) was dissolved in dichloroethane (4 mL) prior to the adddition of 3,3-bis(methoxycarbonyl)propanal (160 mg) (Bunce et al. *Org. Prep. Proc. Int.* 1987, 19, 67–71). The mixture was stirred for 1.5 h before NaBH(OAc)$_3$ (195 mg) was added. After 2 h, EtOAc and saturated NaHCO$_3$ was added. The organic layer was washed with additional saturated NaHCO$_3$ solution. The organic layer was dried, filtered, and concentrated to give (7R,8S)-2-[2-(7-benzenesulfonylmethyl-1,4-dioxa-spiro[4.5]dec-8-ylamino)ethyl]-malonic acid dimethyl ester (203 mg). MS found: (M+H)$^+$=470.4.

(24c) A portion of this material (52 mg) was dissolved in MeOH prior to the addition of 0.5M NaOMe (0.05 mL) in MeOH. The mixture was stirred overnight before being concentrated. EtOAc and 1N HCl was added. The organic layer was washed with additional 1N HCl solution. The organic layer was dried, filtered, and concentrated to give (1-(7-benzenesulfonylmethyl-1,4-dioxa-spiro[4.5]dec-8-yl)-2-oxo-pyrrolidine-3-carboxylic acid methyl ester (42 mg) as a mixture of diastereomers. MS found: (M+H)$^+$=460.3.

(24d) A portion of this material (110 mg) was dissolved in THF (1 mL), MeOH (0.5 mL), and water (0.5 mL) at 0° C. prior to the addition of 1M LiOH (0.25 mL) in water. The reaction was stirred for 2 h. EtOAc and 1N HCl was added. The organic layer was washed with additional 1N HCl solution. The organic layer was dried, filtered, and concentrated to give 1-(7-benzenesulfonylmethyl-1,4-dioxa-spiro[4.5]dec-8-yl)-2-oxo-pyrrolidine-3-carboxylic acid (105 mg). MS found: (M+H)$^+$=424.3.

(24e) This material was dissolved in DMF prior to the addition of 4-methylmorpholine (0.08 mL) and 3-(trifluoromethyl)phenyl aniline (0.05 mL). HATU (114 mg) was added and the mixture was stirred overnight. EtOAc was added along with 1N HCl solution. The EtOAc layer was washed with NaHCO$_3$ solution and brine, dried (MgSO$_4$), filtered, and concentrated. Flash chromatography of the resulting residue gave 1-(7-benzenesulfonylmethyl-1,4-dioxa-spiro[4.5]dec-8-yl)-2-oxo-pyrrolidine-3-carboxylic acid (3-trifluoromethyl-phenyl)-amide. MS found: (M+H)$^+$=567.3.

(24f) A portion of this material (118 mg) was dissolved in acetone (1 mL) prior to the addition of 1N HCl (4 mL). The mixture was heated at reflux for 3 h. After cooling, the solution was concentrated. Flash chromatography of the resulting residue gave two diatereomers of 1-(2-benzenesulfonylmethyl-4-oxo-cyclohexyl)-2-oxo-pyrrolidine-3-carboxylic acid (3-trifluoromethyl-phenyl)-amide as top (MS found: (M–H)$^-$=521.3) and bottom (MS found: (M+Na)$^+$=545.2).

(24g) The above top diastereomer (53 mg) was dissolved in Ti(OiPr)$_4$ (0.74 mL) prior to the addition of isopropylamine (0.08 mL). After 1.5 h, MeOH (1.5 mL) was added followed by NaBH$_4$ (11 mg). After 1 h, the reaction was quenched by the addition of 0.1N NaOH and filtered through celite. The filtrate was concentrated to a mixture of diastereomers. Reverse phase HPLC purification (gradient elution, water/acetonitrile/TFA) of the resulting residue provided the title compound (15 mg) as a mixture of diastereomers. MS found: (M+H)$^+$=566.3.

Example 25

1-((1S,2R)-2-Benzenesulfonylmethyl-4-isopropylamino-cyclohexyl)-2-oxo-pyrrolidine-3-carboxylic acid (3-trifluoromethyl-phenyl)-amide (25a) The above bottom diastereomer from 24f (71 mg) was dissolved in Ti(OiPr)$_4$ (0.7 mL) prior to the addition of isopropylamine (0.08 mL). After 1.5 h, MeOH (1.5 mL) was added followed by NaBH$_4$ (11 mg). After 1 h, the reaction was quenched by the addition of 0.1N NaOH and filtered through celite. The filtrate was concentrated to a mixture of diastereomers. Reverse phase HPLC purification (gradient elution, water/acetonitrile/TFA) of the resulting residue provided the title compound (22 mg) as a mixture of diastereomers. MS found: (M+H)$^+$=566.5.

Example 26

(2-{(3S)-1-[(1S,2R)-2-(4-Methylsulfanyl-benzylamino)-cyclohexyl]-2-oxo-pyrrolidin-3-ylcarbamoyl}-4-trifluoromethyl-phenyl)-carbamic acid tert-butyl ester (26a) Flash chromatography of the mixture of diastereomers in step (1c) gave the clean bottom isomer as {2-[(3S)-1-((1S,2R)-2-benzyloxycarbonylamino-cyclohexyl)-2-oxo-pyrrolidin-3-ylcarbamoyl]-4-trifluoromethyl-phenyl}-carbamic acid tert-butyl ester (MS found: (M–H)$^-$=617.2).

(26b) A portion of this material (50 mg) was dissolved in MeOH (5 mL) prior to the addition of 10% Pd/C (10 mg). A hydrogen balloon was added and the mixture was stirred for 3 h. The Pd/C was filtered off and the solvent was concentrated. The resulting residue was dissolved in dichloroethane (1.4 mL) prior to the adddition of glacial acetic acid (0.009 mL), 4-(methylthio)benzaldehyde (0.02 mL), and NaBH(OAc)$_3$ (31 mg). After 20 h, the solution was concentrated. The resulting residue was dissolved in EtOAc and washed with saturated NaHCO$_3$ solution. The organic layer was dried, filtered, and concentrated. Reverse phase HPLC purification (gradient elution, water/acetonitrile/TFA) of the resulting residue provided the title compound (15 mg). MS found: (M+H)$^+$=621.4.

Example 27

N-{(3S)-1-[(1S,2R,4R)-2-Benzenesulfonylmethyl-4 (R)-(isopropyl-propyl-amino)-cyclohexyl]-2-oxo-pyrrolidin-3-yl}-3-trifluoromethyl-benzamide (27a) Propionaldehyde was incorporated into Example 5 (in the analogous step to 3I) to give two diastereomers. The first diastereomer was the title compound (10 mg). MS found: (M+H)$^+$=608.3.

Example 28

(±) 1-[(1S*,2R*,4R*)-4-Isopropylamino-2-(4-methylsulfanyl-benzenesulfonylmethyl)-cyclohexyl]-4-(3-trifluoromethyl-phenyl)-5,6-dihydro-1H-pyridin-2-one (28a) Vinylmagnesium bromide (40 mL of a 1.0 M THF solution, 40 mmol) was added to a dry round bottom flask under nitrogen. The solution was cooled to −10° C. and charged with meta-trifluoromethylbenzaldehyde (5.0 g, 29 mmol). The reaction was stirred for 1 h, warmed to RT and quenched with sat. NH$_4$Cl. The mixture was extracted with EtOAC three times, and the organic extracts were dried (MgSO$_4$) and concentrated in vacuo. The crude material was purified via flash chromatography to give 1-(3-trifluoromethylphenyl)propen-1-ol as an oil (5.0 g, 87% yield). A portion of 1-(3-trifluoromethylphenyl)propen-1-ol (0.5 g, 2.5 mmol) was dissolved in acetone (20 mL). The resultant solution was cooled to 0° C., treated with Jones reagent (1.14 mL of a 2.6 M solution, 2.96 mmol), and stirred for 10 minutes before being quenched with the addition of isopropyl alcohol (1.5 mL). The mixture was stirred for 5 min at rt, diluted with Et$_2$O, filtered through Celite, washed with 10% Na$_2$SO$_3$. The material was purified via filtration through a plug of silica gel (1:1 Et$_2$O:hexanes as eluant) to provide the 1-(3-trifluoromethylphenyl)propenone as an oil (320 mg, 65% yield), which solidified upon standing in the freezer. $^1$H-NMR (300 MHz, CDCl$_3$): δ 8.20 (s, 1H), 8.13 (d, 1H, J=7.7 Hz), 7.84 (d, 1H, J=9.0 Hz),7.64 (t, 1H, J=7.7 Hz), 7.16 (dd, 1H, J=17.2, 10.6 Hz), 6.49 (dd, 1H, J=17.2, 1.5 Hz), 6.03 (dd, 1H, J=10.6, 1.5 Hz).

(28b) The compound (±) [(1S*,2R*,4R*)-4-azido-2-(4-methylsulfanyl-benzenesulfonylmetyl)-cyclohexyl]-carbamic acid tert-butyl ester (2.36 g, 5.36 mmol, see procedure 10d above) was dissolved in 2:1 CH$_2$Cl$_2$/TFA and stirred at rt for 1 h before being concentrated in vacuo. The resulting residue was redissolved in 1N NaOH and this solution was extracted twice with Et$_2$O. The extracts were combined, washed with brine, dried (MgSO$_4$), filtered, and concentrated in vacuo. The product amine was dissolved in MeOH (40 mL), cooled to −10° C., and treated with a solution of the 1-(3-trifluoromethylphenyl)propenone (1.09 g, 5.23 mmol) in MeOH (10 mL). The reaction was stirred for 30 min at rt, diluted with EtOAc, and washed successively with sat. NaHCO$_3$ and brine. The organic phase was dried (MgSO$_4$), filtered, and concentrated in vacuo. The resultant residue was purified by flash chromatography to give the desired (±) 3-[(1S*,2R*,4R*)-4-azido-2-(4-methylsulfanyl-benzenesulfonylmethyl)-cyclohexylamino]-1-(3-trifluoromethyl-phenyl)-propan-1-one (2.0 g, 69% yield). MS found: (M+H)$^+$=541.3.

(28c) To a cooled (0° C.) solution of dimethylphosphonoacetic acid tert-butyl ester (0.44 mL, 2.22 mmol) in THF (20 mL) was added sodium hydride (94 mg, 60 wt % dispersion in oil, 2.35 mmol) in one portion. The mixture was stirred for 30 minutes at 0° C. and then charged with a solution of (±) 3-[(1S*,2R*,4R*)-4-azido-2-(4-methylsulfanyl-benzenesulfonylmethyl)-cyclohexylamino]-1-(3-trifluoromethyl-phenyl)-propan-1-one (0.75 g, 1.38 mmol) in THF. The reaction was stirred for 64 h at rt, quenched with sat. NH$_4$Cl, and extracted twice with EtOAc. The organic extracts were combined, washed with brine, dried (Na$_2$SO$_4$), filtered, and concentrated in vacuo. The crude residue was purified by flash chromatography to afford diastereomerically-pure (±) E-[5-[(1S*,2R*,4R*)-4-azido-2-(4-methylsulfanyl-benzenesulfonylmethyl)-cyclohexylamino]-3-(3-trifluoromethyl-phenyl)-pent-2-enoic acid tert-butyl ester] (0.26 g, 29% yield) and a number of impure fractions of the same compound contaminated with its Z-diastereomer. MS found: (M+H)$^+$=639.3.

(28d) The compound (±) E-[5-[(1S*,2R*,4R*)-4-azido-2-(4-methylsulfanyl-benzenesulfonylmethyl)-cyclohexylamino]-3-(3-trifluoromethyl-phenyl)-pent-2-enoic acid tert-butyl ester] (0.26 g, 0.4 mmol) was dissolved in 2:1 CH$_2$Cl$_2$/TFA and stirred at rt for 1 h before being concentrated in vacuo. The residue was redissolved in CH$_2$Cl$_2$ and concentrated in vacuo; this procedure was repeated once. The unpurified amino acid was dissolved in CH$_2$Cl$_2$, and the resulting solution was sequentially charged with N,N-diisopropylethylamine (0.3 mL, 1.6 mmol), 4-dimethylaminopyridine (54 mg, 0.44 mmol), and HATU (170 mg, 0.44 mmol). The mixture was stirred for 14 h at rt, quenched with sat. NH$_4$Cl, and extracted twice with EtOAc. The organic extracts were combined, washed with brine, dried (Na$_2$SO$_4$), filtered, and concentrated in vacuo. The crude residue was purified by flash chromatography to afford (±) 1-[(1S*,2R*, 4R*)-4-azido-2-(4-methylsulfanyl-benzenesulfonylmethyl)-cyclohexyl]-4-(3-trifluoromethyl-phenyl)-5,6-dihydro-1H-pyridin-2-one (0.2 g, 89% yield). The entirity of this material was dissolved in MeOH. The resultant solution was charged with 0.1 g of 10% Pd/BaSO$_4$, and the flask was evacuated and then back-filled with hydrogen (1 atm). This procedure was repeated several times. The reaction was stirred for 12 h and then filtered. The resultant solution was concentrated in vacuo to provide (±) 1-[(1S*,2R*,4R*)-4-amino-2-(4-methylsulfanyl-benzenesulfonylmethyl)-cyclohexyl]-4-(3-trifluoromethyl-phenyl)-5,6-dihydro-1H-pyridin-2-one (quantitative; ~90% purity). MS found: (M+H)$^+$=538.

(28e) To a solution of (±) 1-[(1S*,2R*,4R*)-4-amino-2-(4-methylsulfanyl-benzenesulfonylmethyl)-cyclohexyl]-4-(3-trifluoromethyl-phenyl)-5,6-dihydro-1H-pyridin-2-one (0.36 mmol) in dichloroethane (6 mL) was added acetic acid (0.1 mL, 1.8 mmol), acetone (0.08 mL, 1.1 mmol), and sodium triacetoxyborohydride (0.23 g, 1.1 mmol). The mixture was heated at 80° C. for 1 h, cooled to rt, and quenched with sat. NaHCO$_3$, and extracted twice with EtOAc. The

Example 29

(±) 1-[(1S*,2R*,4R*)-4-Isopropylamino-2-(4-benzenesulfonylmethyl)-cyclohexyl]-4-(3-trifluoromethyl-phenyl)-5,6-dihydro-1H-pyridin-2-one (29a) The title compound was isolated from a separate fraction of the reverse-phase HPLC purification described in procedure 28e above. MS found: (M+H)$^+$=535.

Example 30

(±) 1-[(1S*,2R*,4R*)-4-Isopropylmethylamino-2-(4-methylsulfanyl-benzenesulfonylmethyl)-cyclohexyl]-4-(3-trifluoromethyl-phenyl)-5,6-dihydro-1H-pyridin-2-one (30a) To a solution of (±) 1-[(1S*,2R*,4R*)-4-isopropylamino-2-(4-methylsulfanyl-benzenesulfonyl-methyl)-cyclohexyl]-4-(3-trifluoromethyl-phenyl)-5,6-dihydro-1H-pyridin-2-one (0.18 mmol) in MeOH (4 mL) was added formaldehyde (0.09 mL of a 37 wt % solution in water, 1.08 mmol) and sodium cyanoborohydride (0.023 g, 0.36 mmol). The reaction was stirred for 3 h, quenched with sat. NaHCO$_3$, and extracted twice with EtOAc. The organic extracts were combined, washed with brine, dried (Na$_2$SO$_4$), filtered, and concentrated in vacuo. The crude residue was purified by reverse-phase HPLC to provide the title compound. MS found: (M+H)$^+$=595.4.

Example 31

(±) 1-[(1S,2R*,4R*)-4-Amino-2-(4-methylsulfanyl-benzenesulfonylmethyl)-cyclohexyl]-4-(3-trifluoromethoxyphenyl)-5,6-dihydro-1H-pyridin-2-one (31a) meta-Trifluoromethoxybenzaldehyde (4.63 g) was incorporated into procedure (28a) above to provide 1-(3-trifluoromethoxyphenyl)propenone (2.57 g, 50% yield). A portion of this material (0.35 g, 1.75 mmol) was carried through procedures (28b)-(28d) to give a residue, which was purified by reverse-phase HPLC to provide the title compound (0.043 g). MS found: (M+H)$^+$=555.2.

Example 32

(±) 1-[(1S*,2R*,4R*)-4-Isopropylamino-2-(4-methylsulfanyl-benzenesulfonylmethyl)-cyclohexyl]-4-(3-trifluoromethoxyphenyl)-5,6-dihydro-1H-pyridin-2-one (32a) The product of procedure (31a), (±) 1-[(1S*,2R*,4R*)-4-amino-2-(4-methylsulfanyl-benzenesulfonylmethyl)-cyclohexyl]-4-(3-trifluoromethoxyphenyl)-5,6-dihydro-1H-pyridin-2-one (0.026 g, 0.046 mmol), was carried through procedure (28e) above to afford the title compound (0.013 g, 47% yield) after purification by reverse-phase HPLC. MS found: (M+H)$^+$=597.2.

Example 33

(±) 1-[(1S,2R*,4R*)-4-Isopropylamino-2-(4-benzenesulfonylmethyl)-cyclohexyl]-4-(3-trifluoromethyl-phenyl)-piperidin-2-one (33a) The product of procedure (28e), (±) 1-[(1S*,2R*,4R*)-4-isopropylamino-2-(4-methylsulfanyl-benzenesulfonylmethyl)-cyclohexyl]-4-(3-trifluoromethyl-phenyl)-5,6-dihydro-1H-pyridin-2-one (~10 mg), was dissolved in MeOH. The resulting solution was charged with ~20 mg 10% Pd/C, stirred under 1 atm of H$_2$ for 12 h, filtered, and concentrated in vacuo. The residue was redissolved in MeOH. The resulting solution was charged with ~40 mg 10% Pd/C, stirred under 55 atm of H$_2$ for 12 h, filtered, and concentrated in vacuo. The residue was redissolved in MeOH. The resulting solution was charged with ~50 mg 10% Pd/C, stirred under 55 atm of H$_2$ for 36 h, filtered, and concentrated in vacuo. The residue was dissolved in 0.5% TFA/MeCN and concentrated in vacuo to afford a mixture of diastereomers as the title compound as its TFA salt (10 mg). MS found: (M+H)$^+$=537.

Example 34

(S)-3-(3-(trifluoromethyl)benzylamino)-1-((1S,2R,4R)-4-(isopropyl(methyl)amino)-2-((4-(methylthio)phenylsulfonyl)methyl)cyclohexyl)pyrrolidin-2-one (34a) 3-(Trifluoromethyl)benzaldehyde and sodium cyanoborohydride (instead of 3-trifluoromethylphenyl isocyanate) in MeOH (instead of DMF) were incorporated into Example 18 to give the title compound. MS found: (M+H)$^+$=612.3.

Example 35

3(R)-(3-(trifluoromethyl)phenethyl)-1-((1S,2R,4R/S)-4-(isopropylamino)-2-(phenylsulfonylmethyl)cyclohexyl)pyrrolidin-2-one trifluoroacetate (35a) 3-(Trifluoromethyl)phenethyl alcohol (10.0 g, 52.6 mmol), triphenylphosphine (17.9 g, 68.4 mmol), and imidazole (5.00 g, 73.6 mmol) were dissolved in acetonitrile (42 mL) and ether (70 mL), then the mixture was cooled to 0° C. Iodine (18.7 g, 73.6 mmol) was added in portions, then the mixture was stirred for 4 h. The reaction mixture was diluted with ether (1 L), washed with saturated Na$_2$S$_2$O$_3$ (3×300 mL), aqueous CuSO$_4$ (2×300 mL), and brine (2×300 mL), dried over Na$_2$SO$_4$, filtered, and concentrated to a volume of 200 mL. The precipitate of triphenylphosphineoxide was removed by filtration and the filtrate was triturated with ether/hexanes (2:1, 300 mL). Additional triphenylphosphine-oxide was removed by filtration, and the filtrate was concentrated to dryness to provide 1-(2-iodoethyl)-3-trifluoromethylbenzene as a yellow oil (16.5 g, quantitative): $^1$H NMR (300 MHz, CDCl$_3$) δ 7.54–7.35 (m, 4H), 3.37 (t, J=8.3 Hz, 2H), 3.24 (t, J=8.3 Hz, 2H); $^{19}$F NMR (282 MHz, CDCl$_3$) δ –63.1.

(35b) To a 100-mL three-neck round-bottomed flask equipped with a thermometer, addition funnel, and nitrogen inlet was added diisopropylamine (2.4 mL, 17.2 mmol) in THF (4 mL). The solution was cooled to –78° C., then a solution of n-BuLi (2.5 M in hexanes, 6.9 mL) was added slowly, followed by HMPA (3.1 mL, 18.0 mmol) and the reaction was stirred at this temperature for 30 min. A solution of ethylpent-4-enoate (2.0 g, 15.6 mmol) in THF (15.6 mL) was added dropwise, then the mixture was stirred for 45 min. To this mixture was added a solution of 1-(2-iodoethyl)-3-trifluoromethylbenzene (35a) (1.37 g, 4.58 mmol) in THF (2 mL) and the resulting mixture was allowed to warm to room temperature overnight. The mixture was diluted with ether (500 mL), washed with water (2×250 mL), and brine (2×250 mL), dried over $Na_2SO_4$, filtered, and evaporated. The residue was purified by flash chromatography to provide 2-[2-(3-trifluoromethylphenyl)ethyl]pent-4-enoic acid ethyl ester (529 mg, 39%) as a colorless oil: ESI MS m/z 301 $[C_{16}H_{19}F_3O_2+H]^+$.

(35c) 2-[2-(3-Trifluoromethylphenyl)ethyl]pent-4-enoic acid ethyl ester (529 mg, 1.76 mmol) was dissolved in $CH_2Cl_2$ and cooled to −78° C. The resulting solution was treated with ozone until a light blue color was observed. The solution was degassed with $N_2$, then polymer-supported $Ph_3P$ (3 mmol/g, 882 mg, 2.64 mmol) was added and the mixture was stirred for 3 h at room temperature. The solid was removed by filtration and rinsed with $CH_2Cl_2$. Evaporation of the filtrate provided an oil, which was purified by flash column chromatography (hexanes/ether) to give ethyl 2-((1,2,3-trioxolan-4-yl)methyl)-4-(3-(trifluoromethyl)phenyl)butanoate as a colorless oil (151 mg, 25%) and the desired ethyl 2-(2-oxoethyl)-4-(3-(trifluoromethyl)phenyl) butanoate as a colorless oil (83 mg, 16%). A solution of ethyl 2-((1,2,3-trioxolan-4-yl)methyl)-4-(3-(trifluoromethyl)phenyl)butanoate (150 mg, 431 μmol) in $CH_2Cl_2$ (20 mL) was cooled to −78° C., then $Me_2S$ (0.3 mL, 4.1 mmol) was added and the mixture was stirred for 2 d. The reaction mixture was diluted with $CH_2Cl_2$ (300 mL), washed with water (2×100 mL), and brine (100 mL), dried over $Na_2SO_4$, filtered, and evaporated to provide additional ethyl 2-(2-oxoethyl)-4-(3-(trifluoromethyl)phenyl)butanoate (123 mg): $^1H$ NMR (300 MHz $CDCl_3$) δ 7.50–7.30 (m, 4H), 5.26–5.20 (m, 1H), 5.14 (d, J=1.6 Hz, 1H), 5.04 (d, J=6.3 Hz, 1H), 4.37 (q, J=7.0 Hz, 2H), 2.73–2.57 (m, 3H), 2.35–1.77 (m, 4H), 1.29 (t, J=7.1 Hz, 3H); $^{19}F$ NMR (282 MHz, $CDCl_3$) δ −63.0.

(35d) Ethyl 2-(2-oxoethyl)-4-(3-(trifluoromethyl)phenyl) butanoate (83 mg, 275 μmol) and (7R,8S)-7-(benzene-4-sulfonylmethyl)-1,4-dioxa-spiro[4.5]dec-8-ylamine [3 g by substitution of phenyl disulfide into step (3d) and skipping step (3f)] (68 mg, 218 μmol) were dissolved in 1,2-dichloroethane (2.3 mL). The resulting solution was stirred at room temperature for 10 min, then sodium triacetoxyborohydride (58 mg, 275 μmol) was added and the mixture was stirred overnight. The reaction mixture was diluted with $CH_2Cl_2$ (400 mL), washed with saturated $NH_4Cl$ (3×150 mL), and brine (200 mL), dried over $Na_2SO_4$, filtered and evaporated. The residue was purified by flash column chromatography to give an inseparable mixture of diastereomers 4-(7-benzenesulfonylmethyl-1,4-dioxaspiro[4.5]dec-8-ylamino)-2-[2-(3-trifluoromethylphenyl)ethyl]butyric acid ethyl ester (64 mg, 49%): ESI MS m/z 598 $[C_{30}H_{38}F_3NO_6S+H]^+$.

(35e) The mixture of diastereomers from above (35d) (92 mg, 154 mmol) was dissolved in MeOH (10 mL) and NaOMe (85 mg) was added. The mixture was heated at 50° C. for 16 h, then diluted with EtOAc (300 mL). The mixture was washed with water (3×150 mL) and brine (200 mL), dried over $Na_2SO_4$, and evaporated in vacuo to dryness. The residue was purified by flash column chromatography to provide (1S, 2R)-1-(7-benzenesulfonylmethyl-1,4-dioxaspiro[4.5]dec-8-yl)-3(R)-[2-(3-trifluoromethylphenyl)ethyl] pyrrolidin-2-one (upper TLC spot; 30 mg, 35%): 1H NMR (300 MHz, $CDCl_3$) δ 7.88–7.80 (m, 2H), 7.62–7.35 (m, 7H), 4.03–3.70 (m, 6H), 3.52–3.39 (m, 1H), 3.37–3.25 (m, 1H), 3.06 (dd, J=14.6, 2.1 Hz, 1H), 2.88–2.67 (m, 3H), 2.33–1.55 (m, 11H); $^{19}F$ NMR (282 MHz, $CDCl_3$) δ −63.0; ESI MS m/z 552 $[C_{28}H_{32}F_3NO_5S+H]^+$; and (1S, 2R)-1-(7-benzenesulfonylmethyl-1,4-dioxaspiro[4.5]dec-8-yl)-3(S)-[2-(3-trifluoromethylphenyl)ethyl]pyrrolidin-2-one (lower TLC spot; 34 mg, 41%) $^1H$ NMR (300 MHz, $CDCl_3$) δ 7.88–7.80 (m, 2H), 7.60–7.35 (m, 7H), 4.03–3.73 (m, 6H), 3.40–3.25 (m, 2H), 2.97 (dd, J=14.3, 1.9 Hz, 1H), 2.80–2.62 (m, 3H), 2.40–1.40 (m, 11H); $^{19}F$ NMR (282 MHz, $CDCl_3$) δ −63.0; ESI MS m/z 552 $[C_{28}H_{32}F_3NO_5S+H]^+$.

(35f) (1S, 2R)-1-(7-benzenesulfonylmethyl-1,4-dioxaspiro[4.5]dec-8-yl)-3(R)-[2-(3-trifluoromethylphenyl)ethyl] pyrrolidin-2-one (29 mg, 53 mmol) and p-TsOH (4 mg) in acetone (5 mL) was stirred overnight at room temperature. A second portion of p-TsOH (4 mg) was added and the reaction mixture was stirred for an additional 24 h. The solvent was evaporated in vacuo and the residue was purified by flash column chromatography to afford (R)-3-(3-(trifluoromethyl)phenethyl)-1-((1S, 2R)-4-oxo-2-(phenylsulfonylmethyl)cyclohexyl)pyrrolidin-2-one (17 mg, 64%) as a white solid: ESI MS m/z 508 $[C_{26}H_{28}F_3NO_4S+H]^+$.

(35g) To a stirred mixture of the above compound (35f) (17 mg, 34 mmol) and titanium(IV) isopropoxide (0.5 mL, 1.67 mmol) was added 2-propylamine (36 mg, 600 mmol). The mixture was stirred at room temperature for 3 h, then MeOH (5 mL) was added, followed by $NaBH_4$ (3.5 mg, 94 mmol). After 2 h, the reaction mixture was quenched with 0.5 M NaOH (30 mL) and the resulting mixture was stirred for 2 h. The mixture was diluted with EtOAc (400 mL), washed with 0.5 M NaOH (3×150 mL) and brine (200 mL), dried over $Na_2SO_4$, filtered, and evaporated. Purification of the residue by semi-preparative HPLC gave the title compound (10 mg) as a mixture of diastereomers: $^1H$ NMR (300 MHz, $CDCl_3$) δ 8.00–7.75 (m, 2H), 7.73–7.30 (m, 7H), 4.60–1.50 (m, 20H), 1.49–1.20 (m, 6H).

Example 36

3(S)-(3-(Trifluoromethyl)phenethyl)-1-((1S,2R,4R/S)-4-(isopropylamino)-2-(phenylsulfonylmethyl) cyclohexyl)pyrrolidin-2-one trifluoroacetate (36a) (1S, 2R)-1-(7-Benzenesulfonylmethyl-1,4-dioxaspiro[4.5]dec-8-yl)-3(S)-[2-(3-trifluoromethylphenyl)ethyl] pyrrolidin-2-one (see, 35e) was incorporated into Example 35, step (35f) to give the title compound as a mixture of diastereomers. MS found: $(M+H)^+=551.4$.

Example 37

N-((S)-1-((1S, 2R, 4R)-4-(isopropyl(methyl)amino)-2-(phenylsulfonylmethyl)cyclohexyl)-2-oxoazepan-3-yl)-3-(trifluoromethyl)benzamide trifluoroacetate (37a) To a solution of (S)-2-tert-butoxycarbonylamino-6-hydroxy-hexanoic acid (1 g, 6 mmol) in 30 mL of $CH_2Cl_2$ and 5 mL of MeOH at rt was slowly added $TMSCHN_2$ (10 mL), and the reaction mixture was left with stirring for 1 h. The solvent was remove under reduced pressure, and the resulting residue was diluted with water and EtOAc. The organic layer was separated, dried over $Na_2SO_4$, and concentrated to afford an oil (S)-2-tert-butoxycarbonylamino-6-hydroxy-hexanoic acid methyl ester. MS $[M+H]^+$ 262.

(37b) To a solution of oxalyl chloride (0.33 mL, 0.36 mmol) in $CH_2Cl_2$ (10 mL) at −78 C. was added DMSO (0.1 mL, 1.32 mmol). Ten minutes later, a solution of alcohol (S)-2-tert-butoxycarbonylamino-6-hydroxy-hexanoic acid methyl ester (144 mg, 0.55 mmol) in $CH_2Cl_2$ (10 mL) was added and stirred for 15 min before $iPr_2NEt$ (0.5 mL, 2.7 mmol) was added. The reaction mixture was allowed to warm up to 0 C. and left with stirring for 2 h before water and EtOAc were added. The organic layer was separated, dried over Na$_2$SO$_4$, and concentrated to afford to a crude oil (S)-2-tert-butoxycarbonylamino-6-oxo-hexanoic acid methyl ester.

(37c) To a solution of (1S*,2R*,4R*)-4-azido-2-benzenesulfonylmethyl-cyclohexylamine (see example 10, steps 10a–10d with the substitution of methyl phenyl sulfone in step 10a and then treated with TFA) (135 mg, 0.45 mmol) and (S)-2-tert-butoxycarbonylamino-6-oxo-hexanoic acid methyl ester (140 mg, 0.55 mmol) in CH$_2$Cl$_2$ (15 mL) at rt was added NaBH(OAc)$_3$ (194 mg, 0.9 mmol). After 16 h, the solution was concentrated. The resulting residue was re-dissolved in EtOAc and washed with saturated NaHCO$_3$, water, and brine. The organic layer was dried, filtered, and concentrated to afford to a crude oil (1S,2R,3S,4R)-6-(4-azido-2-benzenesulfonylmethyl-cyclohexylamino)-2-tert-butoxycarbonylamino-hexanoic acid methyl ester. MS [M+H]$^+$=538.

(37d) To a solution of (1S,2R,3S,4R)-6-(4-azido-2-benzenesulfonylmethyl-cyclohexylamino)-2-tert-butoxycarbonylamino-hexanoic acid methyl ester (270 mg) in THF (15 mL) and H$_2$O (3 mL) at rt was added LiOH (24 mg). After 1 h, the reaction was diluted with water and EtOAc. Upon adjusting the pH value to 7, the organic layer was collected, dried, and concentrated to afford to a crude oil (140 mg) which was re-dissolved in DMF (15 mL), followed by the addition of HATU (132 mg, 0.34 mmol) and Hunig's base (0.06 mL, 0.34 mmol). The resulting mixture was stirred for 16 before EtOAc layer was added. The EtOAc layer was washed with 1 N HCl, NaHCO$_3$ solution (aq), and brine. The EtOAc was dried (MgSO$_4$), filtered, and concentrated. Flash chromatography of the resulting residue gave [(3S)-1-(1S,2R,4R)-(4-azido-2-benzenesulfonylmethyl-cyclohexyl)-2-oxo-azepan-3-yl]-carbamic acid tert-butyl ester (120 mg). MS found: (M+H)$^+$=506.

(37e) To a solution of [(3S)-1-(1S,2R,4R)-(4-azido-2-benzenesulfonylmethyl-cyclohexyl)-2-oxo-azepan-3-yl]-carbamic acid tert-butyl ester (120 mg) in CH$_2$Cl$_2$ (10 mL) was added TFA (3.3 mL). After 45 min, the solution was diluted with NaHCO$_3$ solution (aq) and EtOAc. The organic layer was collected, dried, and concentrated to afford to a crude oil 3-amino-(3S)-1-(1S,2R,4R)-(4-azido-2-benzenesulfonylmethyl-cyclohexyl)-azepan-2-one. MS [M+H]$^+$=406.

(37f) To a solution of 3-amino-(3S)-1-(1S,2R,4R)-(4-azido-2-benzenesulfonylmethyl-cyclohexyl)-azepan-2-one (50 mg, 0.12 mmol) in DMF (15 mL) was added 3-trifluoromethyl benzoic acid (28 mg, 0.15 mmol), HATU (57 mg, 0.15 mmol) and Hunig's base (0.03 mL, 0.15 mmol). The resulting mixture was stirred for 16 h before EtOAc was added. The EtOAc layer was washed with 1 N HCl, NaHCO$_3$ solution (aq), and brine. The EtOAc was dried (MgSO$_4$), filtered, and concentrated. Flash chromatography of the resulting residue gave N-[(3S)-1-(1S,2R,4R)-(4-azido-2-benzenesulfonylmethyl-cyclohexyl)-2-oxo-azepan-3-yl]-3-trifluoromethyl-benzamide (70 mg). MS found: (M+H)$^+$=578.

(37g) N-[(3S)-1-(1S,2R,4R)-(4-Azido-2-benzenesulfonylmethyl-cyclohexyl)-2-oxo-azepan-3-yl]-3-trifluoromethyl-benzamide (70 mg) was dissolved in MeOH (10 mL) prior to the addition of 10% Pd/C (20 mg). A hydrogen balloon was added and the solution was stirred at rt for 16 h. The palladium was filtered and the solvent was concentrated to N-[(3S)-1-(1S,2R,4R)-(4-amino-2-benzenesulfonylmethyl-cyclohexyl)-2-oxo-azepan-3-yl]-3-trifluoromethyl-benzamide. MS found: (M+H)$^+$=552.

(37h) To a solution of N-[(3S)-1-(1S,2R,4R)-(4-amino-2-benzenesulfonylmethyl-cyclohexyl)-2-oxo-azepan-3-yl]-3-trifluoromethyl-benzamide (30 mg) in CH$_2$Cl$_2$ (15 mL) at rt was added NaBH(OAc)$_3$ (50 mg), acetone (2 mL), and three drops of AcOH. After 2 h, formaldehyde (2 mL) was added and the solution was stirred for another 2 h. The reaction mixture was diluted with EtOAc and washed with saturated NaHCO$_3$, water, and brine. The organic layer was dried, filtered, and concentrated to afford to a crude oil which was purified by semi-preparative HPLC to give the title compound. MS [M+H]$^+$32 608.

Example 38

N-((S)-1-((1S,2R,4R)-4-(dimethylamino)-2-(phenylsulfonylmethyl)cyclohexyl)-2-oxopiperidin-3-yl)-3-(trifluoromethyl)benzamide trifluoroacetate (38a) (S)-2-tert-Butoxycarbonylamino-5-hydroxy-pentanoic acid benzyl ester was incorporated into Example 37 (without acetone in step 37 h) to give the title compound. MS found: (M+H)$^+$=566.

Example 39

(R*)-1-((1S*,2R*,4R*)-4-(isopropyl(methyl)amino)-2-(phenylsulfonylmethyl)cyclohexyl)-3-((2-(3-(trifluoromethyl)phenyl)-1,3-dioxolan-2-yl)methyl)pyrrolidin-2-one (39a) A mixture of methyl 3-bromopropionate (6a, 10.0 g, 60.0 mmol) and sodium iodide (11.2 g, 74.9 mmol) in acetone (60 mL) was stirred for 30 min at room temperature, then heated at reflux for 40 min. The mixture was cooled in an ice/water bath and the white solid was filtered off, rinsing with acetone. The filtrate was evaporated to dryness to provide methyl 3-iodopropionate (12.3 g, 96%) as a yellow oil: $^1$H NMR (300 MHz, CDCl$_3$) δ 3.73 (s, 3H), 3.33 (t, J=7.2 Hz, 2H), 2.99 (t, J=7.2 Hz, 2H).

(39b) To a 250-mL three-neck round-bottomed flask equipped with a thermometer, condenser, and nitrogen inlet was added Zn—Cu couple (3.41 g, 52.1 mmol). A solution of methyl 3-iodopropionate (7.27 g, 34.0 mmol) in benzene (67.7 mL) and DMA (4.5 mL) was added over 5 min and the mixture was stirred at room temperature for 1 h, then heated at 60° C. for 5 h. A mixture of Pd(PPh$_3$)$_4$ (1.05 g, 0.906 mmol) in benzene (22.7 mL) was added to the reaction and stirred at 60° C. for 5 min. The mixture was then removed from heat and 3-(trifluoromethyl)benzoyl chloride (3.4 mL, 23 mmol) in benzene (11.3 mL) was added immediately. After stirring for 2 h, the mixture was diluted with EtOAc, washed with 1 M HCl (3×200 mL), NaHCO$_3$ (2×200 mL) and brine (1×200 mL), dried over Na$_2$SO$_4$, filtered, and evaporated. The crude material was purified by CombiFlash chromatography (silica, 0–70% ether/hexanes) to give 4-oxo-4-(3-trifluoromethylphenyl)butyric acid methyl ester (5.35 g, 91%) as an orange oil: $^1$H NMR (300 MHz CDCl$_3$) δ 8.24 (s, 1H), 8.17 (d, J=7.8 Hz, 1H), 7.84 (d, J=7.8 Hz, 1H), 7.63 (t, J=7.8 Hz, 1H), 3.72 (s, 3H), 3.35 (t, J=6.5 Hz, 2H), 2.81 (t, J=6.5 Hz, 2H); $^{19}$F NMR (282 MHz, CDCl$_3$) δ −63.3; ESI MS m/z 261 [C$_{12}$H$_{11}$F$_3$O$_3$+H]$^+$.

(39c) A solution of 4-oxo-4-(3-trifluoromethylphenyl)butyric acid methyl ester (2.47 g, 9.50 mmol), trimethylorthoformate (4.8 mL), p-TsOH (181 mg, 0.95 mmol) and ethylene glycol (7.3 mL) was heated at 50° C. for 3 h. The mixture was diluted with EtOAc (500 mL), washed with saturated NaHCO$_3$ (3×200 mL), water (2×200 mL), and brine (150 mL), dried over Na$_2$SO$_4$, filtered and evaporated to give a mixture of esters. The mixture was stirred in MeOH (25 mL) with NaOMe (400 mg) at room temperature for 6 h. The reaction was quenched with saturated NH$_4$Cl and the methanol was removed by evaporation. The residue was dissolved in EtOAc, washed with saturated NH$_4$Cl (2×200 mL), water (2×200 mL) and brine (200 mL), dried over Na$_2$SO$_4$, and evaporated to give 3-[2-(3-trifluoromethylphenyl)-[1,3]dioxolan-2-yl]propionic acid methyl ester (2.71 g, 94%) as a light yellow oil: $^1$H NMR (300 MHz, CDCl$_3$) δ 7.73 (s, 1H), 7.65 (d, J=7.7 Hz, 1H), 7.56 (d, J=7.7 Hz, 1H), 7.47 (t, J=7.7 Hz, 1H), 4.10–3.99 (m, 2H), 3.80–3.70 (m, 2H), 3.65 (s, 3H), 2.44 (t, J=7.8 Hz, 2H), 2.24 (t, J=7.8 Hz, 2H); $^{19}$F NMR (282 MHz, CDCl$_3$) δ –62.9; ESI MS m/z 305 [C$_{14}$H$_{15}$F$_3$O$_4$+H]$^+$.

(39d) Diisopropylamine (1.74 mL, 12.5 mmol) was dissolved in THF (6.2 mL) under a nitrogen atmosphere and cooled to –78° C. A solution of n-BuLi (2.5 M in hexanes, 5.3 mL) was added dropwise, keeping the temperature below –67° C. The reaction was warmed to –15° C. for 15 min, then cooled back down to –78° C. A solution of 3-[2-(3-trifluoromethylphenyl)-[1,3]dioxolan-2-yl]propionic acid methyl ester (2.71 g, 8.90 mmol) in THF (1.5 mL) was added and the mixture was stirred for 40 min. Allyl bromide (0.92 mL, 11 mmol) and HMPA (0.46 mL, 2.7 mmol) were added simultan-eously and the reaction was stirred at room temperature overnight. The mixture was diluted with EtOAc (400 mL), washed with saturated NH$_4$Cl (3×150 mL), water (2×150 mL), and brine (200 mL), dried over Na$_2$SO$_4$, filtered, and evaporated. The residue was purified by CombiFlash chromatography (silica, 0–40% ether/heptane) to give 2-[2-(3-trifluoromethylphenyl)-[1,3]dioxolan-2-ylmethyl]pent-4-enoic acid methyl ester (1.82 g, 59%) as a light yellow oil: $^1$H NMR (300 MHz, CDCl$_3$) δ 7.73 (s, 1H), 7.64 (d, J=7.7 Hz, 1H), 7.56 (d, J=7.7 Hz, 1H), 7.46 (t, J=7.7 Hz, 1H), 5.80–5.61 (m, 1H), 5.10–4.97 (m, 2H), 4.10–3.90 (m, 2H), 3.80–3.60 (m, 5H), 2.83–2.68 (m, 1H), 2.50–2.13 (m, 3H), 1.97 (dd, J=14.7, 2.7 Hz, 1H); $^{19}$F NMR (282 MHz, CDCl$_3$) δ –62.9; ESI MS m/z 345 [C$_{17}$H$_{19}$F$_3$O$_4$+H]$^+$.

(39e) A solution of 2-[2-(3-trifluoromethylphenyl)-[1,3]dioxolan-2-ylmethyl]pent-4-enoic acid methyl ester (1.82 g, 5.29 mmol) in CH$_2$Cl$_2$ (250 mL) was cooled to –78° C. and ozone was bubbled into the solution until a light blue solution was obtained. The solution was degassed with nitrogen, then dimethylsulfide (4 mL) was added dropwise. The mixture was stirred overnight at room temperature, then heated at reflux for 24 h. The reaction was diluted with CH$_2$Cl$_2$ (500 mL), washed with 1 M HCl (3×150 mL) and brine (200 mL), dried over Na$_2$SO$_4$, filtered, and evaporated. The residue was purified by CombiFlash chromatography (silica, 0–50% ether/hexanes) to give aldehyde 4-oxo-2-[2-(3-trifluoromethylphenyl)-[1,3]dioxolan-2-ylmethyl]butyric acid methyl ester (1.41 g, 77%) as a yellow oil: $^1$H NMR (300 MHz, CDCl$_3$) δ 9.74 (s, 1H), 7.72 (s, 1H), 7.63 (d, J=7.7 Hz, 1H), 7.57 (d, J=7.7 Hz, 1H), 7.47 (t, J=7.7 Hz, 1H), 4.12–3.95 (m, 2H), 3.83–3.64 (m, 5H), 3.27–3.13 (m, 1H), 2.98–2.70 (m, 2H), 2.40 (dd, J=14.8, 7.2 Hz, 1H), 2.04 (dd, J=14.8, 5.5 Hz, 1H); $^{19}$F NMR (282 MHz, CDCl$_3$) δ –62.9.

(39f) A mixture of (1S*,2R*,4R*)-4-azido-2-benzenesulfonylmethyl-cyclohexylamine (see 37c) (676 mg, 2.30 mmol) and 4-oxo-2-[2-(3-trifluoromethylphenyl)-[1,3]dioxolan-2-ylmethyl]butyric acid methyl ester (794 mg, 2.30 mmol) in 1,2-dichloroethane (46 mL) was stirred at room temperature overnight. The solvent was removed under vacuum, then the residue was dissolved in MeOH (35 mL) and cooled to 0° C. Sodium borohydride (872 mg, 23.0 mmol) was added in one portion and the mixture was stirred for 4 h. The reaction was diluted with EtOAc (500 mL), washed with saturated NaHCO$_3$ (3×150 mL) and brine (200 mL), dried over Na$_2$SO$_4$, filtered, and evaporated. The residue was purified by CombiFlash chromatography (silica, 0–100% ether/hexanes) to give a mixture of diastereomers methyl 4-((1S*,2R*,4R*)-4-azido-2-(phenylsulfonylmethyl)cyclohexylamino)-2-((2-(3-(trifluoromethyl)phenyl)-1,3-dioxolan-2-yl)methyl)butanoate (1.04 g, 70%) as a colorless oil: $^1$H NMR (300 MHz, CDCl$_3$) δ 8.00–7.88 (m, 2H), 7.75–7.52 (m, 6H), 7.51–7.41 (m, 1H), 4.17–3.88 (m, 2H), 3.80–3.60 (m, 5H), 3.59–3.48 (m, 1H), 3.45–3.30 (m, 1H), 3.10–2.98 (m, 1H), 2.85–2.55 (m, 3H), 2.50–2.20 (m, 3H), 2.00–1.30 (m, 9H); $^{19}$F NMR (282 MHz, CDCl$_3$) δ –62.9, –62.8; ESI MS m/z 625 [C$_{29}$H$_{35}$F$_3$N$_4$O$_6$S+H]$^+$.

(39g) A stirred mixture of diastereomers 39f (1.04 g, 1.66 mmol) and NaOMe (90 mg, 1.66 mg) in MeOH (20 mL) was heated at reflux for 4 d. The solvent was removed under vacuum and the residue was dissolved in EtOAc (350 mL). The organic mixture was washed with saturated NH$_4$Cl (3×100 mL), water (200 mL), and brine (200 mL), dried over Na$_2$SO$_4$, filtered, and evaporated. The crude material was purified by CombiFlash chromatography followed by preparative TLC to give (S*)-1-((1S*,2R*,4R*)-4-azido-2-(phenylsulfonylmethyl)cyclohexyl)-3-((2-(3-(trifluoromethyl)phenyl)-1,3-dioxolan-2-yl)methyl)pyrrolidin-2-one (39g-a, 359 mg, 36%) and (R*)-1-((1S*,2R*,4R*)-4-azido-2-(phenylsulfonylmethyl)cyclohexyl)-3-((2-(3-(trifluoromethyl)phenyl)-1,3-dioxolan-2-yl)methyl)pyrrolidin-2-one (39g-b, 322 mg, 33%) as white solids.

For 39g-a: $^1$H NMR (300 MHz, CDCl$_3$) δ 7.90–7.82 (m, 2H), 7.73 (s, 1H), 7.70–7.43 (m, 6H), 4.10–3.90 (m, 3H), 3.81–3.57 (m, 3H), 3.55–3.42 (m, 1H), 3.40–3.20 (m, 3H), 2.61–2.47 (m, 3H), 2.27–2.10 (m, 2H), 2.00–1.63 (m, 7H); $^{19}$F NMR (282 MHz, CDCl$_3$) δ –62.9; ESI MS m/z 593 [C$_{28}$H$_{31}$F$_3$N$_4$O$_5$+H]$^+$.

For 39g-b: $^1$H NMR (300 MHz, CDCl$_3$) δ 7.90–7.82 (m, 2H), 7.73 (s, 1H), 7.69–7.43 (m, 6H), 4.10–3.90 (m, 3H), 3.85–3.57 (m, 3H), 3.44–3.23 (m, 3H), 3.22–3.10 (m, 1H), 2.62–1.60 (m, 12H); $^{19}$F NMR (282 MHz, CDCl$_3$) δ –62.9; ESI MS m/z 593 [C$_{28}$H$_{31}$F$_3$N$_4$O$_5$+H]$^+$.

(39h) A mixture of 39g-b (222 mg, 375 µmol) and 10% Pd/C (239 mg, 112 µmol) in MeOH (150 mL) was hydrogenated (50 psi) for 2 h. The mixture was filtered through diatomaceous earth (infusorial earth) and the filtrate was evaporated under vacuum to give (R*)-1-((1S*,2R*,4R*)-4-amino-2-(phenylsulfonylmethyl)cyclohexyl)-3-((2-(3-(trifluoromethyl)phenyl)-1,3-dioxolan-2-yl)methyl)pyrrolidin-2-one (39h-b, 169 mg, 80%) as a white solid: $^1$H NMR (300 MHz, CDCl$_3$) δ 7.87 (d, J=7.3 Hz, 2H), 7.68–7.35 (m, 7H), 4.22 (s, 1H), 4.02–3.60 (m, 5H), 3.50–3.14 (m, 4H), 2.80–2.63 (m, 1H), 2.60–1.60 (m, 12H); $^{19}$F NMR (282 MHz, CDCl$_3$) δ –62.8; ESI MS m/z 567 [C$_{28}$H$_{33}$F$_3$N$_2$O$_5$S+H]$^+$.

(39i) A mixture of 39h-b (170 mg, 300 µmol), acetone (871 µL, 11.9 µmol), acetic acid (69.1 µL, 1.20 mmol), and sodium triacetoxyborohydride (255 mg, 1.20 mmol) in dichloroethane (17 mL) was stirred at room temperature for 2 h. The reaction was diluted with EtOAc (500 mL), washed with saturated NaHCO$_3$ (3×150 mL), water (2×100 mL), and brine (150 mL), dried over Na$_2$SO$_4$, filtered, and evaporated. The residue was purified by CombiFlash chromatography (silica, 0–10% MeOH/CH$_2$Cl$_2$) to provide (R*)-1-((1S*,2R*,4R*)-4-(isopropylamino)-2-(phenylsulfonylmethyl)cyclohexyl)-3-((2-(3-(trifluoromethyl)phenyl)-1,3-dioxolan-2-yl)methyl)pyrrolidin-2-one (39i-b, 106 mg, 58%) as a white solid: $^1$H NMR (300 MHz, CDCl$_3$) δ 7.89 (d, J=7.2 Hz, 2H), 7.68 (s, 1H), 7.64–7.39 (m, 6H), 4.20 (s, 1H), 4.05–3.90 (m, 2H), 3.81–3.60 (m, 3H), 3.48–3.11 (m, 4H), 3.10–2.88 (m, 1H), 2.60–2.10 (m, 5H), 2.09–1.60 (m, 8H), 1.43–1.00 (m, 6H); $^{19}$F NMR (282 MHz, CDCl$_3$) δ −62.9; ESI MS m/z 609 [C$_{31}$H$_{39}$F$_3$N$_2$O$_5$S+H]$^+$.

(39j) Compound 39i-b (103 mg, 168 µmol) and 37% formaldehyde (50 µL, 1.8 mmol) were dissolved in MeOH (2 mL) and stirred for 3 h at room temperature. Sodium cyanoborohydride (16 mg, 252 µmol) was added and the mixture was stirred for 2 h. The reaction was diluted with EtOAc (400 mL), washed with saturated NaHCO$_3$ (3×150 mL) and brine (100 mL), dried over Na$_2$SO$_4$, filtered, and evaporated. The residue was purified by CombiFlash chromatography (silica, 0–10% CH$_2$Cl$_2$/MeOH) and then lyophilized from CH$_3$CN/H$_2$O to give title compound (77 mg, 74%) as a white solid: $^1$H NMR (300 MHz, CDCl$_3$) δ 7.90–7.82 (m, 2H), 7.71 (s, 1H), 7.68–7.42 (m, 6H), 4.15–3.92 (m, 3H), 3.80–3.00 (m, 7H), 2.71–2.10 (m, 9H), 1.93–1.40 (m, 9H), 1.17–0.95 (m, 6H); $^{19}$F NMR (282 MHz, CDCl$_3$) δ −62.9; ESI MS m/z 623 [C$_{32}$H$_{41}$F$_3$N$_2$O$_5$S+H]$^+$.

Example 40

(S*)-1-((1S*,2R*,4R*)-4-(isopropyl(methyl)amino)-2-(phenylsulfonylmethyl)cyclohexyl)-3-((2-(3-(trifluoromethyl)phenyl)-1,3-dioxolan-2-yl)methyl)pyrrolidin-2-one (40a) Diastereomer 39g-a was incorporated into Example 39 (steps 39h–39j) to give the title compound. MS found: (M+H)$^+$=623.

Example 41

(S*)-3-(2-oxo-2-(3-(trifluoromethyl)phenyl)ethyl)-1-((1S*,2R*,4R*)-4-(isopropyl(methyl)amino)-2-(phenylsulfonylmethyl)cyclohexyl)pyrrolidin-2-one (41a) A solution of Example 40 (74.4 mg, 0.120 mmol) in CH$_3$CN (0.9 mL) and 1 M HCl (0.9 mL) was heated at 60° C. for 5 h. The mixture was diluted with ethyl acetate (500 mL), washed with satd NaHCO$_3$ (3×150 mL) and brine (2×100 mL), dried over Na$_2$SO$_4$, filtered, and evaporated to dryness. The residue was lyophilized from CH$_3$CN/H$_2$O to the title compound as a white solid (70.2 mg, >99): ESI MS m/z 579 [C$_{30}$H$_{37}$F$_3$N$_2$O$_4$S+H]$^+$.

Example 42

(R*)-3-(2-oxo-2-(3-(trifluoromethyl)phenyl)ethyl)-1-((1S*,2R*,4R*)-4-(isopropyl(methyl)amino)-2-(phenylsulfonylmethyl)cyclohexyl)pyrrolidin-2-one (42a) Example 39 was incorporated into Example 41 to give the title compound. MS found: (M+H)$^+$=579.

Example 43

(R*)-3-(2-hydroxy-2-(3-(trifluoromethyl)phenyl)ethyl)-1-((1S*,2R*,4R*)-4-(isopropyl(methyl)amino)-2-(phenylsulfonylmethyl)cyclohexyl)pyrrolidin-2-one trifluoroacetate (43a) To a solution of Example 42 (19.3 mg, 33.4 µmol) in MeOH (2 mL) was added sodium borohydride (6 mg, 167 µmol). After stirring for 1 h, the solvent was removed under vacuum. The residue was dissolved in EtOAc (500 mL), washed with satd NaHCO$_3$ (3×150 mL) and brine (2×100 mL), dried over Na$_2$SO$_4$, filtered, and evaporated to dryness. The residue was purified by preparative TLC (80:12:6:2 EtOAc/CHCl$_3$/MeOH/NH$_4$OH). The middle band was lyophilized from CH$_3$CN/H$_2$O/TFA to give one diastereomer of the title compound 43a-a (7.9 mg, 34%) as a colorless oil. The bottom band was lyophilized from CH$_3$CN/H$_2$O/TFA to give the second diastereomer of the title compound 43a-b (12.1 mg, 66%) as a colorless oil.

For 43a-a: $^1$H NMR (300 MHz, CDCl$_3$) δ 11.13 (br, s, 1H), 8.00–7.89 (m, 2H), 7.75–7.40 (m, 7H), 5.06–4.93 (m, 1H), 4.40–4.29 (m, 1H), 4.10–3.03 (m, 12H), 3.02–2.90 (m, 1H), 2.89–2.50 (m, 5H), 2.41–2.25 (m, 1H), 2.21–1.60 (m, 10H), 1.48–1.40 (m, 3H), 1.38–1.20 (m, 4H); $^{19}$F NMR (282 MHz, CDCl$_3$) δ −62.9, −76.3; ESI MS m/z 581 [C$_{30}$H$_{39}$F$_3$N$_2$O$_4$S+H]$^+$.

For 43a-b: $^1$H NMR (300 MHz, CDCl$_3$) δ 10.95 (br, s, 1H), 7.98–7.89 (m, 2H), 7.76–7.40 (m, 7H), 4.90–4.80 (m, 1H), 4.40–4.30 (m, 1H), 4.10–3.90 (m, 1H), 3.89–3.70 (m, 1H), 3.60–3.48 (m, 1H), 3.42–3.02 (m, 2H), 3.01–2.90 (m, 1H), 2.89–2.55 (m, 6H), 2.40–2.00 (m, 8H), 1.99–1.55 (m, 4H), 1.50–1.40 (m, 3H), 1.37–1.20 (m, 5H); $^{19}$F NMR (282 MHz, CDCl$_3$) δ −63.0, −76.4; ESI MS m/z 581 [C$_{30}$H$_{39}$F$_3$N$_2$O$_4$S+H]$^+$.

Example 44

(S*)-3-(2-hydroxy-2-(3-(trifluoromethyl)phenyl)ethyl)-1-((1S*,2R*,4R*)-4-(isopropyl(methyl)amino)-2-(phenylsulfonylmethyl)cyclohexyl)pyrrolidin-2-one trifluoroacetate (44a) Example 41 was incorporated into Example 43 to give the title compound as a mixture of diastereomers. MS found: (M+H)$^+$=581.

Example 45

((S*)-1-((1S*,2R*,4R*)-4-(isopropyl(methyl)amino)-2-(phenylsulfonylmethyl)cyclohexyl)-3-(-2-(methoxyimino)-2-(3-(trifluoromethyl)phenyl)ethyl)pyrrolidin-2-one trifluoroacetate (45a) A stirred mixture of Example 41 (19.7 mg, 34 µmol), methoxylamine.HCl (17 mg, 204 µmol), NaOAc (17 mg, 204 µmol), and MeOH (2 mL) was heated at 50° C. for 24 h. The solvent was removed under vacuum and the residue was dissolved in EtOAc (500 mL). The organic mixture was washed with satd NaHCO$_3$ (3×100 mL), water (200 mL), and brine (200 mL), dried over Na$_2$SO$_4$, filtered, and evaporated. The residue was lyophilized from CH$_3$CN/H$_2$O/TFA give the title compound as a mixture of (E) and (Z) isomers (26.9 mg, 95%): $^1$H NMR (500 MHz, CDCl$_3$) δ 11.03 (s, 1H), 7.97–7.86 (m, 3H), 7.83–7.76 (m, 1H), 7.70–7.63 (m, 1H), 7.62–7.53 (m, 3H), 7.50–7.41 (m, 1H), 4.32–4.20 (m, 1H), 3.99 (s, 3H), 3.95–3.85 (m, 1H), 3.60–3.43 (m, 2H), 3.32–3.20 (m, 1H), 3.15–2.94 (m, 2H), 2.91–2.77 (m, 2H), 2.75–2.65 (m, 3H), 2.63–2.50 (m, 2H), 2.20–1.68 (m, 7H), 1.50–1.40 (m, 3H), 1.35–1.24 (m, 5H); $^{19}$F NMR (282 MHz, CDCl$_3$) δ −63.1, −76.3; ESI MS m/z 608 [C$_{31}$H$_{40}$F$_3$N$_3$O$_4$S+H]$^+$.1.

Example 46

((R*)-1-((1S*,2R*,4R*)-4-(isopropyl(methyl)amino)-2-(phenylsulfonylmethyl)cyclohexyl)-3-(-2-(methoxyimino)-2-(3-(trifluoromethyl)phenyl)ethyl)pyrrolidin-2-one trifluoroacetate (46a) Example 42 was incorporated into Example 45 to give the title compound as a mixture of (E)/(Z). $^1$H NMR (500 MHz, CDCl$_3$) δ 10.80 (s, 1H), 7.98–7.85 (m, 3H), 7.81–7.40 (m, 6H), 4.40–4.21 (m, 1H), 4.10–3.84 (m, 3H), 3.83–3.77 (m, 1H), 3.74–3.58 (m, 1H), 3.50–3.15 (m, 3H), 3.14–2.89 (m, 3H), 2.85–2.68 (m, 4H), 2.65–2.49 (m 2H), 2.20–1.98 (m, 5H), 1.93–1.62 (m, 2H), 1.50–1.38 (m, 3H), 1.35–1.20 (m, 5H); $^{19}F$ NMR (282 MHz, CDCl$_3$) δ –63.1, –76.3; ESIMS m/z 608 $[C_{31}H_{40}F_3N_3O_4S+H]^+$.

Example 47

1-((1S*,2R*,4R*)-4-(amino)-2-(phenylsulfonylmethyl)cyclohexyl)-3-(7-(trifluoromethyl)-1H-benzo[d]imidazol-2-yl)pyrrolidin-2-one trifluoroacetate (47a) 3-(Trifluoromethyl)benzene-1,2-diamine (257 mg, 1.46 mmol) was dissolved in anhydrous DMF (7.5 mL). The mixture was stirred at 0° C. under N$_2$ as N-methylmorpholine (0.34 mL, 3.09 mmol), compound from Example 24d (456 mg, 1.12 mmol), and benzotriazol-1-yloxy-tris(dimethylamino)phosphonium hexafluorophosphate (BOP reagent, 644 mg, 1.45 mmol) were added sequentially. The mixture was allowed to warm to room temperature and stirred for 14 h, then diluted with EtOAc, washed with 10% aqueous HCl (3×), saturated NaHCO$_3$ (1×), and brine (1×), dried over Na$_2$SO$_4$, filtered and evaporated. The residue was purified by flash column chromatography (silica, 50–100%, EtOAc/hexanes) to provide the two diastereomers of N-(2-amino-3-(trifluoromethyl)phenyl)-1-((1S*,2R*,4R*)-4-(azido)-2-(phenylsulfonylmethyl)cyclohexyl)-2-oxopyrrolidine-3-carboxamide as white crushable foams: ESI MS m/z 565 $[C_{25}H_{27}F_3N_6O_4S+H]^+$.

(47b) The diastereomers from above (47a) (136 mg, 0.241 mmol) and p-toluenesulfonic acid monohydrate (35 mg, 0.18 mmol) were stirred in anhydrous toluene (35 mL). The reaction vessel was fitted with a Dean-Stark trap and the mixture was heated to reflux, at which point 10 mL of toluene was removed. The mixture was further heated at reflux for 2 h, then allowed to cool to room temperature, and the solvent was removed in vacuo. The residue was purified by flash column chromatography (silica, 2–10% MeOH/CH$_2$Cl$_2$) to provide 1-((1S*,2R*,4R*)-4-azido-2-(phenylsulfonylmethyl)cyclohexyl)-3-(7-(trifluoromethyl)-1H-benzo[d]imidazol-2-yl)pyrrolidin-2-one as a mixture of diastereomers (101 mg, 77%): $^1H$ NMR (300 MHz, CDCl$_3$) δ 10.88–10.77 (m, 1H), 7.94–7.76 (m, 3H), 7.65–7.43 (m, 3H), 7.35–7.23 (m, 2H); ESI MS m/z 547 $[C_{25}H_{25}F_3N_6O_3S+H]^+$.

(47c) To a solution of the above compound (47b) (154 mg, 0.282 mmol) in methanol (7 mL) was added 10% Pd/C (wet, 60 mg). The mixture was hydrogenated (1 atm) for 14 h, then filtered through a pad of diatomaceous earth and concentrated. The residue was purified by preparative TLC (80:18:2 CHCl$_3$/MeOH/NH$_4$OH). After concentrating the material in vacuo, the resulting oil was dissolved in CH$_3$CN/H$_2$O/TFA and lyophilized to give the title compound (29 mg, 16%) as a white solid and mixture of diastereomers: ESI MS m/z 521 $[C_{25}H_{27}F_3N_4O_3S+H]^+$.

Example 48

1-((1S*,2R*,4R*)-4-(isopropylamino)-2-(phenylsulfonylmethyl)cyclohexyl)-3-(7-(trifluoromethyl)-1H-benzo[d]imidazol-2-yl)pyrrolidin-2-one trifluoroacetate (48a) To a solution of Example 47 (67 mg, 0.13 mmol) in 1,2-dichloroethane (7.3 mL) was added acetone (0.38 mL, 5.2 mmol) and acetic acid (30 μL, 0.51 mmol). The resulting mixture was stirred for 20 min, then sodium triacetoxyborohydride (110 mg, 0.52 mmol) was added. After stirring for 2 h, the mixture was diluted with EtOAc and washed sequentially with saturated aqueous NaHCO3, water, and brine. The organic phase was dried over Na$_2$SO$_4$, filtered, and the solvent was removed in vacuo. The resulting clear, glassy solid was dissolved in CH$_3$CN/H$_2$O/TFA and lyophilized to provide the title compound (5.1 mg, 6%) as a white solid and mixture of diastereomers: ESI MS m/z 563 $[C_{28}H_{33}F_3N_4O_3S+H]^+$.

Example 49

1-((1S*,2R*,4R*)-4-(isopropyl(methyl)amino)-2-(phenylsulfonylmethyl)cyclohexyl)-3-(7-(trifluoromethyl)-1H-benzo[d]imidazol-2-yl)pyrrolidin-2-one trifluoroacetate (49a) To a solution of Example 48 (25 mg, 44 μmol) in methanol (1.5 mL) was added a solution of 37% aqueous formaldehyde (14 mL, 178 μmol). The resulting mixture was stirred for 2 h, then sodium cyanoborohydride (5 mg, 67 μmol) was added. After stirring for 3 h, the mixture was treated with saturated aqueous NaHCO$_3$ and extracted with EtOAc. The organic layer was washed with brine, dried over Na$_2$SO$_4$, filtered, and the solvent removed in vacuo. The residue was purified by preparative TLC (90:10:1 CHCl$_3$/MeOH/NH$_4$OH). After concentrating the material in vacuo, the resulting oil was dissolved in CH$_3$CN/H$_2$O/TFA and lyophilized to give the title compound (10 mg, 33%) as a white solid and mixture of diastereomers: ESI MS m/z 577 $[C_{29}H_{35}F_3N_4O_3S+H]^+$.

Example 50

1-((1S*,2R*,4R*)-4-(isopropyl(ethyl)amino)-2-(phenylsulfonylmethyl)cyclohexyl)-3-(7-(trifluoromethyl)-1H-benzo[d]imidazol-2-yl)pyrrolidin-2-one trifluoroacetate (50a) To a solution of Example 48 (25 mg, 44 μmol) in 1,2-dichloroethane (3.0 mL) was added acetaldehyde (13 μL, 222 μmol) and acetic acid (30 μL, 0.14 mmol). The resulting mixture was stirred for 20 min, then sodium triacetoxyborohydride (38 mg, 0.18 mmol) was added. After stirring for 2 h, the mixture was diluted with EtOAc and washed sequentially with saturated aqueous NaHCO$_3$, water, and brine. The organic phase was dried over Na$_2$SO$_4$, filtered, and the solvent was removed in vacuo. The residue was purified by preparative TLC (70:30 CH2Cl2/MeOH). After concentrating the material in vacuo, the resulting oil was dissolved in CH$_3$CN/H$_2$O/TFA and lyophilized to provide the title compound (10 mg, 34%) as a white solid and mixture of diastereomers: ESI MS m/z 591 $[C_{30}H_{37}F_3N_4O_3S+H]^+$.

Example 51

1-((1S*,2R*,4R*)-4-(Diethylamino)-2-(phenylsulfonylmethyl)cyclohexyl)-3-(7-(trifluoromethyl)-1H-benzo[d]imidazol-2-yl)pyrrolidin-2-one trifluoroacetate (51a) To a solution of Example 47 (25 mg, 44 μmol) in 1,2-dichloroethane (2.7 mL) was added acetaldehyde (28 μL, 492 μmol) and acetic acid (8 μL, 96 μmol). The resulting mixture was stirred for 20 min, then sodium triacetoxyborohydride (31 mg, 144 μmol) was added. After stirring for 2 h, the mixture was diluted with EtOAc and washed sequentially with saturated aqueous $NaHCO_3$, water, and brine. The organic phase was dried over $Na_2SO_4$, filtered, and the solvent was removed in vacuo. The residue was purified by preparative TLC (90:10:1 $CHCl_3$/MeOH/$NH_4OH$). After concentrating the material in vacuo, the resulting oil was dissolved in $CH_3CN/H_2O$/TFA and lyophilized to provide the title compound (8.5 mg, 26%) as a white solid and mixture of diastereomers: ESI MS m/z 577 $[C_{29}H_{35}F_3N_4O_3S+H]^+$.

Example 52

1-((1S,2R,4R)-4-(Isopropyl(methyl)amino)-2-(phenylsulfonylmethyl)cyclohexyl)-3-(naphthalen-1-ylamino)pyrrolidin-2-one trifluoroacetate (52a) (1S*,2R*,4R*)-4-azido-2-benzenesulfonylmethylcyclohexylamine trifluoroacetate (see 37c) (2.5 g, 6.3 mmol) was dissolved in DMF (15 mL) prior to the addition of BOP reagent (3.4 g) and N-Boc-L-Met-OH (1.9 g). After cooling to 0° C., NMM (2.6 mL) was added. The resulting mixture was warmed to rt and was stirred overnight. The solution was diluted with EtOAc, and was washed successively with brine and sat. $NaHCO_3$. The organic phase was dried ($MgSO_4$), filtered, and concentrated. Flash chromatography of the resulting residue gave tert-butyl (S)-1-((1S*,2R*,4R*)-4-azido-2-(phenylsulfonylmethyl)cyclohexylamino)-4-(methylthio)-1-oxobutan-2-ylcarbamate (2.8 g) as a mixture of diastereomers. MS found: $(M+H)^+$=526.2.

(52b) The above derivative (52a) was dissolved in MeI (30 mL). After stirring overnight at rt, the solution was concentrated and dried. The resulting material was dissolved in DMF (30 mL) prior to the addition of $Cs_2CO_3$ (3.5 g). After stirring 3 h, the solution was diluted with EtOAc and was washed with brine. The organic phase was dried ($MgSO_4$), filtered, and concentrated. Flash chromatography (1:2 up to 2:1 EtOAc/hexane) of the resulting residue provided the bottom diastereomer tert-butyl (S)-1-((1S,2R,4R)-4-azido-2-(phenylsulfonylmethyl)cyclohexyl)-2-oxopyrrolidin-3-ylcarbamate (600 mg). MS found: $(M+H)^+$=478.3.

(52c) A portion of the above material (52b) (30 mg) was dissolved in MeOH (4 mL) prior to the addition of 10% Pd/C (20 mg). A hydrogen balloon was added and the mixture was stirred. After stirring 2 h, the Pd/C was filtered off and the solvent was concentrated to give tert-butyl (S)-1-((1S,2R,4R)-4-amino-2-(phenylsulfonylmethyl)cyclohexyl)-2-oxopyrrolidin-3-ylcarbamate (29 mg). MS found: $(M+H)^+$=452.2.

(52d) The above material (52c) was dissolved in dichloroethane (5 mL) prior to the adddition of glacial acetic acid (0.2 mL), acetone (1.0 mL), and $NaBH(OAc)_3$ (20 mg). After 20 h, MeOH (4 mL) was added prior to the addition of 37% formaldehyde in water (1 mL). After 15 min, $NaBH_3CN$ (20 mg) was added. After 1 h, saturated $NaHCO_3$ was added and some of the MeOH was removed. EtOAc was added and the organic layer was dried, filtered, and concentrated to give tert-butyl (S)-1-((1S,2R,4R)-4-(isopropyl(methyl)amino)-2-(phenylsulfonylmethyl)cyclohexyl)-2-oxopyrrolidin-3-ylcarbamate (15 mg). MS found: $(M+H)^+$=508.3.

(52e) A portion of above material (52b) (160 mg) was dissolved in $CH_2Cl_2$ (3 mL) and cooled to 0° C. prior to the addition of TFA (4 mL). After the reaction was warmed to rt over 1 h, it was concentrated. This material was dissolved in EtOAc (8 mL) prior to the addition of saturated $Na_2CO_3$ solution (3 mL). The organic phase was dried ($Na_2CO_3$), filtered, and concentrated to afford free base (S)-3-amino-1-((1S,2R,4R)-4-(isopropyl(methyl)amino)-2-(phenylsulfonylmethyl)cyclohexyl)pyrrolidin-2-one (130 mg). MS found: $(M+H)^+$=408.2.

(52f) A portion of the above material (52e) (30 mg, 74 μmol), sodium tert-butoxide (14 mg, 140 μmol), and toluene (0.7 mL) were placed in a reaction tube equipped with a stir bar and screw cap. After passing argon through the reaction mixture for 2 min, BINAP (8 mg, 13 μmol), $Pd_2(dba)_3$ (4 mg, 4 μmol) and 1-bromonaphthalene (9 μL, 61 μmol) were added sequentially. The mixture was evacuated again with argon, then sealed and heated to 85° C. overnight. After cooling to room temperature, the mixture was diluted with ether, filtered through a pad of diatomaceous earth, and concentrated. The residue was purified by semi-preparative HPLC, then lyophilized to provide the title compound (9.5 mg) as a gray solid and mixture of diastereomers. ESI MS m/z 534 $[C_{31}H_{39}N_3O_3S+H]^+$.

Example 53

3-(Benzo[b]thiophen-3-ylamino)-1-((1S,2R,4R)-4-(isopropyl(methyl)amino)-2-(phenylsulfonylmethyl)cyclohexyl)pyrrolidin-2-one trifluoroacetate (53a) A portion of the above amine (52e) (27 mg, 66 μmol), sodium tert-butoxide (13 mg, 130 μmol), and toluene (0.7 mL) were placed in a reaction tube equipped with a stir bar and screw cap. After passing argon through the reaction mixture for 2 min, 2-(di-t-butylphosphino)biphenyl (12 mg, 40 μmol), $Pd_2(dba)_3$ (6 mg, 7 μmol) and 3-bromothianaphthene (18 μL, 130 μmol) were added sequentially. The mixture was evacuated again with argon, then sealed and stirred overnight. The mixture was diluted with ether, filtered through a pad of diatomaceous earth, and concentrated. The residue was purified by preparative TLC (9:1 $CH_2Cl_2$/MeOH), then lyophilized to provide the title compound (4.4 mg) as a light yellow solid and mixture of diastereomers. ESI MS M/z 540 $[C_{29}H_{37}N_3O_3S_2+H]^+$.

Example 54

(S)-3-(6-chloroquinazolin-4-ylamino)-1-((1S,2R,4R)-4-(isopropyl(methyl)amino)-2-(phenylsulfonylmethyl)cyclohexyl)pyrrolidin-2-one trifluoroacetate (54a) The above amine (52e) (20 mg), triethylamine (0.03 mL), and 4,6-dichloroquinazoline (15 mg) were dissolved in EtOH (2 mL) and placed in a microwave. The reaction was heated at 100° C. for 22 min. The solution was filtered and the filtrate was subjected to reverse phase HPLC purification (gradient elution, water/acetonitrile/TFA) to provide the title compound (11.3 mg). MS found: $(M+H)^+$=570.2.

Example 55

(S)-3-(6,8-dichloroquinazolin-4-ylamino)-1-((1S,2R,4R)-4-(isopropyl(methyl)amino)-2-(phenylsulfonylmethyl)cyclohexyl)pyrrolidin-2-one trifluoroacetate (55a) 4,6,8-Trichloroquinazoline was incorporated into Example 54 to give the title compound. MS found: $(M+H)^+$=604.2.

Example 56

3,5-Dichloro-N-((S)-1-((1S,2R,4R)-4-(isopropyl (methyl)amino)-2-(phenylsulfonylmethyl)cyclohexyl)-2-oxopyrrolidin-3-yl)benzamide trifluoroacetate (56a) Amine 52e (15 mg) was dissolved in DMF (2 mL) prior to the addition of diisopropylethylamine (0.02 mL) and 3,5-dichlorobenzoic acid (10 mg). After cooling to 0° C., BOP reagent (19 mg) was added. The resulting mixture was warmed to rt and was stirred overnight. The solution was diluted with EtOAc and was washed with sat. NaHCO$_3$. The organic phase was dried (MgSO$_4$), filtered, and concentrated. Reverse phase HPLC purification (gradient elution, water/acetonitrile/TFA) of the resulting residue provided the title compound (1.0 mg). MS found: (M+H)$^+$=580.

Example 57

N-((S)-1-((1S,2R,4R)-4-(isopropyl(methyl)amino)-2-(phenylsulfonylmethyl)cyclohexyl)-2-oxopyrrolidin-3-yl)-3-(trifluoromethoxy)benzamide trifluoroacetate (57a) 3-Trifluoromethoxybenzoic acid was incorporated into Example 56 to give the title compound. MS found: (M+H)$^+$=596.2.

Example 58

3-((E)-3(R*)-(trifluoromethyl)styryl)-1-((1S*,2R*,4R*)-4-(isopropyl(methyl)amino)-2-(phenylsulfonylmethyl)cyclohexyl)pyrrolidin-2-one trifluoroacetate (58a) Compound 39g-b (2.0 g) was dissolved in CH$_3$CN (25 mL) and 1 M HCl (25 mL) was stirred at 60° C. for 6 h. The mixture was diluted with ethyl acetate (500 mL), washed with satd NaHCO$_3$ (3×150 mL) and brine (2×100 mL), dried over Na$_2$SO$_4$, filtered, and evaporated to dryness to give 1-((1S*,2R*,4R*)-4-azido-2-(phenylsulfonylmethyl)cyclohexyl)-3(R*)-(3-(trifluoromethyl)benzoyl)pyrrolidin-2-one as a white solid (1.85 g). ESI MS m/z 549 [C$_{26}$H$_{27}$F$_3$N$_4$O$_4$S+H]$^+$.

(58b) A solution of LiHMDS (5.06 mL, 1 M in hexanes) in THF (50.6 mL) was cooled to −78° C. A precooled solution of compound (58a) (2.80 g, 5.06 mmol) in THF (25 mL) was added dropwise. The mixture was stirred for 1 h at −78° C. then a precooled solution of 2-[(N,N-bistrifluoromethylsulfonyl)amino]-5-chloropyridine (2.90 g, 7.38 mmol) in THF (30 mL) was added. After 90 min, the reaction was warmed to −5° C. and stirred for 2 h. The mixture was diluted with EtOAc (800 mL), washed with satd NH$_4$Cl (3×150 mL) and brine (100 mL), dried over Na$_2$SO$_4$, filtered, and concentrated, filtering off the 2-amino-5-chloropyridine byproduct. The filtrate was evaporated to dryness, and purified by flash chromatography (silica-gel, 0–100% EtOAc/hexanes) to give 2-(1-((1S*,2R*,4R*)-4-azido-2-(phenylsulfonylmethyl)cyclohexyl)-2-oxopyrrolidin-3-yl)-1-(3(R*)-(trifluoromethyl)phenyl)vinyl trifluoromethanesulfonate (2.30 g, 67%) as a white solid:

$^1$H NMR (300 MHz, CDCl$_3$) δ 7.92–7.83 (m, 2H), 7.78–7.50 (m, 7H), 6.07 (d, J=9.0 Hz, 1H), 4.00–3.89 (m, 5H), 3.22 (dd, J=14.7, 3.4 Hz, 1H), 2.80–2.45 (m, 2H), 2.18–1.60 (m, 9H); $^{19}$F NMR (282 MHz, CDCl$_3$) δ −63.4 (3F), −74.1 (3F).

(58c) A mixture of Pd(PPh$_3$)$_4$ (25.5 mg, 22 μmol) and LiCl (140 mg, 3.29 mmol) in THF (3.28 mL) was stirred under argon atmosphere. A solution of compound 58b (750 mg, 1.03 mmol) in THF (3.68 mL) was added, followed by slow addition of tributyltin hydride (μL, 1.32 mmol). The mixture was stirred 4 h at room temperature, diluted with EtOAc (500 mL), washed with satd NaHCO$_3$ (3×100 mL), brine (200 mL), dried over Na$_2$SO$_4$, filtered, and evaporated. The residue was purified by flash chromatography (silica gel with a plug of KF, 0–80% EtOAc/hexanes) to give the 3(R*)-((E)-3-(trifluoromethyl)styryl)-1-((1S*,2R*,4R*)-4-azido-2-(phenylsulfonylmethyl)cyclohexyl)pyrrolidin-2-one (347 mg, 59%) as white solids. ESI MS M/z 533 [C$_{26}$H$_{27}$F$_3$N$_4$O$_3$S+H]$^+$.

(58d) A mixture of 58c (117 mg, 220 μmol) and triphenylphosphine (115 mg, 440 μmol) in THF (10 mL) was stirred at room temperature for 23 h. Water (2 mL) was added and the mixture was stirred for 2 d. The volume was reduced under vacuum and the residue was dissolved in EtOAc (500 mL). The mixture was extracted with 1 M HCl (3×150 mL), and the aqueous layer was made basic with 6 N NaOH, then extracted with EtOAc (3×150 mL). The organic layer was dried over Na$_2$SO$_4$, filtered, and evaporated to give crude free amine. This material (24 mg, 47 μmol), acetone (200 μL, 2.73 mmol), and acetic acid (20 μL, 348 μmol) in 1,2-dichloroethane (4 mL) was stirred for 3 min, then treated with sodium triacetoxyborohydride (20 mg, 95 μmol). After stirring the mixture for 1 h, the solvent was removed under vacuum. The residue was dissolved in MeOH (4 mL), then 37% aqueous formaldehyde (400 μL) and sodium cyanoborohydride (4.5 mg, 71 μmol) were added. The mixture was stirred 18 h, and the solvent was removed under vacuum. The residue was purified by semi-preparative HPLC, and the product lyophilized from CH$_3$CN/H$_2$O/TFA to give the title compound (23.8 mg). ESI MS m/z 563 [C$_{30}$H$_{37}$F$_3$N$_2$O$_3$S+H]$^+$.

Example 59

1-((1S*,2R*,4R*)-4-(isopropyl(methyl)amino)-2-(phenylsulfonylmethyl)cyclohexyl)-3(R*)-((E/Z)-2-(3-(trifluoromethyl)phenyl)prop-1-enyl)pyrrolidin-2-one trifluoroacetate (59a) A suspension of copper bromide.dimethylsulfide (1.03 g, 5.01 mmol) in THF (10 mL) was cooled to −78° C. Methylmagnesium bromide (3 M in ether, 3.34 mL, 10 mmol) was added dropwise, then the mixture was removed from the dry ice bath and THF (3 mL) was added. After stirring for 7 min, the mixture was cooled to −78° C. A solution of compound 58b (569 mg) in THF (11 mL) was added dropwise and the reaction mixture was stirred for 2 h. The mixture was diluted with EtOAc (500 mL), washed with satd NH$_4$Cl (3×100 mL) and brine (200 mL), dried over Na$_2$SO$_4$, filtered, and evaporated. The residue was purified by flash column chromatography (silica-gel, 0–70%, THF/hexanes) to provide 1-((1S*,2R*,4R*)-4-azido-2-(phenylsulfonylmethyl)cyclohexyl)-3(R*)-((E/Z)-2-(3-(trifluoromethyl)phenyl)prop-1-enyl)pyrrolidin-2-one (436 mg). ESI MS m/z 547 [C$_{27}$H$_{29}$F$_3$N$_4$O$_3$S+H]$^+$.

(59b) The above material 59a was incorporated into Example 58 (step 58d) to give the title compound. MS found: (M+H)$^+$=577.

Example 60

N-(1-((1S,2R,4R)-4-(isopropyl(methyl)amino)-2-(phenylsulfonylmethyl)cyclohexyl)-2-oxopyrrolidin-3(R)-yl)benzamidede trifluoroacetate (60a) Benzoic acid was incorporated into Example 56 to give the title compound. MS found: $(M+H)^+=512$.

Example 61

N-((S)-1-((1S,2R,4R)-4-(Isopropyl(methyl)amino)-2-(phenylsulfonylmethyl)cyclohexyl)-2-oxopyrrolidin-3-yl)-3,5-bis(trifluoromethyl)benzamide trifluoroacetate (61a) (1S,2R)-cis-2-Methoxycarbonyl-cyclohex-4-ene-1-carboxylic acid (66.0 g, see Bolm et al. J. Org. Chem. 2000, 65, 6984–6991) was dissolved in dry acetone (815 mL) prior to the addition of triethylamine (43.4 g). This solution was cooled to 0° C. and ethyl chloroformate (46.7 g) was added. The resulting solution was stirred 1 h before $NaN_3$ (35.0 g) was added. The cooling bath was removed, and the reaction was warmed to rt overnight. All solid material was removed by filtration, and the solution was partially concentrated. Water was slowly added and the organic layer was separated. The aqueous layer was extracted with ether. The combined organic layers were washed with water and brine before they were dried, filtered, and concentrated. The resulting oil (66.1 g) was dissolved in benzene (800 mL) and was warmed to a gentle reflux. After 4 h, the solution was cooled back to rt. Benzyl alcohol (37.5 g) and p-TsOH (1.5 g) were added, and the solution was warmed back to a gentle reflux overnight. After cooling to rt, the reaction was washed with $NaHCO_3$ and brine, dried, filtered, and concentrated to give (1R,6S)-6-benzyloxycarbonylamino-cyclohex-3-enecarboxylic acid methyl ester (97.7 g). MS found: $(M+H)^+=290.2$.

(61b) A sample of (1R,6S)-6-benzyloxycarbonylamino-cyclohex-3-enecarboxylic acid methyl ester (91.4 g) was dissolved in MeOH (500 mL) prior to the dropwise addition of NaOH (25.3 g) in water (95 mL). After 3 h, the solution was partially concentrated and an $Et_2O$/water mixture was added. The aqueous layer was separated and was acidified (pH ~2) with concentrated HCl. The resulting mixture was extracted with EtOAc. The combined organic layers were washed with water and brine before they were dried, filtered, and concentrated to give (1R,6S)-6-benzyloxycarbonylamino-cyclohex-3-enecarboxylic acid (72.7 g). MS found: $(M+H)^+=276.2$.

(61c) A sample of (1R,6S)-6-benzyloxycarbonylamino-cyclohex-3-enecarboxylic acid (72 g) was dissolved in $CH_2Cl_2$ (750 mL) prior to the addition of CDI (50.9 g). After 2.5 h water was added, and the solution was extracted with $CH_2Cl_2$. The combined organic layers were dried, filtered, and concentrated. The resulting material was dissolved in $CH_2Cl_2$ and ammonia gas was bubbled through the solution for 1.5 h. After stirring overnight, the majority of the solvent was removed and $Et_2O$ was added. The product precipitated as a white solid and was collected to give (1R,6S)-6-carbamoylcyclohex-3-enyl)carbamic acid benzyl ester (61.5 g). MS found: $(M+H)^+=275.3$.

(61d) A sample of (1R,6S)-6-carbamoylcyclohex-3-enyl)-carbamic acid benzyl ester (30.7 g) was dissolved in THF (1100 mL) and NMP (220 mL). At −78° C., 2.3M n-BuLi (96.3 mL) was added dropwise. After 2 h, a solution of $Boc_2O$ (24.4 g) in THF (40 mL) was added dropwise. This solution was stirred 1.2 h before it was quenched with a saturated $NH_4Cl$ solution. Water and $Et_2O$ were added. The organic layer was filtered then washed with water, brine, dried, filtered, and concentrated. Flash chromatography of the resulting residue gave (1R,6S)-(6-tert-butoxycarbonylaminocarbonyl-cyclohex-3-enyl)-carbamic acid benzyl ester (29.2 g). MS found: $(M+Na)^+=397.4$.

(61e) A sample of (1R,6S)-(6-tert-butoxycarbonyl-aminocarbonylcyclohex-3-enyl)carbamic acid benzyl ester (29.0 g) was dissolved in THF (1290 mL). This was cooled in an ice/brine bath prior to the addition of n-BuLi (1.5 mL, 2.4M). After 30 min, iodine (59.0 g) was added in a single portion. The bath was removed, and the reaction was warmed to rt overnight. The resulting solution was quenched with saturated thiosulfate solution. Water and EtOAc were added. The organic layer was washed with water, brine, dried, filtered, and concentrated. The resulting slurry was diluted with $Et_2O$ and (1R,2S,4S,5R)-2-benzyloxycarbonyl-amino-4-iodo-7-oxo-6-aza-bicyclo[3.2.1]octane-6-carboxylic acid tert-butyl ester (22.8 g) was collected by vacuum filtration. MS found: $M-C_5H_8O_2+H)^+=401.1$.

(61f) A sample of (1R,2S,4S,5R)-2-benzyloxycarbonyl-amino-4-iodo-7-oxo-6-aza-bicyclo[3.2.1]octane-6-carboxylic acid tert-butyl ester (43.3 g) was dissolved in benzene (580 mL) prior to the addition of $Bu_3SnH$ (27.8 g) and AIBN (0.7 g). The resulting mixture was warmed to a gentle reflux for 3 h. After cooling, the solvent was removed and hexane was added. The resulting white solid was collected by vacuum filtration to give (1R,2S,5R)-2-benzyloxycarbonylamino-7-oxo-6-aza-bicyclo[3.2.1]octane-6-carboxylic acid tert-butyl ester (29.5 g). MS found: $(M+Na)^+=397.4$.

(61g) A solution of (1R,2S,5R)-2-benzyloxycarbonyl-amino-7-oxo-6-aza-bicyclo[3.2.1]octane-6-carboxylic acid tert-butyl ester (10.21 g, 27.3 mmol) in tetrahydrofuran (200 mL) was treated with water (40 mL) and then with sodium borohydride (5.16 g, 136 mmol). The mixture was stirred at room temperature for 2 h, then was treated with saturated aqueous sodium bicarbonate and stirred until the bubbling subsided. The mixture was extracted three times with ethyl acetate. The combined extracts were washed with saturated aqueous sodium chloride, dried over sodium sulfate, and concentrated under vacuum. The residue was recrystallized from ethyl acetate-hexane to provide (1R,3R,4S)-(4-benzyloxycarbonylamino-3-hydroxymethylcyclohexyl)carbamic acid tert-butyl ester as a white solid (6.8 g); additional product (2.1 g) was obtained by flash column chromatography of the residue from concentration of the mother liquors, eluting with 40%, then 50% ethyl acetate-hexane. MS found: $(M+H)^+=379.28$.

(61h) A solution of (1R,3R,4S)-(4-benzyloxycarbonyl-amino-3-hydroxymethylcyclohexyl)carbamic acid tert-butyl ester (3.49 g, 9.22 mmol) in tetrahydrofuran (40 mL) was treated with diphenyl disulfide (4.03 g, 18.4 mmol) and tri-n-butylphosphine (4.6 mL, 18.4 mmol) and the solution was heated at reflux for 17 h. The mixture was cooled and concentrated under vacuum, and the residue was purified by flash column chromatography, eluting with 10%, then 20% ethyl acetate-hexane, to provide (1S,2R,4R)-(4-tert-butoxycarbonylamino-2-phenyl-sulfanylmethylcyclohexyl)-carbamic acid benzyl ester (4.37 g) as a white glassy solid. MS found: $(M+H)^+=471.65$.

(61i) A solution of (1S,2R,4R)-(4-tert-butoxycarbonyl-amino-2-phenylsulfanylmethylcyclohexyl)carbamic acid benzyl ester (4.37 g, 9.22 mmol) in 2-propanol (100 mL) was treated with a solution of Oxone (11.34 g, 18.44 mmol) in water (60 mL). The mixture was stirred at room temperature for 18 h, then was diluted with water and extracted with ethyl acetate. The organic phases were washed with water, then with brine, then were dried over sodium sulfate and concentrated under vacuum to provide (1S,2R,4R)-(2-benzene-sulfonylmethyl-4-tert-butoxycarbonylaminocyclohexyl)-carbamic acid benzyl ester (4.77 g) as a white glassy solid, used without further purification. MS found: (M+H)$^+$=503.6.

(61j) A mixture of (1S,2R,4R)-(2-benzene-sulfonylmethyl-4-tert-butoxycarbonylaminocyclohexyl)carbamic acid benzyl ester (2.96 g, 5.9 mmol) and 20% palladium hydroxide on charcoal (Pearlman's catalyst, 2.0 g) in methanol (100 mL) was stirred under one atmosphere of hydrogen at room temperature for 16.5 h. The mixture was filtered through Celite, and the solids were washed with methanol. The filtrate was concentrated under vacuum and the residue was dissolved in dichloromethane. The solution was dried over sodium sulfate and concentrated under vacuum to provide (1R,3R,4S)-(4-amino-3-benzenesulfonylmethylcyclohexyl)-carbamic acid tert-butyl ester (2.02 g) as a white glassy solid, used without further purification. MS found: (M+H)$^+$=369.62.

(61k) This material (61j) was incorporated into Steps 52a to 52b (substituting N-Cbz-L-Met-OH for N-Boc-L-Met-OH) to give tert-butyl (1R,3R,4S)-4-((S)-2-oxo-3-(2-phenylacetamido)pyrrolidin-1-yl)-3-(phenylsulfonylmethyl)cyclohexylcarbamate. MS found: (M+H)$^+$=586.6.

(61l) A portion of above material (61k) (2.0 g) was dissolved in CH$_2$Cl$_2$ (5 mL) and cooled to 0° C. prior to the addition of TFA (7 mL). After the reaction was warmed to rt over 1 h, it was concentrated and dried. This material, acetone (993 mg), and acetic acid (1 mL) in 1,2-dichloroethane (15 mL) was stirred for 3 min, then treated with sodium triacetoxyborohydride (1.4 g). After stirring for 20 h, MeOH (10 mL) was added followed by 37% aqueous formaldehyde (2 mL) and sodium cyanoborohydride (427 mg) were added. The mixture was stirred 3 h, and the solvent was removed under vacuum. The residue was dissolved in EtOAc (200 mL), washed with saturated NaHCO$_3$, dried over Mg$_2$SO$_4$, filtered, and evaporated to provide N-((S)-1-((1S,2R,4R)-4-(isopropyl(methyl)amino)-2-(phenylsulfonylmethyl)cyclohexyl)-2-oxopyrrolidin-3-yl)-2-phenylacetamide (2.7 g). MS found: (M+H)$^+$=542.2.

(61m) A portion of above material (61l) (300 mg) was dissolved in 33% (wt) HBr/AcOH (3 mL). After 30 min, Et$_2$O (20 mL) was added and a white solid precipitated from solution. This solid was collected to give (S)-3-amino-1-((1S,2R,4R)-4-(isopropyl(methyl)amino)-2-(phenylsulfonylmethyl)cyclohexyl)pyrrolidin-2-one dihydrogen bromide (300 mg). MS found: (M+H)$^+$=408.2.

(61n) The above material (61m) was dissolved in EtOAc (8 mL) prior to the addition of saturated Na$_2$CO$_3$ solution (3 mL). The organic phase was dried (Na$_2$CO$_3$), filtered, and concentrated to afford free base (S)-3-amino-1-((1S,2R,4R)-4-(isopropyl(methyl)amino)-2-(phenylsulfonylmethyl)cyclohexyl)pyrrolidin-2-one (210 mg). MS found: (M+H)$^+$=408.2.

(61o) A portion of the above material (61n) (30 mg) was dissolved in DMF (1 mL) prior to the addition of NMM (29.3 mg) and 3,5-ditrifluoromethylbenzoic acid (16.2 mg). After cooling to 0° C., BOP reagent (38 mg) was added. The resulting mixture was warmed to rt and was stirred overnight. The solution was diluted with EtOAc and was washed with sat. NaHCO$_3$. The organic phase was dried (MgSO$_4$), filtered, and concentrated. Reverse phase HPLC purification (gradient elution, water/acetonitrile/TFA) of the resulting residue provided the title compound (X.0 mg). MS found: (M+H)+=648.

Example 62

2-Amino-N-(1-((1S,2R,4R)-4-(isopropyl(methyl)amino)-2-(phenylsulfonylmethyl)cyclohexyl)-2-oxopyrrolidin-3(R)-yl)-5-(trifluoromethoxy)benzamide trifluoroacetate (62a) 2-(tert-Butoxycarbonylamino)-5-(trifluoromethoxy)benzoic acid was incorporated into Step (61o) to give the tert-butyl 2-((1-((1S,2R,4R)-4-(isopropyl(methyl)amino)-2-(phenylsulfonylmethyl)cyclohexyl)-2-oxopyrrolidin-3(R)-yl)carbamoyl)-4-(trifluoromethoxy)phenylcarbamate. MS found: (M+H)$^+$=711.

(62b) The above material (62a) (20 mg) was dissolved in CH$_2$Cl$_2$ (2 mL) and cooled to 0° C. prior to the addition of TFA (4 mL). After the reaction was warmed to rt over 30 min, it was concentrated and dried to provide the title compound. MS found: (M+H)$^+$=611.

Example 63

(R)-1-((1S,2R,4R)-4-(isopropyl(methyl)amino)-2-(phenylsulfonylmethyl)cyclohexyl)-3-(6-(trifluoromethyl)quinolin-4-ylamino)pyrrolidin-2-one trifluoroacetate (63a) Compound (61n) (30 mg), sodium tert-butoxide (10.1 mg), 4-chloro-6-trifluoromethylquinoline (25 mg), and toluene (1.3 mL) were placed in a reaction vial equipped with a stir bar and screw cap. After passing argon through the reaction mixture for 2 min, acetato(2'-di-t-butylphosphino-1,1'-biphenyl-2-yl)palladium(II) (1 mg) was added and the solution was heated to 80° C. overnight. After cooling to room temperature, the mixture was concentrated and then dissolved in MeOH before it was filtered. The filtrate was purified by reverse phase HPLC purification (gradient elution, water/acetonitrile/TFA) to provide two diastereomers. The first diastereomer off the HPLC being the title compound (10.0 mg). MS found: (M+H)+=603.2.

Example 64

(S)-1-((1S,2R,4R)-4-(isopropyl(methyl)amino)-2-(phenylsulfonylmethyl)cyclohexyl)-3-(6-(trifluoromethyl)quinolin-4-ylamino)pyrrolidin-2-one trifluoroacetate (64a) The second diastereomer off the HPLC from Example 63 is the title compound. MS found: (M+H)+=603.2.

Example 65

(R)-1-((1S,2R,4R)-4-(isopropyl(methyl)amino)-2-(phenylsulfonylmethyl)cyclohexyl)-3-(7-(trifluoromethyl)quinolin-4-ylamino)pyrrolidin-2-one trifluoroacetate (65a) 4-Chloro-7-trifluoromethylquinoline was incorporated into Example 63 to give the title compound as the first diastereomer. MS found: (M+H)$^+$=603.2.

Example 66

(S)-1-((1S,2R,4R)-4-(isopropyl(methyl)amino)-2-(phenylsulfonylmethyl)cyclohexyl)-3-(7-(trifluoromethyl)quinolin-4-ylamino)pyrrolidin-2-one trifluoroacetate (66a) The second diastereomer off the HPLC from Example 65 is the title compound. MS found: (M+H)+=603.2.

Example 67

3-(2-(Phenyl)phenylamino)-1-((1S,2R,4R)-4-(isopropyl(methyl)amino)-2-(phenylsulfonylmethyl)cyclohexyl)pyrrolidin-2-one trifluoroacetate (67a) 2-Bromo-biphenyl was incorporated into Example 63 to give the title compound as a mixture of diastereomers. MS found: $(M+H)^+=560.3$.

Example 68

3-(3,5-Bis(trifluoromethyl)phenylamino)-1-((1S,2R,4R)-4-(isopropyl(methyl)amino)-2-(phenylsulfonylmethyl)cyclohexyl)pyrrolidin-2-one trifluoroacetate (68a) 3,5-Ditrifluoromethyl-1-bromobenzene was incorporated into Example 63 to give the title compound as a mixture of diastereomers. MS found: $(M+H)^+=620.2$.

Example 69

1-((1S,2R,4R)-4-(Isopropyl(methyl)amino)-2-(phenylsulfonylmethyl)cyclohexyl)-3-(2-(trifluoromethyl)phenylamino)pyrrolidin-2-one trifluoroacetate (69a) 2-Trifluoromethyl-1-bromobenzene was incorporated into Example 63 to give the title compound as a mixture of diastereomers. MS found: $(M+H)^+=552.3$.

Example 70

1-((1S,2R,4R)-4-(Isopropyl(methyl)amino)-2-(phenylsulfonylmethyl)cyclohexyl)-3-(2-methoxyphenylamino)pyrrolidin-2-one trifluoroacetate (70a) 2-Methoxy-1-bromobenzene was incorporated into Example 63 to give the title compound as a mixture of diastereomers. MS found: $(M+H)^+=568.3$.

Example 71

1-((1S,2R,4R)-4-(Isopropyl(methyl)amino)-2-(phenylsulfonylmethyl)cyclohexyl)-3-(3-(trifluoromethyl)phenylamino)pyrrolidin-2-one trifluoroacetate (71a) 3-Trifluoromethyl-1-bromobenzene was incorporated into Example 63 to give the title compound as a mixture of diastereomers. MS found: $(M+H)^+=552.3$.

Example 72

1-((1S,2R,4R)-4-(Isopropyl(methyl)amino)-2-(phenylsulfonylmethyl)cyclohexyl)-3-(4-(trifluoromethyl)phenylamino)pyrrolidin-2-one trifluoroacetate (72a) 4-Trifluoromethyl-1-bromobenzene was incorporated into Example 63 to give the title compound as a mixture of diastereomers. MS found: $(M+H)^+=552.3$.

Example 73

3-Chloro-N-((S)-1-((1S,2R,4R)-4-(isopropyl(methyl)amino)-2-(phenylsulfonylmethyl)cyclohexyl)-2-oxopyrrolidin-3-yl)benzamide trifluoroacetate (73a) 3-Chlorobenzoic acid was incorporated into Step (61o) to give the title compound. MS found: $(M+H)^+=546$.

Example 74

3-Fluoro-N-((S)-1-((1S,2R,4R)-4-(isopropyl(methyl)amino)-2-(phenylsulfonylmethyl)cyclohexyl)-2-oxopyrrolidin-3-yl)-5-(trifluoromethyl)benzamide trifluoroacetate (74a) 3-Fluoro-5-trifluoromethylbenzoic acid was incorporated into Step (61o) to give the title compound. MS found: $(M+H)^+=598$.

Example 75 tert-Butyl (1R,3R,4S)-4-((S)-2-oxo-3-(3-(trifluoromethyl)benzamido)pyrrolidin-1-yl)-3-(phenylsulfonylmethyl)cyclohexylcarbamate (75a) Compound (61k) (1.0 g) was dissolved in MeOH (15 mL) prior to the addition 10% Pd/C (200 mg). A hydrogen balloon was attached and the solution was stirred 18 h. The mixture was filtered through Celite, and the solids were washed with methanol. The filtrate was concentrated to provide tert-butyl (1R,3R,4S)-4-((S)-3-amino-2-oxopyrrolidin-1-yl)-3-(phenylsulfonylmethyl)cyclohexylcarbamate (980 mg) as a white glassy solid, used without further purification. MS found: $(M+H)^+=452.2$.

(75b) The above material (75a, 980 mg) was dissolved in DMF prior to the addition of 4-methylmorpholine (NMM) (481.5 mg) and 3-trifluoromethyl-benzoic acid (581.7 mg). After cooling to 0° C., BOP reagent (1.4 g) was added. The resulting mixture was warmed to rt and was stirred overnight. EtOAc was added along with saturated NaHCO$_3$ solution. The EtOAc layer was washed with NaHCO$_3$ solution (aq), dried (MgSO$_4$), filtered, and concentrated. Flash chomatography of the resulting residue provided the title compound (978 mg). MS found: $(M+H)^+=624.7$.

Example 76

N—((S)-2-Oxo-1-((1S,2R,4R)-4-(phenylamino)-2-(phenylsulfonylmethyl)cyclohexyl)pyrrolidin-3-yl)-3-(trifluoromethyl)benzamide trifluoroacetate (76a) Example 75 (970 mg) was dissolved in CH$_2$Cl$_2$ (2 mL) and cooled to 0° C. prior to the addition of TFA (7 mL). After the reaction was warmed to rt over 1 h, it was concentrated and dried to provide N—((S)-1-((1S,2R,4R)-4-amino-2-(phenylsulfonylmethyl)cyclohexyl)-2-oxopyrrolidin-3-yl)-3-(trifluoromethyl)benzamide trifluoroacetate (1.01 g). MS found: $(M+H)^+=524.1$.

(76b) The above material (76b) was dissolved in EtOAc (10 mL) prior to the addition of saturated Na$_2$CO$_3$ solution (4 mL). The organic phase was dried (Na$_2$CO$_3$), filtered, and concentrated to afford free base N—((S)-1-((1S,2R,4R)-4-amino-2-(phenylsulfonylmethyl)cyclohexyl)-2-oxopyrrolidin-3-yl)-3-(trifluoromethyl)benzamide (850 mg). MS found: $(M+H)^+=524.1$.

(76c) A portion of compound (76b) (10 mg), sodium tert-butoxide (3.5 mg), bromobenzene (0.1 mL), and toluene (1.0 mL) were placed in a reaction vial equipped with a stir bar and screw cap. After passing argon through the reaction mixture for 2 min, [Pd(µ—Br)(t-Bu$_3$P)]$_2$ (1 mg) was added and the solution was heated to 80° C. overnight. After cooling to room temperature, the mixture was concentrated and then dissolved in MeOH before it was filtered. The filtrate was purified by reverse phase HPLC purification (gradient elution, water/acetonitrile/TFA) to provide the title compound (4.5 mg). MS found: $(M+H)^+=600.1$.

Example 77

N-(2-Oxo-1-((1S,2R,4R)-2-(phenylsulfonylmethyl)-4-(pyridin-4-ylamino)cyclohexyl)pyrrolidin-3-yl)-3-(trifluoromethyl)benzamide trifluoroacetate (77a) Sodium-tert-butoxide (11 mg, 0.114 mmol), 3-bromopyridine (14 mg, 0.086 mmol), and precatalyst acetato (2-di-t-butylphosphino-1,1-biphenyl-2-yl)palladium(II) (2 mg, 0.004 mmol) were added to compound (76b) (30 mg) in toluene (2 mL), degassed by bubbling argon for 30 min. The vial was sealed under argon and the reaction heated overnight at 90° C. Brine (1 mL) was added to quench the reaction and the mixture was evaporated to dryness in vacuo. The crude residue was taken up in acetonitrile/water (1:1, 2.5 mL) and purified by C18 HPLC (acetonitrile/water 0.05% TFA) to give the title compound (6.7 mg) as a mixture of diastereomers. ESI MS m/z 601 $[C_{30}H_{31}F_3N_4O_4S+H]^+$.

Example 78

N-(2-Oxo-1-((1S,2R,4R)-2-(phenylsulfonylmethyl)-4-(thiazol-2-ylamino)cyclohexyl)pyrrolidin-3-yl)-3-(trifluoromethyl)benzamide trifluoroacetate (78a) 2-Bromothiazole was incorporated into Example 77 to give the title compound as a mixture of diastereomers. MS found: $(M+H)^+=607$.

Example 79

Methyl (1R,3R,4S)-4-((S)-2-oxo-3-(3-(trifluoromethyl)benzamido)pyrrolidin-1-yl)-3-(phenylsulfonylmethyl)cyclohexylcarbamate (79a) Compound 76a (20 mg) was dissolved in THF (4 mL) prior to the addition of saturated NaHCO$_3$ solution (0.5 mL) and methyl chloroformate (0.5 mL). After 3 h, EtOAc was added along with saturated NaHCO$_3$ solution. The EtOAc layer was washed with NaHCO$_3$ solution (aq), dried (MgSO$_4$), filtered, and concentrated. Reverse phase HPLC purification (gradient elution, water/acetonitrile/TFA) of the resulting residue provided the title compound (9.3 mg). MS found: $(M+H)^+=582.2$.

Example 80

N-((S)-1-((1S,2R,4R)-4-Formamido-2-(phenylsulfonylmethyl)cyclohexyl)-2-oxopyrrolidin-3-yl)-3-(trifluoromethyl)benzamide (80a) Compound 76a (30 mg) was dissolved in DMF prior to the addition of 4-methylmorpholine (NMM) (481.5 mg) and concentrated formic acid (0.1 mL). After cooling to 0° C., EDC (20 mg) was added. The resulting mixture was warmed to rt and was stirred overnight. EtOAc was added along with saturated NaHCO$_3$ solution. The EtOAc layer was washed with NaHCO$_3$ solution (aq), dried (MgSO$_4$), filtered, and concentrated. Reverse phase HPLC purification (gradient elution, water/acetonitrile/TFA) of the resulting residue provided the title compound (9.1 mg). MS found: $(M+H)^+=552.3$.

Example 81

1-((1R,3R,4S)-4-((S)-2-Oxo-3-(3-(trifluoromethyl)benzamido)pyrrolidin-1-yl)-3-(phenylsulfonylmethyl)cyclohexyl)urea (81a) Compound 76a (77 mg) was dissolved in CH$_2$Cl$_2$ (2 mL) at 0° C. prior to the addition of 2,6-lutidine (51 mg) and phenyl chloroformate (38 mg). After 1 h at rt, CH$_2$Cl$_2$ was added along with saturated NaHCO$_3$ solution. The organic layer was washed with NaHCO$_3$ solution (aq), dried (MgSO$_4$), filtered, and concentrated. Flash chromatography of the resulting residue provided phenyl (1R,3R,4S)-4-((S)-2-oxo-3-(3-(trifluoromethyl)benzamido)pyrrolidin-1-yl)-3-(phenylsulfonylmethyl)cyclohexylcarbamate (43.7 mg). MS found: $(M+H)^+=644.3$.

(81b) A portion of the above compound (81a) (20 mg) was dissolved in DMSO (1 mL) prior to the addition of concentrated ammonium hydroxide solution (0.5 mL). After 1 h, the mixture was filtered. The filtrate was purified by reverse phase HPLC purification (gradient elution, water/acetonitrile/TFA) to provide the title compound (4.9 mg). MS found: $(M+H)^+=567.3$.

Example 82

1-Methyl-3-((1R,3R,4S)-4-((S)-2-oxo-3-(3-(trifluoromethyl)benzamido)pyrrolidin-1-yl)-3-(phenylsulfonylmethyl)cyclohexyl)urea (82a) 2.0 M Methylamine in THF was incorporated into Example 81 to give the title compound. MS found: $(M+H)^+=581.3$.

Example 83

N-((S)-2-Oxo-1-((1S,2R,4R)-4-(2-oxopyrrolidin-1-yl)-2-(phenylsulfonylmethyl)cyclohexyl)pyrrolidin-3-yl)-3-(trifluoromethyl)benzamide (83a) 4-Chlorobutyrylchloride (27 mg, 0.191 mmol) was added dropwise to compound 76b (50 mg) and triethylamine (97 mg, 0.722 mmol) in CH$_2$Cl$_2$ (2 mL) at room temperature under nitrogen. After 1 h the reaction was diluted with ethyl acetate (12 mL) then washed with water (1×5 mL), 10% citric acid (1×5 mL), sat'd NaHCO$_3$ (1×5 mL), and brine (1×5 mL), dried over MgSO$_4$, and evaporated to dryness. The residue was purified by flash chromatography (silica gel, 80% ethyl acetate/hexanes to 10% methanol/ethyl acetate) to provide N-((S)-1-((1S,2R,4R)-4-(4-chlorobutanamido)-2-(phenylsulfonylmethyl)cyclohexyl)-2-oxopyrrolidin-3-yl)-3-(trifluoromethyl)benzamide as a clear film (40 mg). ESI MS m/z 628 $[C_{29}H_{33}ClF_3N_3O_5S+H]^+$.

(83b) The above compound (83a) (40 mg) in THF (1 mL) was added to sodium hydride (60% in mineral oil, 5 mg, 0.128 mmol) in THF (2 mL) at room temperature under nitrogen. After 3 h the reaction was quenched with sat'd NH$_4$Cl (5 mL) and extracted with ethyl acetate (3×5 mL). The combined organic extracts were washed with brine (1×5 mL), dried over MgSO$_4$, then evaporated to dryness. The residue was purified using C18 HPLC (acetonitrile/water 0.05% TFA) to give the title compound (21.7 mg) as a white powder after lyophilization. ESI MS m/z 592 $[C_{29}H_{32}F_3N_3O_5S+H]^+$.

Example 84

N-((S)-1-((1S,2R,4R)-4-(1,1-dioxido-isothiazolidin-2-yl)-2-(phenylsulfonylmethyl)cyclohexyl)-2-oxopyrrolidin-3-yl)-3-(trifluoromethyl)benzamide (84a) 3-Chloropropanesulfonylchloride was incorporated into Example 83 (in place of 4-chlorobutyrylchloride) to give the title compound. MS found: $(M+H)^+=628$.

Example 85

N—((S)-1-((1S,2R,4R)-2-((4-Chlorophenylsulfonyl)methyl)-4-(isopropyl(methyl)amino)cyclohexyl)-2-oxopyrrolidin-3-yl)-3-fluoro-5-(trifluoromethyl)benzamide trifluoroacetate (85a) A portion of compound (61g) (500 mg) and 10% Pd/C (112 mg) in MeOH (150 mL) was hydrogenated at 40 psi on a Paar shaker for 4 h. The mixture was filtered through diatomaceous earth, rinsed with MeOH, then evaporated to dryness to give tert-butyl (1R,3R,4S)-4-amino-3-(hydroxymethyl)cyclohexylcarbamate as a colorless oil (348 mg). ESI MS m/z 245 $[C_{12}H_{24}N_2O_3+H]^+$.

(85b) To a portion of the above (85a) (4.14 g) in $CH_2Cl_2$ (169 mL) was added sodium bicarbonate (1.53 g), followed by dropwise addition of TrocCl (2.48 mL). The mixture was stirred at room temperature overnight, then diluted with $CH_2Cl_2$ (800 mL), washed with satd $NaHCO_3$ (3×150 mL) and brine (100 mL), dried over $Na_2SO_4$, filtered, and concentrated to (1S,2R,4R)-(4-tert-butoxycarbonylamino-2-hydroxymethylcyclohexyl)carbamic acid 2,2,2-trichloroethyl ester (7.14 g) as a white solid. ESI MS m/z 319 $[C_{15}H_{25}Cl_3N_2O_5-Boc+H]^+$.

(85c) A mixture of 85b (7.14 g), bis(p-chlorophenyl)disulfide (9.76 g, 34 mmol), and tri-n-butylphosphine (26 mL, 187 mmol) in THF (426 mL) was stirred under a nitrogen atmosphere at 75° C. for 16 h. The solvent was removed under vacuum, the residue was diluted with MeCN (800 mL), washed with hexanes (4×200 mL), concentrated, and flash chromatography (silica-gel, 0–50% ether/hexanes) afforded (1R,3R,4S)-[3-(4-chlorophenylsulfanylmethyl)-4-(2,2,2-trichloroethoxycarbonylamino)-cyclohexyl]carbamic acid tert-butyl ester (6.73 g) as a white solid: $^1H$ NMR (300 MHz, $CDCl_3$) δ 7.30–7.18 (m, 4H), 5.06 (d, J=9.2 Hz, 1H), 4.78 (d, J=12.1 Hz, 1H), 4.69 (d, J=12.1 Hz, 1H), 4.46 (d, J=7.5 Hz, 1H), 4.20–4.09 (m, 1H), 3.42 (br s, 1H), 2.94 (dd, J=13.4, 7.2 Hz, 1H), 2.69 (dd, J=13.4, 7.2 Hz, 1H), 2.22–2.08 (m, 1H), 2.05–1.78 (m, 3H), 1.68–1.38 (m, 10H), 1.34–0.82 (m, 2H).

(85d) A solution of 85c (6.73 g) in $CH_2Cl_2$ (41 mL) was cooled to 0° C.; 3-chloroperoxy-benzoic acid (70%, 6.38 g, 25.8 mmol) was added portion-wise. The mixture was stirred for 4 h, then diluted with $CH_2Cl_2$ (800 mL), washed with satd $NaHCO_3$ (3×150 mL) and brine (100 mL), dried over $Na_2SO_4$, filtered, and concentrated to give (1R,3R,4S)-[3-(4-chlorobenzenesulfonylmethyl)-4-(2,2,2-trichloroethoxycarbonylamino)cyclohexyl]carbamic acid tert-butyl ester (7.13 g) as an off-white solid. ESI MS m/z 478 $[C_{21}H_{28}Cl_4N_2O_6S-Boc+H]^+$.

(85e) To a solution of 85d (1.00 g) in THF (16 mL) was added glacial acetic acid (33 mL), followed by activated zinc dust (3.00 g). The mixture was stirred for 8 h, then diluted with EtOAc (500 mL), washed with satd $Na_2CO_3$ (3×150 mL) and brine (100 mL), dried over $Na_2SO_4$, filtered, and concentrated. The residue was purified by CombiFlash chromatography (silica-gel, MeOH/$CH_2Cl_2$) to give tert-butyl (1R,3R,4S)-4-amino-3-((4-chlorophenylsulfonyl)methyl)cyclohexylcarbamate (561 mg) as yellow solid. ESI MS m/z 403 $[C_{18}H_{27}ClN_2O_4S+H]^+$.

(85f) To a solution of 85e (561 mg) and N-Cbz-L-methionine (591 mg) in DMF (9.3 mL), cooled to 0° C., was added N-methylmorpholine (458 μL) and BOP reagent (925 mg). The mixture was stirred overnight at room temperature, then diluted with EtOAc (500 mL), washed with satd $NaHCO_3$ (3×150 mL), $NH_4Cl$ (3×150 mL), 5% aqueous LiCl (3×150 mL), and brine (100 mL), dried over $Na_2SO_4$, filtered, and concentrated to give crude (1R,3R,4S)-[4-(2-benzyloxycarbonylamino-4-methylsulfanylbutyrylamino)-3-(4-chlorobenzenesulfonylmethyl)cyclohexyl]carbamic acid tert-butyl ester (953 mg) as a yellow solid. ESI MS m/z 668 $[C_{31}H_{42}ClN_3O_7S_2+H]^+$.

(85g) A mixture of 85f (6.42 g, 9.60 mmol) and iodomethane (70 mL) was stirred overnight at room temperature. Methylene chloride (200 mL) was added and the iodomethane was azeotroped off under vacuum, repeating 6–8 times. The residue was dissolved in $CH_2Cl_2$ (200 mL), concentrated to ¼ volume under vacuum, and the resultant white solid was filtered (2.47 g, sulfonium salt by-product). The filtrate was concentrated to provide a yellow solid (6.80 g), which was used without further purification. This yellow solid (6.80 g), cesium carbonate (5.47 g, 16.8 mmol), and DMF (129 mL) was stirred 6 h at room temperature. More cesium carbonate (5.47 g, 16.8 mmol) was added and the reaction was stirred overnight. The mixture was diluted with EtOAc (1 L), washed with water (3×600 mL), 5% aqueous LiCl (3×600 mL), and brine (450 mL), dried over $Na_2SO_4$, filtered, and concentrated. The residue was purified by flash chromatography (silica-gel, 50–100% EtOAc/hexanes) to give (1S,2R,4R)-{1-[4-tert-butoxycarbonylamino-2-(4-chlorobenzenesulfonylmethyl)cyclohexyl]-2-oxo-pyrrolidin-3-yl}carbamic acid benzyl ester (3.21 g) as white solid. ESI MS m/z 620 $[C_{30}H_{38}ClN_3O_7S+H]^+$.

(85h) Compound 85 g was incorporated into step 62b to give benzyl (S)-1-((1S,2R,4R)-4-amino-2-((4-chlorophenylsulfonyl)methyl)cyclohexyl)-2-oxopyrrolidin-3-ylcarbamate: $^1H$ NMR (300 MHz, $CDCl_3$) δ 10.46 (br, s, 3H), 7.90–7.60 (m, 4H), 7.55–7.42 (m, 2H), 7.40–7.29 (m, 3H), 5.65 (d, J=7.3 Hz, 1H), 4.88 (s, 2H), 4.34–4.09 (m, 2H), 3.86–3.64 (m, 1H), 3.60–3.20 (m, 4H), 2.77–2.30 (m, 3H), 2.20–1.70 (m, 6H).

(85i) A mixture of 85h (875 mg, 1.38 mmol), acetone (3.03 mL, 41.4 mmol), and acetic acid (159 μL, 2.76 mmol) in 1,2-dichloroethane (30 mL) was stirred for 3 min, then treated with sodium triacetoxyborohydride (585 mg, 2.76 mmol). After stirring the mixture for 3 h, more acetone (4 mL), acetic acid (0.4 mL), and sodium triacetoxyborohydride (300 mg, 1.42 mmol) were added. After stirring the reaction mixture overnight, the solvent was removed under vacuum. The residue was dissolved in MeOH (30 mL); 37% aqueous formaldehyde (6 mL) and sodium cyanoborohydride (130 mg, 2.07 mmol) were added. The mixture was stirred 8 h. The solvent was removed under vacuum; the residue was taken up in $CH_2Cl_2$ (300 mL), washed with satd $NaHCO_3$ (3×100 mL) and brine (100 mL), dried over $Na_2SO_4$, filtered, and concentrated under vacuum to afford benzyl (S)-1-((1S,2R,4R)-2-((4-chlorophenylsulfonyl)methyl)-4-(isopropyl(methyl)amino)cyclohexyl)-2-oxopyrrolidin-3-ylcarbamate (707 mg) as a yellow solid. ESI MS m/z 576 $[C_{29}H_{38}ClN_3O_5S+H]^+$.

(85j) A mixture of 85i (536 mg) and 33% HBr in HOAc (15 mL) was stirred 30 minutes at room temperature. The mixture was triturated with ether (3×50 mL) and the residue was dissolved in MeOH (50 mL). The solvent was evaporated under vacuum to provide (S)-3-amino-1-((1S,2R,4R)-2-((4-chlorophenylsulfonyl)methyl)-4-(isopropyl(methyl)amino)cyclohexyl)pyrrolidin-2-one dihydrogen bromide (436 mg) as a tan solid, which was used without further purification in the next step. ESI MS m/z 442 $[C_{21}H_{32}ClN_3O_3S+H]^+$.

(85k) To a solution of crude 85j (92 mg) and 3-fluoro-5-(trifluoromethyl)benzoic acid (48 mg) in DMF (1.01 mL), cooled to 0° C., was added N-methylmorpholine (50 μL) and BOP reagent (101 mg). The mixture was stirred overnight at room temperature, diluted with EtOAc (500 mL), washed with satd $NaHCO_3$ (3×150 mL), $NH_4Cl$ (3×150 mL), 5% aqueous LiCl (3×150 mL), and brine (100 mL), dried over $Na_2SO_4$, filtered, and concentrated. The residue was purified by semi-preparative HPLC to give the title compound (71.2 mg) as a .TFA salt after lyophilization from MeCN/H$_2$O. ESI MS m/z 632 [C$_{29}$H$_{34}$ClF$_4$N$_3$O$_4$S+H]$^+$.

Example 86

3-Chloro-N-((S)-1-((1S,2R,4R)-2-((4-chlorophenylsulfonyl)methyl)-4-(isopropyl(methyl)amino)cyclohexyl)-2-oxopyrrolidin-3-yl)benzamide trifluoroacetate (86a) 3-Chlorobenzoic acid was incorporated into Example 85 (step 85k) to give the title compound. MS found: (M+H)$^+$=580.

Example 87

N—((S)-1-((1S,2R,4R)-2-((4-chlorophenylsulfonyl)methyl)-4-(isopropyl(methyl)amino)cyclohexyl)-2-oxopyrrolidin-3-yl)-3,5-bis(trifluoromethyl)benzamide trifluoroacetate (87a) 3,5-Bis(trifluoromethyl)benzoic acid was incorporated into Example 85 (step 85k) to give the title compound. MS found: (M+H)$^+$=683.

Example 88 tert-Butyl 2-(((S)-1-((1S,2R,4R)-2-((4-chlorophenylsulfonyl)methyl)-4-(isopropyl(methyl)amino)cyclohexyl)-2-oxopyrrolidin-3-yl)carbamoyl)-4-(trifluoromethoxy)phenylcarbamate (88a) 2-tert-Butoxycarbonylamino-5-trifluoromethoxybenzoic acid was incorporated into Example 85 (step 85k) to give the title compound. MS found: (M+H)$^+$=746.

Example 89

2-Amino-N—((S)-1-((1S,2R,4R)-2-((4-chlorophenylsulfonyl)methyl)-4-(isopropyl(methyl)amino)cyclohexyl)-2-oxopyrrolidin-3-yl)-5-(trifluoromethoxy)benzamide trifluoroacetate (89a) Example 88 was incorporated into Example 62 (step 62b) to give the title compound. MS found: (M+H)$^+$=645.

Example 90

N—((S)-1-((1S,2R,4R)-2-((4-Chlorophenylsulfonyl)methyl)-4-(isopropyl(methyl)amino)cyclohexyl)-2-oxopyrrolidin-3-yl)-3-(trifluoromethoxy)benzamide trifluoroacetate (90a) 3-Trifluoromethoxybenzoic acid was incorporated into Example 85 (step 85k) to give the title compound. MS found: (M+H)$^+$=630.2.

Example 91

N—((S)-1-((1S,2R,4R)-2-((4-Chlorophenylsulfonyl)methyl)-4-(isopropyl(methyl)amino)cyclohexyl)-2-oxopyrrolidin-3-yl)-3-(trifluoromethyl)benzamide trifluoroacetate (91a) 3-Trifluoromethylbenzoic acid was incorporated into Example 85 (step 85k) to give the title compound. MS found: (M+H)$^+$=614.0.

Example 92

3,5-Dichloro-N—((S)-1-((1S,2R,4R)-2-((4-chlorophenylsulfonyl)methyl)-4-(isopropyl(methyl)amino)cyclohexyl)-2-oxopyrrolidin-3-yl)benzamide trifluoroacetate (92a) 3,5-Dichlorobenzoic acid was incorporated into Example 85 (step 85k) to give the title compound. MS found: (M+H)$^+$=614.2.

Example 93

3-Chloro-N—((S)-1-((1S,2R,4R)-2-((4-chlorophenylsulfonyl)methyl)-4-(isopropyl(methyl)amino)cyclohexyl)-2-oxopyrrolidin-3-yl)benzamide N-Oxide (93a) A solution of Example 86 (13.6 mg) in CH$_2$Cl$_2$ (1.5 mL) was cooled to 0° C., then 3-chloroperoxybenzoic acid (77%, 10 mg) was added portion-wise. The mixture was stirred for 1.25 h, then diluted with CH$_2$Cl$_2$ (400 mL), washed with satd NaHCO$_3$ (3×100 mL) and brine (100 mL), dried over Na$_2$SO$_4$, filtered, and concentrated. The residue was purified by semi-preparative HPLC to give the title compound (6.8 mg, 57%) as a white solid after lyophilization from MeCN/aqueous TFA. ESI MS m/z 596 [C$_{28}$H$_{35}$Cl$_2$N$_3$O$_5$S+H]$^+$.

Example 94

N—((S)-1-((1S,2R,4R)-2-((4-Chlorophenylsulfonyl)methyl)-4-(isopropyl(methyl)amino)cyclohexyl)-2-oxopyrrolidin-3-yl)-3-(trifluoromethyl)benzamide N-Oxide (94a) Example 91 was incorporated into Example 93 to give the title compound. MS found: (M+H)$^+$=630.3.

Example 95

N—((S)-1-((1S,2R,4R)-2-((4-Chlorophenylsulfonyl)methyl)-4-(isopropyl(methyl)amino)cyclohexyl)-2-oxopyrrolidin-3-yl)-3-fluoro-5-(trifluoromethyl)benzamide N-Oxide (95a) Example 85 was incorporated into Example 93 to give the title compound. MS found: (M+H)$^+$=649.1.

Example 96

N—((S)-1-((1S,2R,4R)-4-(Isopropyl(methyl)amino)-2-(phenylsulfonylmethyl)cyclohexyl)-2-oxopyrrolidin-3-yl)-3-(trifluoromethyl)benzamide N-Oxide (96a) Example 5 was incorporated into Example 93 to give the title compound. MS found: (M+H)$^+$=596.3.

Example 97

N—((S)-1-((1S,2R,4R)-4-(isopropyl(methyl)amino)-2-((4-isopropylphenylsulfonyl)methyl)cyclohexyl)-2-oxopyrrolidin-3-yl)-3-(trifluoromethyl)benzamide Trifluoroacetate (97a) The compound from step 61f (4.0 g) was dissolved in MeOH (30 mL) prior to the addition of 10% Pd/C (600 mg). A hydrogen balloon was added and the mixture was stirred for 3 h. The Pd/C was filtered off and the solvent was concentrated to give (1R,2S,5R)-tert-butyl 2-amino-7-oxo-6-aza-bicyclo[3.2.1]octane-6-carboxylate (2.5 g). MS found: (M+H)$^+$=241.1.

(97b) This material (97a) was incorporated into Steps 52a to 52b (substituting N-Cbz-L-Met-OH for N-Boc-L-Met-OH) to give (1R,2S,5R)-tert-butyl 2-((S)-3-(benzyloxycarbonyl)-2-oxopyrrolidin-1-yl)-7-oxo-6-aza-bicyclo[3.2.1]octane-6-carboxylate. MS found: (M+H)$^+$=458.3.

(97c) A mixture of 97b (1.20 g) and 10% Pd/C (558 mg) in MeOH (200 mL) was hydrogenated at 1 atm for 4 h. The mixture was filtered through diatomaceous earth with MeOH wash and evaporated to dryness to give (1R,2S,5R)-tert-butyl 2-((S)-3-amino-2-oxopyrrolidin-1-yl)-7-oxo-6-aza-bicyclo[3.2.1]octane-6-carboxylate (779 mg) as a yellow solid that was used without further purification in the next step: $^1$H NMR (300 MHz, CDCl$_3$) δ 4.40–4.15 (m, 2H), 3.68 (t, J=9.0 Hz, 1H), 3.53–3.40 (m, 2H), 3.28–3.12 (m, 1H), 2.70–2.60 (m, 1H), 2.46–2.10 (m, 6H), 1.96–1.60 (m, 5H), 1.54 (s, 9H).

(97d) To a mixture of 97c (779 mg), 3-(trifluoromethyl)benzoic acid (687 mg), and DMF (12 mL), cooled to 0° C., was added N-methylmorpholine (793 μL, 7.23 mmol) and BOP reagent (1.60 g, 3.61 mmol). The mixture was stirred overnight at room temperature, diluted with EtOAc (800 mL), washed with satd NaHCO$_3$ (3×150 mL), NH$_4$Cl (3×150 mL), 5% aqueous LiCl (3×150 mL), and brine (100 mL), dried over Na$_2$SO$_4$, filtered, and concentrated. The residue was purified by flash chromatography (silica gel, 0–15% MeOH/CH$_2$Cl$_2$) to give (1R,2S,5R)-tert-butyl 7-oxo-2-((S)-2-oxo-3-(3-(trifluoromethyl)benzamido)pyrrolidin-1-yl)-6-aza-bicyclo[3.2.1]octane-6-carboxylate (1.20 g) as white solid. ESI MS m/z 496 [C$_{24}$H$_{28}$F$_3$N$_3$O$_5$S+H]$^+$.

(97e) To a solution of 97d (1.20 g, 2.42 mmol) in THF (18.6 mL) and water (3.6 mL) was added sodium borohydride (460 mg, 12.1 mmol) portion wise. After stirring the mixture for three hours, satd NaHCO$_3$ (50 mL) was added and the mixture was stirred for an additional 15 min. The mixture was diluted with ethyl acetate (500 mL), washed with satd NaHCO$_3$ (3×150 mL) and brine (100 mL), dried over Na$_2$SO$_4$, filtered, and concentrated to give tert-butyl (1R,3R,4S)-3-(hydroxymethyl)-4-((S)-2-oxo-3-(3-(trifluoromethyl)benzamido)pyrrolidin-1-yl)cyclohexylcarbamate (1.12 g) as a white solid. ESI MS m/z 500 [C$_{24}$H$_{32}$F$_3$N$_3$O$_5$+H]$^+$.

(97f) A mixture of 97e (100 mg), bis(p-1,2-bis(4-isopropylphenyl)disulfane (121 mg), and tri-n-butylphosphine (0.3 mL) in THF (5 mL) was stirred under a nitrogen atmosphere at 75° C. for 16 h. The solvent was removed under vacuum, the residue was diluted with MeCN (500 mL), washed with hexanes (4×200 mL), concentrated, and preparative TLC afforded tert-butyl (1R,3R,4S)-3-((4-isopropylphenylthio)methyl)-4-((S)-2-oxo-3-(3-(trifluoromethyl)benzamido)pyrrolidin-1-yl)cyclohexylcarbamate (79.7 mg) as a mixture of isomers. ESI MS m/z 634 [C$_{24}$H$_{32}$F$_3$N$_3$O$_5$+H]$^+$.

(97g) The compound from above (97f) was incorporated into Step 3e to give tert-butyl (1R,3R,4S)-3-((4-isopropylphenylsulfonyl)methyl)-4-((S)-2-oxo-3-(3-(trifluoromethyl)benzamido)pyrrolidin-1-yl)cyclohexylcarbamate: $^1$H NMR (300 MHz, CDCl$_3$) δ 8.10–7.76 (m, 4H), 7.75–7.62 (m, 1H), 7.61–7.30 (m, 3H), 4.90–4.04 (m, 2H), 3.87–3.20 (m, 4H), 3.13–2.86 (m, 1H), 2.80–2.42 (m, 1H), 2.36–1.50 (m, 25H), 0.99–0.75 (m, 4H); $^{19}$F NMR (282 MHz, CDCl$_3$) δ −63.1, −63.2.

(97h) The compound from above (97g) was incorporated into Step 611 to give the title compound after HPLC. MS found: (M+H)$^+$=622.3.

Example 98

N—((S)-1-((1S,2R,4R)-4-(isopropyl(methyl)amino)-2-(o-tolylsulfonylmethyl)cyclohexyl)-2-oxopyrrolidin-3-yl)-3-(trifluoromethyl)benzamide trifluoroacetate (98a) 1,2-diortho-tolyldisulfane was incorporated into Example 97 from Step 97f to 97h to give the title compound. MS found: (M+H)$^+$=594.6.

Example 99

N—((S)-1-((1S,2R,4R)-2-((4-Fluorophenylsulfonyl)methyl)-4-(isopropyl(methyl)amino)cyclohexyl)-2-oxopyrrolidin-3-yl)-3-(trifluoromethyl)benzamide trifluoroacetate (99a) 1,2-bis(4-Fluorophenyl)disulfane was incorporated into Example 97 from Step 97f to 97h to give the title compound. MS found: (M+H)$^+$=598.5.

Example 100

3-Chloro-N—((S)-1-((1S,2R,4R)-4-(isopropyl(methyl)amino)-2-(tosylmethyl)cyclohexyl)-2-oxopyrrolidin-3-yl)benzamide trifluoroacetate (100a) Compound 97b was incorporated into Step 97e to give (1S,2R,4R)-{1-[4-tert-butoxycarbonylamino-2-(hydroxymethyl)cyclohexyl]-2-oxo-pyrrolidin-3-yl}carbamic acid benzyl ester. MS found: (M+H)$^+$=462.

(100b) Compound 100a was incorporated into Step 97f (with 1,2-dipara-tolyldisulfane instead of bis(p-1,2-bis(4-isopropylphenyl)disulfane) and then Step 97g to give (1S, 2R,4R)-{1-[4-tert-butoxycarbonylamino-2-(4-methylbenzenesulfonylmethyl) cyclohexyl]-2-oxo-pyrrolidin-3-yl}carbamic acid benzyl ester. MS found: (M+H)$^+$=600.

(100c) Compound 100b was taken into Steps 85h-85j to give (S)-3-amino-1-((1S,2R,4R)-2-((4-methylphenylsulfonyl)methyl)-4-(isopropyl(methyl)amino)cyclohexyl)pyrrolidin-2-one dihydrogen bromide. MS found: (M+H)$^+$=584.

(100d) Compound 100c was taken into Step 85k (with 3-chlorobenzoic acid instead 3-fluoro-5-trifluoromethyl-benzoic acid) to give the title compound. MS found: (M+H)$^+$=560.2.

Example 101

2-Amino-N—((S)-1-((1S,2R,4R)-4-(isopropyl(methyl)amino)-2-(tosylmethyl)cyclohexyl)-2-oxopyrrolidin-3-yl)-5-(trifluoromethoxy)benzamidemide trifluoroacetate (101a) 2-(tert-Butoxycarbonyl)-5-(trifluoromethyl)benzoic acid was incorporated into Step (100d) to give tert-butyl 2-(((S)-1-((1S,2R,4R)-4-(isopropyl(methyl)amino)-2-(tosylmethyl)cyclohexyl)-2-oxopyrrolidin-3-yl)carbamoyl)-4-(trifluoromethoxy)phenylcarbamate. MS found: (M+H)$^+$=725.

(101b) The above material (101a) (20 mg) was dissolved in CH$_2$Cl$_2$ (2 mL) and cooled to 0° C. prior to the addition of TFA (4 mL). After the reaction was warmed to rt over 30

Example 102

1-[(1S,2R,4R)-(4-Amino-2-benzenesulfonyl-methyl-cyclohexyl)-4-(3-trifluoromethylphenyl)]-5,6-dihydro-1H-pyridin-2-one (102a) A solution of compound 61j (1.45 g, 3.9 mmol) in methanol (10 mL) was stirred on an ice bath and treated dropwise over 40 min with a solution of 1-(3-trifluoromethylphenyl)propenone (see procedure 28a, 786 mg, 3.9 mmol). The mixture was stirred at room temperature for 2 h, then was concentrated under vacuum. The residue was purified by flash column chromatography, eluting with 55% ethyl acetate-hexane, to provide (1R,3R,4S)-{3-benzene-sulfonylmethyl-4-[3-oxo-3-(3-trifluoromethylphenyl)-propylamino]cyclohexyl}carbamic acid tert-butyl ester (1.16 g) as a white glassy solid. MS found: $(M+H)^+=569.35$.

(102b) A suspension of sodium hydride (60%, 176 mg, 4.4 mmol) in tetrahydrofuran (5 mL) was stirred on an ice bath and treated dropwise over 5 min with dimethylphosphonoacetic acid tert-butyl ester (0.79 mL, 4.0 mmol). The mixture was stirred at room temperature for 25 min, then was cooled on an ice bath and treated with a solution of (1R,3R,4S)-{3-benzenesulfonylmethyl-4-[3-oxo-3-(3-trifluoromethylphenyl)-propylamino]cyclohexyl}carbamic acid tert-butyl ester (1.138 g, 2.0 mmol) in tetrahydrofuran (5 mL). The mixture was stirred at room temperature for 2.5 h, then was treated with saturated aqueous ammonium chloride. The mixture was extracted with ethyl acetate, and the organic extracts were dried over sodium sulfate and concentrated under vacuum. The residue was purified by flash column chromatography, eluting with 25% ethyl acetate-hexane, to provide the E isomer of 5-([1S,2R,4R]-2-benzenesulfonylmethyl-4-tert-butoxycarbonyl-aminocyclohexylamino)-3-(3-trifluoromethylphenyl)pent-2-enoic acid tert-butyl ester (511 mg) as a white solid. MS found: $(M+H)^+=667.41$. Further elution with 40% ethyl acetate-hexane provided the corresponding Z isomer (567 mg) as a white glassy solid. MS found: $(M+H)^+=667.41$.

(102c) A solution of the E isomer of 5-([1S,2R,4R]-2-benzenesulfonylmethyl-4-tert-butoxycarbonylaminocyclohexyl-amino)-3-(3-trifluoromethylphenyl)pent-2-enoic acid tert-butyl ester (495 mg) in dichloromethane (10 mL) was treated with trifluoroacetic acid (5 mL). After standing at room temperature for 4 h, the mixture was concentrated under vacuum to provide the E isomer of 5-([1S,2R,4R]-4-amino-2-benzenesulfonylmethylcyclohexylamino)-3-(3-trifluoromethyl-phenyl)pent-2-enoic acid, bis-trifluoroacetic acid salt, as a white glassy solid (736 mg) containing excess trifluoro-acetic acid. MS found: $(M+H)^+=511.20$. Without further purification, this material was dissolved in dichloromethane (5 mL) and treated sequentially with diisopropylethylamine (0.78 mL, 4.45 mmol), 4-(N,N-dimethylamino)pyridine (91 mg, 0.74 mmol) and TBTU (262 mg, 0.82 mmol). The solution was stirred at room temperature for 17.5 h, then was diluted with dichloromethane, washed with saturated aqueous sodium bicarbonate, dried over sodium sulfate and concentrated under vacuum. The residue was purified by flash column chromatography, eluting with 4% methanol-dichloromethane containing 0.4% aqueous ammonia, and then by reverse phase HPLC. The resulting product was converted to the free base by partitioning between 1N sodium hydroxide and ethyl acetate to provide the title product (130 mg) as a white glassy foam. MS found: $(M+H)^+=493.37$.

min, it was concentrated and dried to provide the title compound. MS found: $(M+H)^+=625.2$.

Example 103

1-([(1S,2R,4R)-2-benzenesulfonylmethyl-4-isopropylamino-cyclohexyl)-4-(3-trifluoromethylphenyl)-5,6-dihydro-1H-pyridin-2-one (103a) A solution of 1-[(1S,2R,4R)-(4-amino-2-benzenesulfonyl-methylcyclohexyl)-4-(3-trifluoromethylphenyl)]-5,6-dihydro-1H-pyridin-2-one (120 mg, 0.243 mmol) in 1,2-dichloroethane (2.5 mL) was treated sequentially with acetone (0.054 mL, 0.071 mmol), acetic acid (0.07 mL, 1.22 mmol) and sodium triacetoxyborohydride (155 mg, 0.731 mmol). The mixture was stirred at room temperature for 3 h, then was concentrated under vacuum. The residue was partitioned between saturated aqueous sodium bicarbonate and ethyl acetate, and the organic extracts were dried over sodium sulfate and concentrated under vacuum to provide the title product (110 mg) as a white glassy solid. MS found: $(M+H)^+=535.21$.

Example 104

1-[(1S,2R,4R)-2-benzenesulfonylmethyl-4-(isopropyl-methyl-amino)cyclohexyl]-4-(3-trifluoromethylphenyl)-5,6-dihydro-1H-pyridin-2-one (104a) A solution of 1-([(1S,2R,4R)-2-benzenesulfonylmethyl-4-isopropylamino-cyclohexyl)-4-(3-trifluoromethylphenyl)-5,6-dihydro-1H-pyridin-2-one (41 mg, 0.077 mmol) in methanol (1 mL) was treated with aqueous formaldehyde (37%, 0.029 mL, 0.383 mmol) and the mixture was stirred for 45 min. Sodium cyanoborohydride (7 mg, 0.115 mmol) was added, and the mixture stirred at room temperature for 2 h. Water was added and the mixture was extracted with ethyl acetate. The extracts were washed with brine, dried over sodium sulfate and concentrated under vacuum to provide the title product (42 mg) as a white glassy solid. MS found: $(M+H)^+=548.67$.

Example 105

1-[(1S,2R,4R)-2-benzenesulfonylmethyl-4-(isopropyl-ethyl-amino)cyclohexyl]-4-(3-trifluoromethylphenyl)-5,6-dihydro-1H-pyridin-2-one (105a) Following the procedure of Example 104 but substituting acetaldehyde for aqueous formaldehyde, 1-([(1S, 2R, 4R)-2-benzenesulfonylmethyl-4-isopropylamino-cyclohexyl)-4-(3-trifluoromethylphenyl)-5,6-dihydro-1H-pyridin-2-one (43 mg, 0.08 mmol) was converted to the title product (45 mg) as a white glassy solid. MS found: $(M+H)^+=563.29$.

Example 106

1-[1S,2R,4R)-2-Benzenesulfonylmethyl-4-(isopropyl-methyl-amino)-cyclohexyl]-(3S)-3-(6-chloro-2-trifluoromethyl-quinazolin-4-ylamino)-pyrrolidin-2-one, TFA salt Part A. Preparation of
6-Chloro-2-trifluoromethyl-quinazolin-4-ol 2-Amino-5-chlorobenzamide (Avocado)(1.00 g, 5.86 mmol, 1.0 eq.) and ethyl trifluoroacetate (4.19 mL, 35.2 mmol, 6.0 eq.) were dissolved in 50 mL of ethanol at rt under nitrogen and followed by the addition of 3.09 M sodium ethoxide in ethanol (11.38 mL, 35.2 mmol, 6.0 eq.) The mixture was refluxed 20 hours. Cooled to rt. Added 10 mL of 10% HOAc/H2O. Solids formed which were filtered, rinsed with 5 mL H2O, then dissolved in 20 mL of EtOAc/THF. Dried and stripped in vacuo to give 1.35 g of amber solids. LCMS detects (M+H)+=249.

Part B. Preparation of
4,6-Dichloro-2-trifluoromethyl quinazoline

6-Chloro-2-trifluoromethyl-quinazolin-4-ol (1.35 g, 5.43 mmol, 1 eq.), phosphorous oxychloride (4.88 mL, 52.4 mmol, 9.64 eq.) and triethylamine (2.43 mL, 17.4 mmol, 3.21 eq.) were refluxed for 2 hours. Stripped 3× from methylene chloride then dissolved in methylene chloride and rinsed 3× with saturated sodium bicarbonate, 1× with brine. Dried and stripped in vacuo to give an amber oil. Purified over silica gel in 9:1 Hexanes/EtOAc. Obtained 800 mg of off-white solids as product. The product was used immediately in Example 1 Part C.

Part C (3S)-3-Amino-1-[(1S,2R,4R)-2-benzenesulfonylmethyl-4-(isopropyl-methyl-amino)-cyclohexyl]-pyrrolidin-2-one (40 mg, 0.0982 mmol, 1 eq., see compound 52e), 4,6-dichloro-2-trifluoromethyl-quinazoline (239 mg, 0.105 mmol, 1 eq.) and triethylamine (55 ul, 0.419, 4 eq.) were dissolved in 3 mL of ethanol then microwaved at 100° C. until reaction was complete by LCMS. Purified by LCMS. Obtained 17 mg of product. LCMS detects (M+H)+=638.

Example 107

1-[(1S,2R,4R)-2-benzenesulfonylmethyl-4-(isopropyl-methyl-amino)-cyclohexyl]-(3S)-3-(7-chloro-quinazol-4-ylamino)-pyrrolidin-2-one, TFA salt Part A. Preparation of 7-Chloro-quinazolin-4-ol 2-Amino-4-chloro-benzoic acid (1.00 g, 11.7 mmol, 1.0 eq.), formamidine acetate (3.64 mL, 35.0 mmol, 3 eq.), and ethoxyethanol (20 mL) were refluxed under nitrogen overnight. Cooled to rt. Added 25 mL of diethyl ether. Solids precipitated. Filtered off solids. Pumped under high vacuum to give 2.75 g of white solids as product. LCMS detects (M+H)+=181.

Part B. Preparation of 4,7-Dichloro-quinazoline

7-Chloro-quinazolin-4-ol (1.1 g, 6.09 mmol, 1 eq.), phosphorous oxychloride (5.47 mL, 58.7 mmol, 9.00 eq.) and triethylamine (2.73 mL, 19.6 mmol, 3.21 eq.) were refluxed for 2 hours. Stripped then restripped 3× from methylene chloride, then dissolved in methylene chloride and rinsed 3× with saturated sodium bicarbonate, 1× with brine. Dried and stripped in vacuo to give an amber oil. Purified over silica gel in 9:1 to 3:1 Hexanes/EtOAc. Obtained 1.00 g of tan solids as product. LCMS detects (M+H)+=199.

107. Part C. Preparation of 1-[(1S,2R,4R)-2-benzenesulfonylmethyl-4-(isopropyl-methyl-amino)-cyclohexyl]-(3S)-3-(7-chloro-quinazol-4-ylamino)-pyrrolidin-2-one, TFA salt Followed the procedure of Example 106c starting from (3S*)-3-amino-1-[(1S*,2R*,4R*)-2-benzenesulfonylmethyl-4-(isopropyl-methyl-amino)-pyrrolidin-2-one and 4,7-dichloro-quinazoline. LCMS detects (M+H)+=570.

Example 108

Part A Preparation of 6-Chloro-quinazoline-2,4-diol

2-Amino-5-chlorobenzamide (Avocado) (3.00 g, 17.5 mmol, 1.0 eq.) was suspended in 105 mL of H2O and 1.75 mL of HOAc at rt. A 12 mL solution of H2O and sodium cyanate (2.80 g, 43.0 mmol, 2.46 eq.) was then added slowly. Stirred at 35° C. for 1 hour. Added 31.26 mL of 1.0 N NaOH slowly. Solids precipitated. Cooled to 0C. Carefully added conc. HCl to pH=3. Filtered solids. Solids were then stirred in diethyl ether then refiltered and pumped under high vacuum to give 3.36 grams of tan solids as product. LCMS detects (M+H)+=197.

Part B. Preparation of 2,4,6-Trichloro-quinazoline

6-Chloro-quinazoline-2,4-diol (0.50 g, 2.54 mmol, 1 eq.), phosphorous oxychloride (2.14 mL, 22.9 mmol, 9 eq.) and 2,6-lutidine (0.44 mL, 3.82 mmol, 1.5 eq.) were refluxed under nitrogen for 2 hours. The reaction was stripped then restripped 3× from methylene chloride, then dissolved in methylene chloride and rinsed 3× with saturated sodium bicarbonate, 1× with brine. Dried and stripped in vacuo to give an amber oil. Purified over silica gel in 9:1 to 3:1 Hexanes/EtOAc. Obtained 0.22 g of light colored solids as product. $^1$H NMR (400 MHz) (CD$_3$OD) δ 8.36 (s, 1H), 8.09 (d, 1H, J=7 Hz), 7.97 (d, 1H, J=7 Hz).

Example 108

Part C. Preparation of 1-[(1S,2R,4R)-2-benzenesulfonylmethyl-4-(isopropyl-methyl-amino)-cyclohexyl]-(3S)-3-(2,6-dichloro-quinazolin-4-ylamino)-pyrrolidin-2-one, TFA salt (3S)-3-Amino-1-[(1S,2R,4R)-2-benzenesulfonylmethyl-4-(isopropyl-methyl-amino)-cyclohexyl]-pyrrolidin-2-one (75 mg, 0.184 mmol, 1 eq.), 2,4,6-trichloro-quinazoline (43 mg, 0.184 mmol, 1 eq.) N,N-diisopropylethylamine (64 mL, 0.368 mmol, 2 eq.) in THF (3 mL) were refluxed overnight. Purified by HPLC. Obtained 62 mg of white solids. LCMS detects (M+H)+=604.

Example 109

Preparation of 1-[(1S,2R,4R)-2-benzenesulfonylmethyl-4-(isopropyl-methyl-amino)-cyclohexyl]-(3S)-3-(6-chloro-2-dimethylamino-quinazolin-4-ylamino)-pyrrolidin-2-one, TFA salt 1-[(1S*,2R*,4R*)-2-benzenesulfonylmethyl-4-(isopropyl-methyl-amino)-cyclohexyl]-(3S*)-3-(2,6-dichloro-quinazolin-4-ylamino)-pyrrolidin-2-one (27 mg, 0.0375 mmol, 1 eq.), 2.0 M dimethylamine in THF (0.94 mL, 1.88 mmol, 50 eq.), and THF (1 mL) were refluxed until reaction was complete by LCMS. Purified by HPLC. Obtained 22 mg of white solids as product. LCMS detects (M+H)+=613.

Example 110

Preparation of 1-[(1S,2R,4R)-2-benzenesulfonylmethyl-4-(isopropyl-methyl-amino)-cyclohexyl]-(3S)-3-(6-chloro-2-hydroxy-quinazolin-4-ylamino)-pyrrolidin-2-one, TFA salt 1-[(1S,2R,4R)-2-benzenesulfonylmethyl-4-(isopropyl-methyl-amino)-cyclohexyl]-(3S)-3-(2,6-dichloro-quinazolin-4-ylamino)-pyrrolidin-2-one (20 mg) and dimethyl sulfoxide (2 mL) were heated at 60° C. under nitrogen until reaction was complete by LCMS. Purified by HPLC to give 6.0 mg of white solids as product. LCMS detects (M+H)+=586.

Example 111

Part A. Preparation of 6-Trifluoromethyl-quinazolin-4-ol

2-Amino-5-trifluoromethyl-benzamide (ButtPark) (1.00 g, 4.90 mmol, 1 eq.) and formic acid (3.30 mL, 87.2 mmol, 17.8 eq.) were refluxed for 2.5 hours. Cooled to rt then added water (10 mL). Stirred 15 minutes then filtered off solids which were present. The solids were dried at 110° C. for 3 hours to give 520 mg of white solids as product. LCMS detects (M+H)+=215.

Part B. Preparation of 4-Chloro-6-trifluoromethyl-quinazoline

6-Trifluoromethyl-quinazolin-4-ol (0.95 g, 4.44 mmol, 1 eq.), phosphorous oxychloride (2.48 mL, 26.6 mmol, 6 eq.) and triethylamine (3.71 mL, 26.6 mmol, 6 eq.) were refluxed for 2.5 hours. Stripped 3× from methylene chloride then dissolved in methylene chloride and rinsed 3× with saturated NaHCO3, 1× with brine. Dried and stripped in vacuo to give and amber oil. Purified over silica gel in 9:1 Hexanes/EtOAc. Obtained 560 mg of off-white solids as product. The product was used immediately in Ex 111 part C.

Example 111

Part C. Preparation of 1-[(1S,2R,4R)-2-benzene-sulfonylmethyl-4-(isopropyl-methyl-amino)-cyclo-hexyl]-(3S)-3-(6-trifluoromethyl-quinazolin-4-ylamino)-pyrrolidin-2-one, TFA salt Followed the procedure of Example 106 Part C starting from (3S)-3-amino-1-[(1S,2R,4R)-2-benzenesulfonylm-ethyl-4-(isopropyl-methyl-amino)-cyclohexyl]-pyrrolidin-2-one and 4-Chloro-6-trifluoromethyl-quinazoline. Purified by HPLC. Obtained 57 mg of white solids as title product. LCMS detects (M+H)+=604.

Example 112

Part A. Preparation of 6-tert-Butyl-thieno[3,2-d]pyrimidin-4-ol

3-Amino-5-tert-butyl-thiophene-2-carboxylic acid methyl ester (1.00 g, 4.69 mmol, 1 eq.), formamidine acetate (1.46 g, 4.69 mmol, 3 eq.) and 2-ethoxyethanol (10 mL) were refluxed under nitrogen for 4 hours. Purified over silica gel in 3:1 to 1:1 Hexanes/ethyl acetate to 100% ethyl acetate to obtain 970 mg of yellow solids as product. LCMS detects (M+H)+=209.

Part B. Preparation of 6-tert-Butyl-4-chloro-thieno[3,2-d]pyrimidine 6-tert-Butyl-thieno[3,2-d]pyrimidin-4-ol (500 mg, 2.40 mmol, 1 eq.) and phosphorous oxychloride (4.48 mL, 48.0 mmol, 20 eq.) were refluxed under nitrogen for 1.5 hours. Stripped 3× from methylene chloride then dissolved in methylene chloride and rinsed 3× with saturated NaHCO3, 1× with brine. Dried and stripped in vacuo to give 250 mg of amber solids as product. LCMS detects (M+H)+=227.

Example 112

Part C. Preparation of 1-[(1S,2R,4R)-2-benzene-sulfonylmethyl-4-(isopropyl-methyl-amino)-cyclo-hexyl]-(3S)-3-(6-tert-butyl-thieno[3,2-d]pyrimidin-4-ylamino)-pyrrolidin-2-one, TFA salt Followed the procedure of Example 106 Part C starting from (3S)-3-amino-1-[(1S,2R,4R)-2-benzenesulfonylm-ethyl-4-(isopropyl-methyl-amino)-cyclohexyl]-pyrrolidin-2-one and 6-tert-butyl-4-chloro-thieno[3,2-d]pyrimidine. Purified by HPLC to give 6.0 mg of white solids as title product. LCMS detects (M+H)+=598.

Example 113

Part A. Preparation of 6-tert-Butyl-2-trifluorom-ethyl-thieno[3,2-d]pyrimidin-4-ol 3-Amino-5-tert-butyl-thiophene-2-carboxylic acid methyl ester (0.50 g, 2.34 mmol, 1 eq.) and trifluoroacetamidine (263 mg, 2.34 mmol, 1 eq.) were heated neat at 150° C. until reaction was complete by TLC. Cooled to rt then dissolved resultant solids in chloroform. Dried and stripped in vacuo to give 540 mg of white solids as product. LCMS detects (M+H)+=277.

Part B. Preparation of 6-tert-Butyl-4-chloro-2-trif-luoromethyl-thieno[3,2-d]pyrimidine Followed the procedure of Example 112 Part B starting from 6-tert-Butyl-2-trifluoromethyl-thieno[3,2-d]pyrimidin-4-ol. LCMS detects (M+H)+=295.

Example 113

Part C Preparation of 1-[(1S,2R,4R)-2-benzene-sulfonylmethyl-4-(isopropyl-methyl-amino)-cyclo-hexyl]-(3S)-3-(6-tert-butyl-2-trifluoromethyl-thieno[3,2-d]pyrimidin-4-ylamino)-pyrrolidin-2-one, TFA salt Followed the procedure of Example 106 Part C starting from 6-tert-butyl-4-chloro-2-trifluoromethyl-thieno[3,2-d]pyrimidine. Purified by HPLC. LCMS detects (M+H)+=666.

Example 114

Part A. Preparation of Ethyl 3-(tert-Butyl)-pyrrole-5-carboxylate

The above compound was synthesized by the methods disclosed in Example 129 employing tert-butylchloride in place of 1-chloroadamantane and foregoing the initial 30 minute heating period. MS found: (M+H)+=196.28.

Part B. Preparation of Ethyl 3-tert-Butyl-1-aminopyrrole-5-carboxylate.

Preparation of monochloramine by the method of John Hynes, Jr., et al., J. Org. Chem., 2004, in press: NH4Cl (3 g, 56 mmol, was mixed in ether (110 mL) and cooled to −5° C. Concentrated NH4OH (4.7 mL) was then added followed by dropwise addition of bleach (Chlorox, 72 mL) over 15 minutes. The mixture was stirred for 15 minutes, the layers separated and the organic layer washed with brine. The organic layer was dried over powdered CaCl2 in the freezer for 1 h and used for the subsequent step immediately.

Ethyl 3-(tert-butyl)pyrrole-5-carboxylate (obtained from Part A) (1.67 g, 8.6 mmol, 1 eq) was dissolved in DMF. Sodium hydride (60% suspension in oil) (0.41 g, 10 mmol, 1.2 eq) was then added thereto cautiously and stirred for 45 minutes at RT under nitrogen. Monochloramine was then added (0.15M in ether, 68.4 mL, 10 mmol, 1.2 eq). The next morning, the reaction is quenched with saturated aqueous $Na_2S_2O_3$, diluted with water and extracted into ether. The ether layer is dried, filtered and stripped to yield 3.19 g of product as a yellow oil which eventually crystallized as long needles. MS found: (M+H)+=211.34.

Part C. Preparation of 6-tert-Butyl-pyrrolo[2,1-f][1,2,4]triazin-4-ol

Ethyl 3-tert-Butyl-1-aminopyrrole-5-carboxylate (1.00 g, 4.76 mmol, 1 eq), formamidine acetate (1.46 g, 14.3 mmol, 3 eq.) and ethoxyethanol (10 mL) were mixed and refluxed for 3 hours. The solvent was stripped and then restripped from chloroform (3×) to yield a solid. This solid was stirred in 5 mL MeOH, filtered, and the collected solids rinsed with $Et_2O$ and dried to yield 233 mg of a white solid as product. LCMS found: (M+H)+$^+$=191.

Part D. Preparation of 6-tert-Butyl-4-chloro-pyrrolo [2,1-f][1,2,4]triazine

The compound from Part C immediately above (0.43 mg, 2.26 mmol, 1 eq.) and POCl3 (4.21 mL, 45.2 mmol, 20 eq.) were mixed and refluxed for 4 hours. The mixture was stripped then restripped 3× from methylene chloride and then dissolved in methylene chloride and rinsed 3× with sat'd NaHCO3, 1× with brine. Dried and stripped in vacuo to give 490 mg of an amber oil. LCMS detects (M+H)+ =210.

Example 114

Part E. Preparation of 1-[(1S,2R,4R)-2-benzenesulfonylmethyl-4-(isopropyl-methyl-amino)-cyclohexyl]-(3S)-3-(6-tert-butyl-pyrrolo[2,1-f][1,2,4]triazin-4-ylamino)-pyrrolidin-2-one The above compound was synthesized using the procedure of Example 106 Part C starting from of 6-tert-Butyl-4-chloro-pyrrolo[2,1-f][1,2,4]triazine. LCMS detects (M+H)+=581.

Example 115

Part A. Preparation of 6-Adamant-1-yl-4-chloropyrrolo[2,1-f][1,2,4]triazine

The above compound was prepared from ethyl 3-(adamanty-1-yl)-pyrrole-5-carboxylate by the procedures in Example 114, parts A, B, and C beginning with ethyl 3-(Adamanty-1-yl)-pyrrole-5-carboxylate (Example 129). Mass found: (M+H)+$^+$=288.22.

Example 115

Part B. Preparation of (3S)-3-(6-Adamantan-1-ylpyrrolo[2,1-f][1,2,4]triazin-4-ylamino)-1-[(1S,2R,4R)-2-benzenesulfonylmethyl-4-(isopropyl-methylamino)-cyclohexyl]-pyrrolidin-2-one 3S-3-Amino-1-[(1S,2R,4R)-2-benzenesulfonylmethyl-4-(isopropyl-methyl-amino)-cyclohexyl]-pyrrolidin-2-one (49 mg, 0.12 mmol, 1 eq), 6-adamant-1-yl-4-chloro-pyrrolo[2, 1-f][1,2,4]triazine (46 mg, 0.18 mmol, 1.5 eq), triethylamine (0.066 mL, 0.48 mmol, 4 eq) and ethanol (1.7 mL) were microwaved at 100° C. for 1 hour. The contents were stripped and flash chromatographed in 100% EtOAc to 4:1 chloroform/methanol to yield 49 mg of a white powder. This powder was taken up in methylene chloride and washed with water (3×). The organic layer was dried and stripped to yield 30 mg of a white powder. Mass found: (M+H)+$^+$=659.49.

Example 116

Part A. Preparation of 2-Phenyl-3H-imidazole-4-carboxylic acid methyl ester

Phenylamidoxime (5.00 g, 36.7 mmol, 1 eq.), methyl propriolate (3.27 mL, 36.7 mmol, 1 eq.), and methanol (25 mL) were refluxed overnight under nitrogen. The reaction was stripped 2× from toluene. Added diphenyl ether (20 mL then heated at 200° C. overnight. Cooled to rt. Added ethyl acetate (50 mL). Rinsed 2× with brine. The organic layer was dried and stripped in vacuo to give an amber oil. Triturated solids with diethyl ether. Obtained 2.84 g of tan solids as product. LCMS detects (M+H)+=203.

Part B. Preparation of 3-Methyl-2-phenyl-3H-imidazole-4-carboxylic acid methyl ester and 1-Methyl-2-phenyl-1H-imidazole-4-carboxylic acid methyl ester 2-Phenyl-3H-imidazole-4-carboxylic acid methyl ester (250 mg, 1.24 mmol, 1 eq.) was dissloved in THF (10 mL) at rt under nitrogen then cooled to 0° C. Potassium hexamethyldisilazane (0.5 M in toluene) (2.72 mL, 1.36 mmol, 1.1 eq.) was added dropwise via an addition funnel. Stirred 10 minutes. Added iodomethane (85 mL, 1.36 mmol, 1.1 eq.). Stirred overnight at rt. Added saturated NH4Cl (20 mL), and extracted 2× with methylene chloride. The organic layers were combined, dried and stripped in vacuo to give 225 mg of an amber oil as product. LCMS detects (M+H)+=217.

Part C. Preparation of 3-Methyl-2-phenyl-3H-imidazole-4-carboxylic acid and 1-Methyl-2-phenyl-1H-imidazole-4-carboxylic acid 3-Methyl-2-phenyl-3H-imidazole-4-carboxylic acid methyl ester and its isomer (225 mg, 1.04 mmol, 1 eq.), 4 N NaOH (1.30 mL, 5.20 mmol, 5 eq.) and THF (5 mL) were mixed at rt then refluxed for 2 hours then stirred overnight at rt. Stripped off the THF, added water then rinsed 1× with diethyl ether. The basic aqueous pH was adjusted to 3 with conc. HCl. The aqueous was then extracted 3× with chloroform (10 mL). The chloroform layers were combined, dried and stripped in vacuo to give 30 mg of a film as product. LCMS detects (M+H)+=203.

Example 116

Part D. Preparation of 3-Methyl-2-phenyl-3H-imidazole- 4-carboxylic acid {(3S)-1-[(1S,2R,4R)-2-benzenesulfonylmethyl-4-(isopropyl-methyl-amino)-cyclohexyl]-2-oxo-pyrrolidin-3-yl}-amide, TFA salt and 1-Methyl-2-phenyl-1H-imidazole-4-carboxylic acid {(3S)-1-[(1S,2R,4R)-2-benzenesulfonylmethyl-4-(isopropyl-methyl-amino)-cyclohexyl]-2-oxo-pyrrolidin-3-yl}-amide (3S)-3-Amino-1-[(1S,2R,4R)-2-benzenesulfonylmethyl-4-(isopropyl-methyl-amino)-cyclohexyl]-pyrrolidin-2-one (and other isomer) (50 mg, 0.124 mmol, 1 eq.), 3-methyl-2-phenyl-3H-imidazole-4-carboxylic acid (30 mg, 0.148 mmol, 1.2 eq.), 1-hydroxybenzotriazole hydrate (HOBT) (20 mg, 0.148 mmol, 1.2 eq.), 1-[3-(dimethylamino)propyl]-3-ethylcarbodiimide HCl (EDCI) (28 mg, 0.148 mmol, 1.2 eq.), triethylamine (35 µL, 0.247 mmol, 2 eq.) and THF (5 mL were stirred at rt under nitrogen overnight. Purified by LCMS. Obtained 50 mg of white solids as product. LCMS detects (M+H)+=592.

Example 117

Part A. Preparation of 3-Benzyl-2-phenyl-3H-imidazole-4-carboxylic acid methyl ester and 1-Benzyl-2-phenyl-1H-imidazole-4-carboxylic acid methyl ester 2-Phenyl-3H-imidazole-4-carboxylic acid methyl ester (250 mg, 1.24 mmol, 1 eq.) was dissloved in THF (10 mL) at rt under nitrogen then cooled to 0° C. Potassium hexamethyldisilazane (0.5 M in toluene) (2.72 mL, 1.36 mmol, 1.1 eq.) was added dropwise via an addition funnel. Stirred 10 minutes. Added benzylbromide (0.16 mL, 1.36 mmol, 1.1 eq.). Stirred overnight at rt. Added saturated NH₄Cl (20 mL), and extracted 2× with methylene chloride. The organic layers were combined, dried and stripped in vacuo to give 200 mg of an amber oil as product. LCMS detects (M+H)+=293.

Part B. Preparation of 3-Benzyl-2-phenyl-3H-imidazole-4-carboxylic acid and 1-Benzyl-2-phenyl-1H-imidazole-4-carboxylic acid 3-Benzyl-2-phenyl-3H-imidazole-4-carboxylic acid methyl ester (200 mg, 0.684 mmol, 1 eq.) and other isomer, 4 N NaOH (0.86mL, 3.42 mmol, 5 eq.) and THF (5 mL) were mixed at rt then refluxed for 2 hours then stirred overnight at rt. Stripped off the THF, added water then rinsed 1× with diethyl ether. The basic aqueous pH was adjusted to 3 with conc. HCl. The aqueous was then extracted 3× with chloroform (10 mL). The chloroform layers were combined, dried and stripped in vacuo to give 390 mg of an amorphous solid as product. LCMS detects (M+H)+=279.

Example 117

Part C. Preparation of 3-Benzyl-2-phenyl-3H-imidazole- 4-carboxylic acid {(3S)-1-[(1S,2R,4R)-2-benzenesulfonylmethyl-4-(isopropyl-methyl-amino)-cyclohexyl]-2-oxo-pyrrolidin-3-yl}-amide, TFA salt and 1-Benzyl-2-phenyl-1H-imidazole-4-carboxylic acid {(3S)-1-[(1S,2R,4R)-2-benzenesulfonylmethyl-4-(isopropyl-methyl-amino)-cyclohexyl]-2-oxo-pyrrolidin-3-yl}-amide, TFA salt Followed the procedure of Example 116, Part D starting from (3S)-3-amino-1-[(1S,2R,4R)-2-benzenesulfonylmethyl-4-(isopropyl-methyl-amino)-cyclohexyl]-pyrrolidin-2-one and 3-benzyl-2-phenyl-3H-imidazole-4-carboxylic acid and its other isomer.
Obtained 21 mg of off-white solids as product. LCMS detects (M+H)+=668.

Example 118

Preparation of 2-Phenyl-3H-imidazole-4-carboxylic acid {(3S)-1-[(1S,2R,4R)-2-benzenesulfonylmethyl-4-(isopropyl-methyl-amino)-cyclohexyl]-2-oxo-pyrrolidin-3-yl}-amide, TFA salt 3-Benzyl-2-phenyl-3H-imidazole-4-carboxylic acid {(3S*)-1-[(1S,2R,4R)-2-benzenesulfonylmethyl-4-(isopropyl-methyl-amino)-cyclohexyl]-2-oxo-pyrrolidin-3-yl}-amide and its other isomer (15 mg) 5 mL methanol, and 20% Pd(OH)₂ (10 mg) were hydrogenated until completion by TLC on a Parr shaker at 50 psi. Filtration through fiberglass filter paper under nitrogen and removal of solvent in vacuo yielded 6 mg of product. LCMS detects (M+H)+=578.

Example 119

Part A. Preparation of 6,7-Dimethoxy-quinazolin-4-ol

Followed the procedure of Example 107 Part A starting from 2-amino-4,5-dimethoxy-benzoic acid. LCMS detects (M+H)+=207.

Part B. Preparation of 4-Chloro-6,7-dimethoxy-quinazoline 6,7-Dimethoxy-quinazolin-4-ol (1.00 g, 4.85 mmol, 1 eq.), phosphorous oxychloride (4.07 mL, 43.6 mmol, 9.00 eq.) and triethylamine (6.08 mL, 43.6 mmol, 9 eq.) were refluxed for 2 hours. Stripped then restripped 3× from methylene chloride then dissolved in methylene chloride and rinsed 3× with saturated sodium bicarbonate, 1× with brine. Dried and stripped in vacuo to give an amber oil. Purified over silica gel in 9:1 to 3:1 Hexanes/EtOAc. Obtained 0.84 g of off-white solids as product. LCMS detects (M+H)+=225.

Example 119

Part C. Preparation of 1-[(1S,2R,4R)-2-benzenesulfonylmethyl-4-(isopropyl-methyl-amino)-cyclohexyl]-(3S)-3-(6,7-dimethoxy-quinazolin-4-ylamino)-pyrrolidin-2-one, TFA salt Followed the procedure of Example 106 Part C starting from (3S)-3-Amino-1-[(1S,2R,4R)-2-benzenesulfonylmethyl-4-(isopropyl-methyl-amino)-cyclohexyl]-pyrrolidin-2-one and 4-chloro-6,7-dimethoxy-quinazoline. LCMS detects (M+H)+=596.

Example 120

Part A. Preparation of 6-Fluoro-quinazolin-4-ol

Followed the procedure of Example 107 Part A starting with 2-amino-5-fluorobenzoic acid. ¹H NMR (400 MHz) (CD3OD) ? 8.06 (s, 1H), 7.87 (m, 1H), 7.75 (m, 1H), 7.62 (m, 1H).

Part B. Preparation of 4-Chloro-6-fluoro-quinazoline

Followed the procedure of Example 112 Part B starting with 6-fluoroquinazolin-4-ol. LCMS detects (M+H)+=183.

Example 120

Part C. Preparation of 1-[(1S,2R,4R)-2-benzenesulfonylmethyl-4-(isopropyl-methyl-amino)-cyclohexyl]-(3S)-3-(6-fluoro-quinazolin-4-ylamino)-pyrrolidin-2-one, TFA salt Followed the procedure of Example 106 Part C starting from (3S)-3-Amino-1-[(1S,2R,4R)-2-benzenesulfonylmethyl-4-(isopropyl-methyl-amino)-cyclohexyl]-pyrrolidin-2-one and 4-chloro-6-fluoro-quinazoline. Purified by HPLC. LCMS detects (M+H)+=554.

Example 121

Part A. Preparation of 6-Methyl-quinazolin-4-ol

Followed the procedure of Example 107 Part A starting from 2-Amino-5-methyl-benzoic acid. $^1$H NMR (400 MHz) (CD3OD) δ 8.00 (m, 2H), 7.68 (d, 1H, J=7 Hz), 7.59 (d, 1H, J=7 Hz), 2.47 (s, 3H).

Part B. Preparation of 4-Chloro-6-methyl-quinazoline

Followed the procedure of Example 111 Part B starting with 6-methylquinazolin-4-ol. LCMS detects (M+H)+=179.

Example 121

Part B. Preparation of 1-[(1S,2R,4R)-2-benzenesulfonylmethyl-4-(isopropyl-methyl-amino)-cyclohexyl]-(3S)-3-(6-methyl-quinazolin-4-ylamino)-pyrrolidin-2-one, TFA salt Followed the procedure of Example 106 Part C starting from (3S)3-amino-1-[(1S,2R,4R)-2-benzenesulfonylmethyl-4-(isopropyl-methyl-amino)-cyclohexyl]-pyrrolidin-2-one and 4-chloro-6-methyl-quinazoline. Purified by HPLC. LCMS detects (M+H)+=550.

Example 122

Part A. Preparation of 6-Phenyl-thieno[2,3-d]pyrimidin-4-ol

Followed the procedure of Example 112 Part A starting from 2-Amino-5-phenyl-thiophene-3-carboxylic acid methyl ester. LCMS detects (M+H)+=229.

Part B. Preparation of 4-Chloro-6-phenyl-thieno[2,3-d]pyrimidine

Followed the procedure of Example 112 Part B starting with 6-Phenyl-thieno[2,3-d]pyrimidin-4-ol. LCMS detects (M+H)+=247.

Example 122

Part C. Preparation of 1-[(1S,2R,4R)-2-benzenesulfonylmethyl-4-(isopropyl-methyl-amino)-cyclohexyl]-(3S)-3-(6-phenyl-thieno[2,3-d]pyrimidin-4-ylamino)-pyrrolidin-2-one, TFA salt Followed the procedure of Example 106 Part C starting from (3S)-3-Amino-1-[(1S,2R,4R)-2-benzenesulfonylmethyl-4-(isopropyl-methyl-amino)-cyclohexyl]-pyrrolidin-2-one and of 4-chloro-6-phenyl-thieno[2,3-d]pyrimidine. Purified by HPLC. LCMS detects (M+H)+=618.

Example 123

Part A. Preparation of 2-Butyrylamino-5-chloro-benzamide

2-Amino-5-chlorobenzamide (1.10 g, 6.5 mmol, 1 eq.), 1.000 N NaOH (6.50 mL, 6.5 mmol, 1 eq.) and THF (20 mL) were mixed and stirred at 0° C. To this mixture was added butyryl chloride dropwise (0.68 mL, 6.50 mmol, 1 eq.). More acid chloride and base were added to drive reaction to completion. The reaction was allowed to warm to rt. After 4 days the reaction was worked up by adding ethyl acetate, washing with 1 N HCl (3×), saturated sodium bicarbonate (1×), and brine (1×). The organic layer was dried and stripped to yield 1.44 g of a white powder as product. LCMS detects (M+H)+=241.0.

Part B. Preparation of 6-Chloro-2-propyl-quinazolin-4-ol

2-Butyrylamino-5-chloro-benzamide (1.08 g, 4.49 mmol, 1 eq.), 1.000 N NaOH (13.46 mL, 13.5 mmol, 3 eq.) and ethanol (10 mL) were mixed and stirred at rt for 15 minutes. The mixture was acidified to pH=2 with 1.000 N HCl. The mixture was extracted with ethyl acetate. Solids that did not dissolve were filtered and rinsed with diethyl ether to dry. Obtained 810 mg of a white solid product. LCMS detects (M+H)+=223.

Part C Preparation of 4,6-Dichloro-2-propyl-quinazoline

6-Chloro-2-propyl-quinazolin-4-ol (810 mg, 3.64 mmol, 1 eq.), phosphorous oxychloride (3.30 mL, 35.1 mmol, 9.64 eq.) and triethylamine (1.63 mL, 11.7 mmol, 3.21 eq.) were refluxed for 2 hours. Stripped 3× from methylene chloride then dissolved in methylene chloride and rinsed 3× with saturated sodium bicarbonate, 1× with brine. Dried and stripped in vacuo to give an amber oil. Purified over silica gel in 9:1 Hexanes/EtOAc. Obtained 510 mg of off-white solids as product. The product was used immediately in Example 121 Part D.

Example 123

Part D. Preparation of 1-[(1S,2R,4R)-2-benzenesulfonylmethyl-4-(isopropyl-methyl-amino)-cyclohexyl]-(3S)-3-(6-chloro-2-propyl-pyrido[2,3-d]pyrimidin-4-ylamino)-pyrrolidin-2-one, TFA salt 1-[(1S,2R,4R)-2-benzenesulfonylmethyl-4-(isopropyl-methyl-amino)-cyclohexyl]-(3S)-3-(6-chloro-2-propyl-pyrido[2,3-d]pyrimidin-4-ylamino)-pyrrolidin-2-one, TFA salt was prepared from (3S)-3-amino-1-[(1S,2R,4R)-2-benzenesulfonylmethyl-4-(isopropyl-methyl-amino)-cyclohexyl]-pyrrolidin-2-one and 4,6-dichloro-2-propyl-quinazoline using the conditions described in Example 106 Part C. MS (ES+)=613 (M+H)+.

Example 124

Part A. Preparation of 1-[(1S,2R,4R)-2-benzenesulfonylmethyl-4-(isopropyl-methyl-amino)-cyclohexyl]-(3S)-3-(6-chloro-2-isopropyl-quinazolin-4-ylamino)-pyrrolidin-2-one, TFA salt The above compound was synthesized from isobutyryl chloride using the procedures found in Example 123, Parts A–D. MS (ES+)=612 (M+H)+.

Example 125

Preparation of 1-[(1S,2R,4R)-2-benzenesulfonylmethyl-4-(isopropyl-methyl-amino)-cyclohexyl]-(3S)-3-(2-tert-butyl-6-chloro-quinazolin-4-ylamino)-pyrrolidin-2-one, TFA salt The above compound was synthesized from 2,2-Dimethyl-propionyl chloride using the procedures found in Example 123, Parts A–D. LCMS detects (M+H)+=626.

Example 126

Part A. Preparation of 6-Chloro-2-methyl-quinazolin-4-ol

2-Amino-5-chlorobenzoic acid (3.58 g, 20.9 mmol, 1 eq.), acetamidine hydrochloride (2.36 g, 25.1 mmol, 1.2 eq.) and 2-ethoxyethanol (70 mL) were mixed and refluxed for 48 h. The resultant solids were filtered and dried to yield 1.57 g of yellow solid product. MS (ES+)=195/197 (M+H)+$^+$.

Part B. Preparation of 4,6-Dichloro-2-methyl-quinazoline

6-Chloro-2-methyl-quinazolin-4-ol (0.75 g, 3.90 mmol, 1 eq.), phosphorous oxychloride (3.47 mL, 37.4 mmol, 9.64 eq.) and triethylamine (1.62 mL, 12.5 mmol, 3.21 eq.) were refluxed for 4 hours. The mixture was stripped twice from toluene and the residue dissolved in ethyl acetate. The organic layer was washed with saturated NH$_4$Cl (2×), dried and stripped. The residue was flash chromatographed in 3:2 ethyl acetate/hexanes to yield 400 mg of a light yellow solid product. MS (ES+)=213/215/217 (M+H)+$^+$.

Example 126

Part C. Preparation of 1-[(1S,2R,4R)-2-benzene-sulfonylmethyl-4-(isopropyl-methyl-amino)-cyclohexyl]-(3S)-3-(6-chloro-2-methyl-quinazolin-4-ylamino)-pyrrolidin-2-one The above compound was synthesized following the procedure of Example 106 Part C using the product from Part B immediately above. MS (ES+)=585 (M+H)+$^+$.

Example 127

Preparation of 1-[(1S,2R,4R)-2-benzenesulfonylmethyl-4-(isopropyl-methyl-amino)-cyclohexyl]-(3S)-3-(6-chloro-2-ethyl-quinazolin-4-ylamino)-pyrrolidin-2-one The above compound was synthesized by the procedures in Example 126 beginning with propionamidine hydrochloride. MS (ES+)=599 (M+H)+$^+$.

Example 128

Part A. Preparation of {(3S)-1-[(1S,2R,4R)-2-benzenesulfonylmethyl-4-(isopropyl-methyl-amino)-cyclohexyl]-2,5-dioxo-pyrrolidin-3-yl}-carbamic acid tert-butyl ester (1S,2R,4R)-2-Benzenesulfonylmethyl-N4-isopropyl-N4-methyl-cyclohexane-1,4-diamine (300 mg, 0.93 mmol, 1 eq.), L-N-BOC-Aspartic acid (216 mg, 0.93 mmol, 1.0 eq.), 1-hydroxybenzotriazole hydrate (HOBT) (275 mg, 2.03 mmol, 2.2 eq.), 1-[3-(dimethylamino)propyl]-3-ethylcarbodiimide HCl (EDCI) (390 mg, 2.03 mmol, 2.2 eq.), triethylamine (0.39 mL, 2.77 mmol, 3 eq.) and methylene chloride (15 mL) were stirred at 0° C. and allowed to warm to rt under nitrogen overnight. The mixture was washed with 2 N sodium carbonate, water (1×) and the organic layer dried and stripped. The residue was purified over silica gel in 100% ethyl acetate to 4:1 methylene chloride/methanol to 4:1 methylene chloride/2N NH3 in methanol. Obtained 60 mg of product. LCMS detects (M+H)+=522.

Part B. Preparation of (3S)-3-Amino-1-[(1S,2R,4R)-2-benzenesulfonylmethyl-4-(isopropyl-methyl-amino)-cyclohexyl]-pyrrolidine-2,5-dione {(3S)-1-[(1S,2R,4R)-2-benzenesulfonylmethyl-4-(isopropyl-methyl-amino)-cyclohexyl]-2,5-dioxo-pyrrolidin-3-yl}-carbamic acid tert-butyl ester (60 mg), TFA (1 mL), and methylene chloride (3 mL) were mixed and stirred overnight at rt. The mixture was stripped and restripped from methylene chloride (3×) to yield 60 mg of an oil. LCMS detects (M+H)+=374.

Example 128

Part C. Preparation of N-{(3S)-1-[(1S,2R, 4R)-2-benzenesulfonylmethyl-4-(isopropyl-methyl-amino)-cyclohexyl]-2,5-dioxo-pyrrolidin-3-yl}-3-trifluoromethyl-benzamide, TFA salt (3S)-3-Amino-1-[(1S,2R,4R)-2-benzenesulfonylmethyl-4-(isopropyl-methyl-amino)-cyclohexyl]-pyrrolidine-2,5-dione (60 mg, 0.092 mmol, 1 eq), 3-trifluoromethylbenzoyl chloride (0.014 mL, 0.092 mmol, 1 eq.), triethylamine (0.039 mL, 0.28 mmol, 3 eq.) and THF (3 mL) were mixed and stirred at rt with the acid chloride being added last. The reaction mixture was stripped and purified by LCMS to yield 5.5 mg of product. LCMS detects (M+H)+=594.

Example 129

Part A. Preparation of Ethyl 3-(Adamanty-1-yl)-pyrrole-5-carboxylate

Ethyl pyrrole-2-carboxylate (2.09 g, 15 mmol, 1 eq), was added to a mixture of gallium(III) chloride (2.90 g, 16.5 mmol, 1.1 eq) in carbon disulfide (40 mL) and the contents heated at 40° C. for 30 min. Afterwards, 1-chloroadamantane (2.82 g, 16.5 mmol, 1.1 eq), was added thereto and the contents heated for another 40 minutes. The reaction was poured onto a mixture of ice and 1N HCl, and extracted with chloroform. The extracts were washed with saturated sodium bicarbonate, dried (MgSO4) and the solvent stripped to yield a crude solid. Recrystallization from EtOAc yielded 2 crops. 1$^{st}$ crop wt.=0.67 grams. 2$^{nd}$ crop wt.=1.10 grams. MS found: (M+H)+=274.44 and 274.45, respectively.

Part B. Preparation of 3-(Adamanty-1-yl)-pyrrole-5-carboxylic Acid

The compound obtained from Part A immediately above (0.29 g, 1.1 mmol, 1 eq), 1.000 N NaOH (2.20 mL, 2.2 mmol, 2 eq) and MeOH (15 mL) were mixed and stirred overnight. After only partial reaction, more 1.000 N NaOH (21 mL) together with more MeOH to dissolve were added and the contents refluxed for 4 hours. The contents were acidified to pH=1 with 1H HCl. The MeOH was stripped off to yield solids and aqueous. The mixture was extracted with EtOAc, the EtOAc layers were combined, washed with brine, dried (MgSO4) and stripped to yield 250 mg of a white powder. MS found: (M+H)+=246.44.

Example 129

Part C. Preparation of N-{(3S)-1-[-(1S,2R,4R)-2-Benzenesulfonylmethyl-4-(isopropyl-methyl-amino)-cyclohexyl]-2-oxo-pyrrolidin-3-yl}-4-adamantan-1-yl-1H-pyrrole-2-carboxamide, TFA salt (3S)-1-[1S,2R,4R-2-benzenesulfonylmethyl-4-(isopropyl-methyl-amino)-cyclohexyl]-pyrrolidin-2-one (45 mg, 0.11 mmol, 1 eq), 3-(adamanty-1-yl)-pyrrole-5-carboxylic acid (27 mg, 0.11 mmol, 1 eq), HOBT (15 mg, 0.11 mmol, 1 eq), 1-[3-(dimethylaminopropyl)]-3-ethylcarbodiimide hydrochloride (EDCI) (21 mg, 0.11 mmol, 1 eq), and methylene chloride (5 mL) were mixed and stirred overnight. The contents were stripped and purified by LCMS. Lyophillization yielded 45 mg of a white solid. MS found: (M+H)+=635.58.s

Example 130

Part A. Preparation of Ethyl 3-(Adamanty-1-yl)-1-methylpyrrole-5-carboxylate Ethyl 3-(adamanty-1-yl)-pyrrole-5-carboxylate (obtained from Example 129) (0.20 g, 0.7 mmol, 1 eq) was dissolved in THF (20 mL). Potassium bis(trimethylsilyl)amide (0.5 M in Tol, 1.62 mL, 0.81 mmol, 1.1 eq) was added thereto followed by iodomethane (0.102 mL, 1.6 mmol, 2.2 eq). The next day, the same amounts of potassium bis(trimethylsilyl) amide and iodomethane were again added to drive the reaction to completion. In 4 h, the reaction was finished. Ethyl acetate was added (100 mL) and the organic layer was washed with water (2×), brine, dried (MgSO4) and stripped to yield 600 mg of product which was used as is in the next step. MS found: (M+H)+=288.16.

Part B. Preparation of 3-(Adamanty-1-yl)-1-methylpyrrole-5-carboxylate

Saponification of ethyl 3-(Adamanty-1-yl)-1-methylpyrrole-5-carboxylate (entire contents from Part A) by the procedure in Example 129 Part B yielded 160 mg of product. MS found: (M−H)+=258.10.

Example 130

Part C. Preparation of N-{(3S)-1-[-(1S,2R,4R)-2-Benzenesulfonylmethyl-4-(isopropyl-methyl-amino)-cyclohexyl]-2-oxo-pyrrolidin-3-yl}-4-adamantan-1-yl-1-methyl-1H-pyrrole-2-carboxamide, TFA salt (3S)-3-Amino-1-[(1S,2R,4R)-2-benzenesulfonylmethyl-4-(isopropyl-methyl-amino)-cyclohexyl]-pyrrolidin-2-one (49 mg, 0.12 mmol, 1 eq), 3-(adamanty-1-yl)-pyrrole-5-carboxylic acid (31 mg, 0.12 mmol, 1 eq), HOBT (16 mg, 0.12 mmol, 1 eq), 1-[3-(dimethylaminopropyl)]-3-ethylcarbodiimide hydrochloride (EDCI) (23 mg, 0.11 mmol, 1 eq), and methylene chloride (5 mL) were mixed and stirred overnight. The contents were stripped and dissolved in EtOAc, washed with 1N HCl (1×), 1N NaOH (2×), brine (1×), dried and stripped. The residue was flash chromatographed in 1:1 hexane/EtOAc to 100% EtOAc to 4:1 chloroform/methanol to yield 31 mg of a yellow glass. MS found: (M+H)+=649.32.

Example 131

Part A. Preparation of 5-Bromo-2-tert-butyl-pyrimidine-4-carboxylic acid

A 22% solution of sodium ethoxide in ethanol (53 mL, 165 mMol) was added dropwise to a magnetically stirred suspension of tert-butylcarbamadine hydrochloride (20.0 g, 146 mMol) in ethanol (100 mL). When the addition was complete, the yellow suspension was warmed to 50° C., the heating mantle was removed, and a solution of mucobromic acid (15.7 g, 61 mMol) in ethanol (50 mL) was added dropwise at a rate which did not allow the temperature to exceed 55° C. When this addition was complete, a 22% solution of sodium ethoxide in ethanol (32 mL, 98 mMol) was added dropwise, then the mixture was allowed to cool to room temperature. The suspension was filtered, the solids were rinsed with ethanol (2×20 mL), and the combined filtrates were concentrated in-vacuo. The residue thus obtained was stirred in 2 N aqueous HCl (30 mL). The resulting solids were collected by filtration, rinsed with ice-cold water (2×20 mL), and air dried to yield 12.1 g of a beige powder as product. MS (ES+)=259, 261 (M+H)+. Yield=76%.

Part B. Preparation of 5-Bromo-2-tert-butyl-pyrimidine-4-carboxylic acid methyl ester A 2.0 M hexanes solution of trimethylsilyldiazomethane (11.8 mL, 23.62 mMol) was added dropwise to a stirring solution of 5-bromo-2-tert-butyl-pyrimidine-4-carboxylic acid (6.12 g, 23.62 mMol) in 9:1 benzene/methanol (100 mL), and the reaction was stirred for 2 days. TLC analysis showed that the reaction was complete, so the mixture was concentrated in-vacuo. The residue was dissolved in ethyl acetate (100 mL), washed with water (3×20 mL), dried over sodium sulfate, then concentrated in-vacuo. Purified over silica gel, eluting with 10% ethyl acetate/hexanes, to yield 5.2 g of a colorless oil as product. MS (ES+)=273, 275 (M+H)+. Yield=81%.

Part C. Preparation of 5-tert-Butoxycarbonylamino-2-tert-butyl-pyrimidine-4-carboxylic acid methyl ester A flame dried reaction tube charged with tert-butylcarbamate (140 mg, 1.2 mMol), cesium carbonate (456 mg, 1.4 mMol), 4,5-bis(diphenylphosphino)-9,9-dimethylxanthane (18 mg, 0.03 mMol), and tris(dibenzylidineacetone)dipalladium (0) (19 mg, 0.02 mMol) was evacuated under vacuum, then backfilled with argon. Dioxane (2 mL) and 5-bromo-2-tert-butyl-pyrimidine-4-carboxylic acid methyl ester (273 mg, 1.0 mMol) were added, and the mixture was degassed under vacuum. The tube was then backfilled with argon, sealed, and heated at 100° C. for 2 hours. Analysis by LC/MS showed complete consumption of starting bromide. The mixture was diluted with methylene chloride (20 mL), filtered to remove solids, and concentrated in-vacuo. The residue was purified over silica gel, eluting with 10% ethyl acetate/heptane, to yield 152 mg of white solids as product. MS (ES+)=310 (M+H)+. Yield=50%.

Part D. Preparation of 5-Amino-2-tert-butyl-pyrimidine-4-carboxylic acid methyl ester, HCl salt 5-tert-Butoxycarbonylamino-2-tert-butyl-pyrimidine-4-carboxylic acid methyl ester (2.4 g, 7.75 mMol) was dissolved in a 4 M solution of HCl in dioxane (30 mL). After 10 minutes of stirring, a thick white solid precipitated. The reaction was allowed to stir overnight, during which time the mixture became a homogenous, amber solution. Concentrated in-vacuo, and the residue was stripped from toluene (2×50 mL) followed by methylene chloride (3×50 mL) to remove excess HCl. The resulting 1.85 g of yellow solids was used without further purification in the next step. MS (ES+)=210 (M+H)+.

Part E. Preparation of 6-tert-Butyl-pyrimido[5,4-d]pyrimidin-4-ol

A mixture of 5-amino-2-tert-butyl-pyrimidine-4-carboxylic acid methyl ester, HCl salt (1.1 g, 4.48 mMol) and formamidine acetate (1.86 g, 17.90 mMol) in 2-ethoxyethanol (20 mL) was heated at reflux for 5 hours. LC/MS analysis showed the reaction to be essentially complete, so the mixture was cooled to room temperature, then concentrated in-vacuo. The residue was purified over silica gel, eluting with ethyl acetate, 1% methanol/ethyl acetate, then 2% methanol/ethyl acetate to yield 1.06 g of a beige solid as product. MS (ES+)=205 (M+H)+. Yield=94%.

Part F. Preparation of 2-tert-Butyl-8-chloro-pyrimido[5,4-d]pyrimidine 6-tert-Butyl-pyrimido[5,4-d]pyrimidin-4-ol (210 mg, 1.03 mMol) was dissolved in phosphorous oxychloride (10 mL), and the mixture was heated at reflux for 4 hours. The solution was concentrated in-vacuo, then stripped from methylene chloride (3×50 mL) to remove excess phosphorous oxychloride. The residue was stirred for 10 minutes in saturated sodium bicarbonate (50 mL), then extracted with ethyl acetate (3×30 mL). The combined organic phases were washed with water (30 mL), followed by brine (30 mL), dried over sodium sulfate, then concentrated in-vacuo. The residue was purified over silica gel, eluting with 50% ethyl acetate/heptane, to yield 150 mg of a white solid as product. NMR (500 MHz, CDCl3) δ 9.61 (s, 1H), 9.15 (S, 1H), 1.52 (s, 9H).

Example 131

Part G. Preparation of 1-[(1S,2R,4R)-2-Benzenesulfonylmethyl-4-(isopropyl-methyl-amino)-cyclohexyl]-(3S)-3-(6-tert-butyl-pyrimido[5,4-d]pyrimidin-4-ylamino)-pyrrolidin-2-one, TFA salt The titled compound was prepared from (3S)-3-amino-1-[(1S,2R,4R)-2-benzenesulfonylmethyl-4-(isopropyl-methyl-amino)-cyclohexyl]-pyrrolidin-2-one and 2-tert-butyl-8-chloro-pyrimido[5,4-d]pyrimidine using the conditions described in JBS Example 106, Part C. MS (ES+)=594 (M+H)+.

Example 132

Example 132 Preparation of 5-Bromo-2-tert-butyl-pyrimidine-4-carboxylic acid {(3S)-1-[(1S,2R,4R)-2-benzenesulfonylmethyl-4-(isopropyl-methyl-amino)-cyclohexyl]-2-oxo-pyrrolidin-3-yl}-amide, TFA salt (3S)-3-Amino-1-[(1S,2R,4R)-2-benzenesulfonylmethyl-4-(isopropyl-methyl-amino)-cyclohexyl]-pyrrolidin-2-one (93 mg, 0.23 mMol), 5-bromo-2-tert-butyl-pyrimidine-4-carboxylic acid, (60 mg, 0.23 mmol), HOBT (68 mg, 0.50 mMol), triethylamine (96 µL, 0.69 mMol), and EDCI (96 mg, 0.50 mMol) were combined in $CH_2Cl_2$ (2 mL), and the mixture was stirred overnight at room temperature. The mixture was diluted with ethyl acetate (15 mL), and washed with saturated $NaHCO_3$ (3×5 mL), water (5 mL), and brine (5 mL). The organic phase was dried over sodium sulfate, and concentrated in-vacuo. The residue was purified by reverse phase HPLC, using a Phenomenex Luna 10µ, C18 (2), 250×50 mm column, under the following conditions: 10% to 70% acetonitrile in water (0.05% TFA in each solvent) over 30 minutes. The reaction yielded 13 mg of white powder as product. MS (ES+)=570 (M+H).

Example 133

Preparation of 2-tert-Butyl-pyrimidine-4-carboxylic acid {(3S*)-1-[(1S*,2R*,4R*)-2-benzenesulfonylmethyl-4-(isopropyl-methyl-amino)-cyclohexyl]-2-oxo-pyrrolidin-3-yl}-amide, TFA salt A solution of 5-bromo-2-tert-butyl-pyrimidine-4-carboxylic acid {(3S)-1-[(1S,2R,4R)-2-benzenesulfonylmethyl-4-(isopropyl-methyl-amino)-cyclohexyl]-2-oxo-pyrrolidin-3-yl}-amide, TFA salt (30 mg, 0.04 mMol) in methanol (10 mL) was hydrogenated at 50 psi in the presence of 1 N aqueous sodium hydroxide (80 µL, 0.08 mMol) and 10% palladium on activated carbon (20 mg) for 2 hours. The catalyst was removed by filtration, and the filtrate was concentrated in-vacuo. The residue was purified by reverse phase HPLC, using a Phenomenex Luna 10µ, C18 (2), 250×50 mm column, under the following conditions: 10% to 70% acetonitrile in water (0.05% TFA in each solvent) over 30 minutes. The reaction yielded 25 mg of white powder as product. MS (ES+)=648 (M+H).

Example 134

Preparation of 2-tert-Butyl-5-phenyl-pyrimidine-4-carboxylic acid {(3S)-1-[(1S,2R,4R)-2-benzenesulfonylmethyl-4-(isopropyl-methyl-amino)-cyclohexyl]-2-oxo-pyrrolidin-3-yl}-amide, TFA salt 5-Bromo-2-tert-butyl-pyrimidine-4-carboxylic acid {(3S)-1-[(1S,2R,4R)-2-benzenesulfonylmethyl-4-(isopropyl-methyl-amino)-cyclohexyl]-2-oxo-pyrrolidin-3-yl}-amide, TFA salt (80 mg, 0.10 mMol), phenyl boronic acid (26 mg, 0.21 mMol), and 2.0 M aqueous $K_3PO_4$ solution (210 µL, 0.42 mMol) were combined in 2 mL of DMF in a microwave reaction tube, and the solution was degassed under vacuum, then backfilled with argon.

Tetrakis(triphenylphosphine)palladium(0) (20 mg, 0.01 mMol) was added, and the mixture was again degassed as described above. The tube was sealed, and the reaction mixture was heated via microwave at 150° C. for 30 minutes. The reaction was cooled, some solids were removed by filtration and rinsed with ethyl acetate, and the combined filtrates were concentrated in-vacuo. The residue was purified by reverse phase HPLC, using a Phenomenex Luna 10µ, C18 (2), 250×50 mm column, under the following conditions: 10% to 70% acetonitrile in water (0.05% TFA in each solvent) over 30 minutes. The reaction yielded 27 mg of white powder as product. MS (ES+)=646 (M+H).

Example 135

Part A. Preparation of 3-tert-Butyl-benzoic acid

A mixture of the commercially available methyl 3-bromo-5-tert-butylbenzoate (700 mg, 2.58 mMol), aqueous NaOH (1 N, 7.75 mL, 7.75 mMol), and Pearlman's catalyst (100 mg) in methanol (20 mL) was hydrogenated at 50 psi for 22 hours. The catalyst was removed by filtration and rinsed with a small amount of methanol. The filtrate was concentrated in-vacuo to remove methanol, and the aqueous mixture was acidified with 1 N HCl (10 mL), then extracted with ethyl acetate (3×20 mL). The combined organic phases were dried over sodium sulfate, then concentrated in-vacuo. Analysis of the resulting material by LC/MS showed that the ester had hydrolyzed to the carboxylic acid, but that the bromide was still present. The material was dissolved in methanol (20 mL), and hydrogenated overnight at 50 psi in the presence of 1 N aqueous NaOH (5.2 mL, 5.2 mMol) and 10% palladium on activated carbon (50 mg). Analysis of the crude reaction mixture by LC/MS showed that the bromine was still present, so Pearlman's catalyst (200 mg) was added, and hydrogenation at 50 psi was continued for 23 hours. MS showed that the reaction was now complete, so the reaction was worked up as described previously in this example to yield 376 mg of white powder as product. MS (AP−)=177 (M−H)+$^+$. Yield=81%.

Example 135

Part B. Preparation of N-{(3S)-1-[(1S,2R,4R)-2-benzenesulfonylmethyl-4-(isopropyl-methyl-amino)-cyclohexyl]-2-oxo-pyrrolidin-3-yl}-3-tert-butyl-benzamide, TFA salt The titled compound was prepared from (3S)-3-amino-1-[(1S,2R,4R)-2-benzenesulfonylmethyl-4-(isopropyl-methyl-amino)-cyclohexyl]-pyrrolidin-2-one and 3-tert-Butyl-benzoic acid using the conditions described in Example 132. MS (ES+)=568 (M+H).

Example 136

Part A. Preparation of Lithium 3-bromo-5-tert-butylbenzoate

A solution of the commercially available methyl-3-bromo-5-tert-butylbenzoate (87 mg, 0.32 mMol) in THF (2 mL) was treated with 0.5 N aqueous lithium hydroxide (0.71 mL, 0.35 mMol), and the mixture was stirred at room temperature for six hours. The THF was stripped in-vacuo, and the aqueous solution was freeze dried to yield 112 mg of light brown solids. This material was used as-is in the next step.

Example 136

Part B. Preparation of N-{(3S)-1-[(1S,2R, 4R)-2-benzenesulfonylmethyl-4-(isopropyl-methyl-amino)-cyclohexyl]-2-oxo-pyrrolidin-3-yl}-3-bromo-5-tert-butyl-benzamide, TFA salt (3S)-3-Amino-1-[(1S,2R,4R)-2-benzenesulfonylmethyl-4-(isopropyl-methyl-amino)-cyclohexyl]-pyrrolidin-2-one (39 mg, 0.10 mMol), lithium-3-bromo-5-tert-butylbenzoate (25 mg, 0.10 mMol), diisoproplyethylamine (84 µL, 0.48 mMol), and HATU (37 mg, 0.10 mMol) were combined in CH$_2$Cl$_2$ (2 mL), and the mixture was stirred overnight at room temperature. The mixture was diluted with ethyl acetate (15 mL), and washed with saturated NaHCO$_3$ (3×5 mL), water (5 mL), and brine (5 mL). The organic phase was dried over sodium sulfate, and concentrated in-vacuo. The residue was purified by reverse phase HPLC, using a Phenomenex Luna 10µ, C18 (2), 250×50 mm column, under the following conditions: 10% to 70% acetonitrile in water (0.05% TFA in each solvent) over 30 minutes. The reaction yielded 17 mg of white powder as product. MS (ES+)=647 (M+H)+$^+$.

Example 137

Part A. Preparation of Pyrido[2,3-d]pyrimidin-4-ol

A mixture of 2-aminonicotinic acid (880 mg, 6.4 mMol) and formamidine acetate (2.0 g, 19.1 mMol) in 2-ethoxy-ethanol (25 mL) was heated at reflux overnight. The solution was allowed to come to room temperature and stand for 2 hours, then the resulting precipitate was collected by filtration, rinsed with 2-ethoxy ethanol (2×5 mL), diethyl ether (20 mL), and air dried to yield 525 mg of a gray powder as product. MS (ES+)=148 (M+H)+$^+$. Yield=56%.

Part B. Preparation of 4-Chloro-pyrido[2,3-d]pyrimidine

A solution of pyrido[2,3-d]pyrimidin-4-ol (490 mg, 3.33 mMol), triethylamine (4.4 mL, 31.6 mMol), and phosphorous oxychloride (2.8 mL, 30 mMol) was heated at reflux for 2 hours. The mixture was concentrated in-vacuo, and the residue was stripped from methylene chloride (3×50 mL) to remove excess phosphorous oxychloride. The residue was dissolved in ethyl acetate (100 mL), saturated sodium bicarbonate (100 mL) was added carefully, causing vigorous gas evolution, and the mixture was stirred for ten minutes. The layers were separated, the organic phase was washed with saturated sodium bicarbonate (30 mL), water (30 mL), brine (30 mL), dried over sodium sulfate, then concentrated in-vacuo. The residue was purified over silica gel, eluting with 40% ethyl acetate/heptane, to yield 92 mg of a tan solid as product. MS (ES+)=166 (M+H)+$^+$. Yield=17%.

Example 137

Part C. Preparation of 1-[(1S,2R,4R)-2-benzenesulfonylmethyl-4-(isopropyl-methyl-amino)-cyclohexyl]-(3S)-3-(pyrido[2,3-d]pyrimidin-4-ylamino)-pyrrolidin-2-one, TFA salt The titled compound was prepared from (3S)-3-amino-1-[(1S ,2R,4R)-2-benzenesulfonylmethyl-4-(isopropyl-methyl-amino)-cyclohexyl]-pyrrolidin-2-one and 4-Chloro-pyrido[2,3-d]pyrimidine using the conditions described in Example 106, Part C. MS (ES+)=537 (M+H)+$^+$.

Example 138

Part A. Preparation of 2-Amino-nicotinic acid ethyl ester

A 60% sodium hydride suspension in mineral oil (1.28 g, 32 mMol) was added to a stirring suspension of 2-aminonicotinic acid (4.21 g, 30 mMol) in DMF (50 mL), and the mixture was gently heated until gas evolution was observed. The suspension was stirred at room temperature for 4 hours, after which a homogeneous amber solution was observed. Iodoethane (4.75 g, 30 mMol) was added, and the mixture was allowed to stir overnight at room temperature. The solution was concentrated in-vacuo, the residue was taken up in 9:1 ethyl acetate/hexane (200 mL), washed with water (5×50 mL), and brine (50 mL), dried over sodium sulfate, then concentrated in-vacuo. The residue was purified over silica gel, eluting with 25%–50% ethyl acetate/hexane, to yield 3.6 g of colorless solids as product. NMR (500 MHz, DMSO) δ 8.20 (dd, 1H, J=5 Hz, 2 Hz), 8.06 (dd, 1H, J=8 Hz, 2 Hz), 7.16 (s, 2H), 6.63 (dd, 1H, J=8 Hz, 5 Hz), 4.28 (q, 2 H, J=7 Hz), 1.30 (t, 3H, J=7 Hz). Yield=72%.

Part B. Preparation of 2-Amino-5-chloro-nicotinic acid ethyl ester

A solution of 2-amino-nicotinic acid ethyl ester (3.60 g, 21.7 mMol) in methanol (100 mL) was treated with HCl gas via sparge tube for 5 minutes, causing the colorless solution to turn yellow. The solution was concentrated in-vacuo, then stripped from methanol (2×50 mL) to remove excess HCl. The residue was dissolved in methanol (100 mL), treated with tert-butyl hypochlorite (2.6 g, 23.8 mMol), and the mixture was allowed to stir overnight at room temperature. Analysis by TLC showed that some starting material remained, so additional tert-butyl hypochlorite (0.47 g, 4.3 mMol) was added, and stirring was continued overnight. Analysis by TLC showed that all starting material had been consumed. The solution was concentrated in-vacuo, the residue was taken up in methylene chloride (150 mL), washed with saturated sodium bicarbonate (3×50 mL), 5% aqueous sodium thiosulfate (3×50 mL), water (50 mL), brine (50 mL), dried over sodium sulfate, and concentrated in-vacuo. The residue was purified over silica gel, eluting with 20%–30% ethyl acetate/heptane, to yield 1.50 g of colorless solids as product. MS (AP+)=201 (M+H)$^+$. Yield=35%.

Part C. Preparation of 6-Chloro-pyrido[2,3-d]pyrimidin-4-ol

A mixture of 2-amino-5-chloro-nicotinic acid ethyl ester (1.5 g, 7.38 mMol) and formamidine acetate (3.1 g, 29.51 mMol) in 2-ethoxyethanol (50 mL) was heated at reflux overnight. The solution was cooled to room temperature, and allowed to stand for 2 hours. The resulting precipitate was collected by filtration, rinsed with a small amount of 2-ethoxyethanol followed by diethyl ether (10 mL), and allowed to air dry. The filtrate was concentrated in-vacuo, and the residue was triturated with methylene chloride. The resulting solids were combined with the solids from the earlier filtration, and this material was crystallized from methanol to yield 475 mg of tan needles as product, in three crops. MS (ES+)=182 (M+H)$^+$. Yield=37%.

Part D. Preparation of 4,6-Dichloro-pyrido[2,3-d]pyrimidine

The titled compound was prepared from 6-Chloro-pyrido[2,3-d]pyrimidin-4-ol using the conditions described in Example 131, Part F. MS (ES+)=201 (M+H)$^+$. Yield=85%.

Example 138

Part E. Preparation of 1-[(1S,2R,4R)-2-benzenesulfonylmethyl-4-(isopropyl-methyl-amino)-cyclohexyl]-(3S)-3-(6-chloro-pyrido[2,3-d]pyrimidin-4-ylamino)-pyrrolidin-2-one, TFA salt The titled compound was prepared from (3S)-3-amino-1-[(1S,2R,4R)-2-benzenesulfonylmethyl-4-(isopropyl-methyl-amino)-cyclohexyl]-pyrrolidin-2-one and 4,6-Dichloro-pyrido[2,3-d]pyrimidine using the conditions described in Example 106, part C. MS (ES+)=572 (M+H)$^+$.

Example 139

Part A. Preparation of 6-Chloro-2-trifluoromethyl-pyrido[2,3-d]pyrimidin-4-ol The titled compound was prepared from 2-Amino-5-chloro-nicotinic acid ethyl ester and trifluoromethylacetamidine using the conditions described in Example 113, part A. MS (ES+)=250 (M+H)$^+$.

Part B. Preparation of 4,6-Dichloro-2-trifluoromethyl-pyrido[2,3-d]pyrimidine The titled compound was prepared from 6-Chloro-2-trifluoromethyl-pyrido[2,3-d]pyrimidin-4-ol using the conditions described in Example 131, part F. MS (ES+)=268 (M+H)+.

Example 139

Part C. Preparation of 1-[(1S,2R,4R)-2-benzenesulfonylmethyl-4-(isopropyl-methyl-amino)-cyclohexyl]-(3S)-3-(6-chloro-2-trifluoromethyl-pyrido[2,3-d]pyrimidin-4-ylamino)-pyrrolidin-2-one The titled compound was prepared from (3S)-3-amino-1-[(1S,2R,4R)-2-benzenesulfonylmethyl-4-(isopropyl-methyl-amino)-cyclohexyl]-pyrrolidin-2-one and 4,6-dichloro-2-trifluoromethyl-pyrido[2,3-d]pyrimidine using the conditions described in Example 106, part C. MS (ES+)=639 (M+H)+.

Example 140

Part A. Preparation of (4-Trifluoromethoxy-phenyl)-carbamic acid tert-butyl ester A solution of 4-(trifluoromethyl)phenyl isocyanate (9.75 g, 48.0 mMol) in THF (100 mL) was cooled to 0° C., and a 1.0 M THF solution of potassium tert-butoxide (53 mL, 53 mMol) was added dropwise. The mixture was allowed to warm to room temperature, and stirred for 7 hours. The solution was poured into a mixture of saturated ammonium chloride solution (200 mL), and diethyl ether (200 mL). Enough water was added to redissolve the ammonium chloride that had crashed out, the mixture was shaken in a separatory funnel, and the layers were separated. The organic phase was washed with saturated ammonium chloride (100 mL), water (100 mL), brine (100 mL), dried over sodium sulfate, and concentrated in-vacuo. The residue was purified over silica gel, eluting with 10%–20% ethyl acetate/heptane to yield 11.7 g of white solids as product. NMR (500 MHz, DMSO) δ9.54 (s, 1H), 7.54 (d, 2H, J=7 Hz), 7.23 (d, 2H, J=8 Hz), 1.45 (s, 9H). Yield=88%.

Part B. Preparation of 2-tert-Butoxycarbonylamino-5-trifluoromethoxy-benzoic acid A solution of (4-trifluoromethoxy-phenyl)-carbamic acid tert-butyl ester (2.31 g, 8.33 mMol) in anhydrous THF (50 mL) at −78° C. was treated with a 1.4 M solution of sec-butyllithium in cyclohexane (13 mL, 18.33 mMol), at a rate which did not allow the internal temperature to exceed −60° C. The solution was stirred at −78° C. for 15 minutes, then allowed to warm to −40° C. and stirred for 2.5 hours. The reaction was treated with gaseous $CO_2$, stirred 30 minutes while warming to −20° C., then quenched with saturated ammonium chloride. The mixture was warmed to room temperature, and extracted with ethyl acetate (3×50 mL). The combined organic phases were washed with water (50 mL), brine (50 mL), dried over sodium sulfate, and concentrated in-vacuo. The residue was triturated with hot heptane to yield 1.9 g of white powder as product. NMR (500 MHz, DMSO) δ 12.89 (s, 1H), 8.24 (d, 1 H, J=9 Hz), 7.84 (s, 1H), 7.21 (d, 1H, J=7 Hz), 1.51 (s, 9 Hz). Yield=72%.

Part C. Preparation of 2-Amino-5-trifluoromethoxy-benzoic acid, HCl salt 2-tert-Butoxycarbonylamino-5-trifluoromethoxy-benzoic acid (1.9 g, 5.91 mMol) was dissolved in a 4 N HCl solution in dioxane (15 mL), and the resulting suspension was stirred at room temperature for 6 hours. Analysis by LC/MS showed that the reaction was incomplete, so concentrated HCl (1 mL) was added, followed by methylene chloride (20 mL) to dissolve the solids, and the reaction was stirred overnight at room temperature. The mixture was concentrated in-vacuo, then stripped from methanol (3×50 mL) to remove any excess HCl. The resulting solids were used as-is in the next step. MS (ES+)=222 (M+H)$^+$.

Part D. Preparation of 6-Trifluoromethoxy-quinazolin-4-ol

A mixture of 2-amino-5-trifluoromethoxy-benzoic acid, HCl salt (1.52 g, 5.91 mMol), and formamidine acetate (1.84 g, 17.73 mMol) in 2-ethoxyethanol (20 mL) was heated at reflux for 2 hours. Analysis by LC/MS showed that the reaction was complete, so the mixture was concentrated in-vacuo, and the residue was purified over silica gel, eluting with 50% ethyl acetate/heptane—100% ethyl acetate, to yield 1.1 g of white solids as product. MS (ES+)=231 (M+H)$^+$. Yield=82%.

Part E. Preparation of 4-Chloro-6-trifluoromethoxy-quinazoline

The titled compound was prepared from 6-trifluoromethoxy-quinazolin-4-ol using the conditions described in example 137, part B. MS (ES+)=249 (M+H)$^+$.

Example 140

Part F. Preparation of 1-[(1S,2R,4R)-2-benzenesulfonylmethyl-4-(isopropyl-methyl-amino)-cyclohexyl]-(3S)-3-(6-trifluoromethoxy-pyrido[2,3-d]pyrimidin-4-ylamino)-pyrrolidin-2-one, TFA salt The titled compound was prepared from (3S)-3-amino-1-[(1S,2R,4R)-2-benzenesulfonylmethyl-4-(isopropyl-methyl-amino)-cyclohexyl]-pyrrolidin-2-one and of 4-chloro-6-trifluoromethoxy-quinazoline using the conditions described in example 106, part C. MS (ES+)=620 (M+H)$^+$.

Example 141

Preparation of 1-[(1S,2R,4R)-2-benzenesulfonylmethyl-4-(isopropyl-methyl-amino)-cyclohexyl]-(3S)-3-(6-chloro-2-methylamino-quinazolin-4-ylamino)-pyrrolidin-2-one, TFA salt 1-[(1S,2R,4R)-2-benzenesulfonylmethyl-4-(isopropyl-methyl-amino)-cyclohexyl]-(3S)-3-(2,6-dichloro-quinazolin-4-ylamino)-pyrrolidin-2-one (35 mg, 0.0487 mmol, 1 eq.), 2.0 M mono-methylamine in THF (1.22 mL, 2.44 mmol, 50 eq.), and THF (1 mL) were microwaved at 100° C. until reaction was complete by LCMS. Purified by HPLC. Obtained 60 mg of white solids as product. LCMS detects (M+H)+=599.

Example 142

Preparation of (3S)-3-(6-Fluoro-quinazolin-4-ylamino)-1-[(1S,2R,4R)-4-(isopropyl-methyl-amino)-2-(toluene-4-sulfonylmethyl)-cyclohexyl]-pyrrolidin-2-one, TFA salt Followed the procedure of Example 106 Part C starting from (3S)-3-amino-1-[(1S,2R,4R)-4-(isopropyl-methyl-amino)-2-(toluene-4-sulfonylmethyl)-cyclohexyl]-pyrrolidin-2-one (100 c) and 4-chloro-6-fluoro-quinazoline. Purified by HPLC. LCMS detects (M+H)+=568.

Example 143

Preparation of N-{1-[(1S,2R,4R)-2-benzenesulfonylmethyl-4-(isopropyl-methyl-amino)-cyclohexyl]-2-oxo-pyrrolidin-(3S)-3-yl}-2-chloro-5-trifluoromethyl-benzamide, TFA salt Followed the procedure of Example 116 Part D starting from 2-chloro-5-trifluoromethyl-benzoic acid. Purified by HPLC. LCMS detects (M+H)+=614.

he next step: ESI MS m/z 507 $[C_{26}H_{29}F_3N_2O_3S+H]^+$.

Example 144

(S)-3-(6-Bromoquinazolin-4-ylamino)-1-((1S,2R,4R)-4-(isopropyl(methyl)amino)-2-(phenylsulfonylmethyl)cyclohexyl)pyrrolidin-2-one, TFA salt (144a) 6-Bromo-4-chloroquinazoline was incorporated into Example 106, Part C give the title compound. MS found: (M+H)$^+$=615.

Example 145

(S)-3-(6,7-Difluoroquinazolin-4-ylamino)-1-((1S,2R,4R)-4-(isopropyl(methyl)amino)-2-(phenylsulfonylmethyl)cyclohexyl)pyrrolidin-2-one, TFA salt (145a) 4-Chloro-6,7-difluoroquinazoline was incorporated into Example 106, Part C give the title compound. MS found: (M+H)$^+$=572.

Example 146

(S)-3-(6-Methoxyquinazolin-4-ylamino)-1-((1S,2R,4R)-4-(isopropyl(methyl)amino)-2-(phenylsulfonylmethyl)cyclohexyl)pyrrolidin-2-one, TFA salt (146a) 4-Chloro-6-methoxyquinazoline was incorporated into Example 106, Part C give the title compound. MS found: (M+H)$^+$=566.

Example 147

((S)-1-((1S,2R,4R)-4-(isopropyl(methyl)amino)-2-(phenylsulfonylmethyl)cyclohexyl)-3-(quinazolin-4-ylamino)pyrrolidin-2-one, TFA salt (147a) 4-Chloroquinazoline was incorporated into Example 106, Part C give the title compound. MS found: (M+H)$^+$=536.

Example 148

3-Phenyl-N—((S)-1-((1S,2R,4R)-4-(isopropyl(methyl)amino)-2-(phenylsulfonylmethyl)cyclohexyl)-2-oxopyrrolidin-3-yl)benzamide, TFA salt (148a) 3-Phenyl-benzoic acid was incorporated into Example 132 give the title compound. MS found: $(M+H)^+$ =588.

Example 149

(S)-3-(6-Iodoquinazolin-4-ylamino)-1-((1S,2R,4R)-4-(isopropyl(methyl)amino)-2-(phenylsulfonylmethyl)cyclohexyl)pyrrolidin-2-one, TFA salt (149a) 4-Chloro-6-iodoquinazoline was incorporated into Example 106, Part C give the title compound. MS found: $(M+H)^+$=662.

Example 150

3-Tert-butyl-4-hydroxy-N—((S)-1-((1S,2R,4R)-4-(isopropyl(methyl)amino)-2-(phenylsulfonylmethyl)cyclohexyl)-2-oxopyrrolidin-3-yl)benzamide, TFA salt (150a) 3-Tert-butyl-4-hydroxybenzoic acid was incorporated into Example 132 give the title compound. MS found: $(M+H)^+$=584.

Example 151

3-Amino-5-tert-butyl-N—((S)-1-((1S,2R,4R)-4-(isopropyl(methyl)amino)-2-(phenylsulfonylmethyl)cyclohexyl)-2-oxopyrrolidin-3-yl)thiophene-2-carboxamide, TFA salt (151a) 3-Amino-5-tert-butylthiophene-2-carboxylic acid was incorporated into Example 132 give the title compound. MS found: $(M+H)^+$=589.

Example 152

N—((S)-1-((1S,2R,4R)-4-(Isopropyl(methyl)amino)-2-(phenylsulfonylmethyl)cyclohexyl)-2-oxopyrrolidin-3-yl)-2-methyl-5-phenylfuran-3-carboxamide, TFA salt (152a) 2-Methyl-5-phenylfuran-3-carboxylic acid was incorporated into Example 132 give the title compound. MS found: $(M+H)^+$=592.

Example 153

N—((S)-1-((1S,2R,4R)-4-(Isopropyl(methyl)amino)-2-(phenylsulfonylmethyl)cyclohexyl)-2-oxopyrrolidin-3-yl)-5-nitrofuran-2-carboxamide, TFA salt (153a) 5-Nitrofuran-2-carboxylic acid was incorporated into Example 132 give the title compound. MS found: $(M+H)^+$=547.

Example 154

N—((S)-1-((1S,2R,4R)-4-(Isopropyl(methyl)amino)-2-(phenylsulfonylmethyl)cyclohexyl)-2-oxopyrrolidin-3-yl)-4-phenylthiophene-2-carboxamide, TFA salt (154a) 4-Phenylthiophene-2-carboxylic acid was incorporated into Example 132 give the title compound. MS found: $(M+H)^+$=594.

Example 155

N—((S)-2-Oxo-1-((1S,2R,4R)-2-(phenylsulfonylmethyl)-4-(pyrrolidin-1-yl)cyclohexyl)pyrrolidin-3-yl)-3-(trifluoromethyl)benzamide, TFA salt (155a) Tert-butyl (S)-1-((1S,2R,4R)-4-amino-2-(phenylsulfonylmethyl)cyclohexyl)-2-oxopyrrolidin-3-ylcarbamate (52c) (80 mg) was dissolved in DMF prior to the addition 1,4-dibromobutane and $K_2CO_3$ (75 mg). After 16 h, water and EtOAc were added. The organic layer was dried, filtered, and concentrated. The resulting residue was dissolved in $CH_2Cl_2$ (2 mL) and cooled to 0° C. prior to the addition of TFA (2 mL). After the reaction was warmed to rt over 1 h, it was concentrated and dried. This material was dissolved in DMF prior to the addition of $(iPr)_2NEt$ (0.03 mL) and 3-trifluoromethylbenzoic acid (33 mg). After cooling to 0° C., HATU (78 mg) was added. The resulting mixture was warmed to rt and was stirred overnight. The solution was diluted with EtOAc and was washed with sat. $NaHCO_3$. The organic phase was dried ($MgSO_4$), filtered, and concentrated. Reverse phase HPLC purification (gradient elution, water/acetonitrile/TFA) of the resulting residue provided the title compound (5 mg). MS found: $(M+H)^+$=578.3.

Table 1 contains representative examples of the present invention. Each of the following structural formulas are to be used in the indicated example (Ex) range paired with the given $R^1$ and $R^2$ substituent. The $R^1$ and $R^2$ described in the tables may be the same or different than those described in the claims

TABLE 1

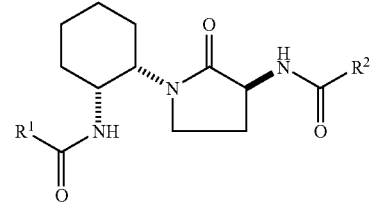

EX. 1–2

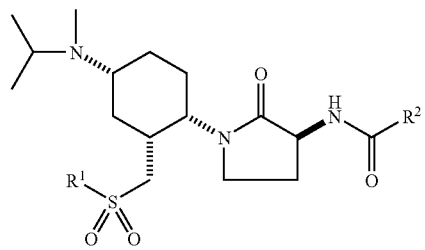

EX. 3, 17, 18, 20, 21

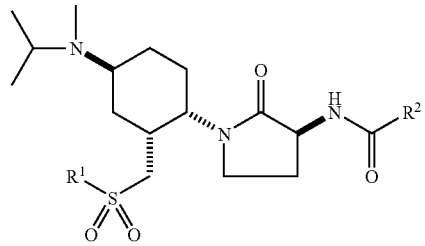

EX. 4, 6

TABLE 1-continued
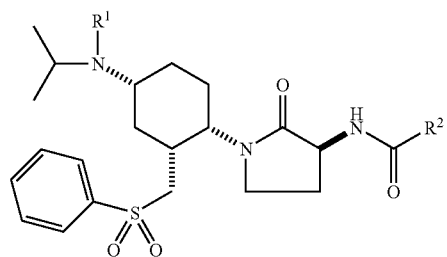
EX. 5, 7, 9, 22, 23, 27, 56, 57, 60
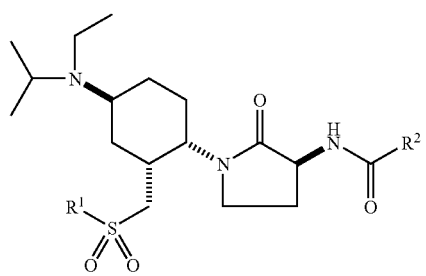
EX. 8
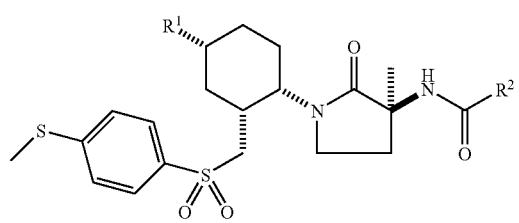
EX. 10–15
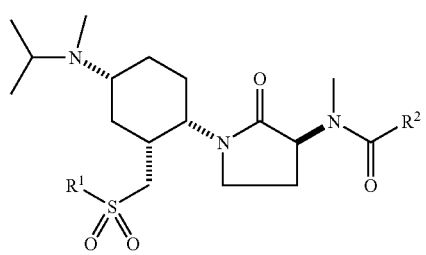
EX. 16
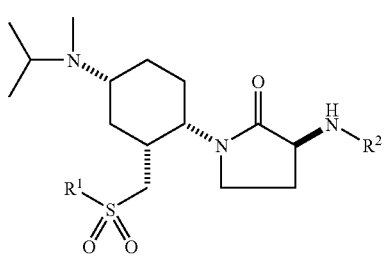
EX. 19, 34
TABLE 1-continued
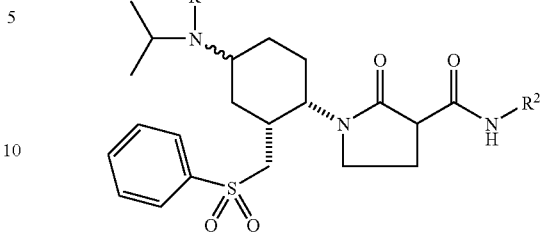
EX. 24, 25
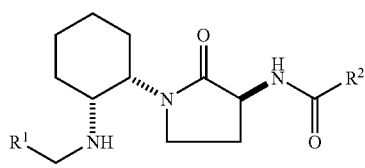
EX. 26
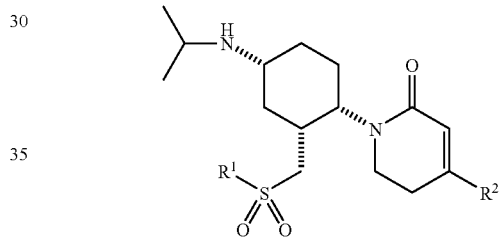
EX. 28, 29, 32
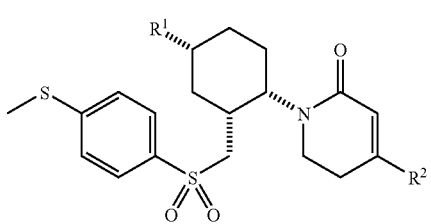
EX. 30, 31
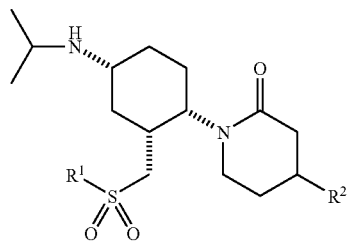
EX. 33

TABLE 1-continued
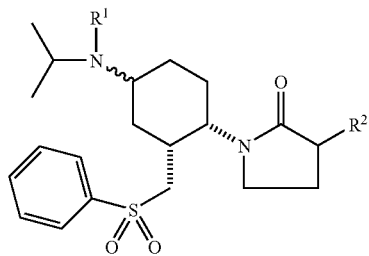
EX. 35, 36
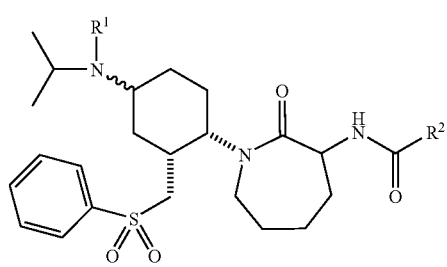
EX. 37
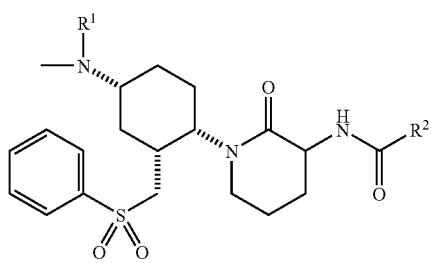
EX. 38
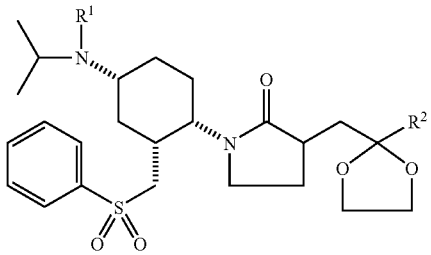
EX. 39, 40
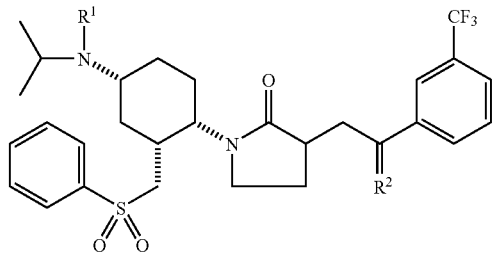
EX. 41, 42, 45, 46
TABLE 1-continued
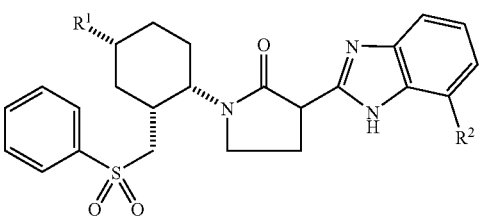
EX. 47–51
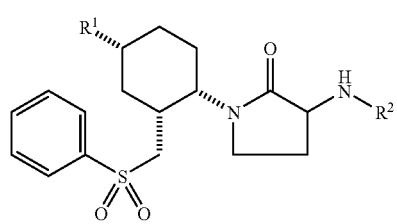
EX. 52, 53, 63–72
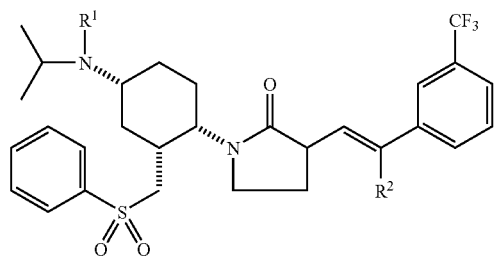
EX. 58, 59
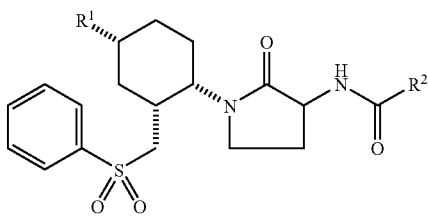
EX. 61, 62, 73–84, 155
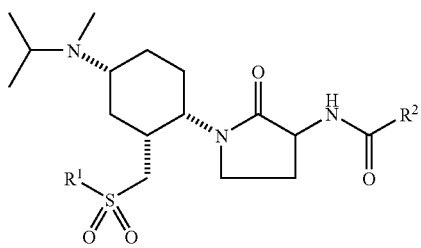
EX. 85–92, 97–101

TABLE 1-continued

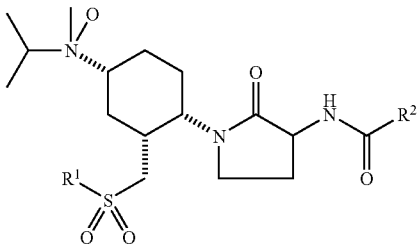

EX. 93–96

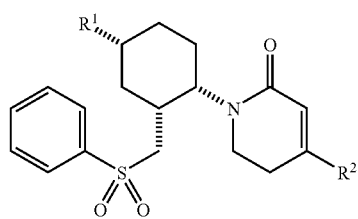

EX. 102–105

| Ex | R¹ | R² | MS [M + H] |
|---|---|---|---|
| 1 | 4-(methylthio)phenyl | 2-(t-butoxycarbonyl) amino-5-trifluoromethylphenyl | 635.4 M + H |
| 2 | 4-(methylthio)phenyl | 2-amino-5-trifluoromethylphenyl | 535.4 M + H |
| 3 | 4-methylphenyl | 3-trifluoromethylphenyl | 594.3 |
| 4 | 4-methylphenyl | 3-trifluoromethylphenyl | 594.3 |
| 5 | methyl | 3-trifluoromethylphenyl | 580.3 |
| 6 | phenyl | 3-trifluoromethylphenyl | 580.3 |
| 7 | ethyl | 3-trifluoromethylphenyl | 594.3 |
| 8 | phenyl | 3-trifluoromethylphenyl | 594.3 |
| 9 | cyclopropylmethyl | 3-trifluoromethylphenyl | 620.3 |
| 10 | azido | 3-trifluoromethylphenyl | 610.5 |
| 11 | amino | 3-trifluoromethylphenyl | 584.5 |
| 12 | isopropylamino | 3-trifluoromethylphenyl | 626.6 |
| 13 | isopropyl (methyl) amino | 3-trifluoromethylphenyl | 640.6 |
| 14 | isopropyl (propargyl) amino | 3-trifluoromethylphenyl | 664.6 |
| 15 | isopropyl (cyclopropyl methyl) amino | 3-trifluoromethylphenyl | 680.6 |
| 16 | 4-(methylthio)phenyl | 3-trifluoromethylphenyl | 640.3 |
| 17 | 4-(methylthio)phenyl | 3-trifluoromethylphenyl | 626.3 |
| 18 | 4-(methylthio)phenyl | 3-(trifluoromethyl)phenyl amino | 641.3 |
| 19 | 4-(methylthio)phenyl | 3-(trifluoromethyl)phenyl sulfonyl | 662.3 |
| 20 | 4-(methylthio)phenyl | phenyl | 558.3 |
| 21 | phenyl | 3-(trifluoromethyl)phenyl amino | 595.3 |
| 22 | H | 3-trifluoromethylphenyl | 566.4 |
| 23 | allyl | 3-trifluoromethylphenyl | 606.3 |
| 24 | H | 3-trifluoromethylphenyl | 566.3 |
| 25 | H | 3-trifluoromethylphenyl | 566.5 |
| 26 | 4-(methylthio)phenyl | 2-(t-butoxycarbonyl)amino-5-trifluoromethylphenyl | 621.4 |
| 27 | propyl | 3-trifluoromethylphenyl | 608.3 |
| 28 | 4-(methylthio)phenyl | 3-trifluoromethylphenyl | 581 |
| 29 | phenyl | 3-trifluoromethylphenyl | 535 |
| 30 | isopropyl (methyl) amino | 3-trifluoromethylphenyl | 595.4 |
| 31 | amino | 3-trifluoromethoxyphenyl | 555.2 |
| 32 | 4-(methylthio)phenyl | 3-trifluoromethoxyphenyl | 597.2 |
| 33 | 4-(methylthio)phenyl | 3-trifluoromethylphenyl | 537 |
| 34 | 4-(methylthio)phenyl | 3-(trifluoromethyl)phenyl methylene | 612.3 |
| 35 | H | 3-(trifluoromethyl)phenyl ethylene | NMR |
| 36 | H | 3-(trifluoromethyl)phenyl ethylene | 551.4 |
| 37 | methyl | 3-trifluoromethylphenyl | 608 |
| 38 | methyl | 3-trifluoromethylphenyl | 566 |
| 39 | methyl | 3-trifluoromethylphenyl | 623 |
| 40 | methyl | 3-trifluoromethylphenyl | 623 |
| 41 | methyl | O | 579 |
| 42 | methyl | O | 579 |
| 43 | methyl | OH | 581 |
| 44 | methyl | OH | 581 |
| 45 | methyl | methoxyamino | 608 |
| 46 | methyl | methoxyamino | 608 |
| 47 | amino | trifluoromethyl | 521 |
| 48 | isopropylamino | trifluoromethyl | 563 |
| 49 | isopropyl (methyl) amino | trifluoromethyl | 577 |
| 50 | isopropyl (ethyl) amino | trifluoromethyl | 591 |
| 51 | diethylamino | trifluoromethyl | 577 |
| 52 | isopropyl (methyl) amino | 1-naphthalenyl | 534 |
| 53 | isopropyl (methyl) amino | 3-benzo[b]thiophenyl | 540 |
| 54 | isopropyl (methyl) amino | 6-chloroquinazolin-4-yl | 570.2 |
| 55 | isopropyl (methyl) amino | 6,8-dichloroquinazolin-4-yl | 604.2 |
| 56 | methyl | 3,5-dichlorophenyl | 580 |
| 57 | methyl | 3-trifluoromethoxylphenyl | 596.2 |
| 58 | methyl | H | 563 |
| 59 | methyl | methyl | 577 |
| 60 | methyl | phenyl | 512 |
| 61 | isopropyl (methyl) amino | 3,5-bis-trifluoromethylphenyl | 648 |
| 62 | isopropyl (methyl) amino | 2-amino-5-trifluoromethoxyphenyl | 611 |
| 63 | isopropyl (methyl) amino | 6-trifluoromethylquinolin-4-yl | 603.2 |
| 64 | isopropyl (methyl) amino | 6-trifluoromethylquinolin-4-yl | 603.2 |
| 65 | isopropyl (methyl) amino | 7-trifluoromethylquinolin-4-yl | 603.2 |
| 66 | isopropyl (methyl) amino | 7-trifluoromethylquinolin-4-yl | 603.2 |
| 67 | isopropyl (methyl) amino | 2-phenyl-phenyl | 560.3 |
| 68 | isopropyl (methyl) amino | 3,5-bis-trifluoromethylphenyl | 620.2 |
| 69 | isopropyl (methyl) amino | 2-trifluoromethylphenyl | 552.3 |
| 70 | isopropyl (methyl) amino | 2-trifluoromethoxyphenyl | 568.3 |
| 71 | isopropyl (methyl) amino | 3-trifluoromethylphenyl | 552.3 |
| 72 | isopropyl (methyl) amino | 4-trifluoromethylphenyl | 552.3 |
| 73 | isopropyl (methyl) amino | 3-chlorophenyl | 546 |
| 74 | isopropyl (methyl) amino | 3-fluoro-5-trifluoromethylphenyl | 648 |
| 75 | t-butoxycarbonylamino | 3-trifluoromethylphenyl | 624.7 |
| 76 | phenyl | 3-trifluoromethylphenyl | 600.1 |
| 77 | pyridin-3-yl | 3-trifluoromethylphenyl | 601 |
| 78 | thiazolin-2-yl | 3-trifluoromethylphenyl | 607 |
| 79 | methoxycarbonylamino | 3-trifluoromethylphenyl | 582.2 |
| 80 | formamidyl | 3-trifluoromethylphenyl | 552.3 |
| 81 | aminocarbonylamino | 3-trifluoromethylphenyl | 567.3 |
| 82 | (methylamino) carbonyl amino | 3-trifluoromethylphenyl | 581.3 |
| 83 | 2-oxo-pyrrolidin-l-yl | 3-trifluoromethylphenyl | 592 |
| 84 | 1,1-dioxido-isothiazolidin-2-yl | 3-trifluoromethylphenyl | 628 |
| 85 | 4-chlorophenyl | 3-fluoro-5-trifluoromethylphenyl | 632 |
| 86 | 4-chlorophenyl | 3-chlorophenyl | 580 |
| 87 | 4-chlorophenyl | 3,5-bis-trifluoromethylphenyl | 683 |

TABLE 1-continued

| No. | | | MS |
|---|---|---|---|
| 88 | 4-chlorophenyl | 2-tert-butoxycarbonylamino-5-trifluoromethoxyphenyl | 746 |
| 89 | 4-chlorophenyl | 2-amino-5-trifluoromethoxyphenyl | 645 |
| 90 | 4-chlorophenyl | 3-trifluoromethoxyphenyl | 630.2 |
| 91 | 4-chlorophenyl | 3-trifluoromethylphenyl | 614.0 |
| 92 | 4-chlorophenyl | 3,5-bis-chloro-phenyl | 614.2 |
| 93 | 4-chlorophenyl | 3-chlorophenyl | 596 |
| 94 | 4-chlorophenyl | 3-trifluoromethylphenyl | 630.3 |
| 95 | 4-chlorophenyl | 3-fluoro-5-trifluoromethylphenyl | 649.1 |
| 96 | phenyl | 3-trifluoromethylphenyl | 596.3 |
| 97 | 4-isopropyl-phenyl | 3-trifluoromethylphenyl | 622.3 |
| 98 | 2-methyl-phenyl | 3-trifluoromethylphenyl | 594.6 |
| 99 | 4-fluoro-phenyl | 3-trifluoromethylphenyl | 598.5 |
| 100 | 4-methyl-phenyl | 3-chloro-phenyl | 560.2 |
| 101 | 4-methyl-phenyl | 2-amino-5-trifluoromethoxyphenyl | 625.2 |
| 102 | amino | 3-trifluoromethylphenyl | 493.4 |
| 103 | isopropylamino | 3-trifluoromethylphenyl | 535.2 |
| 104 | isopropyl (methyl) amino | 3-trifluoromethylphenyl | 548.7 |
| 105 | isopropyl (ethyl) amino | 3-trifluoromethylphenyl | 563.3 |
| 155 | pyrrolidin-1-yl | 3-trifluoromethylphenyl | 578.3 |

TABLE A

| No. | R | MS |
|---|---|---|
| 144 | 6-bromo-quinazolin-4-yl | 615 |
| 145 | 6,7-difluoro-quinazolin-4-yl | 572 |
| 146 | 6-methoxy-quinazolin-4-yl | 566 |

TABLE A-continued

| No. | R | MS |
|---|---|---|
| 137 | pyrido[2,3-d]pyrimidin-4-yl | 537 |
| 147 | quinazolin-4-yl | 536 |
| 140 | 6-trifluoromethoxy-quinazolin-4-yl | 620 |
| 120 | 6-fluoro-quinazolin-4-yl | 554 |
| 138 | 6-chloro-pyrido[2,3-d]pyrimidin-4-yl | 572 |
| 139 | 6-chloro-2-trifluoromethyl-pyrido[2,3-d]pyrimidin-4-yl | 639 |

TABLE A-continued
| No. | R | MS |
|---|---|---|
| 131 | 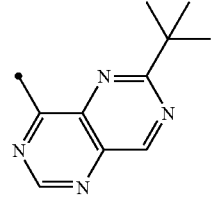 | 594 |
| 135 | 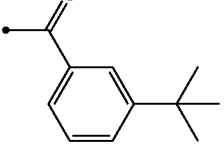 | 568 |
| 132 | 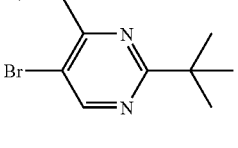 | 648 |
| 136 | 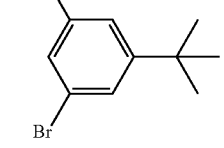 | 647 |
| 150 | 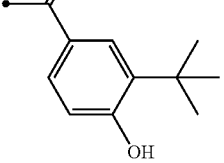 | 584 |
| 133 | 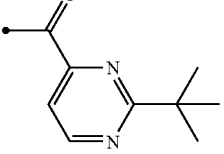 | 570 |
TABLE A-continued
| No. | R | MS |
|---|---|---|
| 148 | 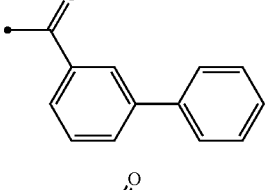 | 588 |
| 134 | 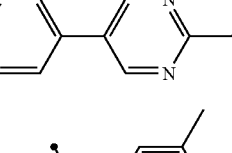 | 646 |
| 121 | 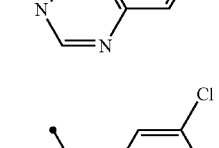 | 550 |
| 109 | 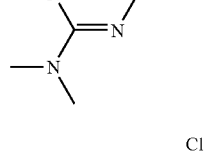 | 613 |
| 110 | 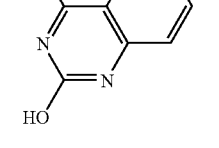 | 586 |
| 111 | 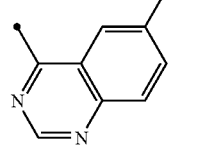 | 604 |

TABLE A-continued

| No. | R | MS |
|---|---|---|
| 112 | 4-tert-butyl-thieno[3,2-d]pyrimidinyl | 598 |
| 113 | 6-tert-butyl-2-trifluoromethyl-thieno[3,2-d]pyrimidinyl | 666 |
| 122 | 6-phenyl-thieno[2,3-d]pyrimidinyl | 618 |
| 124 | 6-chloro-2-isopropyl-quinazolinyl | 612 |
| 115 | 6-adamantyl-pyrrolo[2,1-f][1,2,4]triazinyl | 659 |

TABLE A-continued

| No. | R | MS |
|---|---|---|
| 151 | 3-amino-5-tert-butyl-thiophene-2-carbonyl | 589 |
| 152 | 2-methyl-5-phenyl-furan-3-carbonyl | 592 |
| 153 | 5-nitro-furan-2-carbonyl | 547 |
| 154 | 4-phenyl-thiophene-2-carbonyl | 594 |
| 116 | 1-methyl-2-phenyl-imidazole-5-carbonyl | 592 |
| 117 | 1-benzyl-2-phenyl-imidazole-5-carbonyl | 668 |

TABLE A-continued
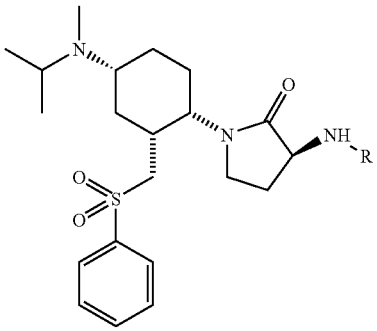
| No. | R | MS |
|---|---|---|
| 118 | 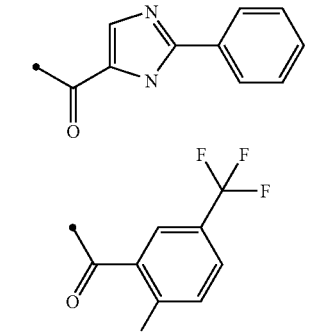 | 577 |
| 143 | 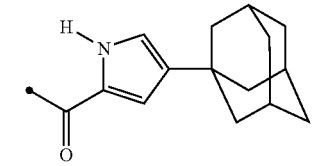 | 614 |
| 129 | 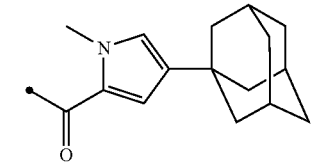 | 636 |
| 130 | 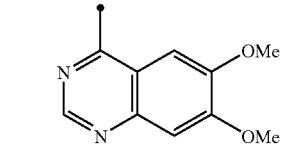 | 649 |
| 119 | 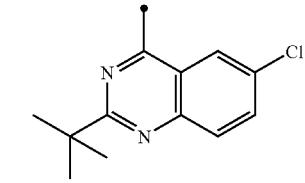 | 596 |
| 125 | 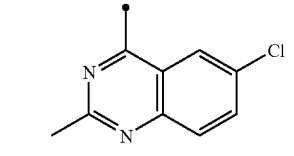 | 626 |
| 126 | 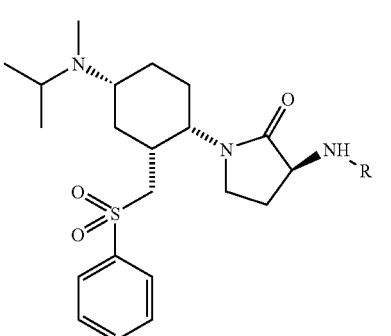 | 585 |
TABLE A-continued
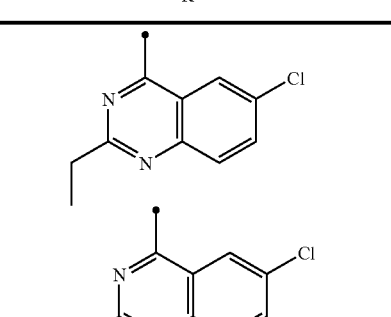
| No. | R | MS |
|---|---|---|
| 127 | 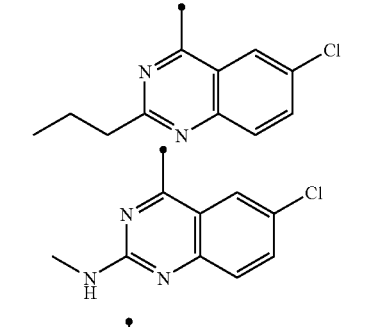 | 599 |
| 106 | 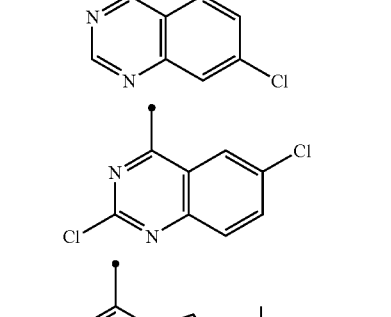 | 638 |
| 123 | 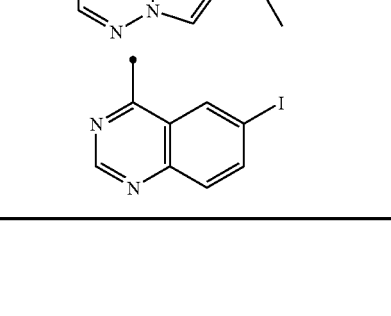 | 613 |
| 141 | 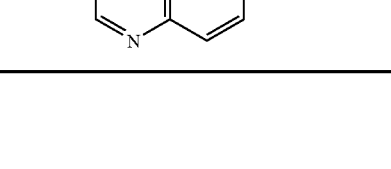 | 599 |
| 107 | | 570 |
| 108 | | 604 |
| 114 | | 581 |
| 149 | | 662 |

TABLE B

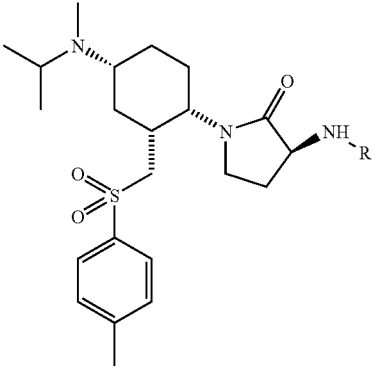

| 142 | | 568 |
|---|---|---|

TABLE C

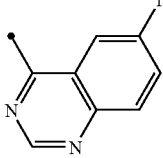

| 128 | | 594 |
|---|---|---|

UTILITY

Compounds of formula I are shown to be modulators of chemokine receptor activity using assays know by those skilled in the art. In this section, we describe these assays and give their literature reference. By displaying activity in these assays of MCP-1 antagonism, compounds of formula I are expected to be useful in the treatment of human diseases associated with chemokines and their cognate receptors. The definition of activity in these assays is a compound demonstrating an $IC_{50}$ of 20 µM or lower in concentration when measured in a particular assay.

Antagonism of MCP-1 Binding to Human PBMC (Yoshimura et al., *J. Immunol.* 1990, 145, 292)

Compounds of the present invention have activity in the antagonism of MCP-1 binding to human PBMC (human peripheral blood mononuclear cells) described here.

Millipore filter plates (#MABVN1250) are treated with 100 µl of binding buffer (0.5% bovine serum albumin, 20 mM HEPES buffer and 5 mM magnesium chloride in RPMI 1640 media) for thirty minutes at room temperature. To measure binding, 50 µl of binding buffer, with or without a known concentration compound, is combined with 50 µl of $^{125}$-I labeled human MCP-1 (to give a final concentration of 150 pM radioligand) and 50 µl of binding buffer containing $5\times10^5$ cells. Cells used for such binding assays can include human peripheral blood mononuclear cells isolated by Ficoll-Hypaque gradient centrifugation, human monocytes (Weiner et al., *J. Immunol. Methods.* 1980, 36, 89), or the THP-1 cell line which expresses the endogenous receptor. The mixture of compound, cells and radioligand are incubated at room temperature for thirty minutes. Plates are placed onto a vacuum manifold, vacuum applied, and the plates washed three times with binding buffer containing 0.5M NaCl. The plastic skirt is removed from the plate, the plate allowed to air dry, the wells punched out and counted. The percent inhibition of binding is calculated using the total counts obtained in the absence of any competing compound and the background binding determined by addition of 100 nM MCP-1 in place of the test compound.

Antagonism of MCP-1-induced Calcium Influx (Sullivan, et al. Methods Mol. Biol., 114, 125–133 (1999)

Compounds of the present invention have activity in the antagonism of MCP-1-induced calcium influx assay described here.

Calcium mobilization is measured using the fluorescent $Ca^{2+}$ indicator dye, Fluo-3. Cells are incubated at $8\times10^5$ cells/ml in phosphate-buffered saline containing 0.1% bovine serum albumin, 20 mM HEPES buffer, 5 mM glucose, 1% fetal bovine serum, 4 µM Fluo-3 AM and 2.5 mM probenecid for 60 minutes at 37° C. Cells used for such calcium assays can include human monocytes isolated as described by Weiner et al., J. Immunol. Methods, 36, 89–97 (1980) or cell lines which expresses the endogenous CCR2 receptor such as THP-1 and MonoMac-6. The cells are then washed three times in phosphate-buffered saline containing 0.1% bovine serum albumin, 20 mM HEPES,5 mM glucose and 2.5 mM probenecid. The cells are resuspended in phosphate-buffered saline containing 0.5% bovine serum albumin, 20 mM HEPES and 2.5 mM probenecid at a final concentration of $2-4\times10^6$ cells/ml. Cells are plated into 96-well, black-wall microplates (100 µl/well) and the plates centrifuged at 200×g for 5 minutes. Various concentrations of compound are added to the wells (50 µl/well) and after 5 minutes, 50 µl/well of MCP-1 is added to give a final concentration of 10 nM. Calcium mobilization is detected by using a fluorescent-imaging plate reader. The cell monolayer is excited with an argon laser (488 nM) and cell-associated fluorescence measured for 3 minutes, (every second for the first 90 seconds and every 10 seconds for the next 90 seconds). Data are generated as arbitrary fluorescence units and the change in fluorescence for each well determined as the maximum-minimum differential. Compound-dependent inhibition is calculated relative to the response of MCP-1 alone.

Antagonism of MCP-1-induced Human PBMC Chemotaxis (Bacon et al., *Brit. J. Pharmacol.* 1988, 95, 966)

Compounds of the present invention have activity in the antagonism of MCP-1-induced human PBMC chemotaxis assay described here.

Neuroprobe MBA96–96-well chemotaxis chamber, Polyfiltronics MPC 96 well plate, and Neuroprobe polyvinylpyrrolidone-free polycarbonate PFD5 8-micron filters are warmed in a 37° C. incubator. Human Peripheral Blood Mononuclear Cells (PBMCs) (Boyum et al., *Scand. J. Clin. Lab Invest. Suppl.* 1968, 97, 31), freshly isolated via the standard ficoll density separation method, are suspended in DMEM at $1 \times 10^7$ c/ml and warmed at 37° C. A 60 nM solution of human MCP-1 is also warmed at 37° C. Dilutions of test compounds are made up at 2× the concentration needed in DMEM. The PBMC suspension and the 60 nm MCP-1 solution are mixed 1:1 in polypropylene tubes with prewarmed DMEM with or without a dilution of the test compounds. These mixtures are warmed in a 37° C. tube warmer. To start the assay, add the MCP-1/compound mixture into the wells of the Polyfiltronics MPC 96 well plate that has been placed into the bottom part of the Neuroprobe chemotaxis chamber. The approximate volume is 400 μl to each well and there should be a positive meniscus after dispensing. The 8 micron filter is placed gently on top of the 96 well plate, a rubber gasket is attached to the bottom of the upper chamber, and the chamber is assembled. A 200 μl volume of the cell suspension/compound mixture is added to the appropriate wells of the upper chamber. The upper chamber is covered with a plate sealer, and the assembled unit is placed in a 37° C. incubator for 45 minutes. After incubation, the plate sealer is removed and all the remaining cell suspension is aspirated off. The chamber is disassembled and the filter gently removed. While holding the filter at a 90 degree angle, unmigrated cells are washed away using a gentle stream of phosphate buffered saline and the top of the filter wiped with the tip of a rubber squeegee. Repeat this wash twice more. The filter is air dried and then immersed completely in Wright Geimsa stain for 45 seconds. The filter is then washed by soaking in distilled water for 7 minutes, and then a 15 second additional wash in fresh distilled water. The filter is again air dried. Migrated cells on the filter are quantified by visual microscopy.

Mammalian chemokine receptors provide a target for interfering with or promoting immune cell function in a mammal, such as a human. Compounds that inhibit or promote chemokine receptor function are particularly useful for modulating immune cell function for therapeutic purposes. Accordingly, the present invention is directed to compounds which are useful in the prevention and/or treatment of a wide variety of inflammatory, infectious, and immunoregulatory disorders and diseases, including asthma and allergic diseases, infection by pathogenic microbes (which, by definition, includes viruses), as well as autoimmune pathologies such as the rheumatoid arthritis and atherosclerosis.

For example, an instant compound which inhibits one or more functions of a mammalian chemokine receptor (e.g., a human chemokine receptor) may be administered to inhibit (i.e., reduce or prevent) inflammation or infectious disease. As a result, one or more inflammatory process, such as leukocyte emigration, adhesion, chemotaxis, exocytosis (e.g., of enzymes, histamine) or inflammatory mediator release, is inhibited.

Similarly, an instant compound which promotes one or more functions of the mammalian chemokine receptor (e.g., a human chemokine) as administered to stimulate (induce or enhance) an immune or inflammatory response, such as leukocyte emigration, adhesion, chemotaxis, exocytosis (e.g., of enzymes, histamine) or inflammatory mediator release, resulting in the beneficial stimulation of inflammatory processes. For example, eosinophils can be recruited to combat parasitic infections. In addition, treatment of the aforementioned inflammatory, allergic and autoimmune diseases can also be contemplated for an instant compound which promotes one or more functions of the mammalian chemokine receptor if one contemplates the delivery of sufficient compound to cause the loss of receptor expression on cells through the induction of chemokine receptor internalization or the delivery of compound in a manner that results in the misdirection of the migration of cells.

In addition to primates, such as humans, a variety of other mammals can be treated according to the method of the present invention. For instance, mammals, including but not limited to, cows, sheep, goats, horses, dogs, cats, guinea pigs, rats or other bovine, ovine, equine, canine, feline, rodent or murine species can be treated. However, the method can also be practiced in other species, such as avian species. The subject treated in the methods above is a mammal, male or female, in whom modulation of chemokine receptor activity is desired. "Modulation" as used herein is intended to encompass antagonism, agonism; partial antagonism and/or partial agonism.

Diseases or conditions of human or other species which can be treated with inhibitors of chemokine receptor function, include, but are not limited to: inflammatory or allergic diseases and conditions, including respiratory allergic diseases such as asthma, allergic rhinitis, hypersensitivity lung diseases, hypersensitivity pneumonitis, eosinophilic cellulitis (e.g., Well's syndrome), eosinophilic pneumonias (e.g., Loeffler's syndrome, chronic eosinophilic pneumonia), eosinophilic fasciitis (e.g., Shulman's syndrome), delayed-type hypersensitivity, interstitial lung diseases (ILD) (e.g., idiopathic pulmonary fibrosis, or ILD associated with rheumatoid arthritis, systemic lupus erythematosus, ankylosing spondylitis, systemic sclerosis, Sjogren's syndrome, polymyositis or dermatomyositis); systemic anaphylaxis or hypersensitivity responses, drug allergies (e.g., to penicillin, cephalosporins), eosinophilia-myalgia syndrome due to the ingestion of contaminated tryptophan, insect sting allergies; autoimmune diseases, such as rheumatoid arthritis, psoriatic arthritis, multiple sclerosis, systemic lupus erythematosus, myasthenia gravis, juvenile onset diabetes; glomerulonephritis, autoimmune thyroiditis, Behcet's disease; graft rejection (e.g., in transplantation), including allograft rejection or graft-versus-host disease; inflammatory bowel diseases, such as Crohn's disease and ulcerative colitis; spondyloarthropathies; scleroderma; psoriasis (including T-cell mediated psoriasis) and inflammatory dermatoses such as an dermatitis, eczema, atopic dermatitis, allergic contact dermatitis, urticaria; vasculitis (e.g., necrotizing, cutaneous, and hypersensitivity vasculitis); eosinophilic myositis, eosinophilic fasciitis; cancers with leukocyte infiltration of the skin or organs. Other diseases or conditions in which undesirable inflammatory responses are to be inhibited can be treated, including, but not limited to, reperfusion injury, atherosclerosis, certain hematologic malignancies, cytokine-induced toxicity (e.g., septic shock, endotoxic shock), polymyositis, dermatomyositis. Infectious diseases or conditions of human or other species which can be treated with inhibitors of chemokine receptor function, include, but are not limited to, HIV.

Diseases or conditions of humans or other species which can be treated with promoters of chemokine receptor function, include, but are not limited to: immunosuppression, such as that in individuals with immunodeficiency syndromes such as AIDS or other viral infections, individuals undergoing radiation therapy, chemotherapy, therapy for autoimmune disease or drug therapy (e.g., corticosteroid therapy), which causes immunosuppression; immunosuppression due to congenital deficiency in receptor function or other causes; and infections diseases, such as parasitic diseases, including, but not limited to helminth infections, such as nematodes (round worms); (Trichuriasis, Enterobiasis, Ascariasis, Hookworm, Strongyloidiasis, Trichinosis, filariasis); trematodes (flukes) (Schistosomiasis, Clonorchiasis), cestodes (tape worms) (Echinococcosis, *Taeniasis saginata*, Cysticercosis); visceral worms, visceral larva migraines (e.g., Toxocara), eosinophilic gastroenteritis (e.g., *Anisaki* sp., *Phocanema* sp.), cutaneous larva migraines (*Ancylostona braziliense, Ancylostoma caninum*). The compounds of the present invention are accordingly useful in the prevention and treatment of a wide variety of inflammatory, infectious and immunoregulatory disorders and diseases. In addition, treatment of the aforementioned inflammatory, allergic and autoimmune diseases can also be contemplated for promoters of chemokine receptor function if one contemplates the delivery of sufficient compound to cause the loss of receptor expression on cells through the induction of chemokine receptor internalization or delivery of compound in a manner that results in the misdirection of the migration of cells.

In another aspect, the instant invention may be used to evaluate the putative specific agonists or antagonists of a G protein coupled receptor. The present invention is directed to the use of these compounds in the preparation and execution of screening assays for compounds that modulate the activity of chemokine receptors. Furthermore, the compounds of this invention are useful in establishing or determining the binding site of other compounds to chemokine receptors, e.g., by competitive inhibition or as a reference in an assay to compare its known activity to a compound with an unknown activity. When developing new assays or protocols, compounds according to the present invention could be used to test their effectiveness. Specifically, such compounds may be provided in a commercial kit, for example, for use in pharmaceutical research involving the aforementioned diseases. The compounds of the instant invention are also useful for the evaluation of putative specific modulators of the chemokine receptors. In addition, one could utilize compounds of this invention to examine the specificity of G protein coupled receptors that are not thought to be chemokine receptors, either by serving as examples of compounds which do not bind or as structural variants of compounds active on these receptors which may help define specific sites of interaction.

The compounds of the present invention are used to treat or prevent disorders selected from rheumatoid arthritis, osteoarthritis, septic shock, atherosclerosis, aneurism, fever, cardiovascular effects, haemodynamic shock, sepsis syndrom, post ischemic reperfusion injury, malaria, Crohn's disease, inflammatory bowel diseases, mycobacterial infection, meningitis, psoriasis, congestive heart failure, fibrotic diseases, cachexia, graft rejection, autoimmune diseases, skin inflammatory diseases, multiple sclerosis, radiation damage, hyperoxic alveolar injury, HIV, HIV dementia, non-insulin dependent diabetes melitus, asthma, allergic rhinitis, atopic dermatitis, idiopathic pulmonary fibrosis, bullous pemphigoid, helminthic parasitic infections, allergic colitis, eczema, conjunctivitis, transplantation, familial eosinophilia, eosinophilic cellulitis, eosinophilic pneumonias, eosinophilic fasciitis, eosinophilic gastroenteritis, drug induced eosinophilia, cystic fibrosis, Churg-Strauss syndrome, lymphoma, Hodgkin's disease, colonic carcinoma, Felty's syndrome, sarcoidosis, uveitis, Alzheimer, Glomerulonephritis, and systemic lupus erythematosus.

In another aspect, the compounds are used to treat or prevent inflammatory disorders selected from from rheumatoid arthritis, osteoarthritis, atherosclerosis, aneurism, fever, cardiovascular effects, Crohn's disease, inflammatory bowel diseases, psoriasis, congestive heart failure, multiple sclerosis, autoimmune diseases, skin inflammatory diseases.

In another aspect, the compounds are used to treat or prevent inflammatory disorders selected from rheumatoid arthritis, osteoarthritis, atherosclerosis, Crohn's disease, inflammatory bowel diseases, and multiple sclerosis.

Combined therapy to prevent and treat inflammatory, infectious and immunoregulatory disorders and diseases, including asthma and allergic diseases, as well as autoimmune pathologies such as rheumatoid arthritis and atherosclerosis, and those pathologies noted above is illustrated by the combination of the compounds of this invention and other compounds which are known for such utilities. For example, in the treatment or prevention of inflammation, the present compounds may be used in conjunction with an anti-inflammatory or analgesic agent such as an opiate agonist, a lipoxygenase inhibitor, a cyclooxygenase-2 inhibitor, an interleukin inhibitor, such as an interleukin-1 inhibitor, a tumor necrosis factor inhibitor, an NMDA antagonist, an inhibitor or nitric oxide or an inhibitor of the synthesis of nitric oxide, a non-steroidal anti-inflammatory agent, a phosphodiesterase inhibitor, or a cytokine-suppressing anti-inflammatory agent, for example with a compound such as acetaminophen, aspirin, codeine, fentaynl, ibuprofen, indomethacin, ketorolac, morphine, naproxen, phenacetin, piroxicam, a steroidal analgesic, sufentanyl, sunlindac, interferon alpha and the like. Similarly, the instant compounds may be administered with a pain reliever; a potentiator such as caffeine, an H2-antagonist, simethicone, aluminum or magnesium hydroxide; a decongestant such as phenylephrine, phenylpropanolamine, pseudophedrine, oxymetazoline, ephinephrine, naphazoline, xylometazoline, propylhexedrine, or levodesoxy-ephedrine; and antitussive such as codeine, hydrocodone, caramiphen, carbetapentane, or dextramethorphan; a diuretic; and a sedating or nonsedating antihistamine. Likewise, compounds of the present invention may be used in combination with other drugs that are used in the treatment/prevention/suppression or amelioration of the diseases or conditions for which compound of the present invention are useful. Such other drugs may be administered, by a route and in an amount commonly used therefore, contemporaneously or sequentially with a compound of the present invention. When a compound of the present invention is used contemporaneously with one or more other drugs, a pharmaceutical composition containing such other drugs in addition to the compound of the present invention may be used. Accordingly, the pharmaceutical compositions of the present invention include those that also contain one or more other active ingredients, in addition to a compound of the present invention.

Examples of other active ingredients that may be combined with a compound of the present invention, either administered separately or in the same pharmaceutical compositions, include, but are not limited to: (a) integrin antagonists such as those for selectins, ICAMs and VLA-4; (b) steroids such as beclomethasone, methylprednisolone, betamethasone, prednisone, dexamethasone, and hydrocortisone; (c) immunosuppressants such as cyclosporin, tacrolimus, rapamycin and other FK-506 type immunosuppressants; (d) antihistamines (H1-histamine antagonists) such as bromopheniramine, chlorpheniramine, dexchlorpheniramine, triprolidine, clemastine, diphenhydramine, diphenylpyraline, tripelennamine, hydroxyzine, methdilazine, promethazine, trimeprazine, azatadine, cyproheptadine, antazoline, pheniramine pyrilamine, astemizole, terfenadine, loratadine, cetirizine, fexofenadine, descarboethoxyloratadine, and the like; (e) non-steroidal anti-asthmatics such as b2-agonists (terbutaline, metaproterenol, fenoterol, isoetharine, albuterol, bitolterol, and pirbuterol), theophylline, cromolyn sodium, atropine, ipratropium bromide, leukotriene antagonists (zafirlukast, montelukast, pranlukast, iralukast, pobilukast, SKB-102,203), leukotriene biosynthesis inhibitors (zileuton, BAY-1005); (f) non-steroidal anti-inflammatory agents (NSAIDs) such as propionic acid derivatives (alminoprofen, benxaprofen, bucloxic acid, carprofen, fenbufen, fenoprofen, fluprofen, flurbiprofen, ibuprofen, indoprofen, ketoprofen, miroprofen, naproxen, oxaprozin, pirprofen, pranoprofen, suprofen, tiaprofenic acid, and tioxaprofen), acetic acid derivatives (indomethacin, acemetacin, alclofenac, clidanac, diclofenac, fenclofenac, fenclozic acid, fentiazac, furofenac, ibufenac, isoxepac, oxpinac, sulindac, tiopinac, tolmetin, zidometacin, and zomepirac), fenamic acid derivatives (flufenamic acid, meclofenamic acid, mefenamic acid, niflumic acid and tolfenamic acid), biphenylcarboxylic acid derivatives (diflunisal and flufenisal), oxicams (isoxicam, piroxicam, sudoxicam and tenoxican), salicylates (acetyl salicylic acid, sulfasalazine) and the pyrazolones (apazone, bezpiperylon, feprazone, mofebutazone, oxyphenbutazone, phenylbutazone); (g) cyclooxygenase-2 (COX-2) inhibitors; (h) inhibitors of phosphodiesterase type IV (PDE-IV); (I) other antagonists of the chemokine receptors; (j) cholesterol lowering agents such as HMG-COA reductase inhibitors (lovastatin, simvastatin and pravastatin, fluvastatin, atorvsatatin, and other statins), sequestrants (cholestyramine and colestipol), nicotonic acid, fenofibric acid derivatives (gemfibrozil, clofibrat, fenofibrate and benzafibrate), and probucol; (k) anti-diabetic agents such as insulin, sulfonylureas, biguanides (metformin), a-glucosidase inhibitors (acarbose) and glitazones (troglitazone ad pioglitazone); (1) preparations of interferons (interferon alpha-2a, interferon-2B, interferon alpha-N3, interferon beta-1a, interferon beta-1b, interferon gamma-1b); (m) antiviral compounds such as efavirenz, nevirapine, indinavir, ganciclovir, lamivudine, famciclovir, and zalcitabine; (o) other compound such as 5-aminosalicylic acid an prodrugs thereof, antimetabolites such as azathioprine and 6-mercaptopurine, and cytotoxic cancer chemotherapeutic agents. The weight ratio of the compound of the present invention to the second active ingredient may be varied and will depend upon the effective doses of each ingredient.

Generally, an effective dose of each will be used. Thus, for example, when a compound of the present invention is combined with an NSAID the weight ratio of the compound of the present invention to the NSAID will generally range from about 1000:1 to about 1:1000, or alternatively from about 200:1 to about 1:200. Combinations of a compound of the present invention and other active ingredients will generally also be within the aforementioned range, but in each case, an effective dose of each active ingredient should be used.

The compounds are administered to a mammal in a therapeutically effective amount. By "therapeutically effective amount" it is meant an amount of a compound of Formula I that, when administered alone or in combination with an additional therapeutic agent to a mammal, is effective to prevent or ameliorate the thromboembolic disease condition or the progression of the disease.

Dosage and Formulation

The compounds of this invention can be administered in such oral dosage forms as tablets, capsules (each of which includes sustained release or timed release formulations), pills, powders, granules, elixirs, tinctures, suspensions, syrups, and emulsions. They may also be administered in intravenous (bolus or infusion), intraperitoneal, subcutaneous, or intramuscular form, all using dosage forms well known to those of ordinary skill in the pharmaceutical arts. They can be administered alone, but generally will be administered with a pharmaceutical carrier selected on the basis of the chosen route of administration and standard pharmaceutical practice.

The dosage regimen for the compounds of the present invention will, of course, vary depending upon known factors, such as the pharmacodynamic characteristics of the particular agent and its mode and route of administration; the species, age, sex, health, medical condition, and weight of the recipient; the nature and extent of the symptoms; the kind of concurrent treatment; the frequency of treatment; the route of administration, the renal and hepatic function of the patient, and the effect desired. A physician or veterinarian can determine and prescribe the effective amount of the drug required to prevent, counter, or arrest the progress of the thromboembolic disorder.

By way of general guidance, the daily oral dosage of each active ingredient, when used for the indicated effects, will range between about 0.001 to 1000 mg/kg of body weight, or between about 0.01 to 100 mg/kg of body weight per day, or alternativley, between about 1.0 to 20 mg/kg/day. Intravenously, the doses will range from about 1 to about 10 mg/kg/minute during a constant rate infusion. Compounds of this invention may be administered in a single daily dose, or the total daily dosage may be administered in divided doses of two, three, or four times daily.

Compounds of this invention can be administered in intranasal form via topical use of suitable intranasal vehicles, or via transdermal routes, using transdermal skin patches. When administered in the form of a transdermal delivery system, the dosage administration will, of course, be continuous rather than intermittent throughout the dosage regimen.

The compounds are typically administered in admixture with suitable pharmaceutical diluents, excipients, or carriers (collectively referred to herein as pharmaceutical carriers) suitably selected with respect to the intended form of administration, that is, oral tablets, capsules, elixirs, syrups and the like, and consistent with conventional pharmaceutical practices.

For instance, for oral administration in the form of a tablet or capsule, the active drug component can be combined with an oral, non-toxic, pharmaceutically acceptable, inert carrier such as lactose, starch, sucrose, glucose, methyl callulose, magnesium stearate, dicalcium phosphate, calcium sulfate, mannitol, sorbitol and the like; for oral administration in liquid form, the oral drug components can be combined with any oral, non-toxic, pharmaceutically acceptable inert carrier such as ethanol, glycerol, water, and the like. Moreover, when desired or necessary, suitable binders, lubricants, disintegrating agents, and coloring agents can also be incorporated into the mixture. Suitable binders include starch, gelatin, natural sugars such as glucose or beta-lactose, corn sweeteners, natural and synthetic gums such as acacia, tragacanth, or sodium alginate, carboxymethylcellulose, polyethylene glycol, waxes, and the like. Lubricants used in these dosage forms include sodium oleate, sodium stearate, magnesium stearate, sodium benzoate, sodium acetate, sodium chloride, and the like. Disintegrators include, without limitation, starch, methyl cellulose, agar, bentonite, xanthan gum, and the like.

The compounds of the present invention can also be administered in the form of liposome delivery systems, such as small unilamellar vesicles, large unilamellar vesicles, and multilamellar vesicles. Liposomes can be formed from a variety of phospholipids, such as cholesterol, stearylamine, or phosphatidylcholines.

Compounds of the present invention may also be coupled with soluble polymers as targetable drug carriers. Such polymers can include polyvinylpyrrolidone, pyran copolymer, polyhydroxypropylmethacrylamide-phenol, polyhydroxyethylaspartamidephenol, or polyethyleneoxide-polylysine substituted with palmitoyl residues. Furthermore, the compounds of the present invention may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacylates, and crosslinked or amphipathic block copolymers of hydrogels. Dosage forms (pharmaceutical compositions) suitable for administration may contain from about 1 milligram to about 100 milligrams of active ingredient per dosage unit. In these pharmaceutical compositions the active ingredient will ordinarily be present in an amount of about 0.5–95% by weight based on the total weight of the composition.

Gelatin capsules may contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract. Liquid dosage forms for oral administration can contain coloring and flavoring to increase patient acceptance. In general, water, a suitable oil, saline, aqueous dextrose (glucose), and related sugar solutions and glycols such as propylene glycol or polyethylene glycols are suitable carriers for parenteral solutions. Solutions for parenteral administration may contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propyl-paraben, and chlorobutanol.

Suitable pharmaceutical carriers are described in *Remington's Pharmaceutical Sciences*, Mack Publishing Company, a standard reference text in this field. Representative useful pharmaceutical dosage-forms for administration of the compounds of this invention can be illustrated as follows:

Capsules

A large number of unit capsules can be prepared by filling standard two-piece hard gelatin capsules each with 100 milligrams of powdered active ingredient, 150 milligrams of lactose, 50 milligrams of cellulose, and 6 milligrams magnesium stearate.

Soft Gelatin Capsules

A mixture of active ingredient in a digestable oil such as soybean oil, cottonseed oil or olive oil may be prepared and injected by means of a positive displacement pump into gelatin to form soft gelatin capsules containing 100 milligrams of the active ingredient. The capsules should be washed and dried.

Tablets

Tablets may be prepared by conventional procedures so that the dosage unit is 100 milligrams of active ingredient, 0.2 milligrams of colloidal silicon dioxide, 5 milligrams of magnesium stearate, 275 milligrams of microcrystalline cellulose, 11 milligrams of starch and 98.8 milligrams of lactose. Appropriate coatings may be applied to increase palatability or delay absorption.

Injectable

A parenteral composition suitable for administration by injection may be prepared by stirring 1.5% by weight of active ingredient in 10% by volume propylene glycol and water. The solution should be made isotonic with sodium chloride and sterilized.

Suspension

An aqueous suspension can be prepared for oral administration so that each 5 mL contain 100 mg of finely divided active ingredient, 200 mg of sodium carboxymethyl cellulose, 5 mg of sodium benzoate, 1.0 g of sorbitol solution, U.S.P., and 0.025 mL of vanillin. Where the compounds of this invention are combined with other anticoagulant agents, for example, a daily dosage may be about 0.1 to 100 milligrams of the compound of Formula I and about 1 to 7.5 milligrams of the second anticoagulant, per kilogram of patient body weight. For a tablet dosage form, the compounds of this invention generally may be present in an amount of about 5 to 10 milligrams per dosage unit, and the second anti-coagulant in an amount of about 1 to 5 milligrams per dosage unit. Where two or more of the foregoing second therapeutic agents are administered with the compound of Formula I, generally the amount of each component in a typical daily dosage and typical dosage form may be reduced relative to the usual dosage of the agent when administered alone, in view of the additive or synergistic effect of the therapeutic agents when administered in combination. Particularly when provided as a single dosage unit, the potential exists for a chemical interaction between the combined active ingredients. For this reason, when the compound of Formula I and a second therapeutic agent are combined in a single dosage unit they are formulated such that although the active ingredients are combined in a single dosage unit, the physical contact between the active ingredients is minimized (that is, reduced). For example, one active ingredient may be enteric coated. By enteric coating one of the active ingredients, it is possible not only to minimize the contact between the combined active ingredients, but also, it is possible to control the release of one of these components in the gastrointestinal tract such that one of these components is not released in the stomach but rather is released in the intestines. One of the active ingredients may also be coated with a material which effects a sustained-release throughout the gastrointestinal tract and also serves to minimize physical contact between the combined active ingredients. Furthermore, the sustained-released component can be additionally enteric coated such that the release of this component occurs only in the intestine. Still another approach would involve the formulation of a combination product in which the one component is coated with a sustained and/or enteric release polymer, and the other component is also coated with a polymer such as a lowviscosity grade of hydroxypropyl methylcellulose (HPMC) or other appropriate materials as known in the art, in order to further separate the active components. The polymer coating serves to form an additional barrier to interaction with the other component.

These as well as other ways of minimizing contact between the components of combination products of the present invention, whether administered in a single dosage form or administered in separate forms but at the same time by the same manner, will be readily apparent to those skilled in the art, once armed with the present disclosure.

Obviously, numerous modifications and variations of the present invention are possible in light of the above teachings. It is therefore to be understood that within the scope of the appended claims, the invention may be practiced otherwise that as specifically described herein.

The invention claimed is:

1. A compound of formula (I):

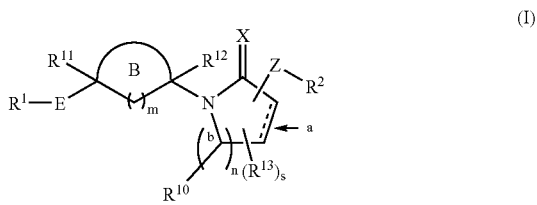

or a stereoisomer or a pharmaceutically acceptable salt thereof, wherein:

ring B is a cyclohexyl group, ring B being substituted with 0–2 $R^5$;

X is selected from O or S;

Z is $-NR^9-$;

wherein neither Z nor $R^{13}$ are connected to a carbon atom labeled (b);

bond (a) is a single bond;

E is selected from $-S(O)_pCHR^e-$, $-CHR^eNR^e-$, $-C(O)-NR^e-$, $-NR^eC(O)NR^e-$, $-SO_2-NR^e-$, and $-NR^eSO_2NR^e-$;

$R^e$ is independently selected from H and $C_{1-3}$ alkyl;

$R^1$ is selected from a $C_{6-10}$ aryl group substituted with 0–5 $R^6$;

$R^2$ is selected from a 5–10 membered heteroaryl system containing 1–4 heteroatoms selected from N, O, and S, substituted with 0–3 $R^7$;

$R^5$, at each occurrence, is independently selected from H, $=$O, $C_{1-6}$ alkyl, $C_{2-8}$ alkenyl, $C_{2-8}$ alkynyl, $(CRR)_rOH$, $(CRR)_rSH$, $(CRR)_rOR^{5d}$, $(CRR)_rSR^{5d}$, $(CRR)_rNR^{5a}R^{5a}$, $(CRR)_rN(\rightarrow O)R^{5a}R^{5a}$, $N_3$, $(CRR)_rC(O)OH$, $(CRR)_rC(O)R^{5b}$, $(CRR)_rC(O)NR^{5a}R^{5a}$, $(CRR)_rNR^{5a}C(O)R^{5b}$, $(CRR)_rOC(O)NR^{5a}R^{5a}$, $(CRR)_rNR^{5a}C(O)OR^{5d}$, $(CRR)_rNR^{5a}C(O)NR^{5a}R^{5a}$, $(CRR)_rNR^{5a}C(O)H$, $(CRR)_rC(O)OR^{5d}$, $(CRR)_rOC(O)R^{5b}$, $(CRR)_rS(O)_pR^{5b}$, $(CRR)_rS(O)_2NR^{5a}R^{5a}$, $(CRR)_rNR^{5a}S(O)_2R^{5b}$, $(CRR)_rNR^{5a}S(O)_2NR^{5a}R^{5a}$, $C_{1-6}$ haloalkyl, a $(CRR)_r$—$C_{3-10}$ carbocyclic residue substituted with 0–3 $R^{5c}$, and a $(CRR)_r$-5–10 membered heterocyclic system containing 1–4 heteroatoms selected from N, O, and S, substituted with 0–2 $R^{5c}$;

$R^{5a}$, at each occurrence, is independently selected from H, methyl substituted with 0–1 $R^{5g}$, $C_{2-6}$ alkyl substituted with 0–2 $R^{5e}$, $C_{3-8}$ alkenyl substituted with 0–2 $R^{5e}$, $C_{3-8}$ alkynyl substituted with 0–2 $R^{5e}$, a $(CH_2)_r$—$C_{3-10}$ carbocyclic residue substituted with 0–5 $R^{5e}$, and a $(CH_2)_r$-5–10 membered heterocyclic system containing 1–4 heteroatoms selected from N, O, and S, substituted with 0–3 $R^{5e}$;

$R^{5b}$, at each occurrence, is selected from $C_{1-6}$ alkyl substituted with 0–3 $R^{5e}$, $C_{3-8}$ alkenyl substituted with 0–2 $R^{5e}$, $C_{3-8}$ alkynyl substituted with 0–2 $R^{5e}$, a $(CH_2)_rC_{3-6}$ carbocyclic residue substituted with 0–2 $R^{5e}$, and a $(CH_2)_r$-5–6 membered heterocyclic system containing 1–4 heteroatoms selected from N, O, and S, substituted with 0–3 $R^{5e}$;

$R^{5c}$, at each occurrence, is selected from $C_{1-6}$ alkyl, $C_{2-8}$ alkenyl, $C_{2-8}$ alkynyl, $(CH_2)_rC_{3-6}$ cycloalkyl, Cl, Br, I, F, $(CF_2)_rCF_3$, $NO_2$, CN, $(CH_2)_rNR^{5f}R^{5f}$, $(CH_2)_rOH$, $(CH_2)_rOC_{1-4}$ alkyl, $(CH_2)_rSC_{1-4}$ alkyl, $(CH_2)_rC(O)OH$, $(CH_2)_rC(O)R^{5b}$, $(CH_2)_rC(O)NR^{5f}R^{5f}$, $(CH_2)_rOC(O)NR^{5f}R^{5f}$, $(CH_2)_rNR^{5f}C(O)R^{5b}$, $(CH_2)_rC(O)OC_{1-4}$ alkyl, $(CH_2)_rNR^{5f}C(O)OC_{1-4}$ alkyl, $(CH_2)_rOC(O)R^{5b}$, $(CH_2)_rC(=NR^{5f})NR^{5f}R^{5f}$, $(CH_2)_rS(O)_pR^{5b}$, $(CH_2)_rNHC(=NR^{5f})NR^{5f}R^{5f}$, $(CH_2)_rS(O)_2NR^{5f}R^{5f}$, $(CH_2)_rNR^{5f}S(O)_2R^{5b}$, and $(CH_2)_r$phenyl substituted with 0–3 $R^{5e}$;

$R^{5d}$, at each occurrence, is selected from methyl, $CF_3$, $C_{2-6}$ alkyl substituted with 0–2 $R^{5e}$, $C_{3-8}$ alkenyl substituted with 0–2 $R^{5e}$, $C_{3-8}$ alkynyl substituted with 0–2 $R^{5e}$, and a $C_{3-10}$ carbocyclic residue substituted with 0–3 $R^{5e}$;

$R^{5e}$, at each occurrence, is selected from $C_{1-6}$ alkyl, $C_{2-8}$ alkenyl, $C_{2-8}$ alkynyl, $C_{3-6}$ cycloalkyl, Cl, F, Br, I, CN, $NO_2$, $(CF_2)_rCF_3$, $(CH_2)_rOC_{1-5}$ alkyl, OH, SH, $(CH_2)_rSC_{1-5}$ alkyl, $(CH_2)_rNR^{5f}R^{5f}$, and $(CH_2)_r$phenyl;

$R^{5f}$, at each occurrence, is selected from H, $C_{1-6}$ alkyl, and $C_{3-6}$ cycloalkyl;

$R^{5g}$ is independently selected from $-C(O)R^{5b}$, $-C(O)OR^{5d}$, $-C(O)NR^{5f}R^{5f}$, $-CN$, and $(CH_2)_r$phenyl;

R, at each occurrence, is selected from H, $C_{1-6}$ alkyl substituted with $R^{5e}$, $C_{2-8}$ alkenyl, $C_{2-8}$ alkynyl, $(CH_2)_rC_{3-6}$ cycloalkyl, and $(CH_2)_r$phenyl substituted with $R^{5e}$;

$R^6$, at each occurrence, is selected from $C_{1-8}$ alkyl, $C_{2-8}$ alkenyl, $C_{2-8}$ alkynyl, $(CH_2)_rC_{3-6}$ cycloalkyl, Cl, Br, I, F, $NO_2$, CN, $(CR'R')_rNR^{6a}R^{6a}$, $(CR'R')_rOH$, $(CR'R')_rO(CR'R')_rR^{6d}$, $(CR'R')_rSH$, $(CR'R')_rC(O)H$, $(CR'R')_rS(CR'R')_rR^{6d}$, $(CR'R')_rSC(O)(CR'R')_rR^{6b}$, $(CR'R')_rC(O)OH$, $(CR'R')_rC(O)(CR'R')_rR^{6b}$, $(CR'R')_rNR^{6a}R^{6a}$, $(CR'R')_rC(O)NR^{6a}R^{6a}$, $(CR'R')_rNR^{6f}C(O)(CR'R')_rR^{6b}$, $(CR'R')_rC(O)O(CR'R')_rR^{6d}$, $(CR'R')_rOC(O)(CR'R')_rR^{6b}$, $(CR'R')_rOC(O)NR^{6a}(CR'R')_rR^{6d}$, $(CR'R')_rNR^{6a}C(O)NR^{6a}(CR'R')_rR^{6d}$, $(CR'R')_rNR^{6a}C(S)NR^{6a}(CR'R')_rR^{6d}$, $(CR'R')_rNR^{6f}C(O)O(CR'R')_rR^{6b}$, $(CR'R')_rC(=NR^{6f})NR^{6a}R^{6a}$, $(CR'R')_rNHC(=NR^{6f})NR^{6f}R^{6f}$, $(CR'R')_rS(O)_p(CR'R')_rR^{6b}$, $(CR'R')_rS(O)_2NR^{6a}R^{6a}$, $(CR'R')_rNR^{6f}S(O)_2NR^{6a}R^{6a}$, $(CR'R')_rNR^{6f}S(O)_2(CR'R')_rR^{6b}$, $C_{1-6}$ haloalkyl, $C_{2-8}$ alkenyl substituted with 0–3 R', $C_{2-8}$ alkynyl substituted with 0–3 R', $(CR'R')_r$phenyl substituted with 0–3 $R^{6e}$, and a $(CH_2)_r$-5–6 membered heterocyclic system containing 1–2 heteroatoms selected from N, O, and S, substituted with 0–2 $R^{6e}$;

alternatively, two $R^6$ on adjacent atoms on $R^1$ may join to form a cyclic acetal;

$R^{6a}$, at each occurrence, is selected from H, methyl substituted with 0–1 $R^{6g}$, $C_{2-6}$ alkyl substituted with 0–2 $R^{6e}$, $C_{3-8}$ alkenyl substituted with 0–2 $R^{6e}$, $C_{3-8}$ alkynyl substituted with 0–2 $R^{6e}$, a $(CH_2)_r$—$C_{3-10}$ carbocyclic residue substituted with 0–5 $R^{6e}$, and a $(CH_2)_r$-5–10 membered heterocyclic system containing 1–4 heteroatoms selected from N, O, and S, substituted with 0–2 $R^{6e}$;

$R^{6b}$, at each occurrence, is selected from H, $C_{1-6}$ alkyl substituted with 0–2 $R^{6e}$, $C_{3-8}$ alkenyl substituted with 0–2 $R^{6e}$, $C_{3-8}$ alkynyl substituted with 0–2 $R^{6e}$, a $(CH_2)_rC_{3-6}$ carbocyclic residue substituted with 0–3 $R^{6e}$, and a $(CH_2)_r$-5–6 membered heterocyclic system containing 1–4 heteroatoms selected from N, O, and S, substituted with 0–2 $R^{6e}$;

$R^{6d}$, at each occurrence, is selected from $C_{3-8}$ alkenyl substituted with 0–2 $R^{6e}$, $C_{3-8}$ alkynyl substituted with 0–2 $R^{6e}$, methyl, $CF_3$, $C_{2-6}$ alkyl substituted with 0–3 $R^{6e}$, $C_{2-4}$ haloalkyl, a $(CH_2)_r$—$C_{3-10}$ carbocyclic residue substituted with 0–3 $R^{6e}$, and a $(CH_2)_r$-5–6 membered heterocyclic system containing 1–4 heteroatoms selected from N, O, and S, substituted with 0–3 $R^{6e}$;

$R^{6e}$, at each occurrence, is selected from $C_{1-6}$ alkyl, $C_{2-8}$ alkenyl, $C_{2-8}$ alkynyl, $(CH_2)_rC_{3-6}$ cycloalkyl, Cl, F, Br, I, CN, $NO_2$, $(CF_2)_rCF_3$, $(CH_2)_rOC_{1-5}$ alkyl, OH, SH, $(CH_2)_rSC_{1-5}$ alkyl, $(CH_2)_rNR^{6f}R^{6f}$, and $(CH_2)_r$phenyl;

$R^{6f}$, at each occurrence, is selected from H, $C_{1-5}$ alkyl, and $C_{3-6}$ cycloalkyl, and phenyl;

$R^{6g}$ is independently selected from —$C(O)R^{6b}$, —$C(O)OR^{6d}$, —$C(O)NR^{6f}R^{6f}$, and $(CH_2)_r$phenyl;

$R^7$, at each occurrence, is selected from $C_{1-8}$ alkyl, $C_{2-8}$ alkenyl, $C_{2-8}$ alkynyl, $(CH_2)_rC_{3-6}$ cycloalkyl, Cl, Br, I, F, $NO_2$, CN, $(CR'R')_rNR^{7a}R^{7a}$, $(CR'R')_rOH$, $(CR'R')_rO(CR'R')_rR^{7d}$, $(CR'R')_rSH$, $(CR'R')_rC(O)H$, $(CR'R')_rS(CR'R')_rR^{7d}$, $(CR'R')_rC(O)OH$, $(CR'R')_rC(O)(CR'R')_rR^{7b}$, $(CR'R')_rC(O)NR^{7a}R^{7a}$, $(CR'R')_rNR^{7f}C(O)(CR'R')_r R^{7b}$, $(CR'R')_rC(O)O(CR'R')_rR^{7d}$, $(CR'R')_rOC(O)(CR'R')_rR^{7b}$, $(CR'R')_rOC(O)NR^{7a}(CR'R')_rR^{7a}$, $(CR'R')_rNR^{7a}C(O)NR^{7a}(CR'R')_rR^{7a}$, $(CR'R')_rNR^{7f}C(O)O(CR'R')_rR^{7d}$, $(CR'R')_rC(\!=\!NR^{7f})NR^{7a}R^{7a}$, $(CR'R')_rNHC(\!=\!NR^{7f})NR^{7f}R^{7f}$, $(CR'R')_rS(O)_p(CR'R')_r R^{7b}$, $(CR'R')_rS(O)_2NR^{7a}R^{7a}$, $(CR'R')_rNR^{7a}S(O)_2 NR^{7a}R^{7a}$, $(CR'R')_rNR^{7f}S(O)_2(CR'R')_rR^{7b}$, $C_{1-6}$ haloalkyl, $C_{2-8}$ alkenyl substituted with 0–3 R', $C_{2-8}$ alkynyl substituted with 0–3 R', $(CR'R')_rC_{3-10}$ carbocyclic residue and $(CR'R')_r$phenyl substituted with 0–3 $R^{7e}$;

alternatively, two $R^7$ on adjacent atoms on $R^2$ may join to form a cyclic acetal;

$R^{7a}$, at each occurrence, is independently selected from H, methyl substituted with 0–1 $R^{7g}$, $C_{2-6}$ alkyl substituted with 0–2 $R^{7e}$, $C_{3-8}$ alkenyl substituted with 0–2 $R^{7e}$, $C_{3-8}$ alkynyl substituted with 0–2 $R^{7e}$, a $(CH_2)_r$—$C_{3-10}$ carbocyclic residue substituted with 0–5 $R^{7e}$, and a $(CH_2)_r$-5–10 membered heterocyclic system containing 1–4 heteroatoms selected from N, O, and S, substituted with 0–2 $R^{7e}$;

$R^{7b}$, at each occurrence, is selected from $C_{1-6}$ alkyl substituted with 0–2 $R^{7e}$, $C_{3-8}$ alkenyl substituted with 0–2 $R^{7e}$, $C_{3-8}$ alkynyl substituted with 0–2 $R^{7e}$, a $(CH_2)_rC_{3-6}$ carbocyclic residue substituted with 0–3 $R^{7e}$, and a $(CH_2)_r$-5–6 membered heterocyclic system containing 1–4 heteroatoms selected from N, O, and S, substituted with 0–2 $R^{7e}$;

$R^{7d}$, at each occurrence, is selected from $C_{3-8}$ alkenyl substituted with 0–2 $R^{7e}$, $C_{3-8}$ alkynyl substituted with 0–2 $R^{7e}$, methyl, $CF_3$, $C_{2-4}$ haloalkyl, $C_{2-6}$ alkyl substituted with 0–3 $R^{7e}$, a $(CH_2)_rC_{3-10}$ carbocyclic residue substituted with 0–3 $R^{7e}$, and a $(CH_2)_r$-5–6 membered heterocyclic system containing 1–4 heteroatoms selected from N, O, and S, substituted with 0–3 $R^{7e}$;

$R^{7e}$, at each occurrence, is selected from $C_{1-6}$ alkyl, $C_{2-8}$ alkenyl, $C_{2-8}$ alkynyl, $(CH_2)_rC_{3-6}$ cycloalkyl, Cl, F, Br, I, CN, $NO_2$, $(CF_2)_rCF_3$, $(CH_2)_rOC_{1-5}$ alkyl, OH, SH, $C(O)OC_{1-5}$ alkyl, $(CH_2)_rSC_{1-5}$ alkyl, $(CH_2)_rNR^{7f}R^{7f}$, and $(CH_2)_r$phenyl;

$R^{7f}$, at each occurrence, is selected from H, $C_{1-5}$ alkyl, and $C_{3-6}$ cycloalkyl, and phenyl;

$R^{7g}$ is independently selected from —$C(O)R^{7b}$, —$C(O)OR^{7d}$, —$C(O)NR^{7f}R^{7f}$, and $(CH_2)_r$phenyl;

R', at each occurrence, is selected from H, $C_{1-6}$ alkyl substituted with $R^{6e}$, $C_{2-8}$ alkenyl, $C_{2-8}$ alkynyl, $(CH_2)_r C_{3-6}$ cycloalkyl, and $(CH_2)_r$phenyl substituted with $R^{6e}$;

$R^9$ is selected from H, $C_{1-4}$ alkyl, $C_{3-4}$ cycloalkyl, —C(O) H, and —C(O)—$C_{1-4}$alkyl;

$R^{10}$ is independently selected from H, and $C_{1-4}$alkyl substituted with 0–1 $R^{10b}$, alternatively, two $R^{10}$ form =O;

$R^{10b}$, at each occurrence, is independently selected from —OH, —SH, —$NR^{10c}R^{10c}$, —$C(O)NR^{10c}R^{10C}$, and —$NHC(O)R^{10c}$;

$R^{10c}$ is selected from H, $C_{1-4}$ alkyl and $C_{3-6}$ cycloalkyl;

$R^{11}$ is selected from H, $C_{1-4}$ alkyl, $(CHR)_qOH$, $(CHR)_q SH$, $(CHR)_qOR^{11d}$, $(CHR)_qS(O)_pR^{11d}$, $(CHR)_rC(O) R^{11b}$, $(CHR)_rNR^{11a}R^{11a}$, $(CHR)_rC(O)NR^{11a}R^{11a}$, $(CHR)_rC(O)R^{11a}OR^{11d}$, $(CHR)_qNR^{11a}C(O)R^{11b}$, $(CHR)_qNR^{11a}C(O)OR^{11d}$, $(CHR)_qOC(O)NR^{11a}R^{11a}$, $(CHR)_rC(O)OR^{11d}$, a $(CHR)_r$—$C_{3-6}$ carbocyclic residue substituted with 0–5 $R^{11e}$, and a $(CHR)_r$-5–10 membered heterocyclic system containing 1–4 heteroatoms selected from N, O, and S, substituted with 0–3 $R^{11e}$;

$R^{11a}$, at each occurrence, is independently selected from H, $C_{1-4}$ alkyl, $C_{3-4}$ alkenyl, $C_{3-4}$ alkynyl, $(CH_2)_rC_{3-6}$ cycloalkyl, a $(CH_2)_rC_{3-6}$ carbocyclic residue substituted with 0–5 $R^{11e}$, and a $(CH_2)_r$-5–6 membered heterocyclic system containing 1–4 heteroatoms selected from N, O, and S, substituted with 0–3 $R^{11e}$;

$R^{11b}$, at each occurrence, is independently selected from $C_{1-4}$ alkyl, $C_{2-4}$ alkenyl, $C_{2-4}$ alkynyl, a $(CH_2)_r$—$C_{3-6}$ carbocyclic residue substituted with 0–2 $R^{11e}$, and a $(CH_2)_r$-5–6 membered heterocyclic system containing 1–4 heteroatoms selected from N, O, and S, substituted with 0–3 $R^{11e}$;

$R^{11d}$, at each occurrence, is independently selected from H, methyl, —$CF_3$, $C_{2-4}$ alkyl, $C_{3-6}$ alkenyl, $C_{3-6}$ alkynyl, a $C_{3-6}$ carbocyclic residue substituted with 0–3 $R^{11e}$, and a $(CH_2)_r$-5–6 membered heterocyclic system containing 1–4 heteroatoms selected from N, O, and S, substituted with 0–3 $R^{11e}$;

$R^{11e}$, at each occurrence, is selected from $C_{1-6}$ alkyl, $C_{2-8}$ alkenyl, $C_{2-8}$ alkynyl, $C_{3-6}$ cycloalkyl, Cl, F, Br, I, CN, $NO_2$, $(CF_2)_rCF_3$, $(CH_2)_rOC_{1-5}$ alkyl, OH, —O—$C_{1-6}$ alkyl, SH, $(CH_2)_rSC_{1-5}$ alkyl, $(CH_2)_rNR^{11f}R^{11f}$, and $(CH_2)_r$phenyl;

$R^{11f}$, at each occurrence, is selected from H, $C_{1-6}$ alkyl, and $C_{3-6}$ cycloalkyl;

$R^{12}$ is selected from H, $C_{1-4}$ alkyl, $(CHR)_qOH$, $(CHR)_q SH$, $(CHR)_qOR^{12d}$, $(CHR)_qS(O)_pR^{12d}$, $(CHR)_rC(O) R^{12b}$, $(CHR)_rNR^{12a}R^{12a}$, $(CHR)_rC(O)NR^{12a}R^{12a}$, $(CHR)_rC(O)NR^{12a}OR^{12d}$, $(CHR)_qNR^{12a}C(O)R^{12b}$, $(CHR)_qNR^{12a}C(O)OR^{12d}$, $(CHR)_qOC(O)NR^{12a}R^{12a}$, $(CHR)_rC(O)OR^{12d}$, a $(CHR)_r$—$C_{3-6}$ carbocyclic residue substituted with 0–5 $R^{12e}$, and a $(CHR)_r$-5–10 membered heterocyclic system containing 1–4 heteroatoms selected from N, O, and S, substituted with 0–3 $R^{12e}$;

$R^{12a}$, at each occurrence, is independently selected from H, $C_{1-4}$ alkyl, $C_{3-4}$ alkenyl, $C_{3-4}$ alkynyl, $(CH_2)_rC_{3-6}$ cycloalkyl, a $(CH_2)_r$—$C_{3-6}$ carbocyclic residue substituted with 0–5 $R^{12e}$, and a $(CH_2)_r$-5–6 membered heterocyclic system containing 1–4 heteroatoms selected from N, O, and S, substituted with 0–3 $R^{12e}$;

$R^{12b}$, at each occurrence, is independently selected from $C_{1-4}$ alkyl, $C_{2-4}$ alkenyl, $C_{2-4}$ alkynyl, a $(CH_2)_rC_{3-6}$ carbocyclic residue substituted with 0–2 $R^{12e}$, and a $(CH_2)_r$-5–6 membered heterocyclic system containing 1–4 heteroatoms selected from N, O, and S, substituted with 0–3 $R^{12e}$;

$R^{12d}$, at each occurrence, is independently selected from H, methyl, —$CF_3$, $C_{2-4}$ alkyl, $C_{3-6}$ alkenyl, $C_{3-6}$ alkynyl, a $C_{3-6}$ carbocyclic residue substituted with 0–3 $R^{12e}$, and a $(CH_2)_r$-5–6 membered heterocyclic system containing 1–4 heteroatoms selected from N, O, and S, substituted with 0–3 $R^{12e}$;

$R^{12e}$, at each occurrence, is selected from $C_{1-6}$ alkyl, $C_{2-8}$ alkenyl, $C_{2-8}$ alkynyl, $C_{3-6}$ cycloalkyl, Cl, F, Br, I, CN, $NO_2$, $(CF_2)_rCF_3$, $(CH_2)_rOC_{1-5}$ alkyl, OH, —O—$C_{1-6}$ alkyl, SH, $(CH_2)_rSC_{1-5}$ alkyl, $(CH_2)_rNR^{12f}R^{12f}$, and $(CH_2)_r$phenyl;

$R^{12f}$, at each occurrence, is selected from H, $C_{1-6}$ alkyl, and $C_{3-6}$ cycloalkyl;

$R^{13}$, at each occurrence, is independently selected from H, and $C_{1-4}$alkyl substituted with 0–1 $R^{13b}$, —OH, —$NH_2$, F, Cl, Br, I, —$OR^{13a}$, —$N(R^{13a})_2$, and $C_{1-4}$ alkyl substituted with 0–3 $R^{13b}$;

$R^{13a}$ is selected from H, $C_{1-4}$ alkyl and $C_{3-6}$ cycloalkyl;

$R^{13b}$, at each occurrence, is independently selected from —OH, —SH, —$NR^{13c}R^{13c}$, —$C(O)NR^{13c}R^{13c}$, and —$NHC(O)R^{13c}$;

$R^{13c}$ is selected from H, $C_{1-4}$ alkyl and $C_{3-6}$ cycloalkyl;

l is selected from 1, 2 and 3;

n is 1;

m is selected from 0 and 1;

p, at each occurrence, is independently selected from 0, 1, and 2;

q, at each occurrence, is independently selected from 1, 2, 3, and 4;

r, at each occurrence, is independently selected from 0, 1, 2, 3, and 4;

t, at each occurrence, is independently selected from 2, 3, and 4;

s is selected from 0 and 1.

2. A compound of claim 1, wherein the compound is of formula (I):

or a stereoisomer or a pharmaceutically acceptable salt thereof, wherein:

ring B is a cyclohexyl group; ring B being substituted with 0–2 $R^5$;

X is selected from O or S;

Z is —$NR^9$—; wherein neither Z nor $R^{13}$ are connected to a carbon atom labeled (b);

bond (a) is a single bond;

E is selected from —$S(O)_pCHR^e$—, —$CHR^eNR^e$—, —$C(O)$—$NR^e$—, —$NR^eC(O)NR^e$—, —$SO_2$—$NR^e$—, and —$NR^eSO_2NR^e$—;

$R^e$ is independently selected from H and $C_{1-3}$ alkyl;

$R^1$ is selected from a $C_{6-10}$ aryl group substituted with 0–5 $R^6$;

$R^2$ is selected from a 5–10 membered heteroaryl system containing 1–4 heteroatoms selected from N, O, and S, substituted with 0–3 $R^7$;

$R^5$, at each occurrence, is independently selected from H, =O, $C_{1-6}$ alkyl, $C_{2-8}$ alkenyl, $C_{2-8}$ alkynyl, $(CRR)_rOH$, $(CRR)_rSH$, $(CRR)_rOR^{5d}$, $(CHR)_rSR^{5d}$, $(CRR)_rNR^{5a}R^{5a}$, $(CRR)_rC(O)OH$, $(CRR)_rC(O)R^{5b}$, $(CRR)_rC(O)NR^{5a}R^{5a}$, $(CRR)_rNR^{5a}C(O)R^{5b}$, $(CRR)_rOC(O)NR^{5a}R^{5a}$, $(CRR)_rNR^{5a}C(O)OR^{5d}$, $(CRR)_rNR^{5a}C(O)NR^{5a}R^{5a}$, $(CRR)_rNR^{5a}C(O)H$, $(CRR)_rC(O)OR^{5d}$, $(CRR)_rOC(O)R^{5b}$, $(CRR)_rS(O)_pR^{5b}$, $(CRR)_rS(O)_2NR^{5a}R^{5a}$, $(CRR)_rNR^{5a}S(O)_2R^{5b}$, $(CRR)_rNR^{5a}S(O)_2NR^{5a}R^{5a}$, $C_{1-6}$ haloalkyl, a $(CRR)_r$—$C_{3-10}$ carbocyclic residue substituted with 0–3 $R^{5c}$, and a $(CRR)_r$-5–10 membered heterocyclic system containing 1–4 heteroatoms selected from N, O, and S, substituted with 0–2 $R^{5c}$;

$R^{5a}$, at each occurrence, is independently selected from H, methyl substituted with 0–1 $R^{5g}$, $C_{2-6}$ alkyl substituted with 0–2 $R^{5e}$, $C_{3-8}$ alkenyl substituted with 0–2 $R^{5e}$, $C_{3-8}$ alkynyl substituted with 0–2 $R^{5e}$, a $(CH_2)_r$—$C_{3-10}$ carbocyclic residue substituted with 0–5 $R^{5e}$, and a $(CH_2)_r$-5–10 membered heterocyclic system containing 1–4 heteroatoms selected from N, O, and S, substituted with 0–3 $R^{5e}$;

$R^{5b}$, at each occurrence, is selected from $C_{1-6}$ alkyl substituted with 0–3 $R^{5e}$, $C_{3-8}$ alkenyl substituted with 0–2 $R^{5e}$, $C_{3-8}$ alkynyl substituted with 0–2 $R^{5e}$, a $(CH_2)_rC_{3-6}$ carbocyclic residue substituted with 0–2 $R^{5e}$, and a $(CH_2)_r$-5–6 membered heterocyclic system containing 1–4 heteroatoms selected from N, O, and S, substituted with 0–3 $R^{5e}$;

$R^{5c}$, at each occurrence, is selected from $C_{1-6}$ alkyl, $C_{2-8}$ alkenyl, $C_{2-8}$ alkynyl, $(CH_2)_rC_{3-6}$ cycloalkyl, Cl, Br, I, F, $(CF_2)_rCF_3$, $NO_2$, CN, $(CH_2)_rNR^{5f}R^{5f}$, $(CH_2)_rOH$, $(CH_2)_rOC_{1-4}$ alkyl, $(CH_2)_rSC_{1-4}$ alkyl, $(CH_2)_rC(O)OH$, $(CH_2)_r(CO)R^{5b}$, $(CH_2)_rC(O)NR^{5f}R^{5f}$, $(CH_2)_rOC(O)NR^{5f}R^{5f}$, $(CH_2)_rNR^{5f}C(O)R^{5b}$, $(CH_2)_rC(O)OC_{1-4}$ alkyl, $(CH_2)_rNR^{5f}C(O)OC_{1-4}$ alkyl, $(CH_2)_rOC(O)R^{5b}$, $(CH_2)_rC(=NR^{5f})NR^{5f}R^{5f}$, $(CH_2)_rS(O)_pR^{5b}$, $(CH_2)_rNHC(=NR^{5f})NR^{5f}R^{5f}$, $(CH_2)_rS(O)_2NR^{5f}R^{5f}$, $(CH_2)_rNR^{5f}S(O)_2R^{5b}$, and $(CH_2)_r$phenyl substituted with 0–3 $R^{5e}$;

$R^{5d}$, at each occurrence, is selected from methyl, $CF_3$, $C_{2-6}$ alkyl substituted with 0–2 $R^{5e}$, $C_{3-8}$ alkenyl substituted with 0–2 $R^{5e}$, $C_{3-8}$ alkynyl substituted with 0–2 $R^{5e}$, and a $C_{3-10}$ carbocyclic residue substituted with 0–3 $R^{5e}$;

$R^{5e}$, at each occurrence, is selected from $C_{1-6}$ alkyl, $C_{2-8}$ alkenyl, $C_{2-8}$ alkynyl, $C_{3-6}$ cycloalkyl, Cl, F, Br, I, CN, $NO_2$, $(CF_2)_rCF_3$, $(CH_2)_rOC_{1-5}$ alkyl, OH, SH, $(CH_2)_rSC_{1-5}$ alkyl, $(CH_2)_rNR^{5f}R^{5f}$, and $(CH_2)_r$phenyl;

$R^{5f}$, at each occurrence, is selected from H, $C_{1-6}$ alkyl, and $C_{3-6}$ cycloalkyl;

$R^{5g}$ is independently selected from —$C(O)R^{5b}$, —$C(O)OR^{5d}$, —$C(O)NR^{5f}R^{5f}$, and $(CH_2)_r$phenyl;

R, at each occurrence, is selected from H, $C_{1-6}$ alkyl substituted with $R^{5e}$, $C_{2-8}$ alkenyl, $C_{2-8}$ alkynyl, $(CH_2)_rC_{3-6}$ cycloalkyl, and $(CH_2)_r$phenyl substituted with $R^{5e}$;

$R^6$, at each occurrence, is selected from $C_{1-8}$ alkyl, $C_{2-8}$ alkenyl, $C_{2-8}$ alkynyl, $(CH_2)_rC_{3-6}$ cycloalkyl, Cl, Br, I, F, $NO_2$, CN, $(CR'R')_rNR^{6a}R^{6a}$, $(CR'R')_rOH$, $(CR'R')_rO(CR'R')_rR^{6d}$, $(CR'R')_rSH$, $(CR'R')_rC(O)H$, $(CR'R')_rS(CR'R')_rR^{6d}$, $(CR'R')_rSC(O)(CR'R')_rR^{6b}$, $(CR'R')_rC(O)OH$, $(CR'R')_rC(O)(CR'R')_rR^{6b}$, $(CR'R')_rNR^{6a}R^{6a}$, $(CR'R')_rC(O)NR^{6a}R^{6a}$, $(CR'R')_rNR^{6f}C(O)(CR'R')_rR^{6b}$, $(CR'R')_rC(O)O(CR'R')_rR^{6d}$, $(CR'R')_rOC(O)(CR'R')_r$ $R^{6b}$, $(CR'R')_rOC(O)NR^{6a}(CR'R')_rR^{6a}$, $(CR'R')_rNR^{6a}C(O)NR^{6a}(CR'R')_rR^{6d}$, $(CR'R')_rNR^{6a}C(S)NR^{6a}(CR'R')_rR^{6d}$, $(CR'R')_rNR^{6a}C(O)O(CR'R')_rR^{6b}$, $(CR'R')_rC(=NR^{6f})NR^{6a}R^{6a}$, $(CR'R')_rNHC(=NR^{6f})NR^{6f}R^{6f}$, $(CR'R')_rS(O)_p(CR'R')_rR^{6b}$, $(CR'R')_rS(O)_2NR^{6a}R^{6a}$, $(CR'R')_rNR^{6f}S(O)_2NR^{6a}R^{6a}$, $(CR'R')_rNR^{6f}S(O)_2(CR'R')_rR^{6b}$, $C_{1-6}$ haloalkyl, $C_{2-8}$ alkenyl substituted with 0–3 R', $C_{2-8}$ alkynyl substituted with 0–3 R', $(CR'R')_r$phenyl substituted with 0–3 $R^{6e}$, and a $(CH_2)_r$-5–6 membered heterocyclic system containing 1–2 heteroatoms selected from N, O, and S, substituted with 0–2 $R^{6e}$;

alternatively, two $R^6$ on adjacent atoms on $R^1$ may join to form a cyclic acetal;

$R^{6a}$, at each occurrence, is selected from H, methyl substituted with 0–1 $R^{6g}$, $C_{2-6}$ alkyl substituted with 0–2 $R^{6e}$, $C_{3-8}$ alkenyl substituted with 0–2 $R^{6e}$, $C_{3-8}$ alkynyl substituted with 0–2 $R^{6e}$, a $(CH_2)_rC_{3-10}$ carbocyclic residue substituted with 0–5 $R^{6e}$, and a $(CH_2)_r$-5–10 membered heterocyclic system containing 1–4 heteroatoms selected from N, O, and S, substituted with 0–2 $R^{6e}$;

$R^{6b}$, at each occurrence, is selected from H, $C_{1-6}$ alkyl substituted with 0–2 $R^{6e}$, $C_{3-8}$ alkenyl substituted with 0–2 $R^{6e}$, $C_{3-8}$ alkynyl substituted with 0–2 $R^{6e}$, a $(CH_2)_rC_{3-6}$ carbocyclic residue substituted with 0–3 $R^{6e}$, and a $(CH_2)_r$-5–6 membered heterocyclic system containing 1–4 heteroatoms selected from N, O, and S, substituted with 0–2 $R^{6e}$;

$R^{6d}$, at each occurrence, is selected from $C_{3-8}$ alkenyl substituted with 0–2 $R^{6e}$, $C_{3-8}$ alkynyl substituted with 0–2 $R^{6e}$, methyl, $CF_3$, $C_{2-6}$ alkyl substituted with 0–3 $R^{6e}$, $C_{2-4}$ haloalkyl, a $(CH_2)_r$—$C_{3-10}$ carbocyclic residue substituted with 0–3 $R^{6e}$, and a $(CH_2)_r$-5–6 membered heterocyclic system containing 1–4 heteroatoms selected from N, O, and S, substituted with 0–3 $R^{6e}$;

$R^{6e}$, at each occurrence, is selected from $C_{1-6}$ alkyl, $C_{2-8}$ alkenyl, $C_{2-8}$ alkynyl, $(CH_2)_rC_{3-6}$ cycloalkyl, Cl, F, Br, I, CN, $NO_2$, $(CF_2)_rCF_3$, $(CH_2)_rOC_{1-5}$ alkyl, OH, SH, $(CH_2)_rSC_{1-5}$ alkyl, $(CH_2)_rNR^{6f}R^{6f}$, and $(CH_2)_r$phenyl;

$R^{6f}$, at each occurrence, is selected from H, $C_{1-5}$ alkyl, and $C_{3-6}$ cycloalkyl, and phenyl;

$R^{6g}$ is independently selected from —$C(O)R^{6b}$, —$C(O)OR^{6d}$, —$C(O)NR^{6f}R^{6f}$, and $(CH_2)_r$phenyl;

$R^7$, at each occurrence, is selected from $C_{1-8}$ alkyl, $C_{2-8}$ alkenyl, $C_{2-8}$ alkynyl, $(CH_2)_rC_{3-6}$ cycloalkyl, Cl, Br, I, F, $NO_2$, CN, $(CR'R')_rNR^{7a}R^{7a}$, $(CR'R')_rOH$, $(CR'R')_rO(CR'R')_rR^{7d}$, $(CR'R')_rSH$, $(CR'R')_rC(O)H$, $(CR'R')_rS(CR'R')_rR^{7d}$, $(CR'R')_rC(O)OH$, $(CR'R')_rC(O)(CR'R')_rR^{7b}$, $(CR'R')_rC(O)NR^{7a}R^{7a}$, $(CR'R')_rNR^{7e}C(O)(CR'R')_rR^{7b}$, $(CR'R')_rC(O)O(CR'R')_rR^{7d}$, $(CR'R')_rOC(O)(CR'R')_rR^{7b}$, $(CR'R')_rOC(O)NR^{7a}(CR'R')_rR^{7a}$, $(CR'R')_rNR^{7a}C(O)NR^{7a}(CR'R')_rR^{7a}$, $(CR'R')_rNR^{7f}C(O)O(CR'R')_rR^{7d}$, $(CR'R')_rC(=NR^{7f})NR^{7a}R^{7a}$, $(CR'R')_rNHC(=NR^{7f})NR^{7f}R^{7f}$, $(CR'R')_rS(O)_p(CR'R')_rR^{7b}$, $(CR'R')_rS(O)_2NR^{7a}R^{7a}$, $(CR'R')_rNR^{7a}S(O)_2(CR'R')_rR^{7a}$, $(CR'R')_rNR^{7f}S(O)_2(CR'R')_rR^{7b}$, $C_{1-6}$ haloalkyl, $C_{2-8}$ alkenyl substituted with 0–3 R', $C_{2-8}$ alkynyl substituted with 0–3 R', and $(CR'R')_r$phenyl substituted with 0–3 $R^{7e}$;

alternatively, two $R^7$ on adjacent atoms on $R^2$ may join to form a cyclic acetal;

$R^{7e}$, at each occurrence, is independently selected from H, methyl substituted with 0–1 $R^{7g}$, $C_{2-6}$ alkyl substituted with 0–2 $R^{7e}$, $C_{3-8}$ alkenyl substituted with 0–2 $R^{7e}$, $C_{3-8}$ alkynyl substituted with 0–2 $R^{7e}$, a $(CH_2)_r$—$C_{3-10}$ carbocyclic residue substituted with 0–5 $R^{7e}$, and a $(CH_2)_r$-5–10 membered heterocyclic system containing 1–4 heteroatoms selected from N, O, and S, substituted with 0–2 $R^{7e}$;

$R^{7b}$, at each occurrence, is selected from $C_{1-6}$ alkyl substituted with 0–2 $R^{7e}$, $C_{3-8}$ alkenyl substituted with 0–2 $R^{7e}$, $C_{3-8}$ alkynyl substituted with 0–2 $R^{7e}$, a $(CH_2)_rC_{3-6}$ carbocyclic residue substituted with 0–3 $R^{7e}$, and a $(CH_2)_r$-5–6 membered heterocyclic system containing 1–4 heteroatoms selected from N, O, and S, substituted with 0–2 $R^{7e}$;

$R^{7d}$, at each occurrence, is selected from $C_{3-8}$ alkenyl substituted with 0–2 $R^{7e}$, $C_{3-8}$ alkynyl substituted with 0–2 $R^{7e}$, methyl, $CF_3$, $C_{2-4}$ haloalkyl, $C_{2-6}$ alkyl substituted with 0–3 $R^{7e}$, a $(CH_2)_r$—$C_{3-10}$ carbocyclic residue substituted with 0–3 $R^{7e}$, and a $(CH_2)_r$-5–6 membered heterocyclic system containing 1–4 heteroatoms selected from N, O, and S, substituted with 0–3 $R^{7e}$;

$R^{7e}$, at each occurrence, is selected from $C_{1-6}$ alkyl, $C_{2-8}$ alkenyl, $C_{2-8}$ alkynyl, $(CH_2)_rC_{3-6}$ cycloalkyl, Cl, F, Br, I, ON, $NO_2$, $(CF_2)_rCF_3$, $(CH_2)_rOC_{1-5}$ alkyl, OH, SH, $C(O)OC_{1-5}$ alkyl, $(CH_2)_rSC_{1-5}$ alkyl, $(CH_2)_rNR^{7f}R^{7f}$, and $(CH_2)_r$phenyl;

$R^{7f}$, at each occurrence, is selected from H, $C_{1-5}$ alkyl, and $C_{3-6}$ cycloalkyl, and phenyl;

$R^{7g}$ is independently selected from —$C(O)R^{7b}$, —$C(O)OR^{7d}$, —$C(O)NR^{7f}R^{7f}$, and $(CH_2)_r$phenyl;

R', at each occurrence, is selected from H, $C_{1-6}$ alkyl substituted with $R^{6e}$, $C_{2-8}$ alkenyl, $C_{2-8}$ alkynyl, $(CH_2)_rC_{3-6}$ cycloalkyl, and $(CH_2)_r$phenyl substituted with $R^{6e}$;

$R^9$ is selected from H, $C_{1-4}$ alkyl, $C_{3-4}$ cycloalkyl, —$C(O)$H, and —$C(O)$—$C_{1-4}$alkyl;

$R^{10}$ is independently selected from H, and $C_{1-4}$alkyl substituted with 0–1 $R^{10b}$;

$R^{10b}$, at each occurrence, is independently selected from —OH, —SH, —$NR^{10c}R^{10c}$, —$C(O)NR^{10c}R^{10c}$, and —$NHC(O)R^{10c}$;

$R^{10c}$ is selected from H, $C_{1-4}$ alkyl and $C_{3-6}$ cycloalkyl;

$R^{11}$ is selected from H, $C_{2-4}$ alkyl, $(CHR)_qOH$, $(CHR)_qSH$, $(CHR)_qOR^{11d}$, $(CHR)_qS(O)_pR^{11d}$, $(CHR)_rC(O)R^{11b}$, $(CHR)_rNR^{11a}R^{11a}$, $(CHR)_rC(O)NR^{11a}R^{11a}$, $(CHR)_rC(O)NR^{11a}OR^{11d}$, $(CHR)_qNR^{11a}C(O)R^{11b}$, $(CHR)_qNR^{11a}C(O)OR^{11d}$, $(CHR)_qOC(O)NR^{11a}R^{11a}$, $(CHR)_rC(O)OR^{11d}$, a $(CHR)_r$—$C_{3-6}$ carbocyclic residue substituted with 0–5 $R^{11e}$, and a $(CHR)_r$-5–10 membered heterocyclic system containing 1–4 heteroatoms selected from N, O, and S, substituted with 0–3 $R^{11e}$;

$R^{11a}$, at each occurrence, is independently selected from H, $C_{2-4}$ alkyl, $C_{3-4}$ alkenyl, $C_{3-4}$ alkynyl, $(CH_2)_rC_{3-6}$ cycloalkyl, a $(CH_2)_r$—$C_{3-6}$ carbocyclic residue substituted with 0–5 $R^{11e}$, and a $(CH_2)_r$-5–6 membered heterocyclic system containing 1–4 heteroatoms selected from N, O, and S, substituted with 0–3 $R^{11e}$;

$R^{11b}$, at each occurrence, is independently selected from 01–4 alkyl, $C_{2-4}$ alkenyl, $C_{2-4}$ alkynyl, a $(CH_2)_r$—$C_{3-6}$ carbocyclic residue substituted with 0–2 $R^{11e}$, and a $(CH_2)_r$-5–6 membered heterocyclic system containing 1–4 heteroatoms selected from N, O, and S, substituted with 0–3 $R^{11e}$;

$R^{11d}$, at each occurrence, is independently selected from H, methyl, —$CF_3$m $C_{2-4}$ alkyl, $C_{3-6}$ alkenyl, $C_{3-6}$ alkynyl, a $C_{3-6}$ carbocyclic residue substituted with 0–3 $R^{11e}$, and a $(CH_2)_r$-5–6 membered heterocyclic system containing 1–4 heteroatoms selected from N, O, and S, substituted with 0–3 $R^{11e}$;

$R^{11e}$, at each occurrence, is selected from $C_{1-6}$ alkyl, $C_{2-8}$ alkenyl, $C_{2-8}$ alkynyl, $C_{3-6}$ cycloalkyl, Cl, F, Br, I, ON, $NO_2$, $(CF_2)_rCF_3$, $(CH_2)_rOC_{1-5}$ alkyl, OH, —O—$C_{1-6}$ alkyl, SH, $(CH_2)_rSC_{1-5}$ alkyl, $(CH_2)_rNR^{11f}R^{11f}$, and $(CH_2)_r$phenyl;

$R^{11f}$, at each occurrence, is selected from H, $C_{1-6}$ alkyl, and $C_{3-6}$ cycloalkyl;

$R^{12}$ is selected from H, $C_{1-4}$ alkyl, $(CHR)_qOH$, $(CHR)_qSH$, $(CHR)_qOR^{12d}$, $(CHR)_qS(O)_pR^{12d}$, $(CHR)_rC(O)R^{12b}$, $(CHR)_rNR^{12a}R^{12a}$, $(CHR)_rC(O)NR^{12a}R^{12a}$, $(CHR)_rC(O)NR^{12a}OR^{12d}$, $(CHR)_qNR^{12a}C(O)R^{12b}$, $(CHR)_qNH^{12a}C(O)OR^{12d}$, $(CHR)_qOC(O)NR^{12a}R^{12a}$, $(CHR)_rC(O)OR^{12d}$, a $(CHR)_r$—$C_{3-6}$ carbocyclic residue substituted with 0–5 $R^{12e}$, and a $(CHR)_r$-5–10 membered heterocyclic system containing 1–4 heteroatoms selected from N, O, and S, substituted with 0–3 $R^{12e}$;

$R^{12a}$, at each occurrence, is independently selected from H, $C_{1-4}$ alkyl, $C_{3-4}$ alkenyl, $C_{3-4}$ alkynyl, $(CH_2)_rC_{3-6}$ cycloalkyl, a $(CH_2)_r$–$C_{3-6}$ carbocyclic residue substituted with 0–5 $R^{12e}$, and a $(CH_2)_r$-5–6 membered heterocyclic system containing 1–4 heteroatoms selected from N, O, and S, substituted with 0–3 $R^{12e}$;

$R^{12b}$, at each occurrence, is selected from $C_{1-4}$ alkyl, $C_{2-4}$ alkenyl, $C_{2-4}$ alkynyl, a $(CH_2)_r$—$C_{3-6}$ carbocyclic residue substituted with 0–2 $R^{12e}$, and a $(CH_2)_r$-5–6 membered heterocyclic system containing 1–4 heteroatoms selected from N, O, and S, substituted with 0–3 $R^{12e}$;

$R^{12d}$, at each occurrence, is independently selected from H, methyl, —$CF_3$, $C_{2-4}$ alkyl, $C_{3-6}$ alkenyl, $C_{3-6}$ alkynyl, a $C_{3-6}$ carbocyclic residue substituted with 0–3 $R^{12e}$, and a $(CH_2)_r$-5–6 membered heterocyclic system containing 1–4 heteroatoms selected from N, O, and S, substituted with 0–3 $R^{12e}$;

$R^{12e}$, at each occurrence, is selected from $C_{1-6}$ alkyl, $C_{2-8}$ alkenyl, $C_{2-8}$ alkynyl, $C_{3-6}$ cycloalkyl, Cl, F, Br, I, CN, $NO_2$, $(CF_2)_rCF_3$, $(CH_2)_rOC_{1-5}$ alkyl, OH, —O—$C_{1-6}$ alkyl, SH, $(CH_2)_rSC_{1-5}$ alkyl, $(CH_2)_rNR^{12f}R^{12f}$, and $(CH_2)_r$phenyl;

$R^{12f}$, at each occurrence, is selected from H, $C_{1-6}$ alkyl, and $C_{3-6}$ cycloalkyl;

$R^{13}$, at each occurrence, is independently selected from H, and $C_{1-4}$alkyl substituted with 0–1 $R^{13b}$, —OH, —$NH_2$, F, Cl, Br, I, —$OR^{13a}$, —$N(R^{13a})_2$, and $C_{1-4}$ alkyl substituted with 0–3 $R^{13b}$;

$R^{13a}$ is selected from H, $C_{1-4}$ alkyl and $C_{3-6}$ cycloalkyl;

$R^{13b}$, at each occurrence, is independently selected from —OH, —SH, —$NR^{13c}R^{13c}$, —$C(O)NR^{13c}R^{13c}$, and —$NHC(O)R^{13c}$;

$R^{13c}$ is selected from H, $C_{1-4}$ alkyl and $C_{3-6}$ cycloalkyl;

l is selected from 1, 2 and 3;

n is 1;

m is selected from 0 and 1;

p, at each occurrence, is independently selected from 0, 1, and 2;

q, at each occurrence, is independently selected from 1, 2, 3, and 4;

r, at each occurrence, is independently selected from 0, 1, 2, 3, and 4;

t, at each occurrence, is independently selected from 2, 3, and 4;

s is selected from 0 and 1.

3. The compound of claim 2, wherein:

m is 0.

4. The compound of claim 3, wherein:

ring B is

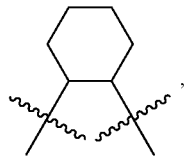

ring B being optionally substituted with 0–1 $R^5$; and $R^{11}$ and $R^{12}$ are H.

5. The compounds of claim 4, wherein:

$R^5$, at each occurrence, is independently selected from H, $C_{1-6}$ alkyl, $C_{2-8}$ alkenyl, $C_{2-8}$ alkynyl, $(CRR)_rOH$, $(CRR)_rSH$, $(CRR)_rOR^{5d}$, $(CRR)_rSR^{5d}$, $(CRR)_rNR^{5a}R^{5a}$, $(CRR)_rC(O)OH$, $(CRR)_rC(O)R^{5b}$, $(CRR)_rC(O)NR^{5a}R^{5a}$, $(CRR)_rNR^{5a}C(O)R^{5b}$, $(CRR)_rNR^{5a}C(O)OR^{5d}$, $(CRR)_rOC(O)NR^{5a}R^{5a}$, $(CHR)_rNR^{5a}C(O)NR^{5a}R^{5a}$, $CRR(CRR)_rNR^{5a}C(O)H$, $(CRR)_rC(O)OR^{5b}$, $(CRR)_rOC(O)R^{5b}$, $(CRR)_rS(O)_pR^{5b}$, $(CRR)_rS(O)_2NR^{5a}R^{5a}$, $(CRR)_rNR^{5a}S(O)_2R^{5b}$, and $C_{1-6}$ haloalkyl;

$R^{5a}$, at each occurrence, is independently selected from H, methyl, $C_{1-6}$ alkyl substituted with 0–2 $R^{5e}$ wherein the alkyl is selected from ethyl, propyl, i-propyl, butyl, i-butyl, pentyl, hexyl, $C_3$ alkenyl, substituted with 0–1 $R^{5e}$, wherein the alkenyl is selected from allyl, $C_3$ alkynyl substituted with 0–1 $R^{5e}$ wherein the alkynyl is selected from propynyl, and a $(CH_2)_r$—$C_{3-4}$ carbocyclic residue substituted with 0–5 $R^{5e}$, wherein the carbocyclic residue is selected from cyclopropyl, and cyclobutyl;

$R^{5b}$, at each occurrence, is selected from $C_{1-6}$ alkyl substituted with 0–2 $R^{5e}$, wherein the alkyl is selected from methyl, ethyl, propyl, i-propyl, butyl, i-butyl, pentyl, and hexyl, a $(CH_2)_r$—$C_{3-4}$ carbocyclic residue substituted with 0–2 $R^{5e}$, wherein the carbocyclic residue is selected from cyclopropyl, and cyclobutyl; and $R^{5d}$, at each occurrence, is selected from methyl, $CF_3$, $C_{2-6}$ alkyl substituted with 0–2 $R^{5e}$, wherein the alkyl is selected from methyl, ethyl, propyl, i-propyl, butyl, i-butyl, pentyl, and hexyl, $C_{3-8}$ alkenyl, $C_{3-8}$ alkynyl, and a $C_{3-10}$ carbocyclic residue substituted with 0–3 $R^{5e}$.

6. The compound of claim 5, wherein:

R, at each occurrence, is independently selected from H, methyl, ethyl, propyl, allyl, propynyl, $(CH_2)_rC_{3-6}$ cycloalkyl, and $(CH_2)_r$phenyl substituted with $R^{6e}$;

$R^5$, at each occurrence, is independently selected from H, methyl, ethyl, propyl, i-propyl, butyl, i-butyl, allyl, propynyl, $(CH_2)_rOH$, $(CH_2)_rOR^{5d}$, $(CH_2)_rNR^{5a}R^{5a}$, $(CH_2)_rC(O)OH$, $(CH_2)_rC(O)R^{5b}$, $(CH_2)_rC(O)NR^{5a}R^{5a}$, $(CH_2)_rNR^{5a}C(O)R^{5b}$, $(CH_2)_rOC(O)NR^{5a}R^{5a}$, $(CH_2)_rNR^{5a}C(O)OR^{5d}$, $(CH_2)_rNR^{5a}C(O)R^{5b}$, $(CH_2)_rC(O)OR^{5b}$, $(CH_2)_rOC(O)R^{5b}$, $(CH_2)_rNR^{5a}C(O)R^{5b}$, and $C_{1-6}$ haloalkyl;

$R^{5a}$, at each occurrence, is independently selected from H, methyl, ethyl, propyl, i-propyl, butyl, i-butyl, pentyl, hexyl, cyclopropyl, and cyclobutyl; and r, at each occurrence, is selected from 0, 1, and 2.

7. The compound of claim 6, wherein:

$R^1$ is selected from phenyl substituted with 0–2 $R^6$, naphthyl substituted with 0–2 $R^6$, $R^2$ is selected from a 5–10 membered heteroaryl system containing 1–4 heteroatoms selected from N, O, and S, substituted with 0–3 $R^7$ wherein the heteroaryl is selected from indolyl, benzimidazolyl, benzofuranyl, benzothiofuranyl, benzoxazolyl, benzthiazolyl, benzo[b]thiophene, benztriazolyl, benztetrazolyl, benzisoxazolyl, benzisothiazolyl, benzimidazalonyl, cinnolinyl, furanyl, imidazolyl, indazolyl, indolyl, isoquinolinyl isothiazolyl, isoxazolyl, oxazolyl, phthalazinyl, pyrazinyl, pyrazolyl, pyridazinyl, pyridyl, pyrido[2,3-d]pyrimidinyl, thieno[3,2-d]pyrimidinyl, pyridinyl, pyrimidinyl, pyrrolyl, pyrrolo[2,1-f][1,2,4]triazine, quinazolinyl, quinolinyl, thiazolyl, thienyl, and tetrazolyl.

8. The compound of claim 7, wherein:

$R_6$, at each occurrence, is selected from $C_{1-8}$ alkyl, $C_{2-8}$ alkenyl, $C_{2-8}$ alkynyl, $(CR'R')_rC_{3-6}$ cycloalkyl, Cl, Br, I, F, $NO_2$, CN, $(CR'R')_rNR^{6a}R^{6a}$, $(CR'R')_rOH$, $(CR'R')_rO(CR'R')_rR^{6d}$, $(CR'R')_rSH$, $(CR'R')_rC(O)H$, $(CR'R')_rS(CR'R')_rR^{6d}$, $(CR'R')_rC(O)OH$, $(CR'R')_rC(O)(CR'R')_rR^{6b}$, $(CR'R')_rC(O)NR^{6a}R^{6a}$, $(CR'R')_rNR^{6f}C(O)(CR'R')_rR^{6b}$, $(CR'R')_rC(O)O(CR'R')_rR^{6d}$, $(CR'R')_rNR^{6a}C(O)NR^{6a}R^{6a}$, $(CR'R')_rNR^{6a}C(S)NR^{6a}R^{6a}$, $(CR'R')_rOC(O)(CR'R')_rR^{5b}$, $(CR'R')_rS(O)_p(CR'R')_rR^{6b}$, $(CR'R')_rS(O)_2NR^{6a}R^{6a}$, $(CR'R')_rNR^{6f}S(O)_2(CR'R')_rR^{6b}$, $(CR'R')_rNR^{6f}S(O)_2 NR^{6a}R^{6a}$, $C_{1-6}$ haloalkyl, and $(CR'R')_r$phenyl substituted with 0–3 $R^{6e}$, and a $(CH_2)_r$-5–6membered heterocyclic system containing 1–2 heteroatoms selected from N, O, and S, substituted with 0–2 $R^{6e}$;

$R^{6a}$, at each occurrence, is independently selected from H, methyl, ethyl, propyl, i-propyl, butyl, i-butyl, t-butyl, pentyl, hexyl, cyclopropyl and phenyl;

$R^{6b}$, at each occurrence, is selected from methyl, ethyl, propyl, i-propyl, butyl, i-butyl, t-butyl, pentyl, hexyl, cyclopropyl, and phenyl;

$R^{6d}$, at each occurrence, is selected from methyl, $CF_3$, ethyl, propyl, i-propyl, butyl, i-butyl, t-butyl, pentyl, hexyl, cyclopropyl, and phenyl;

$R^{6e}$, at each occurrence, is selected from $C_{1-6}$ alkyl, $C_{2-8}$ alkenyl, $C_{2-8}$ alkynyl, $(CH_2)_rC_{3-6}$ cycloalkyl, Cl, F, Br, I, CN, $NO_2$, $(CF_2)_rCF_3$, $(CH_2)_rOC_{1-5}$ alkyl, OH, SH, $(CH_2)_rSC_{1-5}$ alkyl, $(CH_2)_rNR^{6f}R^{6f}$, and $(CH_2)_r$phenyl;

$R^{6f}$, at each occurrence, is selected from H, methyl, ethyl, propyl, i-propyl, butyl, i-butyl, t-butyl, pentyl, hexyl, cyclopropyl, and phenyl;

$R^7$ is selected from methyl, ethyl, propyl, i-propyl, butyl, i-butyl, s-butyl, t-butyl, pentyl, hexyl, $(CR'R')_rC_{3-6}$ cycloalkyl, Cl, Br, I, F, $NO_2$, CN, $(CR'R')_rNR^{7a}R^{7a}$, $(CR'R')_rOH$, $(CR'R')_rO(CH)_rR^{7d}$, $(CR'R')_rSH$, $(CR'R')_rC(O)H$, $(CR'R')_rS(CR'R')_rR^{7d}$, $(CR'R')_rC(O)OH$, $(CR'R')_rC(O)(CR'R')_rR^{7b}$, $(CR'R')_rC(O)NR^{7a}R^{7a}$, $(CR'R')_rNR^{7f}C(O)(CR'R')_rR^{7b}$, $(CR'R')_rC(O)O(CR'R')_rR^{7d}$, $(CR'R')_rOC(O)(CR'R')_rR^{7b}$, $(CR'R')_rNR^{7a}C(O)NR^{7a}R^{7a}$, $(CR'R')_rNR^{7a}C(O)O(CR'R')_rR^{7d}$, $(CR'R')_rS(O)_p(CR'R')_rR^{7b}$, $(CR'R')_rS(O)_2NR^{7a}R^{7a}$, $(CR'R')_rNR^{7f}S(O)_2(CR'R')_rR^{7b}$, $C_{1-6}$ haloalkyl, and $(CR'R')_r$phenyl substituted with 0–3 $R^{7e}$;

$R^{7a}$, at each occurrence, is selected from H, methyl, ethyl, propyl, i-propyl, butyl, i-butyl, t-butyl, pentyl, hexyl, prop-2-enyl, 2-methyl-2-propenyl, cyclopropyl, cyclobutyl, cyclopentyl, cyclohexyl, $CH_2$cyclopropyl, and benzyl;

$R^{7b}$, at each occurrence, is selected from methyl, ethyl, propyl, i-propyl, butyl, i-butyl, t-butyl, pentyl, hexyl, cyclopropyl, cyclopentyl, $CH_2$-cyclopentyl, cyclohexyl, $CH_2$-cyclohexyl, $CF_3$, pyrrolidinyl, morpholinyl, piperizenyl substituted with 0–1 $R^{7e}$, and azetidinyl;

$R^{7d}$, at each occurrence, is selected from methyl, $CF_3$, $CF_2CF_3$, $CHF_2$, $CH_2F$, ethyl, propyl, i-propyl, butyl, i-butyl, t-butyl, pentyl, hexyl, and cyclopropyl;

$R^{7e}$, at each occurrence, is selected from $C_{1-6}$ alkyl, $C_{2-8}$ alkenyl, $C_{2-8}$ alkynyl, $(CH_2)_rC_{3-6}$ cycloalkyl, Cl, F, Br, I, ON, $NO_2$, $(CF_2)_rCF_3$, $(CH_2)_rOC_{1-5}$ alkyl, OH, SH, $C(O)OC_{1-5}$ alkyl, $(CH_2)_rSC_{1-5}$ alkyl, $(CH_2)_rNR^{7f}R^{7f}$, and $(CH_2)_r$phenyl;

$R^{7f}$, at each occurrence, is selected from H, methyl, ethyl, propyl, i-propyl, butyl, i-butyl, t-butyl, pentyl, hexyl, cyclopropyl, and phenyl; and r is 0 or 1.

9. The compound of claim 8, wherein:

$R^7$ is selected from methyl, ethyl, propyl, i-propyl, butyl, i-butyl, s-butyl, pentyl, hexyl, Cl, Br, I, F, ON, $NO_2$, $NR^{7a}R^{7a}$, $NHC(O)NHR^{7a}$, $NR^{7a}C(O)R^{7b}$, $NR^{7a}C(O)OR^{7d}$, $CF_3$, $CF_2CF_3$, $CHF_2$, $CH_2F$, $OCF_3$, $C(O)R^{7b}$, $C(O)OR^{7d}$, $NR^{7f}C(O)NR^{7a}R^{7a}$, $NHS(O)_2R^{7b}$,

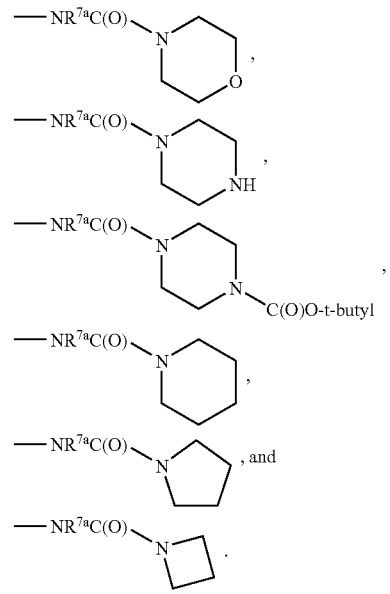

10. The compound of claim 9, wherein:
ring B is

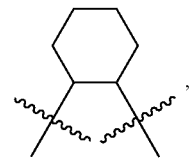

ring B being optionally substituted with 0–1 $R^5$;

$R^1$ is selected from a $C_{6-10}$ aryl group substituted with 0–3 $R^6$ wherein the aryl group is selected from phenyl and naphthyl, $R^6$ is selected from methyl, ethyl, propyl, i-propyl, butyl, F, Cl, Br, I, $NO_2$, CN, $O(CH_2)_rR^{6d}$, $C(O)H$, $C(O)R^{6d}$, $C(O)OH$, $SR^{6d}$, $NR^{6a}R^{6a}$, $NC(O)R^{6b}$, $OC(O)R^{6b}$, $S(O)_pR^{6b}$, $(CHR')_rS(O)_2NR^{6a}R^{6a}$, and $CF_3$;

$R^{6a}$ is H, methyl, or ethyl;

$R^{6b}$ is H, methyl, ethyl, propyl, i-propyl or butyl;

$R^{6d}$ is methyl, phenyl, $CF_3$ and $(CH_2)_r$-phenyl; and r is 0 or 1.

11. The compound of claim 10, wherein:
ring B is

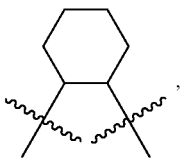

ring B being substituted with 0–1 $R^5$;
$R^1$ is selected from a $C_{6-10}$ aryl group substituted with 0–3 $R^6$ wherein the aryl group is selected from phenyl;
$R^4$ is selected from H, methyl, ethyl, propyl, i-propyl, butyl, i-butyl, t-butyl, pentyl, hexyl, allyl and $(CH_2)_rC(O)R^{4b}$;
$R^5$ is selected from H, OH, $OCH_3$, and $NR^{5a}R^{5a}$;
$R^{5a}$ is selected from H, methyl, ethyl, propyl, i-propyl, butyl, s-butyl, i-butyl, t-butyl, pentyl, hexyl, allyl, propargyl, cyclopropyl, cyclopropylmethyl, acetyl, methylsulfonyl, —$C(O)CF_3$, $C(=N)NH_2$, benzyl, and —$C(O)O$-t-butyl;
$R^6$ is selected from methyl, ethyl, propyl, i-propyl, butyl, vinyl, F, Cl, Br, I, CN, $NR^{6a}R^{6a}$, $C(O)H$, $C(O)OH$, $C(O)R^{6b}$, $SR^{6d}$, $S(O)_pR^{6d}$, $S(O)_2NR^{6a}R^{6a}$, $CF_3$, and $CH_2OH$;
$R^{6b}$ is H, methyl, ethyl, propyl, i-propyl or butyl;
$R^{6d}$ is methyl;
$R^7$ is selected from methyl, ethyl, propyl, i-propyl, butyl, i-butyl, s-butyl, pentyl, hexyl, Cl, Br, I, F, CN, $NO_2$, $NR^{7a}R^{7a}$, $NHC(O)NHR^{7a}$, $NR^{7a}C(O)R^{7b}$, $NR^{7a}C(O)OR^{7d}$, $CF_3$, $CF_2CF_3$, $CHF_2$, $CH_2F$, $OCF_3$, $OCF_2CF_3$, $OCHF_2$, and $OCH_2F$, $C(O)OR^{7d}$, $C(O)R^{7b}$, $NR^{7b}C(O)NR^{7a}R^{7a}$, $NHS(O)_2R^{7b}$,

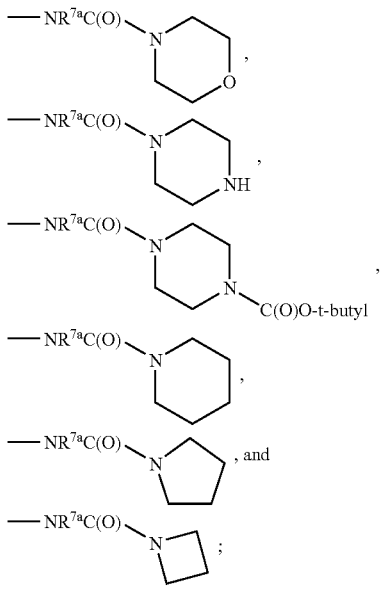

$R^{7a}$ is selected from H, methyl, ethyl, propyl, i-propyl, butyl, i-butyl, t-butyl, pentyl, neo-pentyl, cyclopropyl, cyclobutyl, cyclopentyl, and cyclohexyl;
$R^{7b}$ is selected from cyclohexyl and $CF_3$; and
$R^{7d}$ is selected from methyl, ethyl, propyl, i-propyl, butyl, i-butyl, and t-butyl.

12. The compound of claim 11, wherein:
ring B is selected from

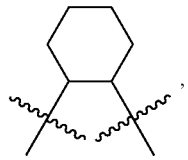

ring B being substituted with 0–1 $R^5$;
$R^1$ is selected from a $C_{6-10}$ aryl group substituted with 0–3 $R^6$ wherein the aryl group is phenyl;
$R^6$ is selected from methyl, ethyl, propyl, i-propyl, F, Cl, Br, CN, $SCH_3$, and $CF_3$;
$R^7$ is selected from methyl, ethyl, propyl, i-propyl, butyl, i-butyl, s-butyl, t-butyl, pentyl, hexyl, phenyl, adamantyl, benzyl, Cl, Br, I, F, ON, $NO_2$, $NR^{7a}R^{7a}$, $OR^{7d}$, $NHC(O)NHR^{7a}$, $NR^{7a}C(O)R^{7b}$, $NR^{7a}C(O)OR^{7d}$, $CF_3$, $CF_2CF_3$, $CHF_2$, $CH_2F$, $OCF_3$, $OCF_2CF_3$, $OCHF_2$, and $OCH_2F$, $C(O)OR^{7d}$, $C(O)R^{7b}$, and $NR^{7f}C(O)NR^{7a}R^{7a}$;
$R^{7a}$ is selected from H, methyl, ethyl, propyl, i-propyl, butyl, i-butyl, t-butyl, pentyl, neo-pentyl, cyclopropyl, cyclobutyl, cyclopentyl, and cyclohexyl.

13. The compound of claim 12, wherein
E is selected from —$CH_2$—NH—, —$C(O)$—NH— and —$SO_2$—$CH_2$—.

14. The compound of claim 1, wherein
B is

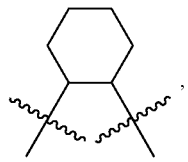

ring B being substituted with 0–1 $R^5$; and
$R^5$ is selected from H, $N(\rightarrow O)R^{5a}R^{5a}$, $N_3$, $NR^{5a}C(O)R^{5b}$, $NR^{5a}C(O)H$, $NR^{5a}C(O)OR^{5d}$, $NR^{5a}C(O)NR^{5a}R^{5a}$, and $NR^{5a}R^{5a}$, and a $(CH_2)_r$-5–6 membered heterocyclic system containing 1–2 heteroatoms selected from N, O, and S, substituted with 0–2 $R^{5e}$, wherein the heterocyclic system is selected from pyrrolidinyl, piperidinyl, pyrrolidin-2-one, and isothiazolidine 1,1-dioxide.

15. The compound of claim 12, wherein
$R^6$ is selected from methyl, ethyl, propyl, i-propyl, butyl, vinyl, F, Cl, Br, I, $C(O)H$, $C(O)R^{6b}$, $SR^{6d}$, $S(O)_pR^{6d}$, $CF_3$, and $CH_2OH$;
$R^{6b}$ is H, methyl, ethyl, propyl, i-propyl or butyl;
$R^{6d}$ is methyl;
$R^7$ is selected from Cl, Br, $NR^{7a}R^{7a}$, $NR^{7a}C(O)OR^{7d}$, $NHC(O)NHR^{7a}$, $OCF_3$, and $CF_3$;
$R^{7a}$ is selected from H, methyl, ethyl, propyl, i-propyl, butyl, i-butyl, t-butyl, pantyl, neo-pentyl, cyclopropyl, cyclobutyl, cyclopentyl, and cyclohexyl;
$R^{7d}$ is selected from methyl, ethyl, propyl, i-propyl, butyl, i-butyl, and t-butyl.

16. The compound of claim 1, wherein the compound is of formula (Ia) or (Ic)

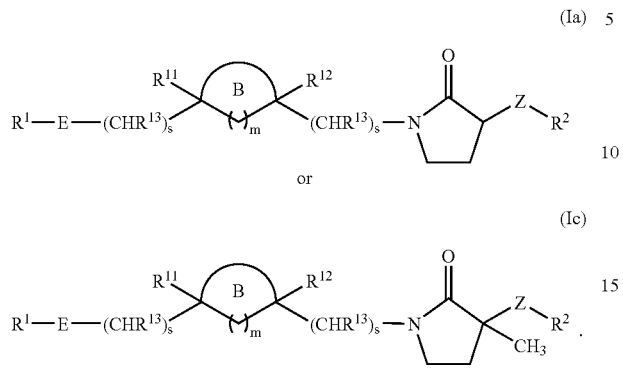

17. The compound of claim 1, wherein the compound of formula (I) is selected:
- 3-(Benzo[b]thiophen-3-ylamino)-1-((1S,2R,4R)-4-(isopropyl(methyl)amino)-2-(phenylsulfonylmethyl)cyclohexyl)pyrrolidin-2-one;
- (S)-3-(6-chloroquinazolin-4-ylamino)-1-((1S,2R,4R)-4-(isopropyl(methyl)amino)-2-(phenylsulfonylmethyl)cyclohexyl)pyrrolidin-2-one;
- (S)-3-(6,8-dichloroquinazolin-4-ylamino)-1-((1S,2R,4R)-4-(isopropyl(methyl)amino)-2-(phenylsulfonylmethyl)cyclohexyl)pyrrolidin-2-one;
- 3-((E)-3(R*)-(trifluoromethyl)styryl)-1-((1S*,2R*,4R*)-4-(isopropyl(methyl)amino)-2-(phenylsulfonylmethyl)cyclohexyl)pyrrolidin-2-one;
- (R)-1-((1S,2R,4R)-4-(isopropyl(methyl)amino)-2-(phenylsulfonylmethyl)cyclohexyl)-3-(6-(trifluoromethyl)quinolin-4-ylamino)pyrrolidin-2-one;
- (S)-1-((1S,2R,4R)-4-(isopropyl(methyl)amino)-2-(phenylsulfonylmethyl)cyclohexyl)-3-(6-(trifluoromethyl)quinolin-4-ylamino)pyrrolidin-2-one;
- (R)-1-((1S,2R,4R)-4-(isopropyl(methyl)amino)-2-(phenylsulfonylmethyl)cyclohexyl)-3-(7-(trifluoromethyl)quinolin-4-ylamino)pyrrolidin-2-one;
- (S)-1-((1S,2R,4R)-4-(isopropyl(methyl)amino)-2-(phenylsulfonylmethyl)cyclohexyl)-3-(7-(trifluoromethyl)quinolin-4-ylamino)pyrrolidin-2-one;
- 1-[(1S,2R,4R)-2-Benzenesulfonylmethyl-4-(isopropyl-methyl-amino)-cyclohexyl]-(3S)-3-(6-chloro-2-trifluoromethyl-quinazolin-4-ylamino)-pyrrolidin-2-one;
- 1-[(1S,2R,4R)-2-benzenesulfonylmethyl-4-(isopropyl-methyl-amino)-cyclohexyl]-(3S)-3-(7-chloro-quinazolin-4-ylamino)-pyrrolidin-2-one;
- 1-[(1S,2R,4R)-2-benzenesulfonylmethyl-4-(isopropyl-methyl-amino)-cyclohexyl]-(3S)-3-(2,6-dichloro-quinazolin-4-ylamino)-pyrrolidin-2-one;
- 1-[(1S,2R,4R)-2-benzenesulfonylmethyl-4-(isopropyl-methyl-amino)-cyclohexyl]-(3S)-3-(6-chloro-2-dimethylamino-quinazolin-4-ylamino)-pyrrolidin-2-one;
- 1-[(1S,2R,4R)-2-benzenesulfonylmethyl-4-(isopropyl-methyl-amino)-cyclohexyl]-(3S)-3-(6-chloro-2-hydroxy-quinazolin-4-ylamino)-pyrrolidin-2-one;
- 1-[(1S,2R,4R)-2-benzenesulfonylmethyl-4-(isopropyl-methyl-amino)-cyclohexyl]-(3S)-3-(6-trifluoromethyl-quinazolin-4-ylamino)-pyrrolidin-2-one;
- 1-[(1S,2R,4R)-2-benzenesulfonylmethyl-4-(isopropyl-methyl-amino)-cyclohexyl]-(3S)-3-(6-tert-butyl-trieno[3,2-d]pyrimidin-4-ylamino)-pyrrolidin-2-one;
- 1-[(1S,2R,4R)-2-benzenesulfonylmethyl-4-(isopropyl-methyl-amino)-cyclohexyl]-(3S)-3-(6-tert-butyl-2-trifluoromethyl-thieno[3,2-d]pyrimidin-4-ylamino)-pyrrolidin-2-one;
- 1-[(1S,2R,4R)-2-benzenesulfonylmethyl-4-(isopropyl-methyl-amino)-cyclohexyl]-(3S)-3-(6-tert-butyl-pyrrolo[2,1-f][1,2,4]triazin-4-ylamino)-pyrrolidin-2-one;
- (3S)-3-(6-Admantan-1-yl-pyrrolo[2,1-f][1,2,4]triazin-4-ylamino)-1-[(1S,2R,4R)-2-benzenesulfonylmethyl-4-(isopropyl-methyl-amino)-cyclohexyl]-pyrrolidin-2-one;
- 1-[(1S,2R,4R)-2-benzenesulfonylmethyl-4-(isopropyl-methyl-amino)-cyclohexyl]-(3S)-3-(6,7-dimethoxy-quinazolin-4-ylamino)-pyrrolidin-2-one;
- 1-[(1S,2R,4R)-2-benzenesulfonylmethyl-4-(isopropyl-methyl-amino)-cyclohexyl]-(3S)-3-(6-fluoro-quinazolin-4-ylamino)-pyrrolidin-2-one;
- 1-[(1S,2R,4R)-2-benzenesulfonylmethyl-4-(isopropyl-methyl-amino)-cyclohexyl]-(3S)-3-(6-methyl-quinazolin-4-ylamino)-pyrrolidin-2-one;
- 1-[(1S,2R,4R)-2-benzenesulfonylmethyl-4-(isopropyl-methyl-amino)-cyclohexyl]-(3S)-3-(6-phenyl-thieno[2,3-d]pyrimidin-4-ylamino)-pyrrolidin-2-one;
- 1-[(1S,2R,4R)-2-benzenesulfonylmethyl-4-(isopropyl-methyl-amino)-cyclohexyl]-(3S)-3-(6-chloro-2-propyl-pyrido[2,3-d]pyrimidin-4-ylamino)-pyrrolidin-2-one;
- 1-[(1S,2R,4R)-2-benzenesulfonylmethyl-4-(isopropyl-methyl-amino)-cyclohexyl]-(3S)-3-(6-chloro-2-isopropyl-quinazolin-4-ylamino)-pyrrolidin-2-one;
- 1-[(1S,2R,4R)-2-benzenesulfonylmethyl-4-(isopropyl-methyl-amino)-cyclohexyl]-(3S)-3-(2-tert-butyl-6-chloro-quinazolin-4-ylamino)-pyrrolidin-2-one;
- 1-[(1S,2R,4R)-2-benzenesulfonylmethyl-4-(isopropyl-methyl-amino)-cyclohexyl]-(3S)-3-(6-chloro-2-methyl-quinazolin-4-ylamino)-pyrrolidin-2-one;
- 1-[(1S,2R,4R)-2-benzenesulfonylmethyl-4-(isopropyl-methyl-amino)-cyclohexyl]-(3S)-3-(6-chloro-2-ethyl-quinazolin-4-ylamino)-pyrrolidin-2-one;
- 1-[(1S,2R,4R)-2-Benzenesulfonylmethyl-4-(isopropyl-methyl-amino)-cyclohexyl]-(3S)-3-(6-tert-butyl-pyrimido[5,4-d]pyrimidin-4-ylamino)-pyrrolidin-2-one;
- 1-[(1S,2R,4R)-2-benzenesulfonylmethyl-4-(isopropyl-methyl-amino)-cyclohexyl]-(3S)-3-(pyrido[2,3-d]pyrimidin-4-ylamino)-pyrrolidin-2-one;
- 1-[(1S,2R,4R)-2-benzenesulfonylmethyl-4-(isopropyl-methyl-amino)-cyclohexyl]-(3S)-3-(6-chloro-pyrido[2,3-d]pyrimidin-4-ylamino)-pyrrolidin-2-one;
- 1-[(1S,2R,4R)-2-benzenesulfonylmethyl-4-(isopropyl-methyl-amino)-cyclohexyl]-(3S)-3-(6-chloro-2-trifluoromethyl-pyrido[2,3-d]pyrimidin-4-ylamino)-pyrrolidin-2-one;
- 1-[(1S,2R,4R)-2-benzenesulfonylmethyl-4-(isopropyl-methyl-amino)-cyclohexyl]-(3S)-3-(6-trifluoromethoxy-pyrrolo[2,3-d]pyrimidin-4-ylamino)-pyrrolidin-2-one;
- 1-[(1S,2R,4R)-2-benzenesulfonylmethyl-4-(isopropyl-methyl-amino)-cyclohexyl]-(3S)-3-(6-chloro-2-methylamino-quinazolin-4-ylamino)-pyrrolidin-2-one;
- (3S)-3-(6-Fluoro-quinazolin-4-ylamino)-1-[(1S,2R,4R)-4-(isopropyl-methyl-amino)-2-(toluene-4-sulfonylmethyl)-cyclohexyl]-pyrrolidin-2-one;

(S)-3-(6-Bromoquinazolin-4-ylamino)-1-((1S,2R,4R)-4-(isopropyl(methyl)amino)-2-(phenylsulfonylmethyl)cyclohexyl)pyrrolidin-2-one;

(S)-3-(6,7-Difluoroquinazolin-4-ylamino)-1-((1S,2R,4R)-4-(isopropyl(methyl)amino)-2-(phenylsulfonylmethyl)cyclohexyl)pyrrolidin-2-one;

(S)-3-(6-Methoxyquinazolin-4-ylamino)-1-((1S,2R,4R)-4-(isopropyl(methyl)amino)-2-(phenylsulfonylmethyl)cyolohexyl)pyrrolidin-2-one;

((S)-1-((1S,2R,4R)-4-(isopropyl(methyl)amino)-2-(phenylsulfonylmethyl)cyclohexyl)-3-(quinazolin-4-ylamino)pyrrolidin-2-one;

(S)-3-(6-Iodoquinazolin-4-ylamino)-1-((1S,2R,4R)-4-(isopropyl(methyl)amino)-2-(phenylsulfonylmethyl)cyclohexyl)pyrrolidin-2-one.

18. A pharmaceutical composition, comprising a pharmaceutically acceptable carrier and a therapeutically effective amount of a compound of claim 1.

19. A pharmaceutical composition, comprising a pharmaceutically acceptable carrier and a therapeutically effective amount of a compound of claim 7.

\* \* \* \* \*

UNITED STATES PATENT AND TRADEMARK OFFICE
CERTIFICATE OF CORRECTION

PATENT NO. : 7,183,270 B2
APPLICATION NO. : 10/776828
DATED : February 27, 2007
INVENTOR(S) : Robert J. Cherney et al.

It is certified that error appears in the above-identified patent and that said Letters Patent is hereby corrected as shown below:

On the Title Page:

Item (56) References Cited, under FOREIGN PATENT DOCUMENTS:

Column 2:

Change "WO 02/01416" to -- WO 02/04416 --.

Delete the following line: "WO WO02060859 8/2002".

In the Claims:

Claim 1:

Column 161, line 48, delete """ before "$(CRR)_rSR^{5d}$".

Column 162, line 4, change "$(CH_2)_rC_{3-6}$" to -- $(CH_2)_r$–$C_{3-6}$ --.

Column 163, line 65, change "$(CH^2)_r phenyl$" to -- $(CH_2)_r phenyl$ --.

Column 164, line 18, change "$(CHR)_rC(O)R^{11a}OR^{11d}$" to -- $(CHR)_rC(O)NR^{11a}OR^{11d}$ --.

Claim 2:

Column 166, line 6, change "$(CHR)_rSR^{5d}$" to -- $(CRR)_rSR^{5d}$ --.

Column 166, line 37, change "$(CH_2)_r(CO)R^{5b}$" to -- $(CH_2)_rC(O)R^{5b}$ --.

Column 167, line 3, change "$(CR'R')_rNR^{6a}C(O)O(CR'R')_rR^{6b}$" to
-- $(CR'R')_rNR^{6f}C(O)O(CR'R')_rR^{6b}$ --.

Column 167, line 16, delete """ after -- $R^{6g}$ --.

Column 167, lines 50 to 51, change "$(CR'R')_rNR^{7e}C(O)(CR'R')_rR^{7b}$" to
-- $(CR'R')_rNR^{7f}C(O)(CR'R')_rR^{7b}$ --.

Column 167, line 63, change "$R^{7e}$" to -- $R^{7a}$ --.

Column 168, line 21, change "ON" to -- CN --.

Signed and Sealed this
Twelfth Day of July, 2011

David J. Kappos
*Director of the United States Patent and Trademark Office*

CERTIFICATE OF CORRECTION (continued)
U.S. Pat. No. 7,183,270 B2

In the Claims:

Claim 2 (continued):

Column 168, line 40, change "$C_{2-4}$ alkyl" to -- $C_{1-4}$ alkyl --.

Column 168, line 51, change "$C_{2-4}$ alkyl" to -- $C_{1-4}$ alkyl --.

Column 168, line 57, change "01-4 alkyl" to -- $C_{1-4}$ alkyl --.

Column 168, line 63, change "–$CF_3$m" to -- –$CF_3$, --.

Column 169, line 2, change "ON" to -- CN --.

Claim 6:

Column 170, lines 55 to 56, change "$(CH_2)_rNR^{5a}C(O)R^{5b}$" to -- $(CH_2)_rNR^{5a}S(O)_2R^{5b}$ --.

Claim 8:

Column 171, line 12, change "$R_6$" to -- $R^6$ --.

Column 171, line 20, change "$(CR'R')_rOC(O)(CR'R')_rR^{5b}$" to -- $(CR'R')_rOC(O)(CR'R')_rR^{6b}$ --.

Column 171, line 24, change "$(CH_2)_r$-5-6membered" to -- $(CH_2)_r$-5-6 membered --.

Column 172, line 6, change "ON" to -- CN --.

Claim 9:

Column 172, line 15, change "ON" to -- CN --.

Claim 11:

Column 173, lines 34 to 35, change "$NR^{7b}C(O)NR^{7a}R^{7a}$" to -- $NR^{7f}C(O)NR^{7a}R^{7a}$ --.

Claim 12:

Column 174, line 21, change "ON" to -- CN --.

Claim 15:

Column 174, line 64, change "pantyl" to -- pentyl --.

Claim 16:

Column 175, line 66, change "-butyl-trieno" to -- -butyl-thieno --.

Column 176, line 60, change "-pyrrolo[2,3-d]pyrimidin-" to -- -pyrido[2,3-d]pyrimidin- --.